US00RE47848E

(19) United States
(12) Reissued Patent
Estrada et al.

(10) Patent Number: US RE47,848 E
(45) Date of Reissued Patent: *Feb. 11, 2020

(54) BIHETEROARYL COMPOUNDS AND USES THEREOF

(71) Applicant: Genentech, Inc., South San Francisco, CA (US)

(72) Inventors: Anthony Estrada, San Carlos, CA (US); Alan G. Olivero, Half Moon Bay, CA (US); Snahel Patel, Foster City, CA (US); Michael Siu, Burlingame, CA (US); Joseph Lyssikatos, Piedmont, CA (US); Malcolm Huestis, San Francisco, CA (US); Terry Kellar, Burlingame, CA (US)

(73) Assignee: Genentech, Inc., South San Francisco, CA (US)

( * ) Notice: This patent is subject to a terminal disclaimer.

(21) Appl. No.: 15/902,746

(22) Filed: Feb. 22, 2018

Related U.S. Patent Documents

Reissue of:
(64) Patent No.: 9,266,862
Issued: Feb. 23, 2016
Appl. No.: 14/267,011
Filed: May 1, 2014

U.S. Applications:
(60) Provisional application No. 61/817,966, filed on May 1, 2013.

(51) Int. Cl.

| | |
|---|---|
| ***A61K 31/55*** | (2006.01) |
| ***C07D 403/14*** | (2006.01) |
| ***A61K 35/30*** | (2015.01) |
| ***C07D 491/08*** | (2006.01) |
| ***C07D 495/08*** | (2006.01) |
| ***C07D 519/00*** | (2006.01) |
| ***C07D 471/08*** | (2006.01) |
| ***A61K 45/06*** | (2006.01) |
| ***A61K 31/5386*** | (2006.01) |
| ***C07D 487/08*** | (2006.01) |
| ***C07D 413/14*** | (2006.01) |
| ***C07D 471/18*** | (2006.01) |
| ***C07D 405/14*** | (2006.01) |
| ***C07D 403/04*** | (2006.01) |
| ***C07D 401/14*** | (2006.01) |
| ***A61K 31/5377*** | (2006.01) |
| ***A61K 31/506*** | (2006.01) |
| ***A61K 31/4545*** | (2006.01) |
| ***A61K 31/444*** | (2006.01) |
| ***A61K 31/553*** | (2006.01) |
| ***A61K 31/155*** | (2006.01) |

(52) U.S. Cl.
CPC ..... *A61K 31/506* (2013.01); *A61K 31/155* (2013.01); *A61K 31/444* (2013.01); *A61K 31/553* (2013.01); *A61K 35/30* (2013.01)

(58) Field of Classification Search
CPC .. A61K 31/506; A61K 31/444; A61K 31/553; A61K 31/5386; A61K 45/06; A61K 35/30; A61K 31/55; A61K 31/5377; A61K 31/4545; C07D 417/14; C07D 487/18; C07D 487/14; C07D 471/08; C07D 401/14; C07D 495/08; C07D 519/00; C07D 403/04; C07D 403/14; C07D 405/14; C07D 413/14; C07D 471/18; C07D 487/08; C07D 491/08
See application file for complete search history.

(56) References Cited

U.S. PATENT DOCUMENTS 3,773,919 A 11/1973 Boswell et al.
4,485,045 A 11/1984 Regen
(Continued)

FOREIGN PATENT DOCUMENTS

CN 103483345 1/2014
CN 103483345 A 1/2014
(Continued)

OTHER PUBLICATIONS

"Polycyclic compound," Wikipedia, pp. 1-2, [online], [retrieved on Oct. 11, 2018], [retrieved from the Internet <URL: https://en.wikipedia.org/wiki/Polycyclic_compound >].*
Patani et al., "Bioisosterism: A Rational Approach in Drug Design", Chem. Rev. 96, pp. 3147-3176, 1996.*
Written Opinion for PCT/CN2014/076654, dated Jul. 30, 2014.
Agid, et al., "How can drug discovery for psychiatric disorders be improved" Nature Reviews/Drug Discovery, 6:189-201 (2007).
Bloom, et al., "The requirement for Phr1 in CNS axon tract formation reveals the corticostriatal boundary as a choice point for cortical axons," Genes & Development, 21:2593-2606 (2007).
(Continued)

*Primary Examiner* — Dwayne C. Jones
(74) *Attorney, Agent, or Firm* — Armstrong Teasdale LLP

(57) ABSTRACT

The present invention provides for compounds of Formula I and embodiments and salts thereof for the treatment of diseases (e.g., neurodegenerative diseases). $R^1$, $R^2$, $R^3$, $X^1$, $X^2$, A and Cy variable in Formula all have the meaning as defined herein.

Formula I

53 Claims, No Drawings

(56) References Cited

U.S. PATENT DOCUMENTS

| | | | |
|---|---|---|---|
| 4,544,545 | A | 10/1985 | Ryan et al. |
| 5,004,697 | A | 4/1991 | Pardridge |
| 5,112,596 | A | 5/1992 | Malfroy-Camine |
| 5,268,164 | A | 12/1993 | Kozarich et al. |
| 5,506,206 | A | 4/1996 | Kozarich et al. |
| 5,686,416 | A | 11/1997 | Kozarich et al. |
| 7,888,344 | B2 | 2/2011 | Alexander et al. |
| 8,217,035 | B2 | 7/2012 | Burger et al. |
| 8,288,378 | B2 | 10/2012 | Kim et al. |
| 8,754,060 | B2 | 6/2014 | DiAntonio et al. |
| 9,266,862 | B2 | 2/2016 | Estrada et al. |
| 10,010,549 | B2 * | 7/2018 | Estrada ..... C07D 401/14 |
| 10,028,954 | B2 | 7/2018 | Estrada et al. |
| 2002/0025313 | A1 | 2/2002 | Micklus et al. |
| 2002/0038086 | A1 | 3/2002 | Hynynen et al. |
| 2002/0065259 | A1 | 5/2002 | Schatzberg et al. |
| 2003/0073713 | A1 | 4/2003 | Shoenhard |
| 2003/0129186 | A1 | 7/2003 | Beliveau et al. |
| 2003/0162695 | A1 | 8/2003 | Schatzberg et al. |
| 2004/0131692 | A1 | 7/2004 | Kreuter et al. |
| 2004/0204354 | A1 | 10/2004 | Nelson et al. |
| 2005/0089473 | A1 | 4/2005 | Black et al. |
| 2005/0124533 | A1 | 6/2005 | Schatzberg et al. |
| 2010/0048547 | A1 | 2/2010 | Atallah et al. |
| 2010/0286135 | A1 | 11/2010 | Reddy et al. |
| 2012/0225859 | A1 | 9/2012 | Burger et al. |
| 2013/0040934 | A1 | 2/2013 | Cmiljanovic et al. |
| 2013/0203838 | A1 | 8/2013 | DiAntonio et al. |
| 2016/0052940 | A1 | 2/2016 | Estrada et al. |
| 2016/0158234 | A1 | 6/2016 | Estrada et al. |
| 2018/0117944 | A1 | 5/2018 | Lee et al. |

FOREIGN PATENT DOCUMENTS

| | | | |
|---|---|---|---|
| EP | 102324 | A2 | 3/1984 |
| EP | 133988 | A2 | 3/1985 |
| JP | 2009527464 | A | 7/2009 |
| JP | 2010518107 | A | 5/2010 |
| JP | 2012506898 | A | 4/2012 |
| JP | 2012508223 | A | 4/2012 |
| JP | 2013504325 | A | 2/2013 |
| WO | 2004029055 | A1 | 4/2004 |
| WO | 2007/084786 | A1 | 7/2007 |
| WO | 2007084786 | A1 | 7/2007 |
| WO | WO 2007/084786 | A1 * | 7/2007 |
| WO | 2008/098058 | A1 | 8/2008 |
| WO | 2008098058 | A1 | 8/2008 |
| WO | 2009/066084 | A1 | 5/2009 |
| WO | 2009066084 | A1 | 5/2009 |
| WO | 2010/049481 | | 5/2010 |
| WO | 2010049481 | A1 | 5/2010 |
| WO | 2010052569 | A2 | 5/2010 |
| WO | 2010052569 | A3 | 5/2010 |
| WO | 2010052569 | A8 | 5/2010 |
| WO | 2011031896 | A2 | 3/2011 |
| WO | 2011050192 | A1 | 4/2011 |
| WO | 2011/114275 | A1 | 9/2011 |
| WO | 2011114275 | A1 | 9/2011 |
| WO | WO 2011/114275 | A1 * | 9/2011 |
| WO | 2011149950 | A2 | 12/2011 |
| WO | 2012/122383 | | 9/2012 |
| WO | 2012122383 | A2 | 9/2012 |

OTHER PUBLICATIONS

Brinkmann, et al., "Fingolimod (FTY720): discovery and development of an oral drug to treat multiple sclerosis," Nature Reviews/Drug Discovery, 9:883-897 (2010).

Chen, et al., "Antiapoptotic and trophic effects of dominant-negative forms of dual leucine zipper kinase in dopamine neurons of the substantia nigra in vivo," J. Neurosci., 28(3):672-680 (Jan. 16, 2008).

Cook, et al., "Treatment of stroke with a PSD-95 inhibitor in the gyrencephalic primate brain," Nature, 483:213-218 (2012).

Fan, et al., "Dual Leucine Zipper-bearing Kinase(DLK) Activates p46 SAPK and p38mapk but not ERK2," J. Biological Chemistry, 271(10):24788-24793 (1996).

Heras-Sandoval, et al., "The Phosphatidylinositol 3-Kinase/m Tor Pathway as a Therapeutic Target for Brain Aging and Neurodegeneration," Pharmaceuticals, 4:1070-1087 (2011).

Hirai, et al., "The c-Jun N-Terminal kinase activator dual leucine zipper kinase regulates axon growth and neuronal migration in the developing cerebral cortex," J. of Neuroscience, 26(46):11992-12002 (2006).

Hunot, et al., "JNK-mediated induction of cyclooxygenase 2 is required for neurodegeneration in a mouse model of Parkinson's disease," Proceedings of the National Academy of Sciences of the USA, 101(2):665-670 (Jan. 2004).

Huntwork-Rodriguez, et al., "JNK-mediated phosphorylation of DLK suppresses its ubiquitination to promote neuronal apoptosis," J. Cell Biology, 202:747-763 (2013).

Itoh, et al., "Impaired regenerative response of primary sensory neurons in ZPK/DLK gene-trap mice," Biochemical and Biophysical Research Communications, 383:258-262 (2009).

Judge, et al., "Potassium channel blockers in multiple sclerosis: Neuronal Kv channels and effects of symptomatic treatment," Pharmacology & Therapeutics, 111:224-259 (2006).

Kovacs, et al., "Distribution of apoptosis-related proteins in sporadic Creutzfeldt-Jakob disease," Brain Research, 1323:192-199 (2010).

Kuan, et al., "A critical role of neural-specific JNK3 for ischemic apoptosis," Proceedings of the National Academy of Sciences of the USA, 100(25)15184-15189 (Dec. 2003).

Kuster, B. (ed.), Kinase Inhibitors Methods and Protocols, Chapters 1-3, Humana Press (2012).

Levkovitch-Verbin, et al., "The transcription factor c-jun is activated in retinal ganglion cells in experimental rat glaucoma," Experimental Eye Research, 80(5):663-670 (2005).

Loopuijt, et al., "The role of NMDA receptors in the slow neuronal degeneration of Parkinson's disease," Amino Acids, 14:17-23 (1998).

Marelli, et al., "Tumor targeting via integrin ligands," Frontiers in Oncology, 3:1-12 (2013).

Morfini, et al., "Pathogenic huntingtin inhibits fast axonal transport by activating JNK3 and phosphorylating kinesin," Nature Neuroscience, 12(7):864-781 (Jul. 2009).

Do, et al., "Expression of c-fos, c-jun, and c-jun N-terminal kinase (JNK) in a Development Model of Induced Apoptotic Death in Neurons of the Subsantia Nigra," Journal of Neurochemistry, 72(2):557-564 (1994).

Patel, et al., "Discovery of dual leucine zipper kinase (DLK, MAP3K12) inhibitors with activity in neurodegeneration models," J. Medicinal Chemistry, 58:401-418 (2015).

Perrin, et al., "Implication of the JNK pathway in a rat model of Huntington's disease," Experimental Neurology, 215:(1):191-200 (2009).

Ries, et al., "JNK2 and JNK3 combined are essentil for apoptosis in dopamine neurons of the substantia nigra, but are not required for axon degeneration," Journal of Neurochemistry, 107(6):1578-1588 (2008).

Sengupta-Ghosh, et al., "DLK induces developmental neuronal degeneration via selective regulation of proapoptotic JNK activity," Journal of Cell Biology, 194(5):751-764 (2011).

Shin, et al., "Dual leucine zipper kinase is required for retrograde injury signaling and axonal regeneration," Neuron, 74:1015-1022 (2012).

Sonkusare, et al., "Dementia of Alzheimer's disease and other neurodegenerative disorders—memantine, a new hope," Pharmacological Research, 51:1-17 (2005).

Steelman, et al., "Galectin-9-Protein Is Up-regulated in Astrocytes by Tumor Necrosis Factor and Promotes Encephalitogenic T-cell Apoptosis," The Journal of Biological Chemistry, 288(33):23776-23787 (Aug. 2013).

Tezel, et al., "Role of tumor necrosis factor receptor-1 in the death of retinal ganglion cells following optic nerve crush injury in mice," Brain Research, 996(2):202-212 (2004).

Thakur, et al., "c-Jun Phosphorylation in Alzheimer Disease," Journal of Neuroscience Research, 85(8):1668-1673 (2007).

(56) References Cited

OTHER PUBLICATIONS

Tran, et al., "Inhibition of JNK by a Peptide Inhibitor Reduces Traumatic Brain Injury Induced Tauopathy in Transgenic Mice," Journal of Neuropathology and Experimental Neurology, 71(2):116-129 (Feb. 2012).
Vulg, et al, "ATF3 expression precedes death of spinal motoneurons in amyotrophic lateral sclerosis-SOD1 transgenic mice and correlates with c-Jun phosphorylation, CHOP expression, somatodendritic ubiquitination and Golgi fragmentation," European Journal of Neuroscience, 22(8):1881-1894 (2005).
Wang, et al., "Mathematical modeling in cancer drug discovery," Drug Discovery Today, 19:154-150 (2014).
Welsbie, et al., "Functional genomic screening identifies dual leucine zipper kinase as a key mediator of retinal ganglion cell death," PNAS, 110(10):4045-4050 (2013).
Yang, et al., "Absence of excitotoxicity induced apoptosis in the hippocampus of mice lacking the Jnk3 gene," Nature, 389(6653):865-870 (1997).
Zakrzewska et al., "Trigeminal neuralgia: the diagnosis and management of this excruciating and poorly understood facial pain," Postgrad Med. J., 87:410-416 (2011).
Office Action issued in U.S. Appl. No. 14/927,267, dated Sep. 22, 2016.
Office action issued in U.S. Appl. No. 15/041,375, dated Aug. 11, 2016.
Office action issued in U.S. Appl. No. 14/267,011, dated Sep. 23, 2015.
Berge, et al., "Pharmaceutical Salts," Journal of Pharmaceutical Science, 66:1-19 (1977).
Bobo et al., "Convection-enhanced delivery of macromolecules in the brain," Proceedings of the National Academy of Sciences U.S.A. 91:2076-2080, 1994.
Bundgaard, H., "(C) Means to enhance penetration: (1) Prodrugs as a means to improve the delivery of peptide drugs," Advanced Drug Delivery Reviews, 8(1):1-38 (1992).
DeYebenes et al., "Continuous intracerebroventricular infusion of dopamine and dopamine agonists through a totally implanted drug delivery system in animal models of Parkinson's disease," Mov. Disord. 2(3): 143-158 (1987).
Epstein et al., "Biological activity of liposome-encapsulated murine interferon gamma is mediated by a cell membrane receptor," Proc. Natl. Acad. Sci. U.S.A. 82(11):3688-3692 (1985).
Fleisher, et al., "Improved oral drug delivery: solubility limitations overcome by the use of prodrugs," Advanced Drug Delivery Reviews, 19(2):115-130 (1996).
Gill et al., "Direct brain infusion of glial cell line-derived neurotrophic factor in Parkinson disease," Nature Medicine, 9 (5): 589-595, 2003.
Harbaugh, "Intracerebroventricular Cholinergic Drug Administration in Alzheimer's Disease: Preliminary Results of a Double-Blind Study," J. Neural Transm. Suppl., 24:271-277 (1987).
Hartwig, J. F., "Palladium-Catalyzed Amination of Aryl Halides: Mechanism and Rational Catalyst Design", Synlett 4: 329-340 (1997).
Hwang et al., "Hepatic uptake and degradation of unilamellar sphingomyelin/cholesterol liposomes: a kinetic study," Proc. Natl. Acad. Sci. U.S.A. 77(7):4030-4034 (1980).
Kakeya, et al., "Studies on Prodrugs of Cephalosporins. I. Synthesis and Biological Properties of Glycyloxybenzoyloxymethyl and Glycylaminobenzoyloxymethyl Esters of 7β-{2-(2-Aminothiazol-4-yl)-(Z)-2-methoxyiminoacetamido]-3-methyl-3-cephem-4-carboxylic Acid," Chem. Pharm. Bull., 32(2):692-698 (1984).
Krogsgaard-Larsen and H. Bundgaard, Editors, A Textbook of Drug Design and Development, Chapter 5 "Design and Application of Prodrugs," by H. Bundgaard p. 113-191 (1991).
Langer et al., "Biocompatibility of polymeric delivery systems for macromolecules," J. Biomed. Mater. Res. 15(2):267-277 (1981).
Miyaura, et al., "Palladium-Catalyzed Cross-Coupling Reactions of Organoboron Comopounds," Chem. Rev., 95(7):2457-2483 (1995).
Nielsen, et al., "Glycolamide esters as biolabile prodrugs of carboxylic acid agents: Synthesis, stability, bioconversion, and physicochemical properties," Journal of Pharmaceutical Sciences, 77(4):285-298 (1988).
Papanastassiou, et al., "The potential for efficacy of the modified (ICP 34.5-) herpes simplex virus HSV1716 following intratumoural injection into human malignant glioma: a proof of principle study," Gene Therapy 9:398-406 (2002).
Robinson, et al., "Discovery of the Hemifumarate and (α-L-Alanylox)methyl Ether as Prodrugs of an Antirheumatic Oxindole: Prodcrugs for the Enolic OH Group," J. Med. Chem., 39(1):10-18 (1996).
Sidman et al., "Controlled release of macromolecules and pharmaceuticals from synthetic poolypeptides based on glutamic acid," Biopolymers 22(1):547-556 (1983).
Widder, K., et al. Editor, Methods in Enzymology, vol. 42, p. 309-396 (Academic Press, 1985).
Bodor, N., "Targeting of Drugs to the Brain", Methods in Enzymology, 1985, vol. 112, pp. 381-396.
Bundgaard, H., "Formation of Prodrugs of Amines, Amides, Ureides and Imides", Methods in Enzymology, 1985, vol. 112, pp. 347-359.
Charton, M., "Prodrug Lability Prediction through the Use of Substituent Effects", Methods in Enzymology, 1985, vol. 112, pp. 323-340.
Fleisher et al., "Design of Prodrugs for Improved Gastrointestinal Absorption by Intestinal Enzyme Targeting", Methods in Enzymology, 1985, vol. 112, pp. 360-381.
Notari, Robert E., "Theory and Practice of Prodrug Kinetics", Methods in Enzymology, 1985, vol. 112, pp. 309-323.
PCT Written Opinion for PCT/CN2014/076654 mailed Jul. 30, 2014.

* cited by examiner

BIHETEROARYL COMPOUNDS AND USES THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application *is a reissue application of U.S. Pat. No. 9,266,862 B2, which was filed as U.S. patent application Ser. No. 14/267,011 on May 1, 2014 and issued on Feb. 23, 2016, and which* claims the benefit of U.S. Provisional Appl. No. 61/817,966, filed on May 1, 2013, *both of* which [is] *are* incorporated herein by reference in [its] *their* entirety.

FIELD OF THE INVENTION

The present invention relates to organic compounds useful for therapy and/or prophylaxis in a mammal, and in particular to inhibitors of DLK useful for treating neurodegeneration diseases and disorders.

BACKGROUND OF THE INVENTION

Neuron or axon degeneration plays a central role in the proper development of the nervous system and is a hall mark of many neurodegenerative diseases including for example, amyotrophic lateral sclerosis (ALS), glaucoma, Alzheimer's disease, and Parkinson's disease, as well a traumatic injury to the brain and spinal cord. Recent patent publication WO2011/050192, incorporated herein by reference, describes the role of the Dual Leucine Zipper Kinase (DLK), also referred to as MAP3K12, to cause neuronal cell death. Neurodegenerative diseases and injuries are devastating to patients and caregivers, and also result in great financial burdens, with annual costs currently exceeding several hundred billion dollars in the United States alone. Most current treatments for these diseases and conditions are inadequate. Adding to the urgency of the problems created by these diseases is the fact that many such diseases are age related, and thus their incidence is increasing rapidly as population demographics change. There is a great need for the development of effective approaches to treating neurodegenerative diseases and nervous system injuries, including for example, through the inhibitors of DLK in neurons.

SUMMARY OF THE INVENTION

In one aspect the present inventions provides for compounds of Formula I (I):

(I)

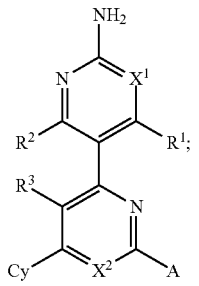

or salts thereof wherein $R^1$, $R^2$ and $R^3$ are each independently H, F, Cl, Br, I, $C_{1-6}$ alkyl or $C_{1-6}$ haloalkyl;

$X^1$ is N or C—$R^4$, wherein $R^4$ is selected from the group consisting of —F, —Cl, —Br, [I-$(L^1)_{0-1}$-$C_{1-6}$ alkyl,] —*I*, -$(L^1)_{0-1}$-$C_{1-6}$*alkyl*, -$(L^1)_{0-1}$-$C_{1-6}$ haloalkyl, -$(L^1)_{0-1}$-$C_{1-6}$ heteroalkyl, -$(L^2)_{0-1}$-$C_{3-8}$cycloalkyl, -$(L^2)_{0-1}$-3 to 7 membered heterocycloalkyl, -$(L^2)_{0-1}$-6-10 membered aryl, *and* -$(L^2)_{0-1}$-5-10 membered heteroaryl, wherein $L^1$ is selected from the group consisting of —O—, —N(H)—, —S—, —N($C_{1-6}$ alkyl)-, [=O] *and* —*C*(=*O*)—, and $L^2$ is selected from the group consisting of —O—, [—N(H] —*N*(*H*)—, —N($C_{1-6}$ alkyl)-, —S—, [=O] —*C*(=*O*)—, $C_{1-4}$ alkylene, $C_{1-4}$ alkenylene, $C_{1-4}$ alkynylene, $C_{1-4}$ alkoxylene, $C_{1-4}$ aminoalkylene, $C_{1-4}$ thioalkylene and $C_{1-4}$ heteroalkylene, and wherein $R^4$ is optionally substituted on carbon atoms and heteroatoms with $R^{R4}$ substituents selected from the group consisting of F, Cl, Br, I, $C_{1-6}$ alkyl, $C_{1-6}$ haloalkyl, 3-5 membered cycloalkyl, 3-5 membered heterocycloalkyl, $C_{1-6}$ alkoxy, $C_{1-6}$ alkylamino, $C_{1-6}$ dialkylamino, $C_{1-6}$ alkylthio, =O, —$NH_2$, —CN, —$NO_2$ and —$SF_5$;

$X^2$ is N or CH;

A is selected from the group consisting of $C_{1-6}$ alkyl, $C_{1-6}$ haloalkyl, $C_{1-6}$ dialkylamino, 3 to 12 membered cycloalkyl, *and* 3 to 12 membered heterocycloalkyl, wherein A is optionally substituted with 1-5 $R^A$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^A)_{0-1}$-3-8 membered cycloalkyl, -$(L^A)_{0-1}$-3-8 membered heterocycloalkyl, -$(L^A)_{0-1}$-5 to 6 membered heteroaryl, -$(L^A)_{0-1}$-$C_6$ aryl, -$(L^A)_{0-1}$-$NR^{R1a}R^{R1b}$, -$(L^A)_{0-1}$-$OR^{R1a}$, -$(L^A)_{0-1}$-$SR^{R1a}$, -$(L^A)_{0-1}$-N($R^{R1a}$)C(=$Y^1$)$OR^{R1c}$, -$(L^A)_{0-1}$-OC(=O)N($R^{R1a}$)($R^{R1b}$), -$(L^A)_{0-1}$-N($R^{R1a}$)C(=O)N($R^{R1a}$)($R^{R1b}$), -$(L^A)_{0-1}$-C(=O)N($R^{R1a}$)($R^{R1b}$), -$(L^A)_{0-1}$-N($R^{R1a}$)C(=O)$R^{R1b}$, -$(L^A)_{0-1}$-C(=O)$OR^{R1a}$, -$(L^A)_{0-1}$-OC(=O)$R^{R1a}$, -$(L^A)_{0-1}$-P(=O)($OR^{R1a}$)($OR^{R1b}$), -$(L^A)_{0-1}$-S(O)$_{1-2}R^{R1c}$, -$(L^A)_{0-1}$-S(O)$_{1-2}$N($R^{R1a}$)($R^{R1b}$), -$(L^A)_{0-1}$-N($R^{R1a}$)S(O)$_{1-2}$N($R^{R1a}$)($R^{R1b}$) and -$(L^A)_{0-1}$-N($R^{R1a}$)S(O)$_{1-2}$($R^{R1c}$), wherein $L^A$ is selected from the group consisting of $C_{1-4}$ alkylene, $C_{1-4}$ heteroalkylene, $C_{1-4}$ alkoxylene, $C_{1-4}$ aminoalkylene, $C_{1-4}$ thioalkylene, $C_{2-4}$ alkenylene, and $C_{2-4}$ alkynylene; wherein $R^{R1a}$ and $R^{R1b}$ are independently selected from the group consisting of hydrogen, $C_{1-8}$ alkyl, $C_{1-8}$ haloalkyl, 3-8 membered cycloalkyl, phenyl, benzyl, 5 to 6 membered heteroaryl and 3 to 8 membered heterocycloalkyl; $R^{R1c}$ is selected from the group consisting of $C_{1-8}$ alkyl, $C_{1-8}$ haloalkyl, 3 to 8 membered cycloalkyl, phenyl, benzyl, 5 to 6 membered heteroaryl and 3 to 7 membered heterocycloalkyl, and wherein $R^A$ is optionally substituted on carbon atoms and heteroatoms with $R^{RA}$ [substitutents] *substituents* selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-S(O)$_{0-2}$—, $C_{1-4}$ (halo)alkyl-N(H)S(O)$_{0-2}$—, $C_{1-4}$ (halo)alkyl-S(O)$_{0-2}$N(H)—, (halo)alkyl-N(H)—S(O)$_{0-2}$N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylthio, $C_{1-4}$ alkylamino and $C_{1-4}$ dialkylamino; and Cy is selected from the group consisting of $C_{1-6}$ alkyl, $C_{1-6}$ haloalkyl, 3 to 12 membered cycloalkyl, *and* 3 to 12 membered heterocycloalkyl, wherein Cy is optionally substituted on carbon or heteroatoms with $R^{Cy}$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^{Cy})_{0-1}$-3-8 membered cycloalkyl, -$(L^{Cy})_{0-1}$-3-8 membered heterocycloalkyl, -$(L^{Cy})_{0-1}$-5 to 6 membered heteroaryl, -$(L^{Cy})_{0-1}$-phenyl, -$(L^{Cy})_{0-1}$-$NR^{RCa}R^{RCb}$, -$(L^{Cy})_{0-1}$-$OR^{RCa}$, -$(L^{Cy})_{0-1}$-$SR^{RCa}$, -$(L^{Cy})_{0-1}$-$N(R^{RCa})C(=Y^1)OR^{RCc}$, -$(L^{Cy})_{0-1}$-$OC(=O)N(R^{RCa})(R^{RCb})$, -$(L^{Cy})_{0-1}$-$N(R^{RCa})C(=O)N(R^{RCa})(R^{RCb})$, -$(L^{Cy})_{0-1}$-$C(=O)N(R^{RCa})(R^{RCb})$, -$(L^{Cy})_{0-1}$-$N(R^{RCa})C(=O)R^{RCb}$, -$(L^{Cy})_{0-1}$-$C(=O)OR^{RCa}$, -$(L^{Cy})_{0-1}$-$OC(=O)R^{RCa}$, [-$(L^{Cy})_{0-1}$-$P(=O)(OR^{RCa})(OR^{RCba})$,] -$(L^{Cy})_{0-1}$-$P(=O)(OR^{RCa})(OR^{RCb})$, -$(L^{Cy})_{0-1}$-$S(O)_{1-2}R^{RCc}$, [-$(L^{Cy})_{0-1}$-$S(O)_{0-2}N(R^{RCa})(R^{RCb})$,] -$(L^{Cy})_{0-1}$-$S(O)_{1-2}N(R^{RCa})(R^{RCb})$, -$(L^{Cy})_{0-1}$-$N(R^{RCa})S(O)_{1-2}N(R^{RCa})(R^{RCb})$ and -$(L^{Cy})_{0-1}$-$N(R^{RCa})S(O)_{1-2}(R^{RCc})$, wherein $L^{Cy}$ is selected from the group consisting of $C_{1-4}$ alkylene, $C_{1-4}$ heteroalkylene, $C_{1-4}$ alkoxylene, $C_{1-4}$ aminoalkylene, $C_{1-4}$ thioalkylene, $C_{2-4}$ alkenylene, and $C_{2-4}$ alkynylene; wherein $R^{RCa}$ and $R^{RCb}$ are independently selected from the group consisting of hydrogen, $C_{1-8}$ alkyl, $C_{1-8}$ haloalkyl, 3-8 membered cycloalkyl, phenyl, benzyl, 5 to 6 membered heteroaryl and 3 to 8 membered heterocycloalkyl; $R^{RCc}$ is selected from the group consisting of $C_{1-8}$ alkyl, $C_{1-8}$ haloalkyl, 3 to 8 membered cycloalkyl, phenyl, benzyl, 5 to 6 membered heteroaryl and 3 to 7 membered heterocycloalkyl, and wherein $R^{Cy}$ is optionally substituted on carbon atoms and heteroatoms with from 1 to 5 $R^{RCy}$ [substitutents] *substituents* selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-$S(O)_{0-2}$—, $C_{1-4}$ (halo)alkyl-N(H)$S(O)_{0-2}$—, $C_{1-4}$ (halo)alkyl-$S(O)_{0-2}$N(H)—, (halo)alkyl-N(H)—$S(O)_{0-2}$N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylthio, $C_{1-4}$ alkylamino and $C_{1-4}$ dialkylamino.

In one embodiment of Formula I or as a sub-embodiment of any other embodiment of Formula I, either A or Cy is a polycyclic carbocycle or polycyclic heterocycle.

In one embodiment of Formula I or as a sub-embodiment of any other embodiment of Formula I, either A or Cy is a bridged bicyclic carbocycle or bridged bicyclic heterocycle.

In one embodiment of Formula I or as a sub-embodiment of any other embodiment of Formula I, either A or Cy is a C-linked carbocycle or C-linked heterocycle.

In one embodiment of Formula I or as a sub-embodiment of any other embodiment of Formula I, $X^1$ is N.

In one embodiment of Formula I or as a sub-embodiment of any other embodiment of Formula I, $X^1$ is C—$R^4$.

In one embodiment of Formula I or as a sub-embodiment of any other embodiment of Formula I, $X^2$ is N.

In one embodiment of Formula I or as a sub-embodiment of any other embodiment of Formula I, $X^2$ is C(H).

In one embodiment of Formula I or as a sub-embodiment of any other embodiment of Formula I, $R^4$ is selected from the group consisting of —F, —Cl, —CN, -$(L^2)_{0-1}$-$C_{3-8}$ cycloalkyl, -$(L^2)_{0-1}$-3 to 7 membered heterocycloalkyl, -$(L^1)_{0-1}$-$C_{1-6}$ alkyl, -$(L^1)_{0-1}$-$C_{1-6}$ haloalkyl, -$(L^1)_{0-1}$-$C_{1-6}$ heteroalkyl, -$(L^2)_{0-1}$-6-10 membered aryl and -$(L^2)_{0-1}$-5-10 membered heteroaryl, and is optionally substituted.

In one embodiment of Formula I or as a sub-embodiment of any other embodiment of Formula I, $R^4$ is selected from the group consisting of —F, —Cl, $C_{3-8}$ cycloalkyl, 3 to 7 membered heterocycloalkyl, $C_{1-6}$ alkyl, $C_{1-6}$ haloalkyl, —(O)—$C_{3-8}$ cycloalkyl, —(O)-3 to 7 membered heterocycloalkyl, —(O)—$C_{1-6}$ alkyl and —(O)—$C_{1-6}$ haloalkyl, and is optionally substituted.

In one embodiment of Formula I or as a sub-embodiment of any other embodiment of Formula I, $R^4$ is selected from the group consisting of methoxy, monofluoromethoxy, difluoromethoxy, trifluoromethoxy, ethoxy, propoxy, isopropoxy, butoxy, isobutoxy, tert-butoxy, cyclopropoxy, cyclobutoxy, cyclopentoxy, methyl, monofluoromethyl difluoromethyl, trifluoromethyl, cyclopropyl, cyclobutyl and cyclopentyl.

In one embodiment of Formula I or as a sub-embodiment of any other embodiment of Formula I, $R^4$ is selected from the group consisting of $(L^2)_{0-1}$-phenyl, -$(L^2)_{0-1}$-pyridyl, -$(L^2)_{0-1}$-pyrimidinyl, -$(L^2)_{0-1}$-pyrazinyl, -$(L^2)_{0-1}$-pyridazinyl, -$(L^2)_{0-1}$-pyrrolyl, -$(L^2)_{0-1}$-pyrazolyl, -$(L^2)_{0-1}$-imidazolyl, -$(L^2)_{0-1}$-thienyl, -$(L^2)_{0-1}$-thiazolyl and -$(L^2)_{0-1}$-thiadiazolyl, -$(L^2)_{0-1}$-triazoloyl, -$(L^2)_{0-1}$-oxazolyl, -$(L^2)_{0-1}$-oxadiazolyl, -$(L^2)_{0-1}$-furanyl and is optionally substituted.

In one embodiment of Formula I or as a sub-embodiment of any other embodiment of Formula I, $R^4$ is selected from the group consisting of -$(L^2)_{0-1}$-phenyl and -$(L^2)_{0-1}$-pyridinyl, and is optionally substituted.

In one embodiment of Formula I or as a sub-embodiment of any other embodiment of Formula I, $R^4$ is —OC(H)($CH_3$)-phenyl wherein said phenyl ring is optionally substituted.

In one embodiment of Formula I or as a sub-embodiment of any other embodiment of Formula I, $R^1$, $R^2$ and $R^3$ are each independently selected from the group consisting of F, Cl, CN, hydrogen, $C_{1-4}$ alkyl and $C_{1-4}$ haloalkyl.

In one embodiment of Formula I or as a sub-embodiment of any other embodiment of Formula I, $R^1$, $R^2$ and $R^3$ are each hydrogen.

In one embodiment of Formula I or as a sub-embodiment of any other embodiment of Formula I, A and Cy are independently selected from the group consisting of pyrrolidine, piperidine, azetidine, azepane, piperazine, 7-azaspiro[3.5]nonane, 3,6-diazabicyclo[3.2.1]octane, 2-oxa-5-azabicyclo[2.2.1]heptane, 2,7-diazaspiro[3.5]nonane, octahydrocyclopenta[c]pyrrole, 2-azaspiro[3.3]heptane, 2,5-diazaspiro[3.4]octane, 6-azaspiro[2.5]octane, 3-azabicyclo[3.1.0]hexane, 3-oxabicyclo[3.1.0]hexane, morpholine, hexahydro-2H-furo[3,2-c]pyrrole, 2-azabicyclo[2.1.1]hexane, 2,5-diazabicyclo[2.2.1]heptane, 2-aza-tricyclo[3.3.1.1-3,7]decane, [2-azabicyclo[2.1.1]hexane,] 9-azabicyclo[4.2.1]nonane, 9-azabicyclo[3.3.1]nonane, cyclobutane, cyclopropane, cyclopentane, 2-Thia-5-azabicyclo[2.2.1]heptane 2,2-dioxide, 2-azabicyclo[2.2.1]heptane, tetrahydro-2H-pyran, 8-azabicyclo[3.2.1]octane and 3-oxa-8-azabicyclo[3.2.1]octane, and is optionally substituted.

In one embodiment of Formula I or as a sub-embodiment of any other embodiment of Formula I, A is selected from the group consisting of pyrrolidine, piperidine, azetidine, azepane, piperazine, cyclopropane, cyclobutane, cyclopentane, 7-azaspiro[3.5]nonane, 3-oxabicyclo[3.1.0]hexane, 3,6-diazabicyclo[3.2.1]octane, 2-oxa-5-azabicyclo[2.2.1]heptane, 2,7-diazaspiro[3.5]nonane, octahydrocyclopenta[c]pyrrole, 2-azaspiro[3.3]heptane, 2,5-diazaspiro[3.4]octane, 6-azaspiro[2.5]octane, 3-azabicyclo[3.1.0]hexane, morpholine, hexahydro-2H-furo[3,2-c]pyrrole and 2-azabicyclo[2.1.1]hexane, and is optionally substituted.

In one embodiment of Formula I or as a sub-embodiment of any other embodiment of Formula I, A is selected from the group consisting of 2-azabicyclo[2.1.1]hexane, 3-azabicyclo

[3.1.0]hexane, 3-oxabicyclo[3.1.0]hexane, azetidine, pyrrolidine, cyclopropane, cyclobutane, cyclopentane, and is optionally substituted.

In one embodiment of Formula I or as a sub-embodiment of any other embodiment of Formula I, A is selected from the group consisting of (1S,4S)-2-oxa-5-azabicyclo[2.2.1]heptane, (1R,4R)-2-oxa-5-azabicyclo[2.2.1]heptane, (1R,5S)-3-azabicyclo[3.1.0]hexane, (1S,5R)-3-azabicyclo[3.1.0]hexane, 3-oxabicyclo[3.1.0]hexane, (1R,5S)-3-oxabicyclo[3.1.0]hexane, (1S,5R)-3-oxabicyclo[3.1.0]hexane, (1S,4S)-2,5-diazabicyclo[2.2.1]heptane and (1R,4R)-2,5-diazabicyclo[2.2.1]heptane, and is optionally substituted.

In one embodiment of Formula I or as a sub-embodiment of any other embodiment of Formula I, A is selected from the group consisting of methyl, ethyl, isopropyl,

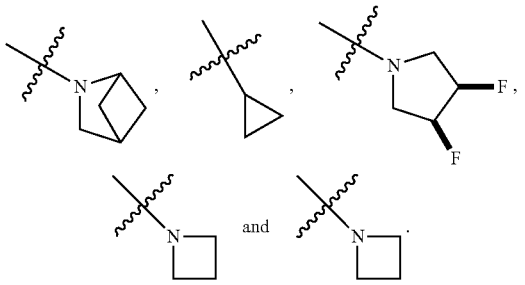

In one embodiment of Formula I or as a sub-embodiment of any other embodiment of Formula I, Cy is selected from the group consisting of 2,5-diazabicyclo[2.2.1]heptane, piperidine, pyrrolidine, azetidine, 2-aza-tricyclo[3.3.1.1-3,7]decane, 2-oxa-5-azabicyclo[2.2.1]heptane, 3-azabicyclo[3.1.0]hexane, 3-oxabicyclo[3.1.0]hexane, 2-azabicyclo[2.1.1]hexane, 9-azabicyclo[4.2.1]nonane, 9-azabicyclo[3.3.1]nonane, cyclobutane, 2-Thia-5-aza-bicyclo[2.2.1]heptane 2,2-dioxide, 2-azabicyclo[2.2.1]heptane, tetrahydro-2H-pyran, 8-azabicyclo[3.2.1]octane, 3-oxa-8-azabicyclo[3.2.1]octane, and is optionally substituted.

In one embodiment of Formula I or as a sub-embodiment of any other embodiment of Formula I, Cy is selected from the group consisting of azetidine, (1S,4S)-2-oxa-5-azabicyclo[2.2.1]heptane, (1R,4R)-2-oxa-5-azabicyclo[2.2.1]heptane, (1R,5S)-3-azabicyclo[3.1.0]hexane, (1S,5R)-3-azabicyclo[3.1.0]hexane, 3-oxabicyclo[3.1.0]hexane, (1R,5S)-3-oxabicyclo[3.1.0]hexane, (1S,5R)-3-oxabicyclo[3.1.0]hexane, (1S,4S)-2,5-diazabicyclo[2.2.1]heptane and (1R,4R)-2,5-diazabicyclo[2.2.1]heptane, and is optionally substituted.

In one embodiment of Formula I or as a sub-embodiment of any other embodiment of Formula I, Cy is a 3-12 membered carbocycle or a C-linked 3-12 membered heterocycle and $X^2$ is C(H).

In one embodiment of Formula I or as a sub-embodiment of any other embodiment of Formula I, Cy is selected from the group consisting of

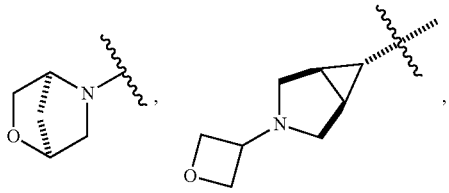

-continued

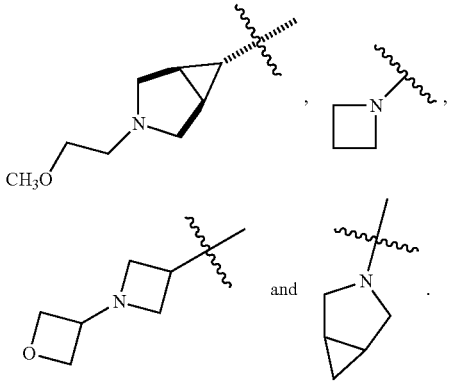

In one embodiment of Formula I or as a sub-embodiment of any other embodiment of Formula I, A is $C_{1-6}$ alkyl or $C_{1-6}$ dialkylamino, and is optionally substituted.

In one embodiment of Formula I or as a sub-embodiment of any other embodiment of Formula I, A is methyl or ethyl.

In one embodiment of Formula I or as a sub-embodiment of any other embodiment of Formula I, Cy is $C_{1-6}$ alkyl, and is optionally substituted.

In one embodiment of Formula I or as a sub-embodiment of any other embodiment of Formula I, A is optionally substituted with from 1 to 5 $R^A$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^A)_{0-1}$-3-8 membered cycloalkyl, -$(L^A)_{0-1}$-3-8 membered heterocycloalkyl, -$(L^A)_{0-1}$-5 to 6 membered [hetero aryl] *heteroaryl*, *and* -$(L^A)_{0-1}$-$C_6$ aryl, wherein $L^A$ is selected from the group consisting of —C(O)—, —C(O)$CH_2$—, —$OCH_2$—, —$CH_2O$—, —$CH_2$—, —$CH_2CH_2$—, —$CH_2OCH_2$—, —N(H)$CH_2$—, —N($C_{1-3}$ alkyl)$CH_2$—, [$CH_2$N(H)—] —*$CH_2$N(H)*—, —$CH_2$N($C_{1-3}$ alkyl)-; wherein said 3-8 membered cycloalkyl is selected from the group consisting of propane, butane, pentane and hexane; wherein said 3 to 8 membered heterocycloalkyl is selected from the group consisting of oxetane, tetrahydrofuran, tetrahydropyran, oxepane, azetidine, pyrrolidine, piperidine and azepane; wherein said 5 to 6 membered heteroaryl is selected from the group consisting of pyrrole, pyrazole, imidazole, thiophene, thiazole, oxazole, [trizole] *triazole*, pyridine, pyrimidine, pyrazine, *and* pyridazine; wherein said $C_6$ aryl is phenyl; and where in $R^A$ is optionally substituted with from 1 to 5 $R^{RA}$ [substitutents] *substituents* selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-S(O)$_{0-2}$—, $C_{1-4}$ (halo)alkyl-N(H)S(O)$_{0-2}$—, $C_{1-4}$ (halo)alkyl-S(O)$_{0-2}$N(H)—, (halo)alkyl-N(H)—S(O)$_{0-2}$N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylthio, $C_{1-4}$ alkylamino and $C_{1-4}$ dialkylamino.

In one embodiment of Formula I or as a sub-embodiment of any other embodiment of Formula I, Cy is optionally substituted with from 1 to 5 $R^{Cy}$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^{Cy})_{0-1}$-3-8 membered cycloalkyl, -$(L^{Cy})_{0-1}$-3-8 membered heterocycloalkyl, -$(L^{Cy})_{0-1}$-5 to 6 membered heteroaryl, *and* -$(L^{Cy})_{0-1}$-$C_6$ aryl, wherein $L^{Cy}$ is selected from the group consisting of —C(O)—, —C(O)$CH_2$—, —$OCH_2$—, —$CH_2O$—, —$CH_2$—, —$CH_2CH_2$—, —$CH_2OCH_2$—, —N(H)$CH_2$—, —N($C_{1-3}$ alkyl)$CH_2$—, [$CH_2$N(H)—] —$CH_2N(H)$—, —$CH_2$N($C_{1-3}$ alkyl)-; wherein said 3-8 membered cycloalkyl is selected from the group consisting of propane, butane, pentane and hexane; wherein said 3 to 8 membered heterocycloalkyl is selected from the group consisting of oxetane, tetrahydrofuran, tetrahydropyran, oxepane, azetidine, pyrrolidine, piperidine and azepane; wherein said 5 to 6 membered heteroaryl is selected from the group consisting of pyrrole, pyrazole, imidazole, thiophene, thiazole, oxazole, [trizole] *triazole*, pyridine, pyrimidine, pyrazine, *and* pyridazine; wherein said $C_6$ aryl is phenyl; and where in $R^{Cy}$ is optionally substituted with from 1 to 5 $R^{RCy}$ [substitutents] *substituents* selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-S(O)$_{0-2}$—, $C_{1-4}$ (halo)alkyl-N(H)S(O)$_{0-2}$—, $C_{1-4}$ (halo)alkyl-S(O)$_{0-2}$N(H)—, (halo)alkyl-N(H)—S(O)$_{0-2}$N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylthio, $C_{1-4}$ alkylamino and $C_{1-4}$ dialkylamino.

In one embodiment of Formula I or as a sub-embodiment of any other embodiment of Formula I, Cy is optionally substituted with 1 to 5 $R^{Cy}$ substituents selected from the group consisting of F, Cl, Br, I, CN, OH, 2,3-difluorophen-1-yl-C(=O)—, 4-fluorophen-1-yl-C(=O)—, 3-fluorophen-1-yl-C(=O)—, 3,5-difluorophen-1-yl-C(=O)—, 3-fluoro-4-methyl-phen-1-yl-C(=O)—, 2,5-difluorophen-1-yl-C(=O)—, oxetane, oxetan-3-yl, thiazole, thiazol-2-yl, —$CH_3CH_2$C(=O)—, $CH_3$C(=O)—, $CF_3CH_2$—, (HO)C$(CH_3)_2CH_2$—, $CH_3OCH_2CH_2$—, $CH_3OC(CH_3)_2$C(=O)—, $CH_3OCH_2$C(=O)—, isopropyl, ethyl and methyl.

In one embodiment of Formula I or as a sub-embodiment of any other embodiment of Formula I, A is optionally substituted with 1 to 5 $R^A$ substituents selected from the group consisting of F, Cl, Br, I, CN, $CH_3O$—, $CH_3$, cyclopropylmethyl, $CF_3$ and butyl.

In one embodiment of Formula I or as a sub-embodiment of any other embodiment of Formula I, said compound is selected from the subformula consisting of

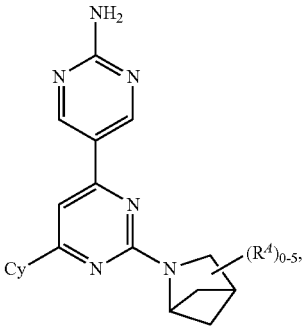

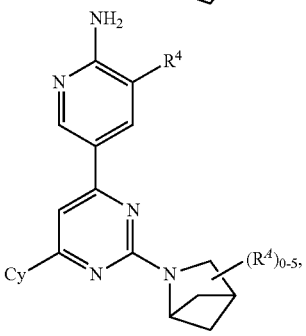

-continued

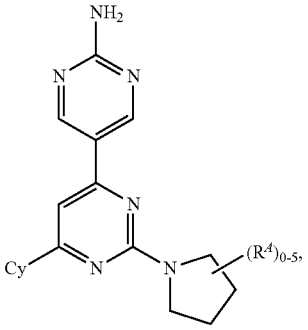

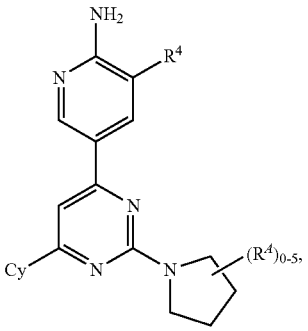

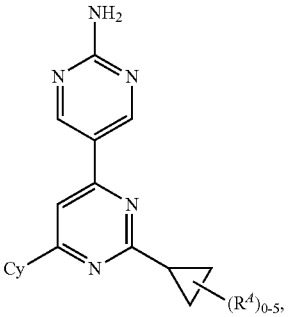

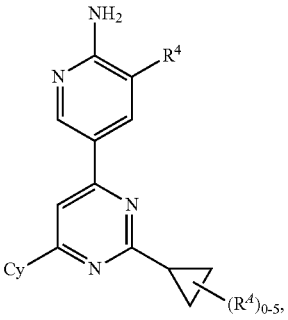

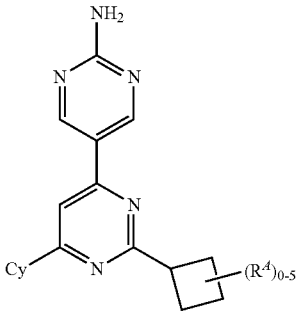

and

-continued

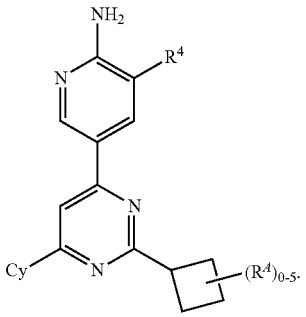

In one embodiment of Formula I or as a sub-embodiment of any other embodiment of Formula I, said compound is selected from the subformula consisting of

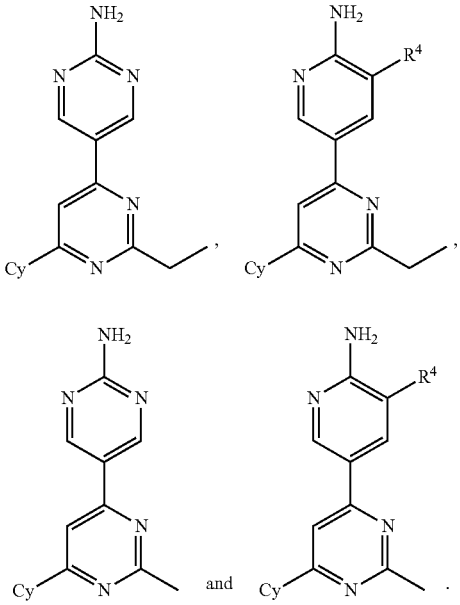

In one embodiment of Formula I or as a sub-embodiment of any other embodiment of Formula I, said compound is selected from the subformula consisting of

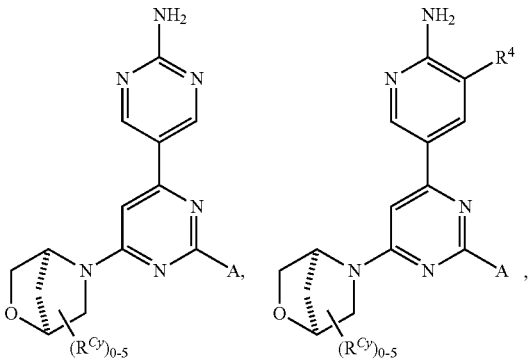

-continued

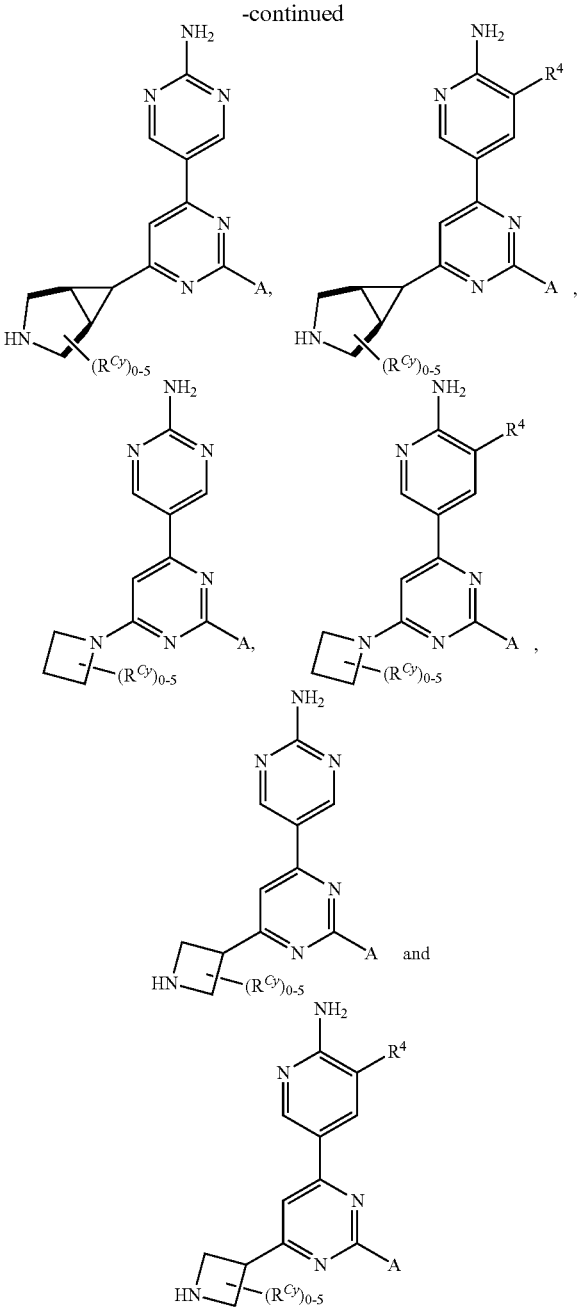

wherein $R^{Cy}$ if present replaces a hydrogen atom attached to a carbon or nitrogen atom of the Cy ring.

In one embodiment of Formula I the compound is selected from the group as set forth in Table 1.

In another aspect, the present invention provides for compositions comprising a compound of Formula I as defined above, or any embodiment thereof and a pharmaceutically acceptable carrier, diluent or excipient.

In another aspect, the present invention provides for a method for inhibiting or preventing degeneration of a central nervous system (CNS) neuron or a portion thereof, the method comprising administering to the CNS neuron a compound of formula I. In certain embodiments, said administering to the CNS neuron is performed in vitro. In other embodiments, said the method further comprises grafting or implanting the CNS neuron into a human patient after administration of the agent. In other embodiment, said CNS neuron is present in a human patient. In other embodiments, said administering to the CNS neuron comprises administration of said compound of formula I in a pharmaceutically acceptable carrier, diluent or excipient. In another embodiment said administering to the CNS neuron is carried out by an administration route selected from the group consisting of parenteral, subcutaneous, intravenous, intraperitoneal, intracerebral, intralesional, intramuscular, intraocular, intraarterial interstitial infusion and implanted delivery device. In another embodiment, said method further comprising administering one or more additional pharmaceutical agents. In another embodiment, said administering of a compound of formula I results in a decrease in JNK phosphorylation, JNK activity and/or JNK expression. In another embodiment, said the administering of a compound of formula I results in a decrease of cJun phosphorylation, cJun activity, and/or cJun expression. In another embodiment, said the administering of a compound of formula I results in a decrease in p38 phosphorylation, p38 activity, and/or p38 expression.

In another aspect, the present invention provides for a method for inhibiting or preventing degeneration of a central nervous system (CNS) neuron in a patient having or at risk of developing a neurodegenerative disease or condition comprising administering to said patient a therapeutically effective amount of a compound of formula I, or a pharmaceutically acceptable salt thereof.

In another aspect, the present invention provides for a method for decreasing or preventing one or more symptoms of a neurodegenerative disease or condition in a patient suffering therefrom comprising administering to said patient a therapeutically effective amount of a compound of formula I or a pharmaceutically acceptable salt thereof.

In another aspect, the present invention provides for a method for decreasing the progression of a neurodegenerative disease or condition in a patient suffering therefrom comprising administering to said patient a therapeutically effective amount of a compound of formula I or a pharmaceutically acceptable salt thereof. In certain embodiments, said neurodegenerative disease of condition is selected from the group consisting of: Alzheimer's disease, Huntington's disease, Parkinson's disease, Parkinson's-plus diseases, amyotrophic lateral sclerosis (ALS), ischemia, stroke, intracranial hemorrhage, cerebral hemorrhage, trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, multiple system atrophy, progressive supranuclear palsy, corticobasal degeneration, dementia with Lewy bodies, frontotemporal dementia, demyelinating diseases, Guillain-Barré syndrome, multiple sclerosis, Charcot-Marie_Tooth disease, prion disease, Creutzfeldt-Jakob disease, Gerstmann-Strässler-Scheinker syndrome (GSS), fatal familial insomnia (FFI), bovine spongiform encephalopathy, Pick's disease, epilepsy, AIDS demential complex, nerve damage caused by exposure to toxic compounds selected from the group consisting of heavy metals, industrial solvents, drugs and chemotherapeutic agents; injury to the nervous system caused by physical, mechanical or chemical trauma, glaucoma, lattice dystrophy, retinitis pigmentosa, age-related macular degeneration (AMD), photoreceptor degeneration associated with wet or dry AMD, other retinal degeneration, optic nerve drusen, optic neuropthy and optic neuritis. In certain embodiment, said neurodegenerative disease of condition in a patient is selected from the group consisting of: Alzheimer's disease, Parkinson's disease, and amyotrophic lateral sclerosis (ALS), In certain embodiment, said the compound of formula I is administered in combination with one or more additional pharmaceutical agents.

DETAILED DESCRIPTION OF THE INVENTION

A. Definitions

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include linear and branched groups including vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl," "carbocyclic," or "carbocycle" refers to hydrocarbon ring system having specified overall number of ring atoms (e.g., 3 to 12 ring atoms in a 3 to 12 membered cycloalkyl or $C_{3-12}$ cycloalkyl) and being fully saturated or having no more than one double bond between ring vertices for a 3-5 membered cycloalkyl and being saturated or having no more than two double bonds between ring vertices for 6 or larger membered cycloalkyl. The monocyclic or polycyclic ring may be optionally substituted with one or more oxo groups. As used herein, "cycloalkyl," "carbocyclic," or "carbocycle" is also meant to refer to polycyclic (including fused and bridged bicyclic, fused and bridged polyclic and spirocyclic) hydrocarbon ring system such as, for example, bicyclo[2.2.1]heptane, pinane, bicyclo[2.2.2]octane, adamantane, norborene, spirocyclic $C_{5-12}$ alkane, etc. As used herein, the terms, "alkenyl," "alkynyl," "cycloalkyl,", "carbocycle," and "carbocyclic," are meant to include mono and polyhalogenated variants thereof.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include $—CH_2—CH_2—O—CH_3$, $—CH_2—CH_2—O—CF_3$, $—CH_2—CH_2—NH—CH_3$, $—CH_2—CH_2—N(CH_3)—CH_3$, $—CH_2—S—CH_2—CH_3$, $—S(O)—CH_3$, $—CH_2—CH_2—S(O)_2—CH_3$, $—CH=CH—O—CH_3$, $—Si(CH_3)_3$, $—CH_2—CH=N—OCH_3$, and $—CH=CH=N(CH_3)—CH_3$. Up to two heteroatoms can be consecutive, such as, for example, $—CH_2—NH—OCH_3$ and $—CH_2—O—Si(CH_3)_3$.

The term "heterocycloalkyl," "heterocyclic," or "heterocycle" refers to a saturated or partially unsaturated ring system radical having from the indicated number of overall number of stated ring atoms and containing from one to five heteroatoms selected from N, O, and S, wherein the nitrogen and sulfur atoms are optionally oxidized, nitrogen atom(s) are optionally quaternized, as ring atoms (e.g., a 3 to 12 membered heterocycloalkyl that would have 3 to 12 ring atoms and include at least one heteroatom, which also could be referred to as a $C_{2-11}$ heterocycloalkyl). Unless otherwise stated, a "heterocycloalkyl," "heterocyclic," or "heterocycle" ring system can be a monocyclic or a fused, bridged, or spirocyclic polycyclic (including a fused bicyclic, bridged bicyclic or spirocyclic) ring system. The monocyclic or polycyclic ring may be optionally substituted with one or more oxo groups. A "heterocycloalkyl," "heterocyclic," or "heterocycle" group can be attached to the remainder of the molecule through one or more ring carbons or heteroatoms. Non limiting examples of "heterocycloalkyl," "heterocyclic," or "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-5-oxide, thiomorpholine-S,S-oxide, piperazine, pyran, pyridone, 3-pyrroline, thiopyran, pyrone, tetrahydrofuran, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and the like. A "heterocycloalkyl," "heterocyclic," or "heterocycle" can include mono- and poly-halogenated variants thereof.

The term "alkylene" by itself or as part of another substituent means a divalent radical derived from an alkane, as exemplified by $—CH_2CH_2CH_2CH_2—$, and can be branched. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively. "Alkylene", "alkenylene" and "alkynylene" are also meant to include mono and poly-halogenated variants.

The term "heteroalkylene" by itself or as part of another substituent means a divalent radical, saturated or unsaturated or polyunsaturated, derived from heteroalkyl, as exemplified by $—CH_2—CH_2—S—CH_2CH_2—$ and $—CH_2—S—CH_2—CH_2—NH—CH_2—$, $—CH_2—CH{=}C(H)CH_2—O—CH_2—$ and $S—CH_2—C{\equiv}C—$. The term "heteroalkylene" is also meant to include mono and poly-halogenated variants.

The term "alkoxylene" and "aminoalkylene" and "thioalkylene" by itself or as part of another substituent means a divalent radical, saturated or unsaturated or polyunsaturated, derived from alkoxy, alkylamino and alkylthio, respectively, as exemplified by $—OCH_2CH_2—$, $—O—CH_2—CH{=}CH—$, $—N(H)CH_2C(H)(CH_3)CH_2—$ and $—S—CH_2—C{\equiv}C—$. The term "alkoxylene" and "aminoalkylene" and "thioalkylene" are meant to include mono and poly halogenated variants The terms "alkoxy," "alkylamino" and "alkylthio", are used in their conventional sense, and refer to those alkyl groups attached to the remainder of the molecule via an oxygen atom ("oxy"), an amino group ("amino") or thio group, and further include mono- and poly-halogenated variants thereof. Additionally, for dialkylamino groups, the alkyl portions can be the same or different.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, difluoromethyl, and the like. The term "(halo)alkyl" as used herein includes optionally halogenated alkyl. Thus the term "(halo)alkyl" includes both alkyl and haloalkyl (e.g., monohaloalkyl and polyhaloalkyl).

The term "aryl" means, unless otherwise stated, a polyunsaturated, typically aromatic, hydrocarbon ring, which can be a single ring or multiple rings (up to three rings) which are fused together. The term "heteroaryl" refers to aryl ring(s) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Optional substituents for each of the above noted aryl and heteroaryl ring systems can be selected from the group of acceptable substituents described further below.

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkyl and cycloalkyl) can be a variety of groups including, but not limited to, -halogen, $=O$, $—OR'$, $—NR'R''$, $—SR'$, $—SiR'R''R'''$, $—OC(O)R'$, $—C(O)R'$, $—CO_2R'$, $—CONR'R''$, $—OC(O)NR'R''$, $—NR''C(O)R'$, $—NR'''C(O)NR'R''$, $—NR''C(O)_2R'$, $—NHC(NH_2){=}NH$, $—NR'C(NH_2){=}NH$, $—NHC(NH_2){=}NR'$, $—NR'''C(NR'R''){=}N—CN$, $—NR'''C(NR'R''){=}NOR'$, $—NHC(NH_2){=}NR'$, $—S(O)R'$, $—S(O)_2R'$, $—S(O)_2NR'R''$, $—NR'S(O)_2R''$, $—NR'''S(O)_2NR'R''$, $—CN$, $—NO_2$, $—(CH_2)_{1-4}—OR'$, $—(CH_2)_{1-4}—NR'R''$, $—(CH_2)_{1-4}—SR'$, $—(CH_2)_{1-4}—SiR'R''R'''$, $—(CH_2)_{1-4}—OC(O)R'$, $—(CH_2)_{1-4}—C(O)R'$, $—(CH_2)_{1-4}—CO_2R'$, $—(CH_2)_{1-4}CONR'R''$, in a number ranging from zero to (2m'+1), where m' is the total number of carbon atoms in such radical. R', R'' and R''' each independently refer groups including, for example, hydrogen, unsubstituted $C_{1-6}$ alkyl, unsubstituted heteroalkyl, unsubstituted aryl, aryl substituted with 1-3 halogens, unsubstituted $C_{1-6}$ alkyl, $C_{1-6}$ alkoxy or $C_{1-6}$ thioalkoxy groups, or unsubstituted aryl-$C_{1-4}$ alkyl groups, unsubstituted heteroaryl, *or* substituted heteroaryl, among others. When R' and R'' are attached to the same nitrogen atom, they can be combined with the nitrogen atom to form a 3-, 4-, 5-, 6-, or 7-membered ring. For example, $—NR'R''$ is meant to include 1-pyrrolidinyl and 4-morpholinyl. Other [substitutents] *substituents* for alkyl radicals, including heteroalkyl[,] *and* alkylene, include for example, $=O$, $=NR'$, $=N—OR'$, $=N—CN$, *and* $=NH$, wherein R' include substituents as described above. When a substituent for the alkyl radicals (including those groups often referred to as alkylene, alkenyl, alkynyl, heteroalkyl and cycloalkyl) contains an alkylene, alkenylene, *or* alkynylene linker (e.g., —$(CH_2)_{1-4}$—NR'R" for alkylene), the alkylene linker includes halo variants as well. For example, the linker "—$(CH_2)_{1-4}$—" when used as part of a substituent is meant to include difluoromethylene, 1,2-difluoroethylene, etc.

Similarly, substituents for the aryl and heteroaryl groups are varied and are generally selected from the group including, but not limited to, -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"$C(O)_2$R', —NR'C(O)NR"R'", —NHC($NH_2$)═NH, —NR'C($NH_2$)═NH, —NHC($NH_2$)═NR', —S(O)R', —$S(O)_2$R', —$S(O)_2$NR'R", —NR'$S(O)_2$R", —$N_3$, perfluoro-$C_{1-4}$ alkoxy, and perfluoro-$C_{1-4}$ alkyl, —$(CH_2)_{1-4}$—OR', —$(CH_2)_{1-4}$—NR'R", —$(CH_2)_{1-4}$—SR', —$(CH_2)_{1-4}$—SiR'R"R'", —$(CH_2)_{1-4}$—OC(O)R', —$(CH_2)_{1-4}$—C(O)R', —$CH_2)_{1-4}$—$CO_2$R', —$(CH_2)_{1-4}$CONR'R", in a number ranging from zero to the total number of open valences on the aromatic ring system; and where R', R" and R'" are independently selected from hydrogen, $C_{1-6}$ alkyl, $C_{3-6}$ cycloalkyl, $C_{2-6}$ alkenyl, $C_{2-6}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms. When a substituent for the aryl or heteroaryl group contains an alkylene, alkenylene, alkynylene linker (e.g., —$(CH_2)_{1-4}$—NR'R" for alkylene), the alkylene linker includes halo variants as well. For example, the linker "—$(CH_2)_{1-4}$—" when used as part of a substituent is meant to include difluoromethylene, 1,2-difluoroethylene, etc.

As used herein, the term "heteroatom" is meant to include oxygen (O), nitrogen (N), sulfur (S) and silicon (Si).

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "〰" that intersects a bond in a chemical structure fragment indicates the point of attachment of the bond to which the wavy bond intersects in the chemical structure fragment to the remainder of a molecule or structural formula.

As used herein, the representation of a group (e.g., $X^d$) in parenthesis followed by a subscript integer range (e.g., $(X^d)_{0-2}$) means that the group can have the number of occurrences as designated by the integer range. For example, $(X^d)_{0-1}$ means the group $X^d$ can be absent or can occur one time.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl)

ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis $4^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, the term "salts" is meant to include salts of the active compounds which are prepared with relatively nontoxic acids or bases (e.g., those salts that are pharmaceutically acceptable), depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-($(C_{1-6})$alkanoyloxy)ethyl, 1-methyl-1-($(C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, bur the for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include istopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically labeled compounds of the present invention (e.g., those labeled with $^{3}H$ or $^{14}C$) are useful in compound and/or substrate tissue distribution assays. Tritiated ($^{3}H$) and carbon-14 ($^{14}C$) isotopes are usefule for their ease of preparation and detectability. Further substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In some embodiments, a therapeutically effective amount is an amount of a chemical entity described herein sufficient to significantly decrease or delay neuronal cell death.

The term "administering" as used herein refers to contacting a neuron or portion thereof with a compound described herein. This includes administration of the compound to a subject (e.g., a patient, mammal) in which the neuron or portion thereof is present, as well as introducing the inhibitor into a medium in which a neuro or portion thereof is cultured.

The term "patient" as used herein refers to any mammal, including humans, higher non-human primates, rodenst domestic and farm animals such as cow, horses, dogs and cats. In one embodiment, the patient is a human patient.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The phrases "preventing axon degeneration," "preventing neuron degeneration," "preventing CNS neuron degeneration," "inhibiting axon degeneration," "inhibiting neuron degeneration" "inhibiting CNS neuron degeneration" as used herein include (i) the ability to inhibit or presenve axon or neuron degeration in patients diagnosed as having a neurodegerative disease or risk of developing a neurodegenerative disease and (ii) the ability to inhibit or prevent further axon or neuron degeneration in patients who are already suffering from, or have symptoms of a neurodegenerative disease. Preventing axon or neuron degeneration includes decreasing or inhbiting axon or neuron degeneration, which may be characterized by complete or partial inhibition or neuron or axon degeneration. This can be assessed, for example, by analysis of neurological function. The above-listed terms also include in vitro and ex vivo methods. Further, the pharases "preventing neuron degeneration" and "inhibiting neuron degeneration" in clued such inhibiton with respect to the entire neuron or a portion thereof, such as the neuron ell body, axons and dendrites. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90% or even 100% decrease in one or more symptoms of a disorder of the nervous system, a condition of the nervous system that is secondary to a disease, condition, or therapy having a primary effect outside of the nervous system; an inusry to the nervous system caused by physical, mechanical or chemical trauma, pain; and ocular related neurodegeneration; memory loss; or a psychiatric disorder (e.g., tremors, slowness of movement, ataxia, loss of balance, depressioin, decreased cognitive function, short term memory loss, long term memory loss, confusion, changes in personality, language difficultities, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity) in a subject or population compared to a control subject or population that does not receive the one or more agent described herein. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the agents described herein. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the likelihood of developing a disorder of the nervous system; a condition of the nervous system that is secondary to a disease, condition, or therapy having a primary effect outside of the nervous system; an injury to the nervous system caused by physical, mechanical, or chemical trauma, pain; an ocular-related neurodegeneration; memory loss; or a psychiatric disorder in a subject or a subject population compared to a control subject or population not treated with the one or more compounds described herein.

The term "neuron" as used herein denotes nervous system cells that include a central cell body or soma, and two types of extensions or projections: dendrites, by which, in general, the majority of neuronal signals are conveyed to the cell body, and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column) Certain specific examples of neuron types that may be subject to treatment according to the invention include cerebellar granule neurons, dorsal root ganglion neurons, and cortical neurons.

B. Compounds

In one aspect the present invention provides for novel compounds. In a first embodiment of such compounds (Embodiment 1; abbreviated as "E1") the invention provides for compounds of Formula I (I):

(I)

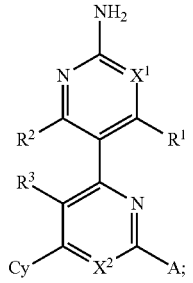

or salts thereof wherein $R^1$, $R^2$ and $R^3$ are each independently H, F, Cl, Br, I, $C_{1-6}$ alkyl or $C_{1-6}$haloalkyl;

$X^1$ is N or C—$R^4$, wherein $R^4$ is selected from the group consisting of —F, —Cl, —Br, [I-$(L^I)_{0-1}$-$C_{1-6}$ alkyl,] —*I*, -$(L^I)_{0-1}$-$C_{1-6}$ *alkyl*, -$(L^1)_{0-1}$-$C_{1-6}$ haloalkyl, -$(L^1)_{0-1}$-$C_{1-6}$ heteroalkyl, -$(L^2)_{0-1}$-$C_{3-8}$ cycloalkyl, -$(L^2)_{0-1}$-3 to 7 membered heterocycloalkyl, -$(L^2)_{0-1}$-6-10 membered aryl, *and* -$(L^2)_{0-1}$-5-10 membered heteroaryl, wherein $L^1$ is selected from the group consisting of —O—, —N(H)—, —S—, —N($C_{1-6}$ alkyl)-, [=O] *and* —*C*(=*O*)—, and $L^2$ is selected from the group consisting of —O—, —N(H)—, —N($C_{1-6}$ alkyl)-, —S—, [=O] —*C*(=*O*)—, $C_{1-4}$ alkylene, $C_{1-4}$ alkenylene, $C_{1-4}$ alkynylene, $C_{1-4}$ alkoxylene, $C_{1-4}$ aminoalkylene, $C_{1-4}$ thioalkylene and $C_{1-4}$ heteroalkylene, and wherein $R^4$ is optionally substituted on carbon atoms and heteroatoms with $R^{R4}$ substituents selected from the group consisting of F, Cl, Br, I, $C_{1-6}$ alkyl, $C_{1-6}$ haloalkyl, 3-5 membered cycloalkyl, 3-5 membered heterocycloalkyl, $C_{1-6}$ alkoxy, $C_{1-6}$ alkylamino, $C_{1-6}$ dialkylamino, $C_{1-6}$ alkylthio, =O, —$NH_2$, —CN, —$NO_2$ and —$SF_5$;

$X^2$ is N or CH;

A is selected from the group consisting of $C_{1-6}$ alkyl, $C_{1-6}$ haloalkyl, $C_{1-6}$ dialkylamino, 3 to 12 membered cycloalkyl, *and* 3 to 12 membered heterocycloalkyl, wherein A is optionally substituted with 1-5 $R^A$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^A)_{0-1}$-3-8 membered cycloalkyl, -$(L^A)_{0-1}$-3-8 membered heterocycloalkyl, -$(L^A)_{0-1}$-5 to 6 membered heteroaryl, -$(L^A)_{0-1}$-$C_6$ aryl, -$(L^A)_{0-1}$-$NR^{R1a}R^{R1b}$, -$(L^A)_{0-1}$-$OR^{R1a}$, -$(L^A)_{0-1}$-$SR^{R1a}$, -$(L^A)_{0-1}$-N($R^{R1a}$)C(=$Y^1$)$OR^{R1c}$, -$(L^A)_{0-1}$-OC(=O)N($R^{R1a}$)($R^{R1b}$), -$(L^A)_{0-1}$-N($R^{R1a}$)C(=O)N($R^{R1a}$)($R^{R1b}$), -$(L^A)_{0-1}$-C(=O)N($R^{R1a}$)($R^{R1b}$), -$(L^A)_{0-1}$-N($R^{R1a}$)C(=O)$R^{R1b}$, -$(L^A)_{0-1}$-C(=O)$OR^{R1a}$, -$(L^A)_{0-1}$-OC(=O)$R^{R1a}$, -$(L^A)_{0-1}$-P(=O)($OR^{R1a}$)($OR^{R1b}$), -$(L^A)_{0-1}$-S(O)$_{1-2}R^{R1c}$, -$(L^A)_{0-1}$-S(O)$_{1-2}$N($R^{R1a}$)($R^{R1b}$), -$(L^A)_{0-1}$-N($R^{R1a}$)S(O)$_{1-2}$N($R^{R1a}$)($R^{R1b}$) and -$(L^A)_{0-1}$-N($R^{R1a}$)S(O)$_{1-2}$($R^{R1c}$), wherein $L^A$ is selected from the group consisting of $C_{1-4}$ alkylene, $C_{1-4}$ heteroalkylene, $C_{1-4}$ alkoxylene, $C_{1-4}$ aminoalkylene, $C_{1-4}$ thioalkylene, $C_{2-4}$ alkenylene, and $C_{2-4}$ alkynylene; wherein $R^{R1a}$ and $R^{R1b}$ are independently selected from the group consisting of hydrogen, $C_{1-8}$ alkyl, $C_{1-8}$ haloalkyl, 3-8 membered cycloalkyl, phenyl, benzyl, 5 to 6 membered heteroaryl and 3 to 8 membered heterocycloalkyl; $R^{R1c}$ is selected from the group consisting of $C_{1-8}$ alkyl, $C_{1-8}$ haloalkyl, 3 to 8 membered cycloalkyl, phenyl, benzyl, 5 to 6 membered heteroaryl and 3 to 7 membered heterocycloalkyl, and wherein $R^{A}$ is optionally substituted on carbon atoms and heteroatoms with $R^{RA}$ [substitutents] *substituents* selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-S(O)$_{0-2}$—, $C_{1-4}$ (halo)alkyl-N(H)S(O)$_{0-2}$—, $C_{1-4}$ (halo)alkyl-S(O)$_{0-2}$N(H)—, (halo)alkyl-N(H)—S(O)$_{0-2}$N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylthio, $C_{1-4}$ alkylamino and $C_{1-4}$ dialkylamino; and Cy is selected from the group consisting of $C_{1-6}$ alkyl, $C_{1-6}$ haloalkyl, 3 to 12 membered cycloalkyl, *and* 3 to 12 membered heterocycloalkyl, wherein Cy is optionally substituted on carbon or heteroatoms with $R^{Cy}$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^{Cy})_{0-1}$-3-8 membered cycloalkyl, -$(L^{Cy})_{0-1}$-3-8 membered heterocycloalkyl, -$(L^{Cy})_{0-1}$-5 to 6 membered heteroaryl, -$(L^{Cy})_{0-1}$-phenyl, -$(L^{Cy})_{0-1}$-$NR^{RCa}R^{RCb}$, -$(L^{Cy})_{0-1}$-$OR^{RCa}$, -$(L^{Cy})_{0-1}$-$SR^{RCa}$, -$(L^{Cy})_{0-1}$-$N(R^{RCa})C(=Y^1)OR^{RCc}$, -$(L^{Cy})_{0-1}$-$OC(=O)N(R^{RCa})(R^{RCb})$, -$(L^{Cy})_{0-1}$-$N(R^{RCa})C(=O)N(R^{RCa})(R^{RCb})$, -$(L^{Cy})_{0-1}$-$C(=O)N(R^{RCa})(R^{RCb})$, -$(L^{Cy})_{0-1}$-$N(R^{RCa})C(=O)R^{RCb}$, -$(L^{Cy})_{0-1}$-$C(=O)OR^{RCa}$, -$(L^{Cy})_{0-1}$-$OC(=O)R^{RCa}$, [-$(L^{Cy})_{0-1}$-$P(=O)(OR^{RCa})(OR^{RCba})$,] -$(L^{Cy})_{0-1}$-$P(=O)(OR^{RCa})(OR^{RCb})$, -$(L^{Cy})_{0-1}$-$S(O)_{1-2}R^{RCc}$, [-$(L^{Cy})_{0-1}$-$S(O)_{0-2}N(R^{RCa})(R^{RCb})$,] -$(L^{Cy})_{0-1}$-$S(O)_{1-2}N(R^{RCa})(R^{RCb})$, -$(L^{Cy})_{0-1}$-$N(R^{RCa})S(O)_{1-2}N(R^{RCa})(R^{RCb})$ and [-$(L^{Cy})_{0-1}$-$N(R^{RCa})S(O)_{1-2}(R^{RCc})$,] -$(L^{Cy})_{0-1}$-$N(R^{RCa})S(O)_{1-2}(R^{RCc})$, wherein $L^{Cy}$ is selected from the group consisting of $C_{1-4}$ alkylene, $C_{1-4}$ heteroalkylene, $C_{1-4}$ alkoxylene, $C_{1-4}$ aminoalkylene, $C_{1-4}$ thioalkylene, $C_{2-4}$ alkenylene, and $C_{2-4}$ alkynylene; wherein $R^{RCa}$ and $R^{RCb}$ are independently selected from the group consisting of hydrogen, $C_{1-8}$ alkyl, $C_{1-8}$haloalkyl, 3-8 membered cycloalkyl, phenyl, benzyl, 5 to 6 membered heteroaryl and 3 to 8 membered heterocycloalkyl; $R^{RCc}$ is selected from the group consisting of $C_{1-8}$ alkyl, $C_{1-8}$ haloalkyl, 3 to 8 membered cycloalkyl, phenyl, benzyl, 5 to 6 membered heteroaryl and 3 to 7 membered heterocycloalkyl, and wherein $R^{Cy}$ is optionally substituted on carbon atoms and heteroatoms with from 1 to 5 $R^{RCy}$ [substitutents] *substituents* selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-S(O)$_{0-2}$—, $C_{1-4}$ (halo)alkyl-N(H)S(O)$_{0-2}$—, $C_{1-4}$ (halo)alkyl-S(O)$_{0-2}$N(H)—, (halo)alkyl-N(H)—S(O)$_{0-2}$N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylthio, $C_{1-4}$ alkylamino and $C_{1-4}$ dialkylamino.

Further embodiments (E) of the first embodiment of compounds of the invention, are described below E2. A compound according to E1, wherein either A or Cy is a polycyclic carbocycle or polycyclic heterocycle.

E3. A compound according to E1 or E2, wherein $X^1$ is N.

E4. A compound according to E1 or E2, wherein $X^1$ is C—$R^4$.

E5. A compound of claim E1, E2, E3 or E4, wherein $X^2$ is N.

E6. A compound of claim, E1, E2, E3 or E4, wherein $X^2$ is C(H).

E7. A compound according to claim E1, E2, E4, E5 or E6, wherein $R^4$ is selected from the group consisting of —F, —Cl, —CN, -$(L^2)_{0-1}$-$C_{3-8}$ cycloalkyl, -$(L^2)_{0-1}$-3 to 7 membered heterocycloalkyl, -$(L^1)_{0-1}$-$C_{1-6}$ alkyl, -$(L^1)_{0-1}$-$C_{1-6}$ haloalkyl, -$(L^1)_{0-1}$-$C_{1-6}$ heteroalkyl, -$(L^2)_{0-1}$-6-10 membered aryl and -$(L^2)_{0-1}$-5-10 membered heteroaryl, and is optionally substituted.

E8. A compound according to claim E1, E2, E4, E5, E6 or E7, wherein $R^4$ is selected from the group consisting of —F, —Cl, $C_{3-8}$ cycloalkyl, 3 to 7 membered heterocycloalkyl, $C_{1-6}$ alkyl, $C_{1-6}$ haloalkyl, —(O)—$C_{3-8}$ cycloalkyl, —(O)-3 to 7 membered heterocycloalkyl, —(O)—$C_{1-6}$ alkyl and —(O)—$C_{1-6}$ haloalkyl, and is optionally substituted.

E9. A compound of claim E1, E2, E4, E5, E6, E7 or E8, wherein $R^4$ is selected from the group consisting of methoxy, monofluoromethoxy, difluoromethoxy, trifluoromethoxy, ethoxy, propoxy, isopropoxy, butoxy, isobutoxy, tert-butoxy, cyclopropoxy, cyclobutoxy, cyclopentoxy, methyl, monofluoromethyl difluoromethyl, trifluoromethyl, cyclopropyl, cyclobutyl and cyclopentyl.

E10. A compound of claim E1, E2, E4, E5, E6 or E7, wherein $R^4$ is selected from the group consisting of $(L^2)_{0-1}$-phenyl, -$(L^2)_{0-1}$-pyridyl, -$(L^2)_{0-1}$-pyrimidinyl, -$(L^2)_{0-1}$-pyrazinyl, -$(L^2)_{0-1}$-pyridazinyl, -$(L^2)_{0-1}$-pyrrolyl, -$(L^2)_{0-1}$-pyrazolyl, -$(L^2)_{0-1}$-imidazolyl, -$(L^2)_{0-1}$-thienyl, -$(L^2)_{0-1}$-thiazolyl and -$(L^2)_{0-1}$-thiadiazolyl, -$(L^2)_{0-1}$-triazoloyl, -$(L^2)_{0-1}$-oxazolyl, -$(L^2)_{0-1}$-oxadiazolyl, -$(L^2)_{0-1}$-furanyl and is optionally substituted.

E11. A compound of claim E1, E2, E4, E5, E6, E7 or E10, wherein $R^4$ is selected from the group consisting of -$(L^2)_{0-1}$-phenyl and -$(L^2)_{0-1}$-pyridinyl, and is optionally substituted.

E12. A compound of claim E1, E2, E4, E5, E6, E7, E10 or E11, wherein $R^4$ is —OC(H)($CH_3$)-phenyl wherein said phenyl ring is optionally substituted.

E13. A compound of claim E1, E2, E3, E4, E5, E6, E7, E8, E9, E10, E11 or E12, wherein $R^1$, $R^2$ and $R^3$ are each independently selected from the group consisting of F, Cl, CN, hydrogen, $C_{1-4}$ alkyl and $C_{1-4}$ haloalkyl.

E14. A compound of claim E1, E2, E3, E 4, E5, E6, E7, E8, E9, E10, E11, E12 or E13, wherein $R^1$, $R^2$ and $R^3$ are each hydrogen.

E15. A compound of claim E1, E2, E3, E4, E5, E6, E7, E8, E9, E10, E11, E12, E13 or E14, wherein A and Cy are independently selected from the group consisting of pyrrolidine, piperidine, azetidine, azepane, piperazine, 7-azaspiro[3.5]nonane, 3,6-diazabicyclo[3.2.1]octane, 2-oxa-5-azabicyclo[2.2.1]heptane, 2,7-diazaspiro[3.5]nonane, octahydrocyclopenta[c]pyrrole, 2-azaspiro[3.3]heptane, 2,5-diazaspiro[3.4]octane, 6-azaspiro[2.5]octane, 3-azabicyclo[3.1.0]hexane, 3-oxabicyclo[3.1.0]hexane, morpholine, hexahydro-2H-furo[3,2-c]pyrrole, 2-azabicyclo[2.1.1]hexane, 2,5-diazabicyclo[2.2.1]heptane, 2-aza-tricyclo[3.3.1.1-3,7]decane, [2-azabicyclo[2.1.1]hexane], 9-azabicyclo[4.2.1]nonane, 9-azabicyclo[3.3.1]nonane, cyclobutane, cyclopropane, cyclopentane, 2-Thia-5-aza-bicyclo[2.2.1]heptane 2,2-dioxide, 2-azabicyclo[2.2.1]heptane, tetrahydro-2H-pyran, 8-azabicyclo[3.2.1]octane and 3-oxa-8-azabicyclo[3.2.1]octane, and is optionally substituted.

E16. A compound of claim E1, E2, E3, E4, E5, E6, E7, E8, E9, E10, E11, E12, E13, E14 or E15, wherein A is selected from the group consisting of pyrrolidine, piperidine, azetidine, azepane, piperazine, cyclopropane, cyclobutane, cyclopentane, 7-azaspiro[3.5]nonane, 3-oxabicyclo[3.1.0]hexane, 3,6-diazabicyclo[3.2.1]octane, 2-oxa-5-azabicyclo[2.2.1]heptane, 2,7-diazaspiro[3.5]nonane, octahydrocyclopenta[c]pyrrole, 2-azaspiro[3.3]heptane, 2,5-diazaspiro[3.4]octane, 6-azaspiro[2.5]octane, 3-azabicyclo[3.1.0]hexane, morpholine, hexahydro-2H-furo[3,2-c]pyrrole and 2-azabicyclo[2.1.1]hexane, and is optionally substituted.

E17. A compound of claim E1, E2, E3, E4, E5, E6, E7, E8, E9, E10, E11, E12, E13, E14, E15 or E16, wherein A is selected from the group consisting of 2-azabicyclo[2.1.1]hexane, 3-azabicyclo[3.1.0]hexane, 3-oxabicyclo[3.1.0]hexane, azetidine, pyrrolidine, cyclopropane, cyclobutane, cyclopentane, and is optionally substituted.

E18. A compound of claim E1, E2, E3, E4, E5, E6, E7, E8, E9, E10, E11, E12, E13, E14, E15, E16 or E17, wherein A is selected from the group consisting of (1S,4S)-2-oxa-5-azabicyclo[2.2.1]heptane, (1R,4R)-2-oxa-5-azabicyclo[2.2.1]heptane, (1R,5S)-3-azabicyclo[3.1.0]hexane, (1S,5R)-3-azabicyclo[3.1.0]hexane, 3-oxabicyclo[3.1.0]hexane, (1R,5S)-3-oxabicyclo[3.1.0]hexane, (1S,5R)-3-oxabicyclo[3.1.0]hexane, (1S,4S)-2,5-diazabicyclo[2.2.1]heptane and (1R,4R)-2,5-diazabicyclo[2.2.1]heptane, and is optionally substituted.

E19. A compound of claim E1, E2, E3, E4, E5, E6, E7, E8, E9, E10, E11, E12, E13 or E14, wherein is A is selected from the group consisting of methyl, ethyl, isopropyl,

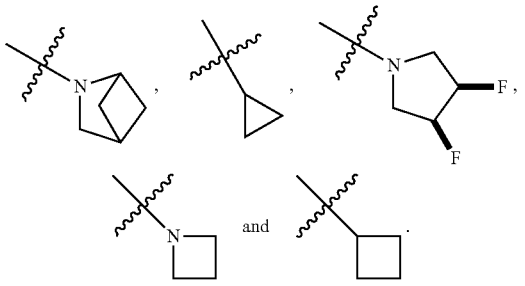

E20. A compound of claim E1, E2, E3, E4, E5, E6, E7, E8, E9, E10, E11, E12, E13, E14, E15, E16, E17, E18 or E19, wherein Cy is selected from the group consisting of 2,5-diazabicyclo[2.2.1]heptane, piperidine, pyrrolidine, azetidine, 2-aza-tricyclo[3.3.1.1-3,7]decane, 2-oxa-5-azabicyclo[2.2.1]heptane, 3-azabicyclo[3.1.0]hexane, 3-oxabicyclo[3.1. 0]hexane, 2-azabicyclo[2.1.1]hexane, 9-azabicyclo[4.2.1]nonane, 9-azabicyclo[3.3.1]nonane, cyclobutane, 2-Thia-5-aza-bicyclo[2.2.1]heptane 2,2-dioxide, 2-azabicyclo[2.2.1]heptane, tetrahydro-2H-pyran, 8-azabicyclo[3.2.1]octane, 3-oxa-8-azabicyclo[3.2.1]octane, and is optionally substituted.

E21. A compound of claim E1, E2, E3, E4, E5, E 6, E7, E8, E9, E10, E11, E12, E13, E14, E15, E16, E17, E18, E19 or E20, wherein Cy is selected from the group consisting of azetidine, (1S,4S)-2-oxa-5-azabicyclo[2.2.1]heptane, (1R,4R)-2-oxa-5-azabicyclo[2.2.1]heptane, (1R,5S)-3-azabicyclo[3.1.0]hexane, (1S,5R)-3-azabicyclo[3.1.0]hexane, 3-oxabicyclo[3.1.0]hexane, (1R,5S)-3-oxabicyclo[3.1.0]hexane, (1S,5R)-3-oxabicyclo[3.1.0]hexane, (1S,4S)-2,5-diazabicyclo[2.2.1]heptane and (1R,4R)-2,5-diazabicyclo[2.2.1]heptane, and is optionally substituted.

E22. A compound of claim E1, E2, E3, E4, E5, E6, E7, E8, E9, E10, E11, E12, E13 or E14, wherein Cy is selected from the group consisting of

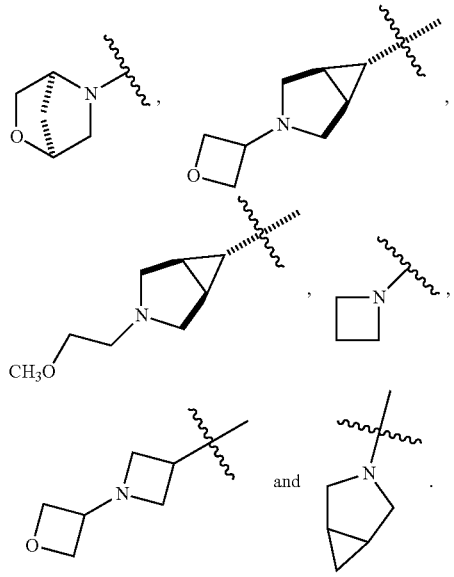

E23. A compound of claim E1, E2, E3, E4, E5, E6, E7, E8, E9, E10, E11, E12, E13 or E14, wherein A is $C_{1-6}$ alkyl or $C_{1-6}$ dialkylamino, and is optionally substituted.

E24. A compound of claim E1, E2, E3, E4, E5, E6, E7, E8, E9, E10, E11, E12, E13 or E14, wherein A is methyl or ethyl.

E25. A compound of claim E1, E2, E3, E4, E5, E6, E7, E8, E9, E10, E11, E12, E13 or E14, wherein Cy is $C_{1-6}$ alkyl, and is optionally substituted.

E26. A compound of claim E1, E2, E3, E4, E5, E6, E7, E8, E9, E10, E11, E12, E13, E14, E15, E16, E17, E18 or E23, wherein A is optionally substituted with from 1 to 5 $R^A$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^A)_{0-1}$-3-8 membered cycloalkyl, -$(L^A)_{0-1}$-3-8 membered heterocycloalkyl, -$(L^A)_{0-1}$-5 to 6 membered heteroaryl, *and* -$(L^A)_{0-1}$-$C_6$ aryl, wherein $L^A$ is selected from the group consisting of —C(O)—, —C(O)$CH_2$—, —$OCH_2$—, —$CH_2O$—, —$CH_2$—, —$CH_2CH_2$—, —$CH_2OCH_2$—, —N(H)$CH_2$—, —N($C_{1-3}$ alkyl)$CH_2$—, [$CH_2$N(H)—] —*$CH_2N$(H)*—, —$CH_2$N($C_{1-3}$ alkyl)-; wherein said 3-8 membered cycloalkyl is selected from the group consisting of propane, butane, pentane and hexane; wherein said 3 to 8 membered heterocycloalkyl is selected from the group consisting of oxetane, tetrahydrofuran, tetrahydropyran, oxepane, azetidine, pyrrolidine, piperidine and azepane; wherein said 5 to 6 membered heteroaryl is selected from the group consisting of pyrrole, pyrazole, imidazole, thiophene, thiazole, oxazole, [trizole] *triazole*, pyridine, pyrimidine, pyrazine, *and* pyridazine; wherein said $C_6$ aryl is phenyl; and [where in] *wherein* $R^A$ is optionally substituted with from 1 to 5 $R^{RA}$ [substitutents] *substituents* selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(═O)—, $C_{1-4}$ (halo)alkyl-S(O)$_{0-2}$—, $C_{1-4}$ (halo)alkyl-N(H)S(O)$_{0-2}$—, $C_{1-4}$ (halo)alkyl-S(O)$_{0-2}$N(H)—, (halo)alkyl-N(H)—S(O)$_{0-2}$N(H)—, $C_{1-4}$ (halo)alkyl-C(═O)N(H)—, $C_{1-4}$ (halo)alkyl-N(H)—C(═O)—, ((halo)alkyl)$_2$N—C(═O)—, $C_{1-4}$ (halo)alkyl-OC(═O)N(H)—, $C_{1-4}$ (halo)alkyl-OC(═O)N(H)—, (halo)alkyl-N(H)—C(═O)O—, ((halo)alkyl)$_2$N—C(═O)O—, $C_{1-4}$ alkylthio, $C_{1-4}$ alkylamino and $C_{1-4}$ dialkylamino.

E27. A compound of claim E1, E2, E3, E4, E5, E6, E7, E8, E9, E10, E11, E12, E13, E14, E15, E20, E21 or E25, wherein Cy is optionally substituted with from 1 to 5 $R^{Cy}$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -($L^{Cy}$)$_{0-1}$-3-8 membered cycloalkyl, -($L^{Cy}$)$_{0-1}$-3-8 membered heterocycloalkyl, -($L^{Cy}$)$_{0-1}$-5 to 6 membered heteroaryl, *and* -($L^{Cy}$)$_{0-1}$-$C_6$ aryl, wherein $L^{Cy}$ is selected from the group consisting of —C(O)—, —C(O)$CH_2$—, —$OCH_2$—, —$CH_2O$—, —$CH_2$—, —$CH_2CH_2$—, —$CH_2OCH_2$—, —N(H)$CH_2$—, —N($C_{1-3}$ alkyl)$CH_2$—, [$CH_2N$(H)—] —*$CH_2N$(H)*—, *and* —$CH_2N$($C_{1-3}$ alkyl)-; wherein said 3-8 membered cycloalkyl is selected from the group consisting of propane, butane, pentane and hexane; wherein said 3 to 8 membered heterocycloalkyl is selected from the group consisting of oxetane, tetrahydrofuran, tetrahydropyran, oxepane, azetidine, pyrrolidine, piperidine and azepane; wherein said 5 to 6 membered heteroaryl is selected from the group consisting of pyrrole, pyrazole, imidazole, thiophene, thiazole, oxazole, [trizole] *triazole*, pyridine, pyrimidine, pyrazine, *and* pyridazine; wherein said $C_6$ aryl is phenyl; and [where in] *wherein* $R^{Cy}$ is optionally substituted with from 1 to 5 $R^{RCy}$ [substitutents] *substituents* selected from, F, Cl, Br, I, —$NH_2$, —OH, —CN, —$NO_2$, ═O, —$SF_5$, $C_{1-4}$ alkyl, $C_{1-4}$ haloalkyl, $C_{1-4}$ alkoxy, $C_{1-4}$ (halo)alkyl-C(═O)—, $C_{1-4}$ (halo)alkyl-S(O)$_{0-2}$—, $C_{1-4}$ (halo)alkyl-N(H)S(O)$_{0-2}$—, $C_{1-4}$ (halo)alkyl-S(O)$_{0-2}$N(H)—, (halo)alkyl-N(H)—S(O)$_{0-2}$N(H)—, $C_{1-4}$ (halo)alkyl-C(═O)N(H)—, $C_{1-4}$ (halo)alkyl-N(H)—C(═O)—, ((halo)alkyl)$_2$N—C(═O)—, $C_{1-4}$ (halo)alkyl-OC(═O)N(H)—, $C_{1-4}$ (halo)alkyl-OC(═O)N(H)—, (halo)alkyl-N(H)—C(═O)O—, ((halo)alkyl)$_2$N—C(═O)O—, $C_{1-4}$ alkylthio, $C_{1-4}$ alkylamino and $C_{1-4}$ dialkylamino.

E28. A compound of claim of claim E1, E2, E3, E4, E5, E6, E7, E8, E9, E10, E11, E12, E13, E14, E15, E20, E21, E24, E25 or E26, wherein Cy is optionally substituted with 1 to 5 $R^{Cy}$ substituents selected from the group consisting of F, Cl, Br, I, CN, OH, 2,3-difluorophen-1-yl-C(═O)—, 4-fluorophen-1-yl-C(═O)—, 3-fluorophen-1-yl-C(═O)—, 3,5-difluorophen-1-yl-C(═O)—, 3-fluoro-4-methyl-phen-1-yl-C(═O)—, 2,5-difluorophen-1-yl-C(═O)—, oxetane, oxetan-3-yl, thiazole, thiazol-2-yl, —$CH_3CH_2C$(═O)—, $CH_3C$(═O)—, $CF_3CH_2$—, (HO)C($CH_3$)$_2CH_2$—, $CH_3OCH_2CH_2$—, $CH_3OC(CH_3)_2C$(═O)—, $CH_3OCH_2C$(═O)—, isopropyl, ethyl and methyl.

E29. A compound of claim E1, E2, E3, E4, E5, E6, E7, E8, E9, E10, E11, E12, E13, E14, E15, E16, E17, E18, E23 or E26, wherein A is optionally substituted with 1 to 5 $R^A$ substituents selected from the group consisting of F, Cl, Br, I, CN, $CH_3O$—, $CH_3$, cyclopropylmethyl, $CF_3$ and butyl.

E30. A compound of claim E1, E2, E3, E4, E5, E6, E7, E8, E9, E10, E11, E12, E13, E14, E15, E16, E17, E18, E19, E20, E21, E22, E25, E26, E27, E28 or E29, wherein said compound is selected from the subformula consisting of

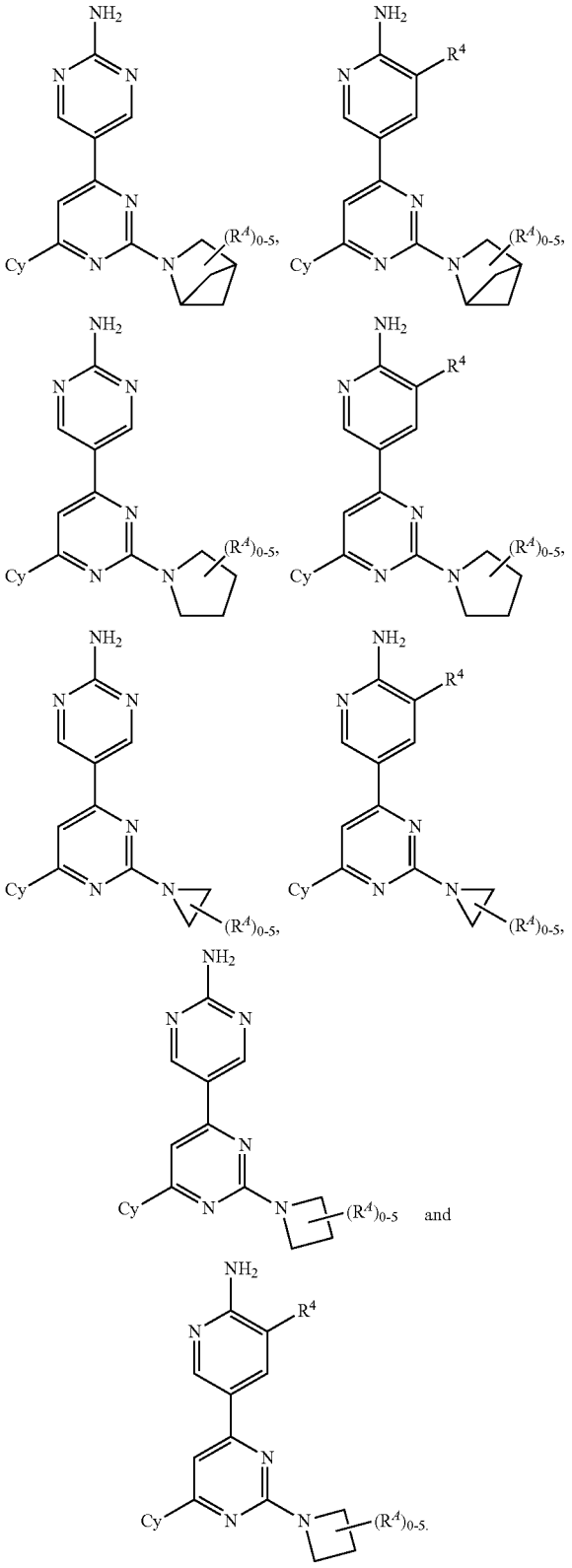

E31. A compound of claim E1, E2, E3, E4, E5, E6, E7, E8, E9, E10, E11, E12, E13, E14, E20, E21, E22, E25, E27, E28 or E29, wherein said compound is selected from the subformula consisting of

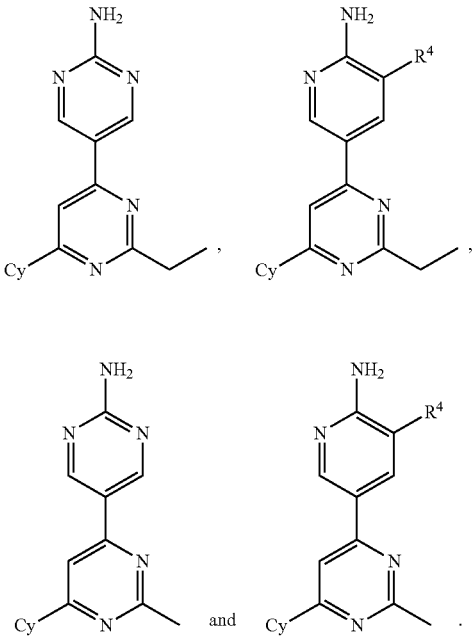

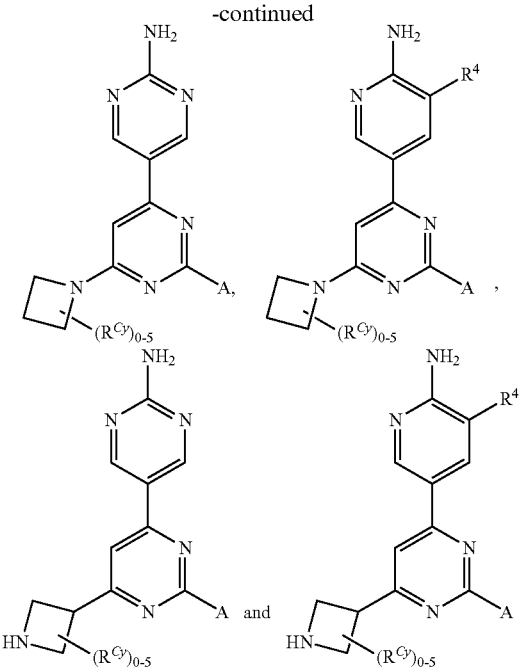

E32. A compound of claim E1, E2, E3, E4, E5, E6, E7, E8, E9, E10, E11, E12, E13, E14, E15, E16, E17, E18, E19, E20, E21, E22, E24, E26, E27, E28 or E29, wherein said compound is selected from the subformula consisting of

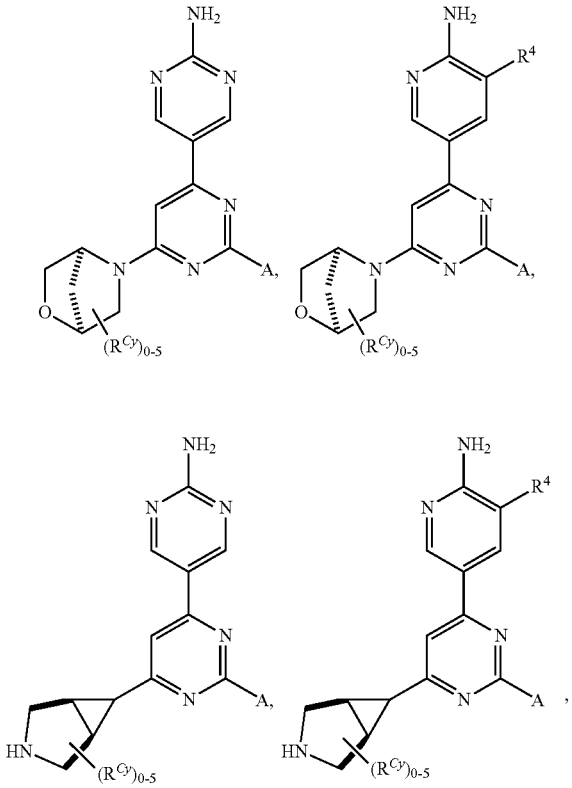

wherein $R^{Cy}$ if present replaces a hydrogen atom attached to a carbon or nitrogen atom of the Cy ring E33. A compound of claim 1 selected from the group as set forth in Table 1.

C. Synthesis of Compounds

Compounds of the invention as well as key intermediates can be prepared following the general synthetic schemes described below (Scheme 1-4). In Schemes 1-4, $R^1$, $R^2$, $R^3$, $R^4$, $X^1$ and $X^2$ have the meaning as described for compounds of Formula I; halo refers to a halogen atom, e.g., Cl, F, Br, I; and R where present means a cyclic or noncyclic noninterferring substituent. More detailed description of the individual reaction steps, is found in the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of the invention, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethylenoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

As illustrated in Scheme 1, compounds or intermediates of the inventions can be prepared by displacement of a halogen atom from a dihalothiopyrimidine compound (i) with an amine group under basic conditions. Further treatment of the alkylthio compound (II) under oxidative conditions provides the oxidized sulfone (iii) compound. A Suzuki-Miyaura coupling reaction between (iii) and a boronate reagent (iv) with a Pd(0) catalyst yields compounds and or intermediates of the invention (v) (See, Miyaura, N.; Suzuki, A. Chem. Rev. 1995, 95, 2457-2483).

Scheme 1

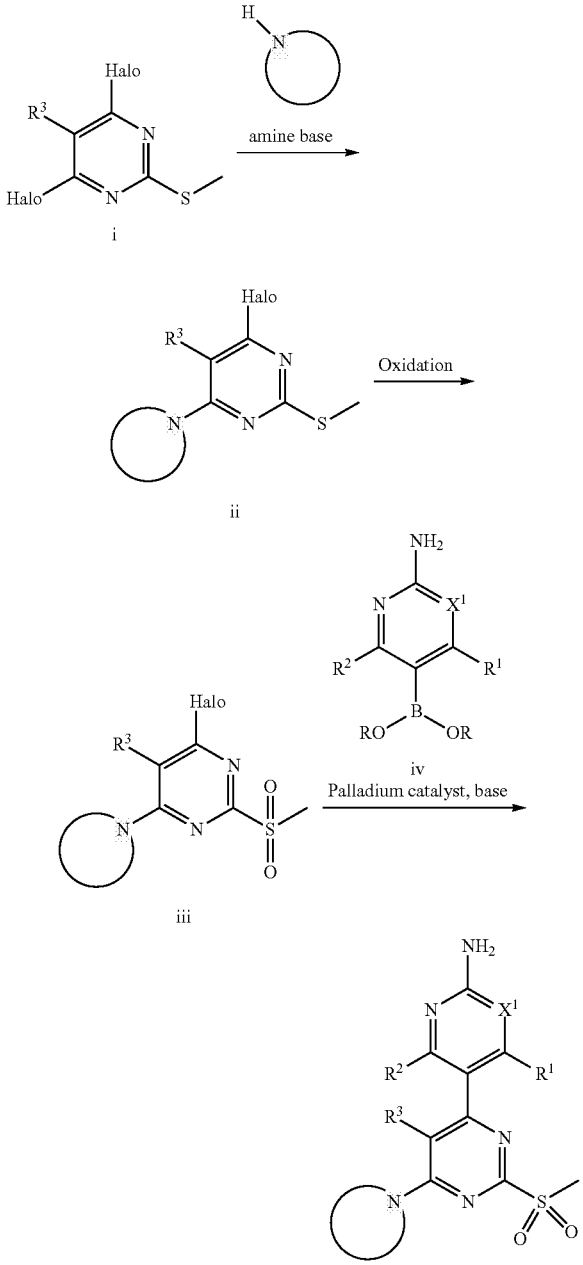

As illustrated in Scheme 2, compounds or intermediates of the invention can be prepared by reaction of a trihalo pyrimidine (vi) with a boronate ester under Pd(0) coupling conditions to provide biheteroaryl (vii). Subsequent sequential displacement of a halogens atom of vii with an the same of different amine reagents under basic conditions, provide biheteroaryl compounds (ix).

Scheme 2

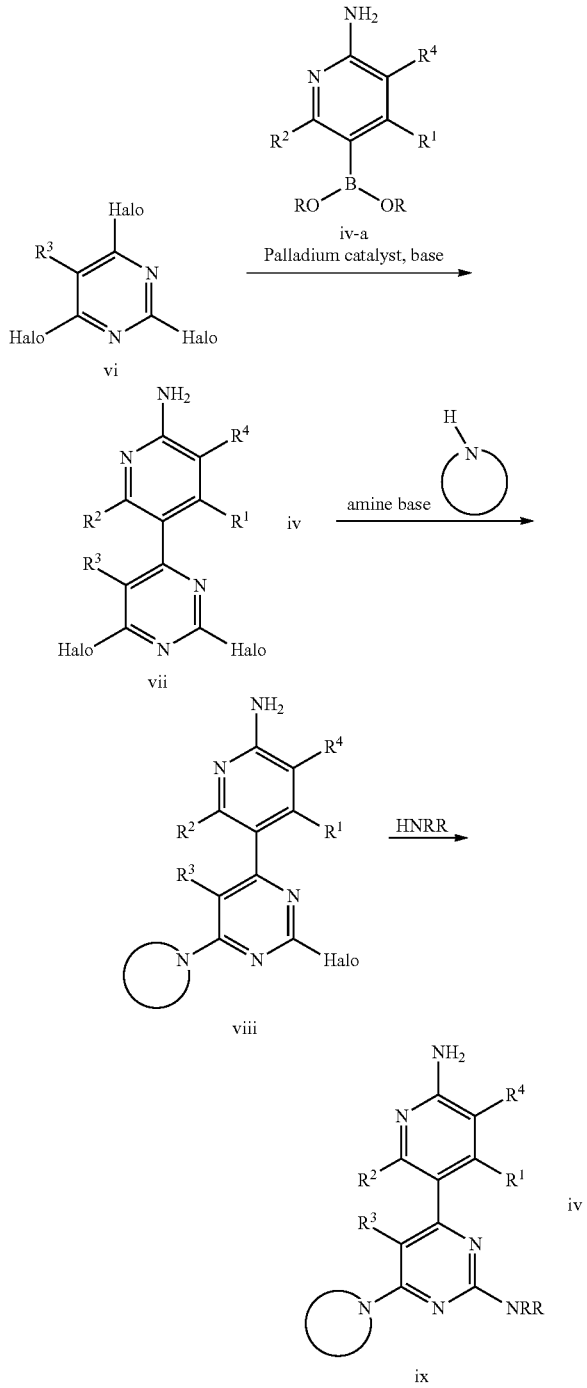

As illustrated in Scheme 3, compounds or intermediates of the invention can be prepared by Suzuki-Miyaura coupling of dichloroodopyridine (x) with an amine under Pd(0) catalyzed conditions (See, Hartwig, J. F. (1997), "Palladium-Catalyzed Amination of Aryl Halides: Mechanism and Rational Catalyst Design", Synlett 4: 329-340). Displacement of a chloro group in xi with an amine followed by Suzuki coupling of the resultant product (xii) with a boronate ester (iv-b) provides compounds and or intermediates of the invention xiii.

Scheme 3

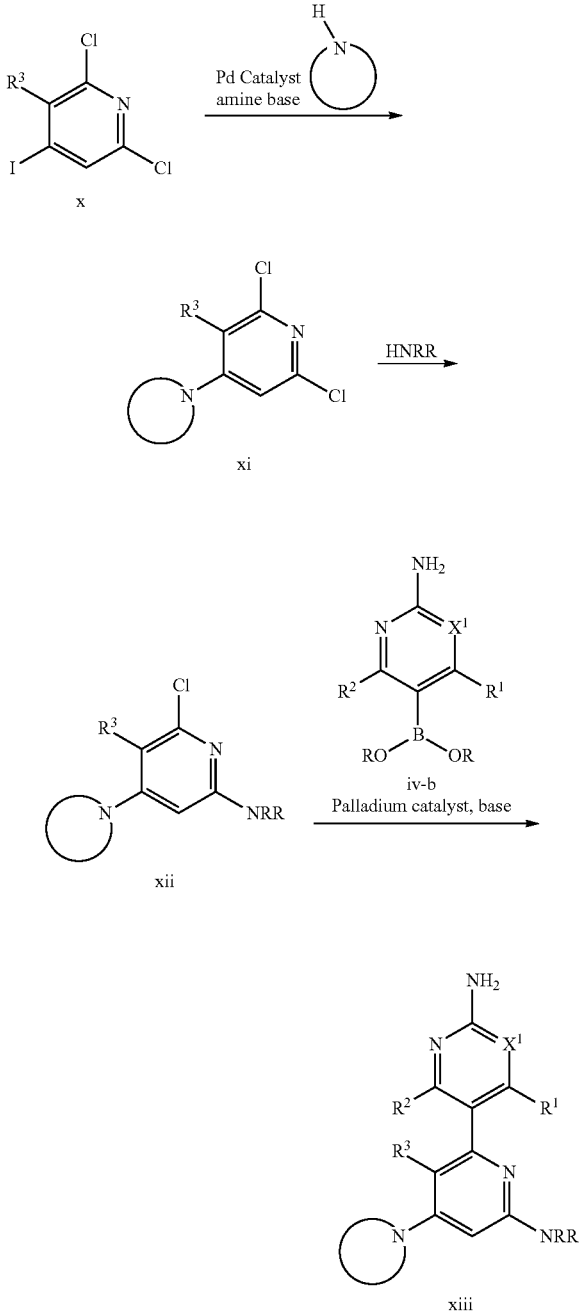

Scheme 4

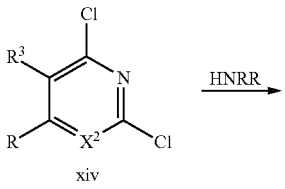

-continued

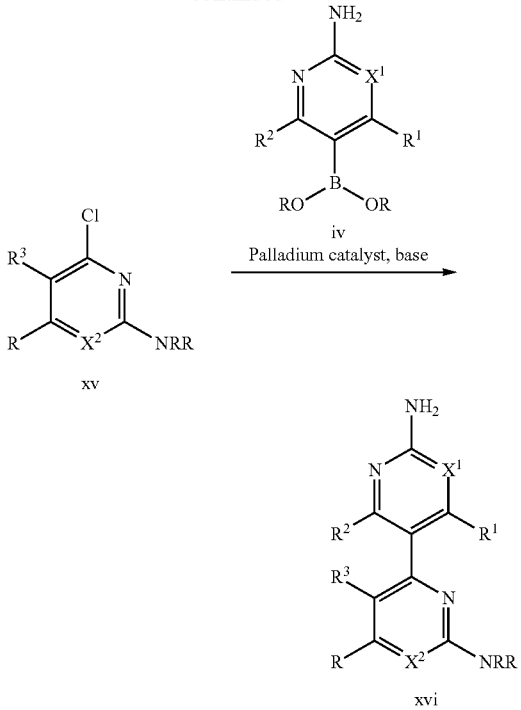

As illustrated in Scheme 4, compounds and or intermediates of the invention can be prepared by treating a R substituted dichloro compound (xiv) with an amine under base conditions to produce compound xv. Subsequent treatment of compound xv under Pd(0) catalyst couplingh conditions provides compounds and intermediates of the inventions (xvi).

D. Pharmaceutical Compositions and Administrations

In addition to one or more of the compounds provided above (or stereoisomers, geometric isomers, tautomers, solvates, metabolites, isotopes, (pharmaceutically acceptable) salts, or prodrugs thereof), the invention also provides for compositions and medicaments comprising a compound of Formula I or any subformula or any embodiment thereof and at least one pharmaceutically acceptable carrier, diluent or excipient. The compositions of the invention can be used for inhibiting DLK activity in patients (e.g., humans) pharmaceutically acceptable carrier, diluent or excipient.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof In one embodiment, the invention provides for pharmaceutical compositions (or medicaments) comprising a compound of Formula I (or stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of Formula I or I-I and compositions comprising compounds of Formula I or any embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit DLK activity as required to prevent or treat the undesired disease or disorder, such as for example, neurodegeneration, amyloidosis, formation of neurofibrillary tangles, or undesired cell growth. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of Formula I any embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of Formula I or any embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21$^{st}$ Edition, Lippincott Williams & Wilkins, Philidelphia, Pa.

Sustained-release preparations of a compound of the invention (e.g., compound of Formula I or any embodiment thereof) can be prepared. Suitable examples of sustained-release preparations include semipermeable matrices of solid hydrophobic polymers containing a compound of Formula I or an embodiment thereof, which matrices are in the form of shaped articles, e.g., films, or microcapsules.

Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) 21st Edition, Lippincott Williams & Wilkins, Philidelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of Formula I or any embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of Formula I or an embodiment thereof is formulated in an acetate buffer, at pH 5. In another embodiment, the compounds of Formula I or an embodiment thereof are sterile. The compound may be stored, for example, as a solid or amorphous composition, as a lyophilized formulation or as an aqueous solution.

Formulations of a compound of the invention (e.g., compound of Formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of a compound of the invention (e.g., compound of Formula I or an embodiment thereof) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of Formula I or I-I) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford. Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I or I-I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I or I-I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

A compound of formula I (or an embodiment thereof) used in the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. A compound of formula I (or an embodiment thereof) need not be, but is optionally formulated with one or more agent currently used to prevent or treat the disorder in question. The effective amount of such other agents depends on the amount of a compound of the invention present in the formulation, the type of disorder or treatment, and other factors discussed above.

These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a compound of formula I or I-I (or an embodiment thereof) (when used alone or in combination with other agents) will depend on the type of disease to be treated, the properties of the compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 μg/kg to 15 mg/kg (e.g., 0.1 mg/kg-10 mg/kg) of compound can be an initial candidate dosage for administration to the patient, whether, for example, by one or more separate administrations, or by continuous infusion. One typical daily dosage might range from about 1 μg kg to 100 mg/kg or more, depending on the factors mentioned above. For repeated administrations over several days or longer, depending on the condition, the treatment would generally be sustained until a desired suppression of disease symptoms occurs. One exemplary dosage of a compound of formula I (or an embodiment thereof) would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg kg of the compound. However, other dosage regimens may be useful. The progress of this therapy is easily monitored by conventional techniques and assays.

Other typical daily dosages might range from, for example, about 1 g/kg to up to 100 mg/kg or more (e.g., about 1 μg kg to 1 mg/kg, about 1 μg/kg to about 5 mg/kg, about 1 mg kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer a compound until a dosage is reached that results in improvement in or, optimally, elimination of, one or more symptoms of the treated disease or condition. The progress of this therapy is easily monitored by conventional assays. One or more agent provided herein may be administered together or at different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

E. Indications and Methods of Treatment

In another aspect, the invention provides for methods of inhibiting the Dual Leucine Zipper Kinase (DLK) in an in vitro (e.g., a nerve graft of nerve transplant) or in vivo setting (e.g., in a patient) by contacting DLK present in an in vitro or in vivo setting with compounds of Formula I or an embodiment thereof. In these methods of the invention, the inhibition of DLK signaling or expression with a compound of formula I or an embodiment thereof results in a downstream decrease in JNK phosphorylation (e.g., a decrease in JNK2 and/or JNK3 phosphorylation), JNK activity (e.g., a decrease in JNK2 and/or JNK3 activity), and/or JNK expression (e.g., a decrease in JNK2 and/or JNK3 expression). Accordingly, administering one or more compounds of Formula I or an embodiment thereof according to the methods of the invention can result in decrease in activity of kinase targets downstream of the DLK signalling cascade, e.g, (i) a decrease in JNK phosphorylation, JNK activity, and/or JNK expression, (ii) a decrease in cJun phosphorylation, cJun activity, and/or cJun expression, and/or (iii) a decrease in p38 phosphorylation, p38 activity, and/or p38 expression.

Compounds of the invention can be used in methods for inhibiting neuron or axon degeneration. The inhibitors are, therefore, useful in the therapy of, for example, (i) disorders of the nervous system (e.g., neurodegenerative diseases), (ii) conditions of the nervous system that are secondary to a disease, condition, or therapy having a primary effect outside of the nervous system, (iii) injuries to the nervous system caused by physical, mechanical, or chemical trauma, (iv) pain, (v) ocular-related neurodegeneration, (vi) memory loss, and (vii) psychiatric disorders. Non-limiting examples of some of these diseases, conditions, and injuries are provided below.

Examples of neurodegenerative diseases and conditions that can be prevented or treated according to the invention include amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson's-plus diseases (e.g., multiple system atrophy, progressive supranuclear palsy, and corticobasal degeneration), dementia with Lewy bodies, frontotemporal dementia, demyelinating diseases (e.g., Guillain-Barre syndrome and multiple sclerosis), Charcot-Marie-Tooth disease (CMT; also known as Hereditary Motor and Sensory Neuropathy (HMSN), Hereditary Sensorimotor Neuropathy (HSMN), and Peroneal Muscular Atrophy), prion disease (e.g., Creutzfeldt-Jakob disease, Gerstmann-Straussler-Scheinker syndrome (GSS), fatal familial insomnia (FFI), and bovine spongiform encephalopathy (BSE, commonly known as mad cow disease)), Pick's disease, epilepsy, and AIDS demential complex (also known as HIV dementia, HIV encephalopathy, and HIV-associated dementia).

The methods of the invention can also be used in the prevention and treatment of ocular-related neurodegeneration and related diseases and conditions, such as glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis. Non-limiting examples of different types of glaucoma that can be prevented or treated according to the invention include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochromic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphema and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neovascular glaucoma, drug-induced glaucoma (e.g., corticosteroid induced glaucoma and alpha-chymotrypsin glaucoma), toxic glaucoma, and glaucoma associated with intraocular tumors, retinal deatchments, severe chemical burns of the eye, and iris atrophy.

Examples of types of pain that can be treated according to the methods of the invention include those associated with the following conditions: chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neuogenic or neuropathic pain, nerve inflammation or damage, shingles, herniated disc, torn ligament, and diabetes.

Certain diseases and conditions having primary effects outside of the nervous system can lead to damage to the nervous system, which can be treated according to the methods of the present invention. Examples of such conditions include peripheral neuropathy and neuralgia caused by, for example, diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, and amyloidosis.

In addition, the methods of the invention can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine. Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexyline), and Metronidazole.

The methods of the invention can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), as well as damage to the central nervous system due to, e.g., stroke or intracranial hemorrhage (such as cerebral hemorrhage).

Further, the methods of the invention can be used in the prevention or treatment of memory loss such as, for example, age-related memory loss. Types of memory that can be affected by loss, and thus treated according to the invention, include episodic memory, semantic memory, short-term memory, and long-term memory. Examples of diseases and conditions associated with memory loss, which can be treated according to the present invention, include mild cognitive impairment, Alzheimer's disease, Parkinson's disease, Huntington's disease, chemotherapy, stress, stroke, and traumatic brain injury (e.g., concussion).

The methods of the invention can also be used in the treatment of psychiatric disorders including, for example, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders (e.g., kleptomania, pathological gambling, pyromania, and trichotillomania).

In addition to the in vivo methods described above, the methods of the invention can be used to treat nerves ex vivo, which may be helpful in the context of nerve grafts or nerve transplants. Thus, the inhibitors described herein can be useful as components of culture media for use in culturing nerve cells in vitro.

Accordingly, in another aspect, the invention provides for a method for inhibiting or preventing degeneration of a central nervous system (CNS) neuron or a portion thereof, the method comprising administering to the CNS neuron a compound of formula I or an embodiment thereof In one embodiment, of the method for inhibiting or preventing degeneration of a central nervous system neuron or a portion thereof, the administering to the CNS neuron is performed in vitro.

In another embodiment, of the method for inhibiting or preventing degeneration of a central nervous system neuron or a portion thereof, the method further comprises grafting or implanting the CNS neuron into a human patient after administration of the agent.

In another embodiment, of the method for inhibiting or preventing degeneration of a central nervous system neuron or a portion thereof, the CNS neuron is present in a human patient.

In another embodiment, of the method for inhibiting or preventing degeneration of a central nervous system neuron or a portion thereof, the administering to the CNS neuron comprises administration of said compound of formula I or an embodiment thereof in a pharmaceutically acceptable carrier, diluent or excipient.

In another embodiment, of the method for inhibiting or preventing degeneration of a central nervous system neuron or a portion thereof, the administering to the CNS neuron is carried out by an administration route selected from the group consisting of parenteral, subcutaneous, intravenous, intraperitoneal, intracerebral, intralesional, intramuscular, intraocular, intraarterial interstitial infusion and implanted delivery device.

In another embodiment, of the method for inhibiting or preventing degeneration of a central nervous system neuron or a portion thereof, the method further comprises administering one or more additional pharmaceutical agents.

The inhibitors can be optionally combined with or administered in concert with each other or other agents known to be useful in the treatment of the relevant disease or condition. Thus, in the treatment of ALS, for example, inhibitors can be administered in combination with Riluzole (Rilutek), minocycline, insulin-like growth factor 1 (IGF-1), and/or methylcobalamin. In another example, in the treatment of Parkinson's disease, inhibitors can be administered with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In a further example, in the treatment of Alzheimer's disease, inhibitors can be administered with acetylcholinesterase inhibitors (e.g., donepezil, galantamine, and rivastigmine) and/or NMDA receptor antagonists (e.g., memantine). The combination therapies can involve concurrent or sequential administration, by the same or different routes, as determined to be appropriate by those of skill in the art. The invention also includes pharmaceutical compositions and kits comprising combinations as described herein.

In addition to the combinations noted above, other combinations included in the invention are combinations of inhibitors of degeneration of different neuronal regions. Thus, the invention includes combinations of agents that (i) inhibit degeneration of the neuron cell body, and (ii) inhibit axon degeneration. For example, inhibitors of GSK and transcription are found to prevent degeneration of neuron cell bodies, while inhibitors of EGFR and p38 MAPK are found to prevent degeneration of axons. Thus, the invention includes combinations of inhibitors of GSK and EGFR (and/or p38 MAPK), combinations of transcription inhibitors and EGF (and/or p38 MAPK), and further combinations of inhibitors of dual leucine zipper-bearing kinase (DLK), glycogen synthase kinase 3β (GSK3), p38 MAPK, EGFF, phosphoinositide 3-kinase (PI3K), cyclin-dependent kinase 5 (cdk5), adenylyl cyclase, c-Jun N-terminal kinase (JNK), BCL2-associated X protein (Bax), In channel, calcium/calmodulin-dependent protein kinase kinase (CaMKK), a G-protein, a G-protein coupled receptor, transcription factor 4 (TCF4), and β-catenin. The inhibitors used in these combinations can be any of those described herein, or other inhibitors of these targets as described in WO 2011/050192, incorporated herein by reference.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

F. Examples

The invention will be more fully understood by reference to the following examples. They should not, however, be construed as limiting the scope of the invention. These examples are not intended to limit the scope of the present invention, but rather to provide guidance to a skilled artisan to prepare and use the compounds, compositions, and methods of the present invention. While particular embodiments of the present invention are described, the skilled artisan will appreciate that various changes and modifications can be made without departing from the spirit and scope of the invention.

The chemical reactions in the Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interferring groups, by utilizing other suitable reagents known in the art other than those described, and/or by making routine modifications of reaction conditions. Alternatively, other reactions disclosed herein or known in the art will be recognized as having applicability for preparing other compounds of the invention. Accordingly, the following examples are provided to illustrate but not limit the invention.

In the Examples described below, unless otherwise indicated all temperatures are set forth in degrees Celsius. Commercially available reagents were purchased from suppliers such as Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters); or alternatively column chromatography was carried out using on an ISCO chromatography system (Manufacturer: Teledyne ISCO) having a silica gel column. $^1$H NMR spectra were recorded on a Varian instrument operating at 400 MHz. $^1$H NMR spectra were obtained in deuterated $CDCl_3$, $d_6$-DMSO, $CH_3OD$ or $d_6$-acetone solutions (reported in ppm), using tetramethylsilane (TMS) as the reference standard (0 ppm). When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

When possible, product formed in the reaction mixtures were monitored by LC/MS. High Pressure Liquid Chromatography—Mass Spectrometry (LCMS) experiments. Example conditions for analysis include monitoring on an Agilent 1200 Series LC coupled to a 6140 quadrupole mass spectrometer using a Supelco Ascentis Express C18 column with a linear gradient of 5%-95% acetonitrile/water (with 0.1% trifluoroacetic acid in each mobile phase) within 1.4 minutes and held at 95% for 0.3 minute, or on a PE Sciex API 150 EX using a Phenomenex DNYC monolithic C18 column with a linear gradient of 5%-95% acetonitrile/water (with 0.1% trifluoroacetic acid in each mobile phase) within 5 minutes and held at 95% for 1 minute to determine retention times ($R_T$) and associated mass ions.

All abbreviations used to described reagents, reaction conditions, or equipment used are consistent with the definitions set forth in the "List of standard abbreviations and acronyms" published yearly by the Journal of Organic Chemistry (an American Chemical Society journal). The chemical names of discrete compounds of the invention were obtained using the structure naming features of commonly used programs including ChemBioDraw Version 11.0, Accelrys' Pipeline Pilot IUPAC compound naming program.

Example 1

Method A:

2-(2-azabicyclo[2.1.1]hexan-2-yl)-6-((1S,4S)-2-oxa-5-azabicyclo[2.2.1]heptan-5-yl)-[4,5'-bipyrimidin]-2'-amine

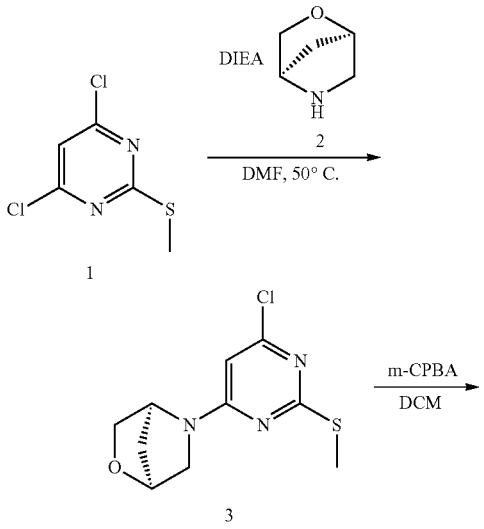

-continued

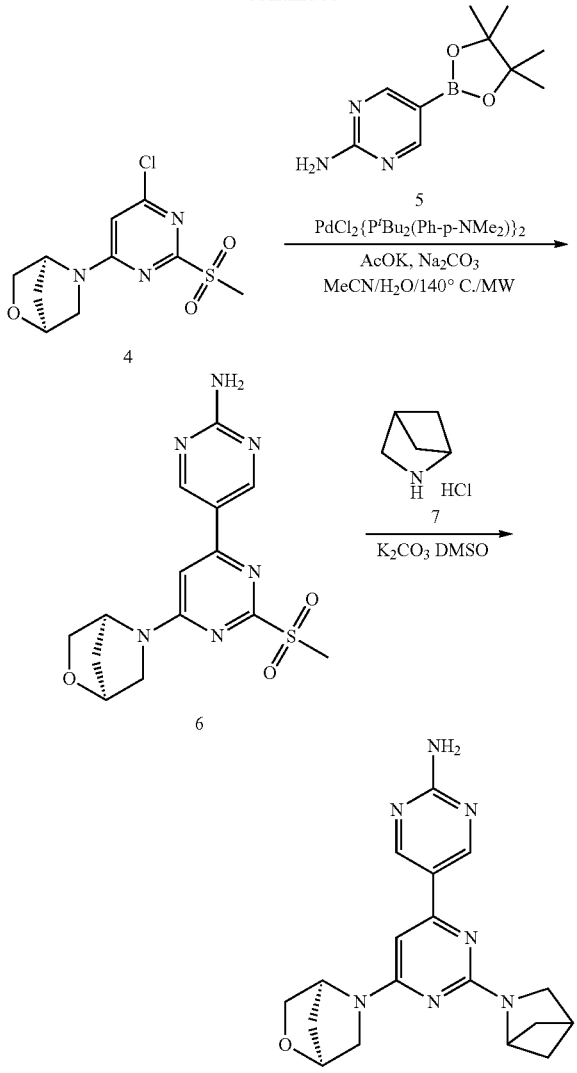

Step 1: Synthesis of (1S,4S)-5-(6-chloro-2-(methylthio)pyrimidin-4-yl)-2-oxa-5-azabicyclo[2.2.1]-heptane

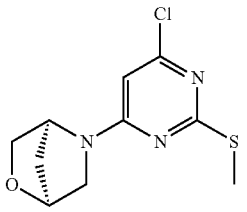

The mixture of 4,6-dichloro-2-(methylthio)pyrimidine (450 mg, 2.31 mmol), DIEA (894 mg, 6.92 mmol) and 2-oxa-5-azabicyclo[2.2.1]heptane (328 mg, 2.42 mmol) in DMF (5 mL) was stirred at 50° C. for 12 h. Water (20 mL) was added to and extracted with ethyl acetate (2×20 mL). The organic layers were dried over $Na_2SO_4$, filtered and concentrated to give (1S,4S)-5-(6-chloro-2-(methylthio)pyrimidin-4-yl)-2-oxa-5-azabicyclo-[2.2.1]heptane (550 mg, 92.5% yield) as a white solid, which was used for next step without further purification LCMS (ESI): $[MH]^+$=258.0.

Step 2: Synthesis of (1S,4S)-5-(6-chloro-2-(methylsulfonyl)pyrimidin-4-yl)-2-oxa-5-azabicyclo-[2.2.1]heptane

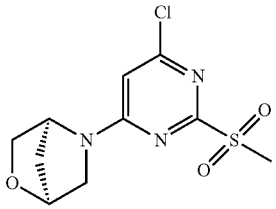

To a mixture of (1S,4S)-5-(6-chloro-2-(methylthio)pyrimidin-4-yl)-2-oxa-5-azabicyclo[2.2.1]heptane (550 mg, 2.13 mmol) in DCM (50 mL) was added m-CPBA (1.73 g, 8.53 mmol) portionwise. The reaction mixture was stirred at room temperature for 1 h. The mixture was washed with $Na_2SO_3$ (sat aq, 20 mL) and was concentrated in vacuo to afford (1S,4S)-5-(6-chloro-2-(methylsulfonyl)pyrimidin-4-yl)-2-oxa-5-azabicyclo[2.2.1]--heptane (600 mg, 97.0% yield) as a white solid, LCMS (ESI): $[MH]^+$=289.7, which was used for next step without further purification.

Step 3: Synthesis of 6-((1S,4S)-2-oxa-5-azabicyclo[2.2.1]heptan-5-yl)-2-(methylsulfonyl)-[4,5'-bipyrimidin]-2'-amine

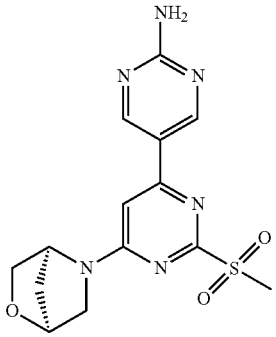

To a microwave vial charged with (1S,4S)-5-(6-chloro-2-(methylsulfonyl)pyrimidin-4-yl)-2-oxa-5-azabicyclo[2.2.1]-heptane (600 mg, 2.07 mmol), 5-(4,4,5,5-tetramethyl-1,3,2-dioxaborolan-2-yl)pyrimidin-2-amine (641 mg, 2.90 mmol), potassium acetate (284 mg, 2.90 mmol) and sodium carbonate (307 mg, 2.90 mmol) in acetonitrile/water (1 (5:1, 6.0 mL) was added $PdCl_2\{PtBu_2(Ph\text{-}p\text{-}NMe_2)\}_2$ (147 mg, 0.21 mmol) under nitrogen. The vial was sealed and heated by microwave irradiation at 140° C. for 40 min. The reaction mixture was concentrated in vacuo, and resulting residue was purified by flash column chromatography (5% methanol in dichloromethane) to provide 6-((1S,4S)-2-oxa-5-azabicyclo[2.2.1]heptan-5-yl)-2-(methylsulfonyl)-[4,5'-bipyrimidin]-2'-amine (380 mg, 52.7% yield). LCMS (ESI): $[MH]^+$=349.0.

Step 4: Synthesis of 2-(2-azabicyclo[2.1.1]hexan-2-yl)-6-((1S,4S)-2-oxa-5-azabicyclo[2.2.1]heptan-5-yl)-[4,5'-bipyrimidin]-2'-amine

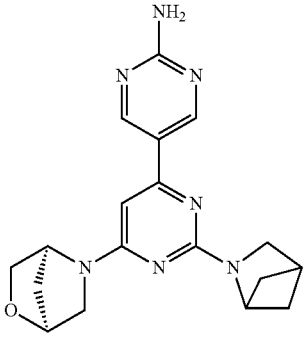

To the mixture of 6-((1S,4S)-2-oxa-5-azabicyclo[2.2.1]heptan-5-yl)-2-(methylsulfonyl)-[4,5'-bipyrimidin]-2'-amine (380 mg, 1.09 mmol) and potassium carbonate (754 mg, 5.45 mmol) in DMSO (5 mL) was added 2-azabicyclo[2.1.1]hexane hydrochloride (326 mg, 2.73 mmol). The mixture was stirred at 100° C. for 5 h. After removal of the solvent, the residue was purified by Prep-HPLC (formic acid) to afford 2-(2-azabicyclo[2.1.1]hexan-2-yl)-6-((1S,4S)-2-oxa-5-azabicyclo[2.2.1]heptan-5-yl)-[4,5'-bipyrimidin]-2'-amine (220 mg, 57% yield). LCMS (ESI): $[MH]^+$=352.1; $^1$H NMR (400 MHz, DMSO-d6) δ 8.91 (s, 2H), 7.00 (s, 2H), 6.30-6.10 (m, 1H), 5.10-4.90 (m, 1H), 4.83 (d, J=6.4 Hz, 1H), 4.70-4.64 (m, 1H), 3.78-3.76 (m, 1H), 3.66-3.64 (m, 1H), 3.45-3.38 (m, 4H), 2.89-2.87 (m, 1H), 1.93-1.86 (m, 4H), 1.32-1.31 (m, 2H).

Method B:

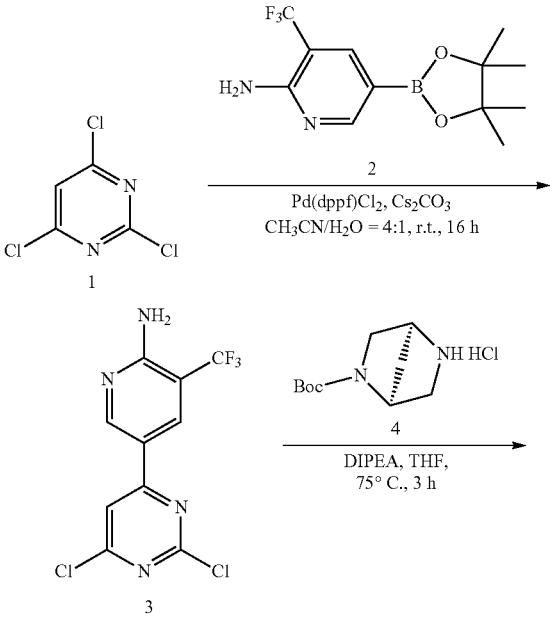

-continued

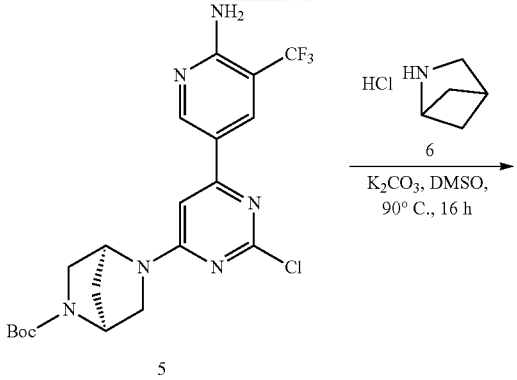

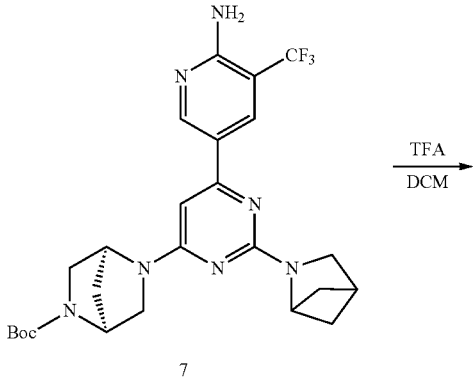

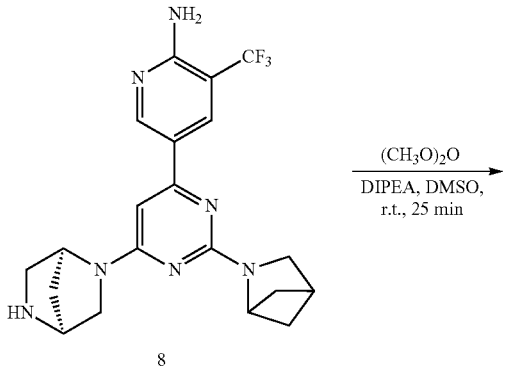

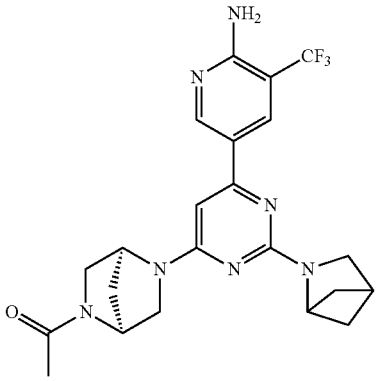

Step 1: Synthesis of 5-(2,6-dichloropyrimidin-4-yl)-3-(trifluoromethyl)pyridin-2-amine

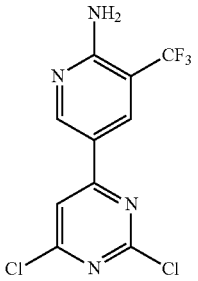

To a microwave vial charged with 2,4,6-trichloropyrimidine (300 mg, 1.64 mmol), 5-(4,4,5,5-tetramethyl-1,3,2-dioxaborolan-2-yl)-3-(trifluoromethyl)pyridin-2-amine (518 mg, 1.80 mmol) and cesium carbonate (1.07 g, 3.27 mmol) in acetonitrile/water (4:1, 30 mL) was added 1,1'-bis(diphenylphosphino)ferrocene-palladium(II)dichloride (60 mg, 0.05 mmol) under nitrogen. The mixture was stirred at room temperature for 16 h. The reaction mixture was concentrated in vacuo, and resulting residue was purified by flash column chromatography (15% ethyl acetate in petroleum ether to 50% ethyl acetate in petroleum ether) to provide 5-(2,6-dichloropyrimidin-4-yl)-3-(trifluoromethyl)pyridin-2-amine (300 mg, 59.3% yield). LCMS (ESI): $[MH]^+$=308.7.

Step 2: Synthesis of (1S,4S)-tert-butyl 5-(6-(6-amino-5-(trifluoromethyl)pyridin-3-yl)-2-chloropyrimidin-4-yl)-2,5-diazabicyclo[2.2.1]heptane-2-carboxylate

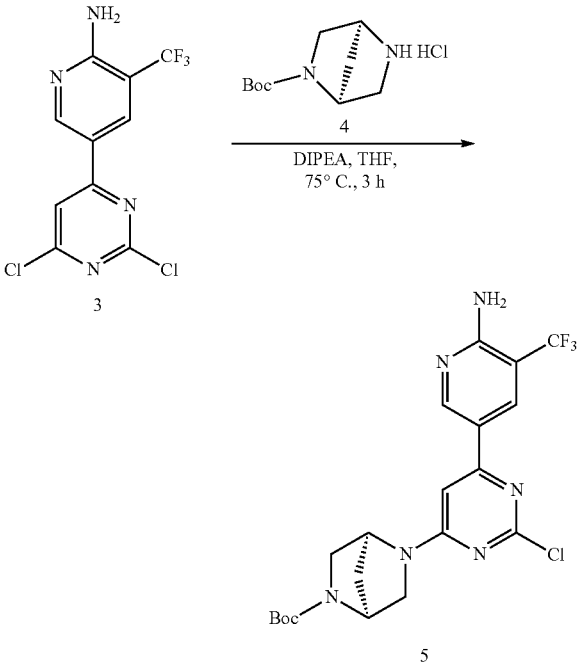

To a solution of 5-(2,6-dichloropyrimidin-4-yl)-3-(trifluoromethyl)pyridin-2-amine (300 mg, 0.84 mmol) in tetrahydrofuran (60 mL) was added (1S,4S)-tert-butyl 2,5-diazabicyclo[2.2.1]heptane-2-carboxylate hydrochloride (197 mg, 0.84 mmol) and N-ethyl-N-isopropylpropan-2-amine (2 mL). The mixture was heated at 75° C. for 3 h. After cooling to room temperature, water (50 mL) was added to. The mixture was extracted with ethyl acetate (3×30 mL). The organic layer was dried over sodium sulfate, concentrated and purified by flash column chromatography (25% ethyl acetate in petroleum ether to 100% ethyl acetate) to provide (1S,4S)-tert-butyl 5-(6-(6-amino-5-(trifluoromethyl)pyridin-3-yl)-2-chloropyrimidin-4-yl)-2,5-diazabicyclo[2.2.1]heptane-2-carboxylate (220 mg, 48.1% yield). TLC (Thin layer chromatography) (petroleum ether (PE): ethyl acetate (EA)=3:1, $R_f$=0.3-0.4).

Step 3: Synthesis of (1S,4S)-tert-butyl 5-(6-(6-amino-5-(trifluoromethyl)pyridin-3-yl)-2-(2-azabicyclo[2.1.1]hexan-2-yl)pyrimidin-4-yl)-2,5-diazabicyclo[2.2.1]heptane-2-carboxylate

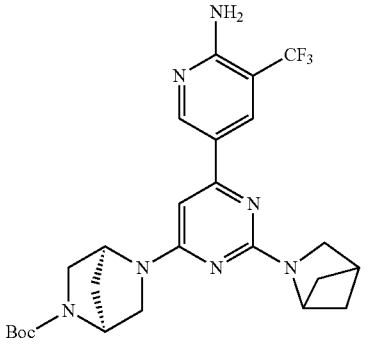

To a solution of (1S,4S)-tert-butyl 5-(6-(6-amino-5-(trifluoromethyl)pyridin-3-yl)-2-chloropyrimidin-4-yl)-2,5-diazabicyclo[2.2.1]heptane-2-carboxylate (220 mg, 0.47 mmol) in DMSO (2 mL) was added 2-azabicyclo[2.1.1]hexane hydrochloride (68 mg, 0.56 mmol) and potassium carbonate (130 mg, 0.93 mmol). The mixture was heated at 90° C. for 16 h. After cooling to room temperature, water (50 mL) was added to. The mixture was extracted with ethyl acetate (30 mL (3 times)). The organic layer was dried over sodium sulfate, concentrated and purified by flash column chromatography (50% ethyl acetate in petroleum ether to 100% ethyl acetate) to provide (1S,4S)-tert-butyl 5-(6-(6-amino-5-(trifluoromethyl)pyridin-3-yl)-2-(2-azabicyclo[2.1.1]hexan-2-yl)pyrimidin-4-yl)-2,5-diazabicyclo[2.2.1]heptane-2-carboxylate (130 mg, 53.7% yield). LCMS (ESI): $[MH]^+$=518.0.

Step 4: Synthesis of 5-(2-(2-azabicyclo[2.1.1]hexan-2-yl)-6-((1S,4S)-2,5-diazabicyclo[2.2.1]heptan-2-yl)pyrimidin-4-yl)-3-(trifluoromethyl)pyridin-2-amine

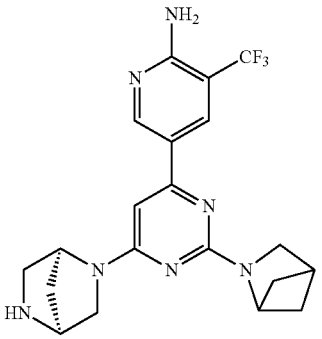

To an ice-cooled solution of (1S,4S)-tert-butyl 5-(6-(6-amino-5-(trifluoromethyl)pyridin-3-yl)-2-(2-azabicyclo[2.1.1]hexan-2-yl)pyrimidin-4-yl)-2,5-diazabicyclo[2.2.1]heptane-2-carboxylate (130 mg, 0.25 mmol) in dichloromethane (6 mL) was added trifluoroacetic acid (3 mL). The mixture was stirred at room temperature for 0.5 h. After removal of the solvent, the residue was dissolved with water (30 mL), basified and extracted with dichloromethane (3×30 mL). The organic layer was dried over sodium sulfate, concentrated to provide 5-(2-(2-azabicyclo[2.1.1]hexan-2-yl)-6-((1S,4S)-2,5-diazabicyclo[2.2.1]heptan-2-yl)pyrimidin-4-yl)-3-(trifluoromethyl)pyridin-2-amine (80 mg, 75.0% yield). LCMS (ESI): $[MH]^+$=417.9.

Step 5: Synthesis of 1-((1S,4S)-5-(6-(6-amino-5-(trifluoromethyl)pyridin-3-yl)-2-(2-azabicyclo[2.1.1]hexan-2-yl)pyrimidin-4-yl)-2,5-diazabicyclo[2.2.1]heptan-2-yl)ethanone

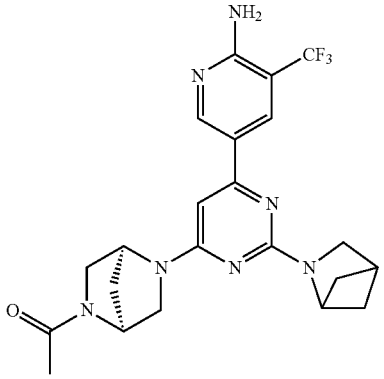

To a solution of 5-(2-(2-azabicyclo[2.1.1]hexan-2-yl)-6-((1S,4S)-2,5-diazabicyclo[2.2.1]heptan-2-yl)pyrimidin-4-yl)-3-(trifluoromethyl)pyridin-2-amine (80 mg, 0.22 mmol) in DMSO (2 mL) was added acetic anhydride (46 mg, 0.44 mmol) and N-ethyl-N-isopropylpropan-2-amine (0.1 mL). The mixture was stirred at room temperature for 25 min. The mixture was concentrated in vacuum and the residue was purified by Prep-HPLC (BASE) to provide 1-((1S,4S)-5-(6-(6-amino-5-(trifluoromethyl)pyridin-3-yl)-2-(2-azabicyclo[2.1.1]hexan-2-yl)pyrimidin-4-yl)-2,5-diazabicyclo[2.2.1]heptan-2-yl)ethanone (46.34 mg, 40.0% yield). LCMS (ESI): $[MH]^+$=459.9; $^1H$ NMR (400 MHz, DMSO-d6) δ 8.91 (s, 1H), 8.36 (s, 1H), 6.79 (s, 2H), 6.53-6.21 (m, 1H), 5.10-4.89 (m, 1H), 4.80-4.78 (m, 1H), 4.74-4.63 (m, 1H), 3.55-3.51 (m, 1H), 3.44-3.35 (m, 2H), 3.23-2.84 (m, 4H), 2.82 (s, 1H), 2.00 (s, 1H), 1.91 (s, 3H), 1.83-1.81 (m, 2H), 1.29 (d, J=2.0 Hz, 2H).

Method C:

(1R,5S,6r)-tert-butyl 6-(2'-amino-2-(2-azabicyclo[2.1.1]hexan-2-yl)-[4,5'-bipyrimidin]-6-yl)-3-azabicyclo[3.1.0]hexane-3-carboxylate

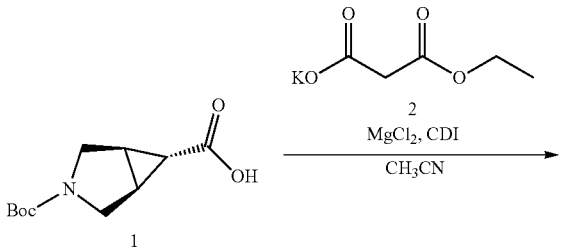

-continued

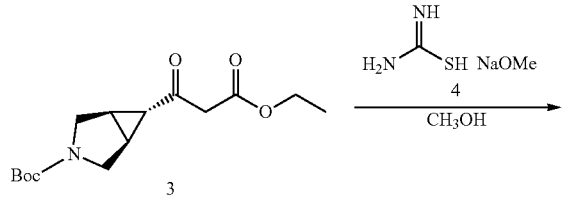

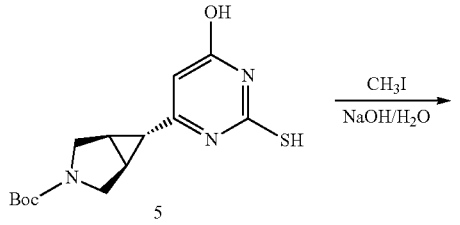

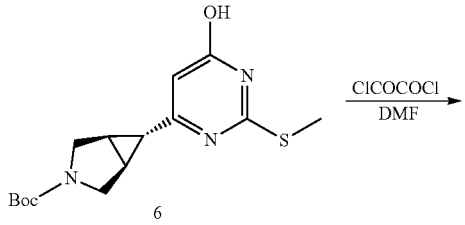

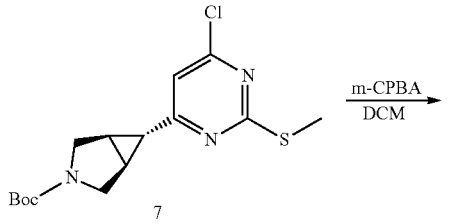

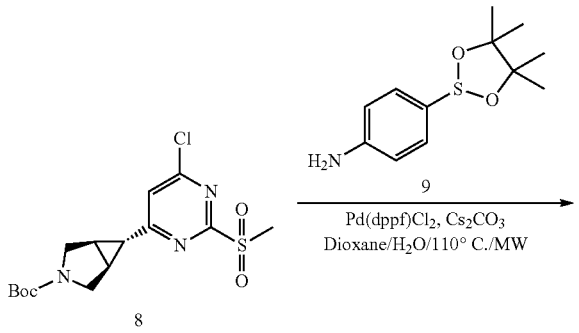

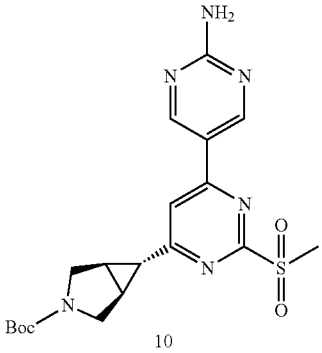

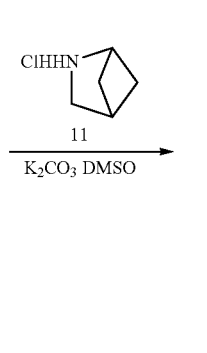

-continued

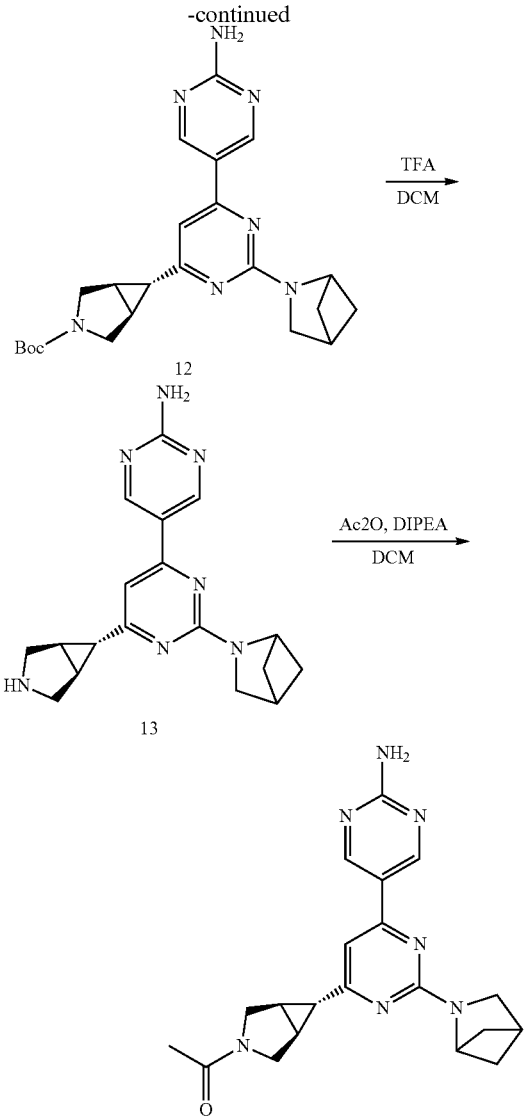

Step 1: Synthesis of (1R,5S,6r)-tert-butyl 6-(3-ethoxy-3-oxopropanoyl)-3-azabicyclo[3.1.0]hexane-3-carboxylate

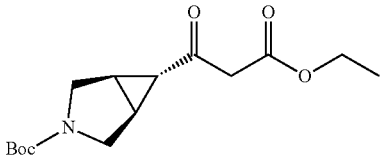

To a solution of (1R,5S,6r)-3-(tert-butoxycarbonyl)-3-azabicyclo[3.1.0]hexane-6-carboxylic acid (2 g, 8.8 mmol) in acetonitrile (150 mL) was added 1,1'-carbonyldiimidazole (1.71 g, 10.56 mmol). After stirring at 20° C. for 1 h, magnesium chloride (827 mg, 8.8 mmol) and potassium 3-ethoxy-3-oxopropanoate (1.5 g, 8.8 mmol) was added to and the reaction mixture was stirred at 20° C. for 16 h. The reaction solution was filtered, concentrated and purified by flash column (60% ethyl acetate in petroleum ether) to afford (1R,5S,6r)-tert-butyl 6-(3-ethoxy-3-oxopropanoyl)-3-azabicyclo[3.1.0]hexane-3-carboxylate (1.5 g, 57.7% yield). $^1$H NMR (400 MHz, Chloroform-d) δ 4.21-4.16 (m, 2H), 3.66-3.64 (m, 1H), 3.54 (s, 3H), 3.42-3.90 (m, 2H), 2.15-2.13 (m, 2H), 1.90-1.88 (m, 1H), 1.42 (s, 9H), 1.28-1.24 (m, 3H)

Step 2: Synthesis of (1R,5S,6r)-tert-butyl 6-(6-hydroxy-2-mercaptopyrimidin-4-yl)-3-azabicyclo[3.1.0]hexane-3-carboxylate

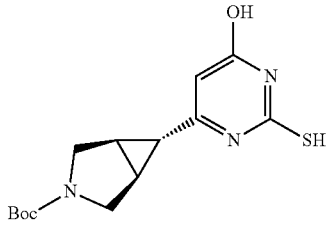

The mixture of (1R,5S,6r)-tert-butyl 6-(3-ethoxy-3-oxopropanoyl)-3-azabicyclo[3.1.0]hexane-3-carboxylate (7.6 g, 25.6 mmol), carbamimidothioic acid (7.77 g, 102.3 mmol) and sodium methanolate (5.52 g, 102.3 mmol) in anhydrous methonal (250 mL) was refluxed under $N_2$ for 16 h. After removal of the solvent, the residue was adjusted pH to 6 with hydrogen chloride aqueous solution (2 M). The mixture was filtered and the solid was the desired product of (1R,5S,6r)-tert-butyl 6-(6-hydroxy-2-mercaptopyrimidin-4-yl)-3-azabicyclo[3.1.0]hexane-3-carboxylate (7 g, 88.6% yield). $^1$H NMR (400 MHz, DMSO-d6) δ 12.30 (d, J=13.6 Hz, 2H), 5.45 (s, 1H), 3.57-3.53 (m, 2H), 3.33-3.29 (m, 2H), 2.05-1.99 (m, 2H), 1.58-1.57 (m, 1H), 1.39 (s, 9H).

Step 3: Synthesis of (1R,5S,6r)-tert-butyl 6-(6-hydroxy-2-(methylthio)pyrimidin-4-yl)-3-azabicyclo[3.1.0]hexane-3-carboxylate

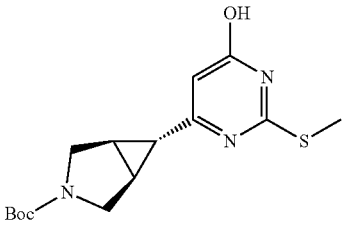

To the solution of (1R,5S,6r)-tert-butyl 6-(6-hydroxy-2-mercaptopyrimidin-4-yl)-3-azabicyclo[3.1.0]hexane-3-carboxylate (7 g, 22.65 mmol) in sodium hydroxide aqueous solution (8%) was added iodomethane (6.43 g, 45.3 mmol). The resulting solution was stirred at room temperature for 1 h. The reaction mixture was adjusted pH=5~6 with hydrogen chloride aqueous solution (2 M). The mixture was filtered and the solid was the desired product of (1R,5S,6r)-tert-butyl 6-(6-hydroxy-2-(methylthio)pyrimidin-4-yl)-3-azabicyclo[3.1.0]hexane-3-carboxylate (6 g, crude, about 65%, 53.4% yield). LCMS (ESI): $[MH]^+$=324.1.

Step 4: Synthesis of (1R,5S,6r)-tert-butyl 6-(6-chloro-2-(methylthio)pyrimidin-4-yl)-3-azabicyclo[3.1.0]hexane-3-carboxylate

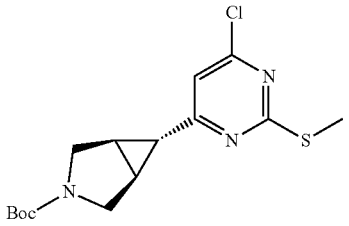

To a solution of (1R,5S,6r)-tert-butyl 6-(6-hydroxy-2-(methylthio)pyrimidin-4-yl)-3-azabicyclo[3.1.0]hexane-3-carboxylate (6 g, 18.57 mmol, 65%) in dry dichloromethane (250 mL) was added oxalyl dichloride (2.83 g, 22.3 mmol) and DMF (0.5 mL) at 0° C. The mixture was stirred at 0° C. for 2 h and was poured into ice water including $Et_3N$. The mixture was extracted with dichloromethane (250 mL*2). The organic layer was washed with brine (100 mL), dried over sodium sulfate, concentrated and purified by flash column chromatography (20% ethyl acetate in petroleum ether) to afford (1R,5S,6r)-tert-butyl 6-(6-chloro-2-(methylthio)pyrimidin-4-yl)-3-azabicyclo[3.1.0]hexane-3-carboxylate (3.8 g, 92.7% yield).

Step 5: Synthesis of (1R,5S,6r)-tert-butyl 6-(6-chloro-2-(methylsulfonyl)pyrimidin-4-yl)-3-azabicyclo[3.1.0]hexane-3-carboxylate

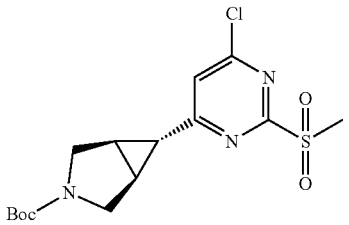

To a solution of (1R,5S,6r)-tert-butyl 6-(6-chloro-2-(methylthio)pyrimidin-4-yl)-3-azabicyclo[3.1.0]hexane-3-carboxylate (800 mg, 2.35 mmol) in anhydrous dichloromethane (40 mL) was added m-CPBA (2 g, 11.7 mmol). The reaction mixture was stirred at room temperature for 1 h. The mixture was extracted with dichloromethane (2×50 mL). The organic layer was washed with brine (50 mL), dried over sodium sulfate, concentrated and purified by flash column chromatography (30% ethyl acetate in petroleum ether) to provide (1R,5S,6r)-tert-butyl 6-(6-chloro-2-(methylsulfonyl)pyrimidin-4-yl)-3-azabicyclo[3.1.0]hexane-3-carboxylate (700 mg, 80% yield) $^1$H NMR (400 MHz, Chloroform-d) δ 7.40 (s, 1H), 3.82-3.70 (m, 2H), 3.54-3.50 (m, 2H), 3.33 (s, 3H), 2.38 (s, 2H), 1.96-1.94 (m, 1H), 1.47 (s, 1H).

Step 6: Synthesis of (1R,5S,6r)-tert-butyl 6-(2'-amino-2-(methylsulfonyl)-[4,5'-bipyrimidin]-6-yl)-3-azabicyclo[3.1.0]hexane-3-carboxylate

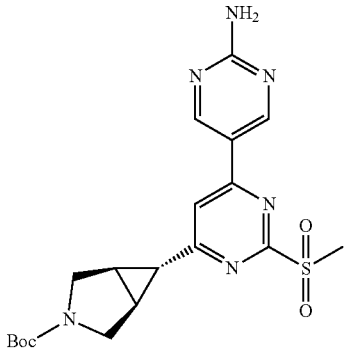

To a microwave vial charged with (1R,5S,6r)-tert-butyl 6-(6-chloro-2-(methylsulfonyl)pyrimidin-4-yl)-3-azabicyclo[3.1.0]hexane-3-carboxylate (820 mg, 2.2 mmol), 4-(4,4,5,5-tetramethyl-1,3,2-dioxaborolan-2-yl)aniline (972 mg, 4.4 mmol), and cesium carbonate (1.43 g, 4.4 mmol) in dioxane/water (5:1, 15 mL) was added 1,1'-bis(diphenylphosphino)ferrocene-palladium(II) dichloride (161 mg, 0.22 mmol) under nitrogen. The vial was sealed and heated by microwave irradiation at 110° C. for 30 min. The reaction mixture was concentrated in vacuo, and resulting residue was purified by flash column chromatography (25% ethyl acetate in petroleum ether to 100% ethyl acetate) to provide (1R,5S,6r)-tert-butyl 6-(2'-amino-2-(methylsulfonyl)-[4,5'-bipyrimidin]-6-yl)-3-azabicyclo[3.1.0]hexane-3-carboxylate (700 mg, 94.7% yield) LCMS (ESI): $[MH]^+$=432.8.

Step 7: Synthesis of (1R,5S,6r)-tert-butyl 6-(2'-amino-2-(2-azabicyclo[2.1.1]hexan-2-yl)-[4,5'-bipyrimidin]-6-yl)-3-azabicyclo[3.1.0]hexane-3-carboxylate

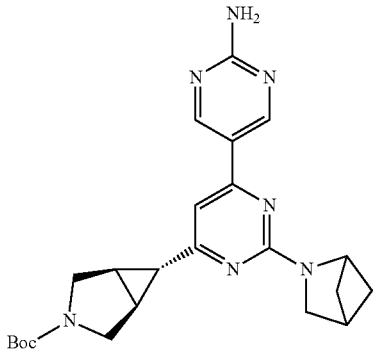

To a solution of (1R,5S,6r)-tert-butyl 6-(2'-amino-2-(methylsulfonyl)-[4,5'-bipyrimidin]-6-yl)-3-azabicyclo[3.1.0]hexane-3-carboxylate (200 mg, 0.46 mmol) in DMSO (15 mL) was added 2-azabicyclo[2.1.1]hexane hydrochloride (109.5 mg, 0.92 mmol) and potassium carbonate (127 mg, 0.92 mmol). The mixture was stirred at 120° C. for 2 h. After cooling to room temperature, the mixture was extracted with ethyl acetate (2×20 mL). The organic layer was concentrated and purified by flash column chromatography (75% ethyl acetate in petroleum ether) to provide (1R,5S,6r)-tert-butyl 6-(2'-amino-2-(2-azabicyclo[2.1.1]hexan-2-yl)-[4,5'-bipyrimidin]-6-yl)-3-azabicyclo[3.1.0]hexane-3-carboxylate (140 mg, 70% yield). TLC (EA, $R_f$=0.3~0.4).

Step 8: Synthesis of 2-(2-azabicyclo[2.1.1]hexan-2-yl)-6-((1R,5S,6r)-3-azabicyclo[3.1.0]hexan-6-yl)-[4,5'-bipyrimidin]-2'-amine

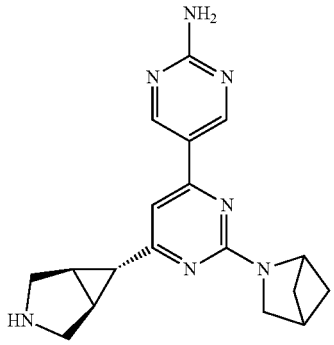

To an ice-cooled solution of (1R,5S,6r)-tert-butyl 6-(2'-amino-2-(2-azabicyclo[2.1.1]hexan-2-yl)-[4,5'-bipyrimidin]-6-yl)-3-azabicyclo[3.1.0]hexane-3-carboxylate (120 mg, 0.276 mmol) in dichloromethane (6 mL) was added trifluoroacetic acid (3 mL). The mixture was warmed to room temperature. After 3 h, the reaction mixture was concentrated in vacuo to provide 2-(2-azabicyclo[2.1.1]hexan-2-yl)-6-((1R,5S,6r)-3-azabicyclo[3.1.0]hexan-6-yl)-[4,5'-bipyrimidin]-2'-amine (90 mg, 97.3% yield). The resulting residue was used without further purification. TLC (EA, $R_f$=0).

Step 9: Synthesis of 1-((1R,5S,6r)-6-(2'-amino-2-(2-azabicyclo[2.1.1]hexan-2-yl)-[4,5'-bipyrimidin]-6-yl)-3-azabicyclo[3.1.0]hexan-3-yl)ethanone

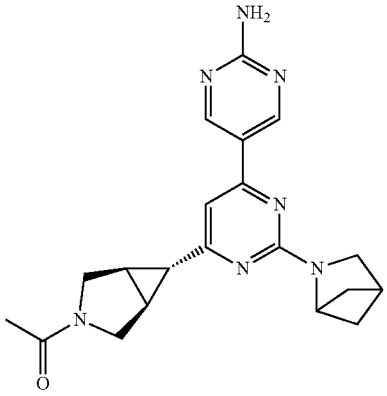

To a solution of 2-(2-azabicyclo[2.1.1]hexan-2-yl)-6-((1R,5S,6r)-3-azabicyclo[3.1.0]hexan-6-yl)-[4,5'-bipyrimidin]-2'-amine (80 mg, 0.24 mmol) and N-ethyl-N-isopropylpropan-2-amine (62 mg, 0.48 mmol) in dichloromethane (15 mL) was added acetic anhydride (49 mg, 0.48 mmol). The mixture was stirred at room temperature for 30 min. After removal of the solvent, the residue was purified by PR-HPLC (BASE) to provide 1-((1R,5S,6r)-6-(2'-amino-2-(2-azabicyclo[2.1.1]hexan-2-yl)-[4,5'-bipyrimidin]-6-yl)-3-azabicyclo[3.1.0]hexan-3-yl)ethanone (88 mg, 97.2% yield). LCMS (ESI): $[MH]^+$=377.8; $^1$H NMR (400 MHz, Chloroform-d) δ 8.94 (s, 2H), 6.65 (s, 1H), 5.49 (s, 2H), 4.95 (d, J=6.0 Hz, 1H), 3.97 (d, J=12.0 Hz, 1H), 3.72 (s, 2H), 3.54 (s, 3H), 2.95 (s, 1H), 2.30 (s, 2H), 2.06 (s, 3H), 2.00 (s, 2H), 1.70 (s, 1H), 1.45 (s, 2H).

Method D:

Preparation of 5-[6-(3-azabicyclo[2.1.1]hexan-3-yl)-4-[(1S,4S)-2-oxa-5-azabicyclo[2.2.1]heptan-5-yl]-2-pyridyl]-3-(difluoromethoxy)pyridin-2-amine

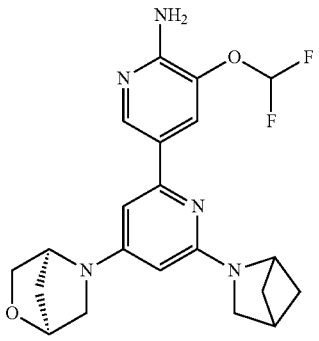

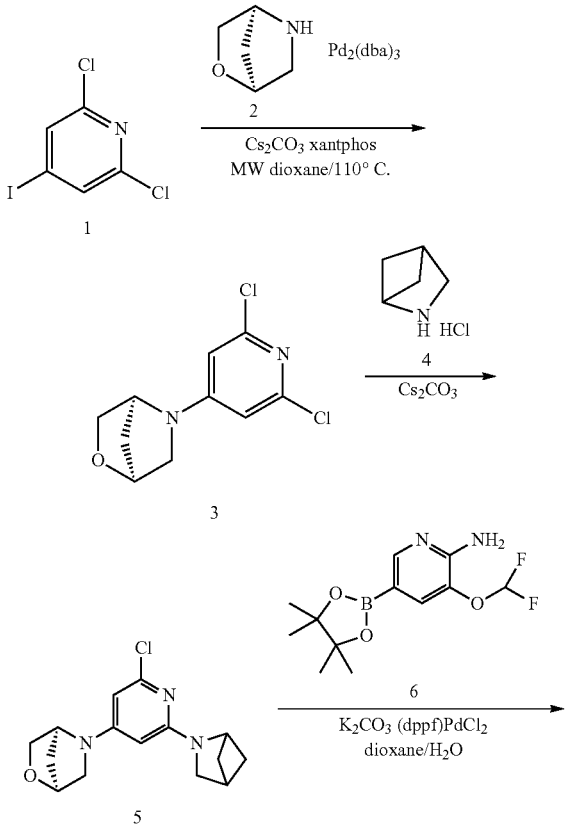

-continued

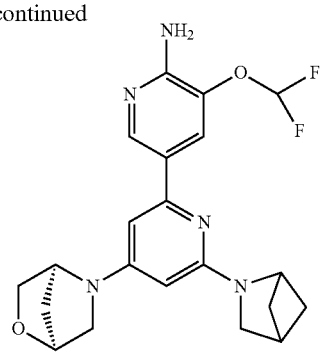

Step 1: Synthesis of (1S,4S)-5-(2,6-dichloropyridin-4-yl)-2-oxa-5-azabicyclo[2.2.1]heptane

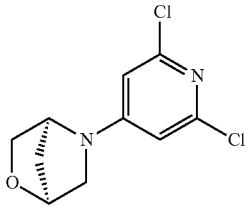

To a microwave vial charged with 2,6-dichloro-4-iodopyridine (100 mg, 0.37 mmol), (1S,4S)-2-oxa-5-azabicyclo[2.2.1]heptane (49.19 mg, 0.44 mmol) and cesium carbonate (66.29 mg, 0.48 mmol) in dioxane (5 mL) was added $Pd_2(dba)_3$ (3.5 mg, 0.048 mmol) and xantphos (3.5 mg, 0.048 mmol) under nitrogen. The vial was sealed and heated by microwave irradiation at 140° C. for 1 h. The reaction mixture was concentrated in vacuo, and resulting residue was purified by TLC (PE:EA=2:1) to afford (1S,4S)-5-(2,6-dichloropyridin-4-yl)-2-oxa-5-azabicyclo[2.2.1]heptane (40 mg, 35% yield).

Step 2: Synthesis of (1S,4S)-5-(2-(2-azabicyclo[2.1.1]hexan-2-yl)-6-chloropyridin-4-yl)-2-oxa-5-azabicyclo[2.2.1]heptane

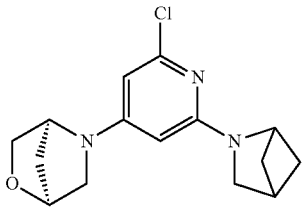

To a microwave vial charged with (1S,4S)-5-(2,6-dichloropyridin-4-yl)-2-oxa-5-azabicyclo[2.2.1]heptane (100 mg, 0.41 mmol) and 2-azabicyclo[2.1.1]hexane hydrochloride (244 mg, 2.04 mmol) in NMP (3 mL) was added cesium carbonate (1.33 g, 4.08 mmol). The vial was sealed and heated by microwave irradiation at 150° C. for 18 h. The reaction mixture was concentrated in vacuo, and resulting residue was purified by TLC (PE:EA=1:1) to afford compound 5 (80 mg, 77.7% yield). LCMS (ESI) $[MH]^+$=291.8.

Step 3: Synthesis of 5-[6-(3-azabicyclo[2.1.1]hexan-3-yl)-4-[(1S,4S)-2-oxa-5-azabicyclo[2.2.1]heptan-5-yl]-2-pyridyl]-3-(difluoromethoxy)pyridin-2-amine

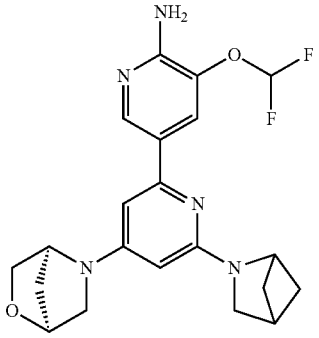

To a microwave vial charged with (1S,4S)-5-(2-(2-azabicyclo[2.1.1]hexan-2-yl)-6-chloropyridin-4-yl)-2-oxa-5-azabicyclo[2.2.1]heptane (70 mg, 0.24 mmol), 3-(difluoromethoxy)-5-(4,4,5,5-tetramethyl-1,3,2-dioxaborolan-2-yl)pyridin-2-amine (75.53 mg, 0.26 mmol) and potassium carbonate (66.29 mg, 0.48 mmol) in dioxane/water (5:1, 3.0 mL) was added 1,1'-bis(diphenylphosphino)ferrocene-palladium(II)dichloride (3.5 mg, 0.048 mmol) under nitrogen. The vial was sealed and heated by microwave irradiation at 120° C. for 1 h. The reaction mixture was concentrated in vacuo, and resulting residue was purified by PR-HPLC (Basic) to afford 5-[6-(3-azabicyclo[2.1.1]hexan-3-yl)-4-[(1S,4S)-2-oxa-5-azabicyclo[2.2.1]heptan-5-yl]-2-pyridyl]-3-(difluoromethoxy)pyridin-2-amine (24.55 mg, 24.6% yield). LCMS (ESI) $[MH]^+$=416.1; $^1H$ NMR (400 MHz, DMSO-d6) δ 8.48 (s, 1H), 7.91 (s, 1H), 7.15 (t, J=74.0 Hz, 1H), 6.42 (s, 1H), 6.21 (s, 2H), 5.54 (s, 1H), 4.76-4.74 (m, 2H), 4.62 (s, 1H), 3.73 (d, J=6.8 Hz, 1H), 3.63 (d, J=7.6 Hz, 1H), 3.45 (d, J=8.8 Hz, 1H), 3.33 (s, 2H), 3.10 (d, J=10.4 Hz, 1H), 2.88-2.86 (m, 1H), 1.88-1.81 (m, 4H), 1.27-1.26 (m, 2H).

Method E:

Step 1-Synthesis of (1S,4S)-5-(6-chloro-2-methylsulfonyl-pyrimidin-4-yl)-2-oxa-5-azabicyclo[2.2.1]heptane (70929-339-C)

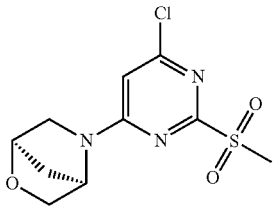

To a solution of 4,6-dichloro-2-methylsulfonyl-pyrimidine (3.41 g, 15 mmol) and (1S,4S)-2-oxa-5-azabicyclo[2.2.1]heptane hydrochloride (2.03 g, 15.0 mmol) in N,N-dimethylacetamide (40.5 mL), was added N,N-diisopropylethylamine (6.60 mL). The resulting mixture was stirred at room temperature. After 30 min, the reaction mixture was concentrated to a solid. The crude material was purified by column chromatography using an 80 g column, with a gradient of 0% to 100% ethyl acetate in heptane. The combined fractions containing product were concentrated under reduced pressure to provide (1S,4S)-5-(6-chloro-2-methylsulfonyl-pyrimidin-4-yl)-2-oxa-5-azabicyclo[2.2.1]heptane (3.03 g). 1H NMR (400 MHz, Chloroform-d) δ 6.30 (s, 1H), 3.98-3.81 (m, 3H), 3.45-3.35 (m, 2H), 3.28 (s, 3H), 2.16-1.98 (m, 2H), 1.95-1.86 (m, 1H).

Step 2 Synthesis of 6-((1S,4S)-2-oxa-5-azabicyclo[2.2.1]heptan-5-yl)-2-(methylsulfonyl)-[4,5'-bipyrimidin]-2'-amine (70929-339-E)

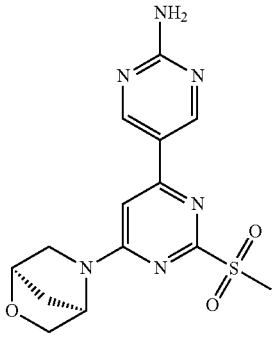

To a solution of (1S,4S)-5-(6-chloro-2-methylsulfonyl-pyrimidin-4-yl)-2-oxa-5-azabicyclo[2.2.1]heptane (500 mg, 1.73 mmol), 5-(4,4,5,5-tetramethyl-1,3,2-dioxaborolan-2-yl)pyrimidin-2-amine (382 mg, 1.73 mmol), and [1,1'-bis(diphenylphosphino)ferrocene]dichloropalladium (II) (63.8 mg, 0.0863 mmol) in acetonitrile (6.90 mL) was added potassium acetate in water (3.45 mL) in a microwave vial equipped with a stirbar. The mixture was microwaved at 110° C. for 5 min. The solid was and washed with ethyl acetate (5 mL) filtered under vacuum, providing 6-((1S,4S)-2-oxa-5-azabicyclo[2.2.1]heptan-5-yl)-2-(methylsulfonyl)-[4,5'-bipyrimidin]-2'-amine (598 mg, crude). $^1$H NMR (400 MHz, DMSO-d6) δ 9.02 (d, J=5.6, 2.8 Hz, 2H), 7.40-6.97 (m, 1H), 7.28 (s, 2H), 5.14 (d, J=16.0 Hz, 1H), 4.76 (d, J=27.9 Hz, 1H), 3.82 (d, J=7.7, 1.5 Hz, 1H), 3.76-3.66 (m, 1H), 3.60-3.51 (m, 1H), 3.50-3.41 (m, 1H), 3.35 (d, J=6.1 Hz, 3H), 1.95 (d, J=22.0 Hz, 2H).

Step 3 Synthesis of 2-(azetidin-1-yl)-6-(1S,4S)-2-oxa-5-azabicyclo[2.2.1]heptan-5-yl)-[4,5'-bipyrimidin]-2'-amine

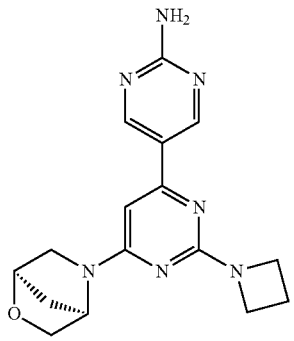

5-[2-methylsulfonyl-6-[(1S,4S)-2-oxa-5-azabicyclo[2.2.1]heptan-5-yl]pyrimidin-4-yl]pyrimidin-2-amine (30.0 mg, 0.861 mmol), azetidine hydrochloride (24.7 mg, 0.258 mmol), potassium carbonate (71.4 mg, 0.517 mmol), and 1-methyl-2-pyrrolidinone (0.861 mL) were combined in a reaction flask and heated to 130° C. for 16 hrs. The reaction was filtered and purified by reverse phase column chromatography using a gradient of 20% to 60% acetonitrile in 0.1% ammonium hydroxide in water. The combined fractions containing product were concentrated under reduced pressure to provide 2-(azetidin-1-yl)-6-((1S,4S)-2-oxa-5-azabicyclo[2.2.1]heptan-5-yl)-[4,5'-bipyrimidin]-2'-amine 1H NMR (400 MHz, DMSO-d6) δ 8.87 (s, 2H), 6.97 (s, 2H), 4.95 (s, 1H), 4.66 (s, 1H), 3.99 (t, J=7.5 Hz, 4H), 3.77 (dd, J=7.3, 1.5 Hz, 1H), 3.64 (d, J=7.3 Hz, 1H), 3.43 (dd, J=10.5, 1.5 Hz, 1H), 3.40-3.32 (m, 1H), 3.17 (s, 1H), 2.24 (p, J=7.5 Hz, 2H), 1.85 (s, 2H).

Method F:

Preparation of 6-(3-methoxyazetidin-1-yl)-4-(1-(oxetan-3-yl)piperidin-4-yl)-5'-(trifluoromethyl)-[2,3'-bipyridin]-6'-amine

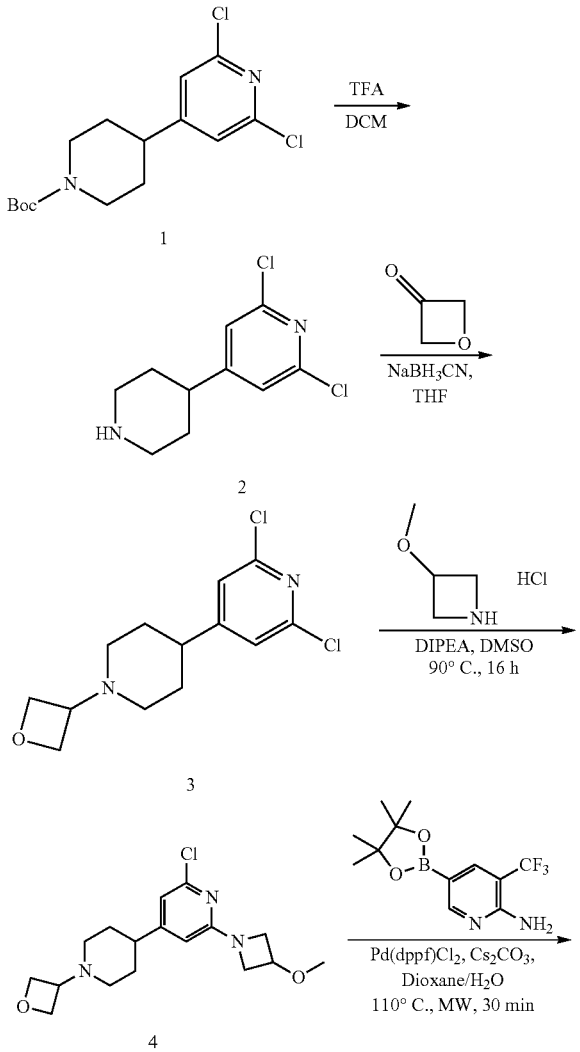

-continued

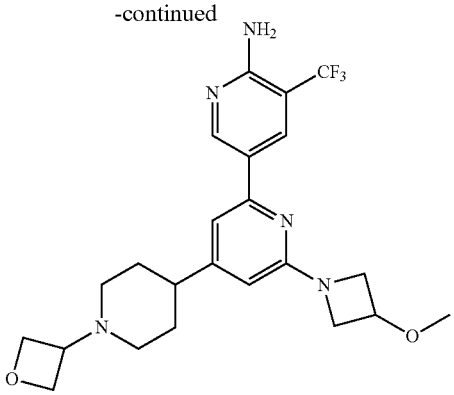

Step 1: Synthesis of 2,6-dichloro-4-(piperidin-4-yl)pyridine

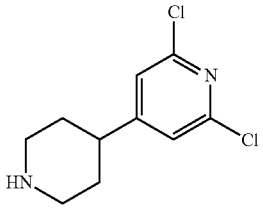

To a solution of tert-butyl 4-(2,6-dichloropyridin-4-yl) piperidine-1-carboxylate (2 g, 6.06 mmol) in DCM (2 mL) was added TFA (3 mL). The solution was stirred at room temperature for 30 min. The reaction solution was concentrated to afford 2,6-dichloro-4-(piperidin-4-yl)pyridine as TFA salt, which was used without further purification. LCMS (ESI) [MH]+=231.1.

Step 2: Synthesis of 2,6-dichloro-4-(1-(oxetan-3-yl) piperidin-4-yl)pyridine

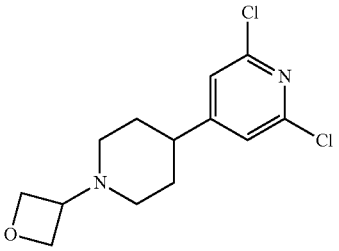

A solution of 2,6-dichloro-4-(piperidin-4-yl)pyridine (2 g, 8.7 mmol) and oxetan-3-one (6.26 g, 87 mmol) in THF (50 mL) was stirred at 70° C. for 30 min and then sodium cyanoborohydride (2.74 g, 43.5 mmol) was added to the mixture and the mixture solution was stirred at 70° C. for additional 30 min. The reaction solution was filtered and the filtrate was concentrated to give crude product which was purified by flash column chromatography on silica gel (30% ethyl acetate in petroleum ether) to afford 2,6-dichloro-4-(1-(oxetan-3-yl)piperidin-4-yl)pyridine. (2 g, 88.7% yield). LCMS (ESI) [MH]+=286.7.

Step 3: Synthesis of 2-chloro-6-(3-methoxyazetidin-1-yl)-4-(1-(oxetan-3-yl)piperidin-4-yl)pyridine

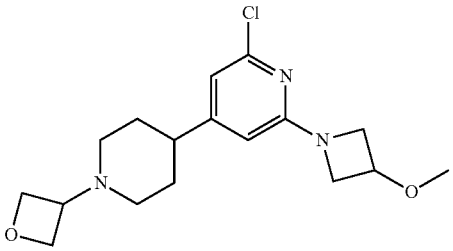

A mixture of 2,6-dichloro-4-(1-(oxetan-3-yl)piperidin-4-yl)pyridine (450 mg, 1.57 mmol), 3-methoxyazetidine hydrochloride (963 mg, 7.83 mmol) and DIPEA (3 mL, 16.9 mmol) in DMSO (5 mL) was stirred at 100° C. for 16 h. The mixture was poured into water and extracted with EtOAc. The organic layer was washed with brine, dried over Na2SO4, evaporated and purified by flash column chromatography on silica gel (30% ethyl acetate in petroleum ether) to give 2-chloro-6-(3-methoxyazetidin-1-yl)-4-(1-(oxetan-3-yl)piperidin-4-yl)pyridine (320 mg, 60.3% yield). LCMS (ESI) [MH]+=337.8

Step 4: Synthesis of 6-(3-methoxyazetidin-1-yl)-4-(1-(oxetan-3-yl)piperidin-4-yl)-5'-(trifluoromethyl)-[2,3'-bipyridin]-6'-amine

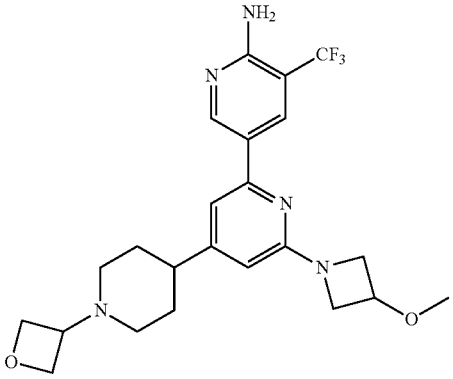

To a solution of 2-chloro-6-(3-methoxyazetidin-1-yl)-4-(1-(oxetan-3-yl)piperidin-4-yl)pyridine (80 mg, 0.24 mmol), 5-(4,4,5,5-tetramethyl-1,3,2-dioxaborolan-2-yl)-3-(trifluoromethyl)pyridin-2-amine (140 mg, 0.48 mmol) and cesium carbonate (160 mg, 0.48 mmol) in dioxane/H2O (5:1, 4 mL) was added [1,1'-bis(diphenylphosphino)ferrocene]dichloropalladium (II) (18 mg, 0.024 mmol) under nitrogen. The mixture was irradiated by microwave at 110° C. for 30 min. The reaction mixture was filtered, the filtrate was concentrated and purified by Prep-HPLC to afford 6-(3-methoxyazetidin-1-yl)-4-(1-(oxetan-3-yl)piperidin-4-yl)-5'-(trifluoromethyl)-[2,3'-bipyridin]-6'-amine (68.3 mg 61.5%, yield). LCMS (ESI) [MH]+=464, 1HNMR (400 MHz, $CDCl_3$), δ8.745(s,1H), δ8.363(s,1H), δ8.232(s,1H), δ8.832 (s,1H), δ6.109(s,1H), δ5.642(s,2H), δ4.74- 4.67(m,4H), δ 4.39-4.22 (m, 3H), δ 3.94-3.90 (m, 2H), δ 3.63-3.56(m, 1H), δ 3.346(s, 3H), δ 2.980(d, J=10.8 Hz, 2H), δ 2.55-2.46 (m,1H), δ 2.06-1.99 (m, 1H), δ 1.93-1.87(m, 4H). LCMS: 464.0(M+1).

Method G:

6-(3-methoxyazetidin-1-yl)-4-(1-(oxetan-3-yl)piperidin-4-yl)-5'-(trifluoromethyl)-[2,3'-bipyridin]-6'-amine Step 1:
1-(2,6-dichloro-4-pyridyl)cyclobutanecarbonitrile

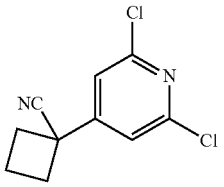

To a stirring solution of 2,4,6-trichloropyridine (1.00 g, 5.48 mmol) and cyclobutanecarbonitrile (0.53 mL, 5.5 mmol) in anhydrous THF (27 mL) at −78° C. and under nitrogen was added lithium bis(trimethylsilyl)amide (6.0 mL, 6.0 mmol, 1.0 M solution in THF). The cooling bath was removed and stirring continued for 1 h. The reaction was quenched by the addition of sat. aq. $NH_4Cl$, extracted with $CH_2Cl_2$ and organics dried over $MgSO_4$. Following concentration, the reaction residue was purified by flash column chromatography (100:0 heptanes/EtOAc 85:15 heptanes/EtOAc) to afford the title compound as a white solid (0.995 g, 76%); $^1$H NMR (400 MHz, $CDCl_3$) δ 7.34 (s, 2H), 2.92-2.80 (m, 2H), 2.68-2.40 (m, 3H), 2.23-2.08 (m, 1H).

Step 2: 1-[2-(2-aminopyrimidin-5-yl)-6-(3-azabicyclo[2.1.1]hexan-3-yl)-4-pyridyl]cyclobutanecarbonitrile

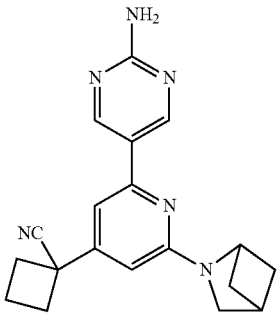

To a solution of 1-(2,6-dichloro-4-pyridyl)cyclobutanecarbonitrile (100 mg, 0.440 mmol) in anhydrous DMSO (0.44 mL) was added 2-azabicyclo[2.1.1]hexane hydrochloride (60 mg, 0.48 mmol) and potassium carbonate (122 mg, 0.881 mmol). The vessel was sealed and the reaction mixture stirred at 100° C. for 92 h. After cooling to rt, the mixture was diluted with diethyl ether and washed with water (2×), brine (1×) and dried over $MgSO_4$ and concentrated to dryness. The following compounds were added to the crude product: 2-aminopyridine-5-boronic acid pinacol ester (110 mg, 0.48 mmol), chloro(2-dicyclohexylphosphino-2',4',6'-triisopropyl-1,1'-biphenyl)[2-(2-aminoethyl)phenyl)]palladium(II) (16.6 mg, 0.0220 mmol), 2-Dicyclohexylphosphino-2',4',6'-triisopropylbiphenyl (21.4 mg, 0.0440 mmol), and potassium phosphate tribasic (289 mg, 1.32 mmol). Under a stream of nitrogen, anhydrous, degassed THF (1.3 mL) and degassed water (0.22 mL) were added and the vial was sealed tightly. The reaction mixture was stirred at 80° C. for 3 h, cooled to rt, and filtered through Celite, rinsing with $CH_2Cl_2$. The residue obtained after concentration was purified by RPLC to afford the title compound as a white solid (85.4 mg, 58% over 2 steps); $^1$H NMR (400 MHz, DMSO) δ 8.92 (s, 2H), 7.10 (d, J=1.1 Hz, 1H), 6.91 (br s, 2H), 6.46 (d, J=1.1 Hz, 1H), 4.95-4.81 (m, 1H), 3.44 (s, 2H), 3.01-2.90 (m, 1H), 2.75-2.64 (m, 4H), 2.39-2.18 (m, 1H), 2.11-1.92 (m, 3H), 1.41-1.27 (m, 2H).

Method H:

[3-[6-[2-amino-4-(trifluoromethyl)pyrimidin-5-yl]-2-methyl-pyrimidin-4-yl]-1-piperidyl]-phenyl-methanone

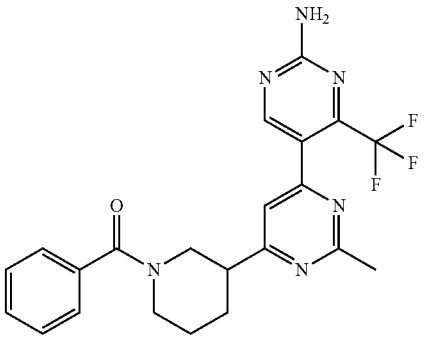

A solution of tert-butyl 3-(6-chloro-2-methyl-pyrimidin-4-yl)piperidine-1-carboxylate (40 mg, 0.13 mmol, 1.00 equiv), 5-(4,4,5,5-tetramethyl-1,3,2-dioxaborolan-2-yl)-4-(trifluoromethyl)pyrimidin-2-amine (40 mg, 0.14 mmol, 1.10 equiv) and [1,1'-BIS(DIPHENYLPHOSPHINO)FERROCENE]DICHLOROPALLADIUM(II) (10 mg, 0.013 mmol, 0.1 equiv) in Acetonitrile (1.0 mL) was mixed with 1M potassium carbonate solution in water (420 uL, 0.42 mmol, 3.2 equiv) and stirred at 90° C. for 2 hr. The reaction mixture was extracted with DCM (3 mL) and H2O (2 mL). The organic phase was removed, dried over sodium sulfate, and passed through a filter. The resulting organic phase was concentrated under vacuum. The crude product was mixed with methanol (1.0 mL) and 4M hydrogen chloride in dioxane (325 uL, 1.3 mmol, 10 equiv). The resulting solution was stirred at room temperature overnight. The reaction mixture was concentrated under vacuum. A solution of crude product, benzoic acid (15 mg, 0.13 mmol, 1.0 equiv), HBTU (50 mg, 0.13 mmol, 1.0 equiv) and Triethylamine (90 uL, 0.65 mmol, 5.0 equiv) in DMF (1.0 mL) was stirred at room temperature overnight. The reaction mixture was concentrated under vacuum and the crude product was purified by Prep-HPLC (Column, Sunfire C18 19×150; mobile phase, CH3CN:NH4CO3/H2O (10 mmol/L)=5%-85%, 10 min; Detector, UV 254 nm) to give 21.8 mg (38%) of [3-[6-[2-amino-4-(trifluoromethyl)pyrimidin-5-yl]-2-methyl-pyrimidin-4-yl]-1-piperidyl]-phenyl-methanone as an off white solid, $^1$H NMR (400 MHz, DMSO-d6) δ 8.63 (s, 1H), 7.66 (s, 2H), 7.46-7.42 (m, 3H), 7.42-7.36 (m, 2H), 7.01 (s, 1H), 4.65-4.37 (m, 1H), 4.08 (q, J=5.3 Hz, 1H), 3.77-3.51 (m, 1H), 3.17 (d, J=5.3 Hz, 2H), 3.14-2.89 (m, 3H), 2.10-2.02 (m, 1H), 1.91-1.50 (m, 3H).

Method I:

1-[6-[6-amino-5-(difluoromethoxy)-3-pyridyl]-2-(3-azabicyclo[2.1.1]hexan-3-yl)pyrimidin-4-yl]cyclobutanecarbonitrile Step 1: 1-(2,6-dichloropyrimidin-4-yl)cyclobutanecarbonitrile

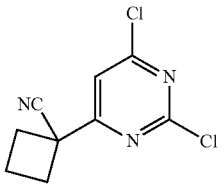

To a stirring solution of 2,4,6-trichloropyrimidine (1.00 g, 5.45 mmol) and cyclobutanecarbonitrile (0.53 mL, 5.5 mmol) in anhydrous THF (27 mL) at −78° C. and under nitrogen was added lithium bis(trimethylsilyl)amide (6.0 mL, 6.0 mmol, 1.0 M solution in THF) over 3 min. The cooling bath was removed after 5 further min, and stirring continued for 3 h. The reaction was quenched by the addition of sat. aq. $NH_4Cl$, extracted with $CH_2Cl_2$ and organics dried over $MgSO_4$. Following concentration, the reaction residue was purified by flash column chromatography (100:0 heptanes/EtOAc-85:15 heptanes/EtOAc) to afford the title compound as a colorless solid (0.147 g, 12%); $^1$H NMR (400 MHz, $CDCl_3$) δ 7.54 (s, 1H), 2.97-2.82 (m, 2H), 2.82-2.67 (m, 2H), 2.51-2.35 (m, 1H), 2.35-2.16 (m, 1H).

Step 2: 1-[6-[6-amino-5-(difluoromethoxy)-3-pyridyl]-2-(3-azabicyclo[2.1.1]hexan-3-yl)pyrimidin-4-yl]cyclobutanecarbonitrile

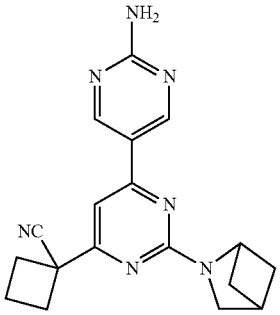

Into a vial was weighed 1-(2,6-dichloropyrimidin-4-yl) cyclobutanecarbonitrile (64.2 mg, 0.281 mmol), 2-aminopyridine-5-boronic acid pinacol ester (64.2 mg, 0.281 mmol), tetrakis(triphenylphosphine)palladium(0) (16.3 mg, 5 mol %), and sodium carbonate (90 mg, 0.84 mmol). Under a stream of nitrogen, anhydrous, degassed THF (0.84 mL) and degassed water (0.14 mL) were added and the vial was sealed tightly. The reaction mixture was stirred at 90° C. for 68 h, cooled to rt, filtered through Celite rinsing with $CH_2Cl_2$, and concentrated to dryness. To this crude product was added 2-azabicyclo[2.1.1]hexane hydrochloride (49 mg, 0.39 mmol), N,N-diisopropylethylamine (0.147 mL, 0.844 mmol), and anhydrous DMF (1.1 mL). The vessel was sealed and the reaction mixture stirred at 80° C. for 4.5 h. After cooling to rt, the mixture was concentrated and the residue subjected to RPLC purification to yield the title compound as a white solid (36.9 mg, 39% over 2 steps); $^1$H NMR (400 MHz, DMSO) δ 8.69 (s, 1H), 8.05 (s, 1H), 7.23 (t, J=74.0 Hz, 2H), 7.20 (s, 1H), 6.70 (br s, 2H), 4.95 (m, 1H), 3.54 (s, 2H), 2.99-2.91 (m, 1H), 2.81 (m, 2H), 2.72-2.60 (m, 2H), 2.32-2.18 (m, 1H), 2.13-1.94 (m, 3H), 1.45-1.38 (m, 2H).

Method J:

Step 1: tert-butyl 3-(2,6-dichloropyridin-4-yl)azetidine-1-carboxylate

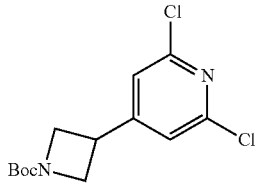

Under a nitrogen atmosphere, zinc dust (6.91 g, 105 mmol) was suspended in N,N-dimethylacetamide (10 mL) and 1,2-dibromoethane (1.08 mL, 12.4 mmol) was added, followed by careful addition of trimethylsilylchloride (1.61 mL, 12.4 mmol) and was added cautiously over 5 min while the flask sat on a bed of ice. The bath was removed, and after stirring for a further 15 min, a solution of N-(tert-butoxycarbonyl)-3-iodoazetidine (25.1 g, 86.9 mmol) in N,N-dimethylacetamide (30 mL) was added over 30 min and stirring was continued for an additional 30 min. In the open atmosphere, this mixture was filtered through Celite as quickly as possible, rinsing with N,N-dimethylacetamide (100 mL). The resulting yellow solution was injected into a separately prepared, nitrogen flushed vessel containing [1,1-bis(diphenylphosphino)ferrocene]dichloropalladium(II) (2.56 g, 3.10 mmol), copper(I) iodide (1.18 g, 6.21 mmol) and 2,6-dichloro-4-iodopyridine (17.0 g, 62.1 mmol) and this mixture was stirred at 80° C. for 19.5 h. After cooling to rt, the mixture was diluted with EtOAc and washed with water (3×). On the third time, filtration through Celite was necessary to break the emulsion, following which, the organics were washed with brine and then dried over $MgSO_4$. After being freed of volatiles, the resultant residue was purified by flash column chromatography (100:0-70:30 heptanes/EtOAc) to afford tert-butyl 3-(2,6-dichloropyridin-4-yl)azetidine-1-carboxylate as a white solid (10.98 g, 58%); $^1$H NMR (400 MHz, $CDCl_3$) δ 7.22 (s, 2H), 4.35 (dd, J=8.7, 5.6 Hz, 2H), 3.92 (dd, J=8.7, 5.6 Hz, 2H), 3.73-3.61 (m, 1H), 1.47 (s, 9H).

Step 2: 2,6-dichloro-4-(1-(oxetan-3-yl)azetidin-3-yl) pyridine

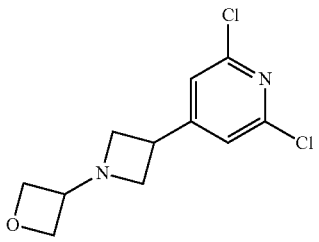

A solution of tert-butyl 3-(2,6-dichloropyridin-4-yl)azetidine-1-carboxylate (0.940 g, 3.10 mmol) in trifluoroacetic acid (3.1 mL) was stirred for 1 h, and then concentrated to dryness to afford the TFA salt as a white solid. The solid was re-suspended in anhydrous THF (12.4 mL) and submitted to the action of triethylamine (2.62 mL, 18.6 mmol) and 3-oxetanone (0.60 mL, 9.3 mmol). After stirring for 10 min, sodium triacetoxyborohydride (2.07 g, 9.30 mmol) was added and stirring continued for 18.5 h at 35° C. The reaction mixture was diluted with $CH_2Cl_2$ and washed with sat. aq. $NaHCO_3$ and organics dried over $MgSO_4$. Concentration gave sufficiently pure 2,6-dichloro-4-(1-(oxetan-3-yl)azetidin-3-yl)pyridine as a yellow liquid (640 mg, 80% over 2 steps); $^1$H NMR (400 MHz, $CDCl_3$) δ 7.27 (s, 2H), 4.72 (dd, J=6.5, 5.3 Hz, 2H), 4.54 (dd, J=6.5, 5.3 Hz, 2H), 3.82-3.77 (m, 1H), 3.77-3.71 (m, 2H), 3.67-3.58 (m, 1H), 3.32-3.27 (m, 2H).

Step 3: 6-cyclopropyl-5'-(difluoromethoxy)-4-(1-(oxetan-3-yl)azetidin-3-yl)-[2,3'-bipyridin]-6'-amine

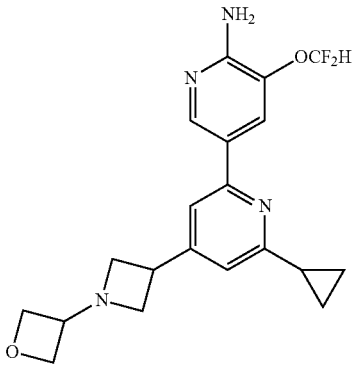

A vial was charged with 2,6-dichloro-4-(1-(oxetan-3-yl)azetidin-3-yl)pyridine (133 mg, 0.513 mmol), palladium(II) acetate (5.8 mg, 5 mol %), butyldi-1-adamantylphosphine (14.5 mg, 7.5 mol %), potassium cyclopropyltrifluoroborate (79.9 mg, 0.523 mmol), and cesium carbonate (502 mg, 1.54 mmol) and purged under nitrogen before the addition of degassed toluene (2.6 mL) and deionized water (0.25 mL). The mixture was stirred at 110° C. overnight and then cooled to rt. To the mixture was added 3-(difluoromethoxy)-5-(4,4,5,5-tetramethyl-1,3,2-dioxaborolan-2-yl)pyridin-2-amine (220 mg, 0.770 mmol), chloro(2-dicyclohexylphosphino-2',4',6'-triisopropyl-1,1'-biphenyl)[2-(2-aminoethyl)phenyl)] palladium(II) (38.7 mg, 0.0513 mmol), 2-dicyclohexylphosphino-2',4',6'-triisopropylbiphenyl (50.0 mg, 0.103 mmol), and potassium phosphate tribasic monohydrate (366 mg, 1.54 mmol). The vial was purged with nitrogen gas, sealed, and stirred at 110° C. for 2 h. After cooling to rt, the mixture was concentrated to dryness. The reaction residue thus obtained was purified by flash column chromatography (100:0-80:20 $CH_2Cl_2$/MeOH) and by RPLC to afford the title compound as a white solid (22.9 mg, 12% over 2 steps); $^1$H NMR (400 MHz, DMSO) δ 8.53 (d, J=1.9 Hz, 1H), 7.94 (s, 1H), 7.50 (d, J=1.9 Hz, 1H), 7.17 (t, J=74.0 Hz, 1H), 7.16 (s, 1H), 6.35 (br s, 2H), 4.62-4.50 (m, 2H), 4.45-4.32 (m, 2H), 3.82-3.70 (m, 1H), 3.70-3.60 (m, 3H), 3.28-3.23 (m, 2H), 2.17-2.03 (m, 1H), 1.05-0.85 (m, 4H).

Example 2

The compounds disclosed in Table 1 were prepared following the synthetic steps described in general Methods A-J as described above in Example 1 with modifying the starting reactants and/or intermediates and in those methods as would be known to one skilled in the art in view of the final compound structures to arrive at the compounds in Table 1. The compounds disclosed in Table 1 were tested for DLK inhibitory activity as described in Example 3.

TABLE 1

| No | DLK Ki (μM) | Structure | $^1$H NMR | MS [MS]$^+$ | Method |
|---|---|---|---|---|---|
| 1 | 6.43 | 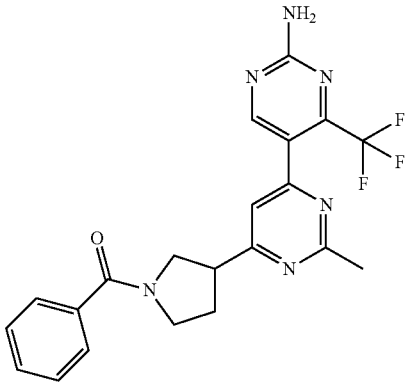 [3-[6-[2-amino-4-(trifluoromethyl) pyrimidin-5-yl]-2-methyl-pyrimidin-4-yl]pyrrolidin-1-yl]-phenyl-methanone | 1H NMR (400 MHz, DMSO-d6) δ 8.63 (d, J = 21.2 Hz, 1H), 7.66 (s, 2H), 7.58-7.40 (m, 6H), 4.12-3.89 (m, 1H), 3.80-3.52 (m, 4H), 3.17 (d, J = 4.7 Hz, 1H), 2.66-2.56 (m, 3H), 2.41-2.04 (m, 2H). | 429 | H |

TABLE 1-continued

| No | DLK Ki (μM) | Structure | $^1$H NMR | MS [MS]$^+$ | Method |
|---|---|---|---|---|---|
| 2 | 1.7 | 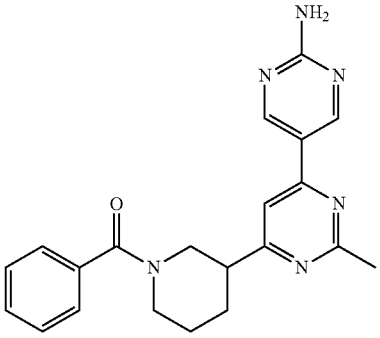 <br>[3-[6-(2-aminopyrimidin-5-yl)-2-methyl-pyrimidin-4-yl]-1-piperidyl]-phenyl-methanone | 1H NMR (400 MHz, DMSO-d6) δ 9.02 (s, 2H), 7.79-7.59 (m, 1H), 7.50-7.41 (m, 3H), 7.41-7.36 (m, 2H), 7.24 (s, 2H), 7.12-6.91 (m, 1H), 4.62-4.44 (m, 1H), 3.76-3.53 (m, 1H), 3.19-2.80 (m, 3H), 2.64-2.59 (m, 2H), 2.10-2.02 (m, 1H), 1.89-1.47 (m, 3H). | 375 | H |
| 3 | 6.43 | 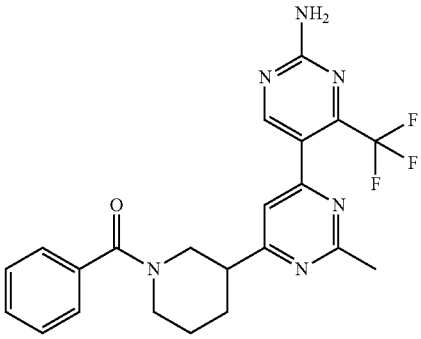 <br>[3-[6-[2-amino-4-(trifluoromethyl) pyrimidin-5-yl]-2-methyl-pyrimidin-4-yl]-1-piperidyl]-phenyl-methanone | 1H NMR (400 MHz, DMSO-d6) δ 8.63 (s, 1H), 7.66 (s, 2H), 7.46-7.42 (m, 3H), 7.42-7.36 (m, 2H), 7.01 (s, 1H), 4.65-4.37 (m, 1H), 4.08 (q, J = 5.3 Hz, 1H), 3.77-3.51 (m, 1H), 3.17 (d, J = 5.3 Hz, 2H), 3.14-2.89 (m, 3H), 2.10-2.02 (m, 1H), 1.91-1.50 (m, 3H). | 443 | H |
| 4 | 1.73 | 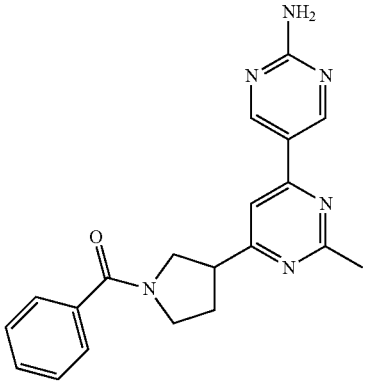 <br>[3-[6-(2-aminopyrimidin-5-yl)-2-methyl-pyrimidin-4-yl]pyrrolidin-1-yl]-phenyl-methanone | 1H NMR (400 MHz, DMSO-d6) δ 9.05 (s, 1H), 9.00 (s, 1H), 7.83-7.68 (m, 1H), 7.58-7.50 (m, 2H), 7.51-7.39 (m, 3H), 7.28-7.22 (m, 2H), 4.00-3.43 (m, 4H), 2.65-2.55 (m, 3H), 2.42-2.06 (m, 2H). | 361 | H |

TABLE 1-continued

| No | DLK Ki (μM) | Structure | $^1$H NMR | MS [MS]$^+$ | Method |
|---|---|---|---|---|---|
| 5 | 0.83 | 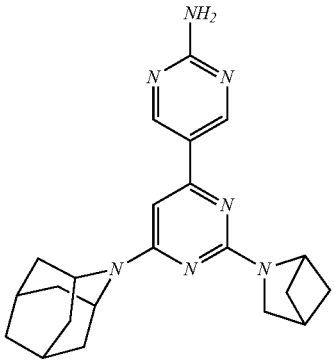 *6((1R,3R,5R,7R)-2-azaadamantan-2-yl)-2-(2-azabicyclo[2.1.1]hexan-2-yl)-[4,5'-bipyrimidin]-2'amine* | | 390 | I |
| 6 | 0.001 | 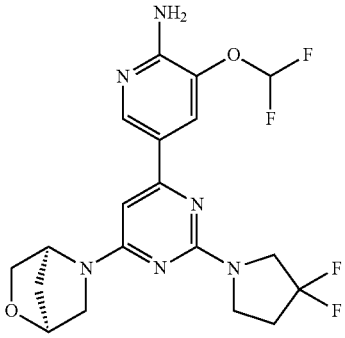 3-(difluoromethoxy)-5-[2-(3,3-difluoropyrrolidin-1-yl)-6-[(1S,4S)-2-oxa-5-azabicyclo[2.2.1]heptan-5-yl]pyrimidin-4-yl]pyridin-2-amine | 1H NMR (400 MHz, DMSO-d6) δ 8.61 (s, 1H), 7.98 (s, 1H), 7.17 (t, J = 73.9 Hz, 1H), 6.45 (s, 2H), 5.01 (s, 1H), 4.68 (s, 1H), 3.91 (t, 2H), 3.81-3.69 (m, 3H), 3.66 (d, J = 7.4 Hz, 1H), 3.47 (d, J = 10.6, 1.5 Hz, 1H), 3.40-3.23 (m, 1H), 2.46 (q, J = 7.4, 6.9 Hz, 1H), 1.87 (s, 2H). | 441 | E |
| 7 | 0.10 | 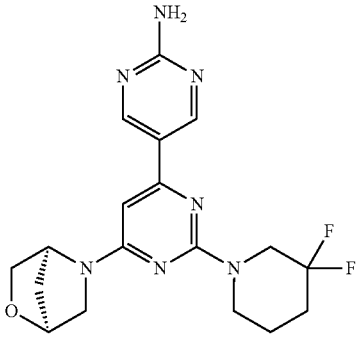 5-[2-(3,3-difluoro-1-piperidyl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.91 (s, 2H), 7.00 (s, 2H), 4.98 (s, 1H), 4.67 (s, 1H), 4.08 (t, J = 12.1 Hz, 2H), 3.88-3.71 (m, 3H), 3.65 (d, J = 7.4 Hz, 1H), 3.47 (d, J = 10.3 Hz, 1H), 3.37 (s, 1H), 2.17-1.95 (m, 2H), 1.88 (s, 2H), 1.78-1.58 (m, 2H). | 390 | E |

TABLE 1-continued
| No | DLK Ki (μM) | Structure | $^1$H NMR | MS [MS]$^+$ | Method |
|---|---|---|---|---|---|
| 8 | 0.22 | 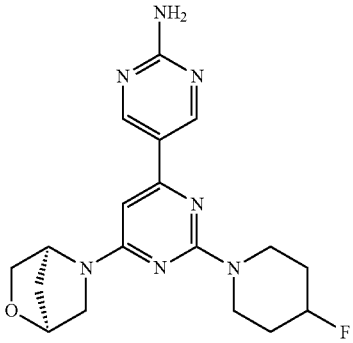 5-[2-(4-fluoro-1-piperidyl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.90 (s, 2H), 6.98 (s, 2H), 5.11-4.74 (m, 2H), 4.67 (s, 1H), 3.98 (s, 2H), 3.78 (d, J = 7.0 Hz, 1H), 3.73-3.55 (m, 3H), 3.45 (d, 1H), 2.00-1.76 (m, 4H), 1.76-1.58 (m, 2H). | 372 | E |
| 9 | 0.11 | 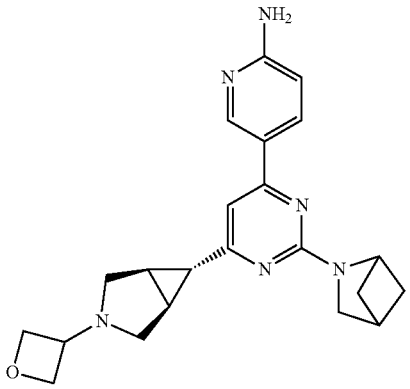 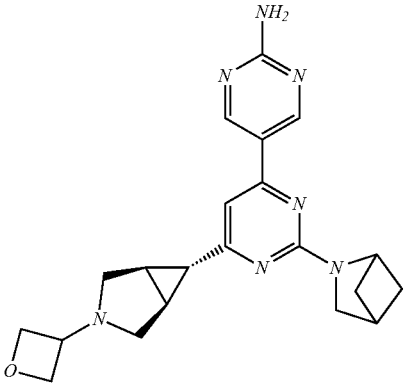 5-[2-(3-azabicyclo[2.1.1]hexan-3-yl)-6-[(1R,5S)-3-(oxetan-3-yl)-3-azabicyclo[3.1.0]hexan-6-yl]pyrimidin-4-yl]pyrimidin-2-amine | $^1$H NMR (400 MHz, Chloroform-d) δ 8.94 (s, 2H), 6.68 (s, 1H), 5.34 (s, 2H), 4.97-4.95 (m, 1H), 4.69-4.62 (m, 4H), 3.83-3.78 (m, 1H), 3.55 (s, 2H), 3.14 (d, J = 8.8 Hz, 2H), 2.94-2.93 (m, 1H), 2.50 (d, J = 8.4 Hz, 2H), 2.35-2.33 (m, 1H), 2.13 (s, 2H), 1.99 (s, 2H), 1.46-1.44 (m, 2H). | 392.2 | C |

TABLE 1-continued

| No | DLK Ki (μM) | Structure | $^1$H NMR | MS [MS]$^+$ | Method |
|---|---|---|---|---|---|
| 10 | 0.01 | 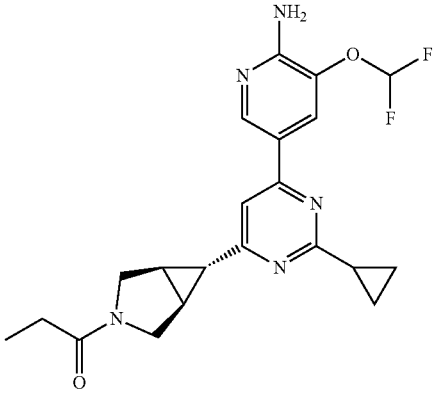 1-[(1R,5S)-6-[6-[6-amino-5-(difluoromethoxy)-3-pyridyl]-2-cyclopropyl-pyrimidin-4-yl]-3-azabicyclo[3.1.0]hexan-3-yl]propan-1-one | $^1$H NMR (400 MHz, DMSO-d6) δ 8.65 (s, 1H), 8.01 (s, 1H), 7.64 (s, 1H), 7.21 (t, J = 73.6 Hz, 1H), 6.72 (s, 2H), 3.78-3.73 (m, 2H), 3.65-3.60 (m, 1H), 3.40-3.35 (m, 1H), 2.27-2.16 (m, 5H), 1.85 (t, J = 3.2 Hz, 1H), 1.00-0.93 (m, 7H). | 416.1 | C |
| 11 | 0.01 | 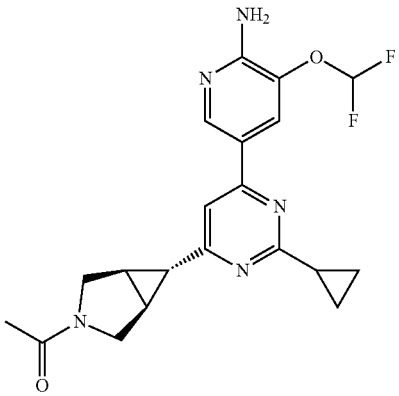 1-[(1R,5S)-6-[6-[6-amino-5-(difluoromethoxy)-3-pyridyl]-2-cyclopropyl-pyrimidin-4-yl]-3-azabicyclo[3.1.0]hexan-3-yl]ethanone | $^1$H NMR (400 MHz, DMSO-d6) δ 8.65 (s, 1H), 8.01 (s, 1H), 7.64 (s, 1H), 7.21 (t, J = 73.6 Hz, 1H), 6.72 (s, 2H), 3.76-3.73 (m, 2H), 3.69-3.68 (m, 1H), 3.39-3.36 (m, 1H), 2.26-2.24 (m, 1H), 2.18-2.17 (m, 1H), 2.11-2.10 (m, 1H), 1.94 (s, 3H), 1.86 (t, J = 3.2 Hz, 1H), 1.00-0.97 (m, 4H). | 402.1 | C |
| 12 | 0.01 | 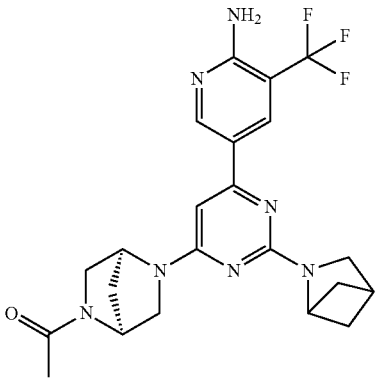 1-[(1S,4S)-5-[6-[6-amino-5-(trifluoromethyl)-3-pyridyl]-2-(3-azabicyclo[2.1.1]hexan-3-yl)pyrimidin-4-yl]-2,5-diazabicyclo[2.2.1]heptan-2-yl]ethanone | $^1$H NMR (400 MHz, DMSO-d6) δ 8.91 (s, 1H), 8.36 (s, 1H), 6.79 (s, 2H), 6.53-6.21 (m, 1H), 5.10-4.89 (m, 1H), 4.80-4.78 (m, 1H), 4.74-4.63 (m, 1H), 3.55-3.51 (m, 1H), 3.44-3.35 (m, 2H), 3.23-2.84 (m, 4H), 2.82 (s, 1H), 2.00 (s, 1H), 1.91 (s, 3H), 1.83-1.81 (m, 2H), 1.29 (d, J = 2.0 Hz, 2H). | 459.9 | B |

TABLE 1-continued

| No | DLK Ki (μM) | Structure | $^1$H NMR | MS [MS]$^+$ | Method |
|---|---|---|---|---|---|
| 13 | 0.20 | 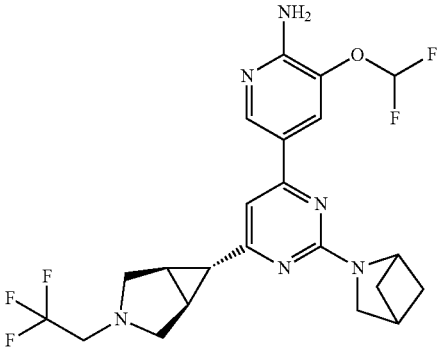 5-[2-(3-azabicyclo[2.1.1]hexan-3-yl)-6-[(1R,5S)-3-(2,2,2-trifluoroethyl)-3-azabicyclo[3.1.0]hexan-6-yl]pyrimidin-4-yl]-3-(difluoromethoxy)pyridin-2-amine | $^1$H NMR (400 MHz, Chloroform-d) δ 8.59 (s, 1H), 8.02 (s, 1H), 6.72 (s, 1H), 6.58 (t, J = 73.6 Hz, 1H), 4.97-4.94 (m, 3H), 3.56 (s, 2H), 3.28 (d, J = 8.4 Hz, 2H), 3.15-3.08 (m, 2H), 2.95-2.93 (m, 1H), 2.78 (d, J = 8.4 Hz, 2H), 2.25 (d, J = 2.8 Hz, 1H), 2.12 (s, 2H), 1.99 (s, 2H), 1.49-1.43 (m, 2H). | 483.14 | C |
| 14 | 0.43 | 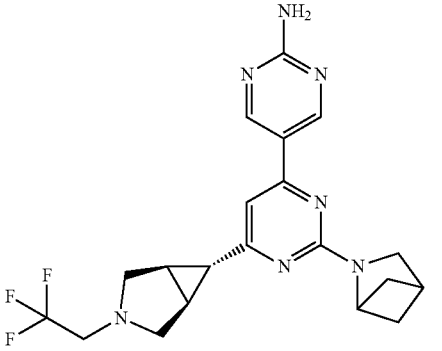 5-[2-(3-azabicyclo[2.1.1]hexan-3-yl)-6-[(1R,5S)-3-(2,2,2-trifluoroethyl)-3-azabicyclo[3.1.0]hexan-6-yl]pyrimidin-4-yl]pyrimidin-2-amine | $^1$H NMR (400 MHz, DMSO-d6) δ 8.92 (s, 2H), 7.09 (s, 2H), 7.03 (s, 1H), 4.83 (br.s, 1H), 3.43 (s, 2H), 3.26-3.24 (m, 2H), 3.13 (d, J = 8.8 Hz, 2H), 2.89-2.87 (m, 1H), 2.74-2.72 (m, 2H), 2.12-2.11 (m, 1H), 2.03 (s, 2H), 1.93 (s, 2H), 1.30-1.29 (m, 2H). | 418.1 | C |
| 15 | 0.001 | 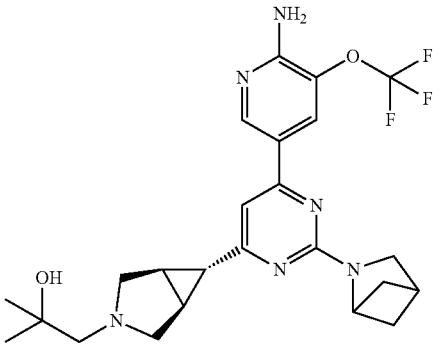 1-[(1R,5S)-6-[6-[6-amino-5-(trifluoromethoxy)-3-pyridyl]-2-(3-azabicyclo[2.1.1]hexan-3-yl)pyrimidin-4-yl]-3-azabicyclo[3.1.0]hexan-3-yl]-2-methyl-propan-2-ol | $^1$H NMR (400 MHz, DMSO-d6) δ 8.74 (s, 1H), 8.16 (s, 1H), 7.04 (s, 1H), 6.91 (s, 2H), 4.84-4.82 (m, 1H), 4.05 (s, 1H), 3.45 (s, 3H), 3.19 (d, J = 8.8 Hz, 2H), 2.91-2.89 (m, 1H), 2.35 (s, 2H), 2.26 (s, 1H), 1.98-1.95 (m, 4H), 1.33-1.32 (m, 2H), 1.08 (s, 6H). | 491.2 | C |

TABLE 1-continued

| No | DLK Ki (μM) | Structure | $^1$H NMR | MS [MS]$^+$ | Method |
|---|---|---|---|---|---|
| 16 | 0.001 | 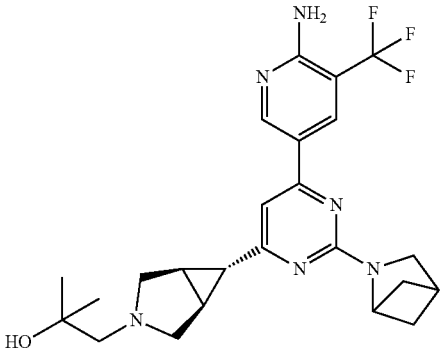 1-[(1R,5S)-6-[6-[6-amino-5-(trifluoromethyl)-3-pyridyl]-2-(3-azabicyclo[2.1.1]hexan-3-yl)pyrimidin-4-yl]-3-azabicyclo[3.1.0]hexan-3-yl]-2-methyl-propan-2-ol | $^1$H NMR (400 MHz, DMSO-d6) δ 8.94 (s, 1H), 8.39 (s, 1H), 7.06 (s, 1H), 6.91 (s, 2H), 4.83-4.81 (m, 1H), 4.02 (s, 1H), 3.42 (s, 2H), 3.16-3.14 (m, 2H), 2.87-2.85 (m, 1H), 2.48 (s, 2H), 2.31 (s, 2H), 2.23 (s, 1H), 1.95-1.92 (m, 4H), 1.29 (d, J = 2.8 Hz, 2H), 1.05 (s, 6H). | 475.0 | C |
| 17 | 0.001 | 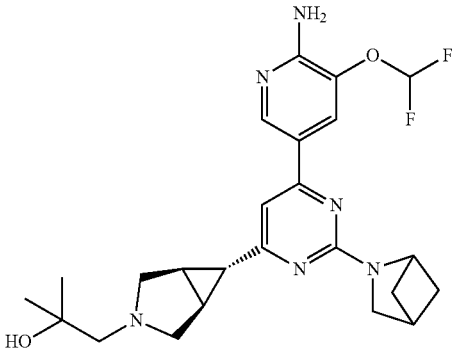 [[6-amino-5-(difluoromethoxy)-3-pyridyl]-] [2-(3-azabicyclo[2.1.1]hexan-] [3-yl)pyrimidin-4-yl]-3-azabicyclo[3.1.0]] [hexan-3-yl]-2-methyl-propan-2-ol] *1-[(1R,5S)-6-[6-[6-amino-5-(difluoromethoxy)-3-pyridyl]-2-(3-azabicyclo[2.1.1]hexan-3-yl)-pyrimidin-4-yl]-3-azabicyclo[3.1.0]hexane-3-yl]-2-methyl-propan-2-ol* | $^1$H NMR (400 MHz, Chloroform-d) δ 8.59 (s, 1H), 8.02 (s, 1H), 6.68 (s, 1H), 6.58 (t, J = 73.6 Hz, 1H), 4.98 (s, 3H), 3.56 (s, 2H), 3.31-3.28 (m, 2H), 3.01-2.94 (m, 2H), 2.75 (d, J = 8.4 Hz, 2H), 2.50 (s, 2H), 2.26 (s, 1H), 2.10 (s, 2H), 1.99 (s, 2H), 1.80-1.70 (m, 2H), 1.19 (s, 6H). | 473.17 | C |
| 18 | 0.05 | 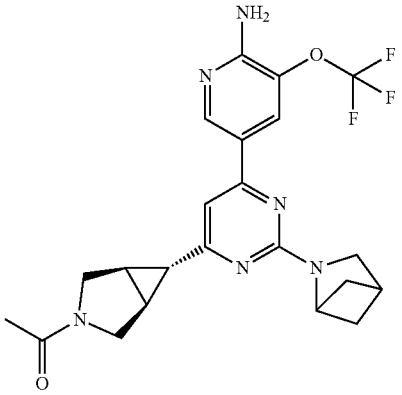 1-[(1R,5S)-6-[6-[6-amino-5-(trifluoromethoxy)-3-pyridyl]-2-(3-azabicyclo[2.1.1]hexan-3-yl)pyrimidin-4-yl]-3-azabicyclo[3.1.0]hexan-3-yl]ethanone | $^1$H NMR (400 MHz, DMSO-d6) δ 8.72 (s, 1H), 8.13 (s, 1H), 7.07 (s, 1H), 6.94 (s, 2H), 4.85-4.83 (m, 1H), 3.74-3.65 (m, 3H), 3.45-3.40 (m, 3H), 2.95-2.91 (m, 1H), 2.23-2.17 (m, 2H), 1.96-1.93 (m, 4H), 1.74 (s, 1H), 1.33 (s, 2H), 1.30-1.22 (m, 1H). | 460.9 | C |

TABLE 1-continued

| No | DLK Ki (μM) | Structure | $^1$H NMR | MS [MS]$^+$ | Method |
|---|---|---|---|---|---|
| 19 | 0.03 | 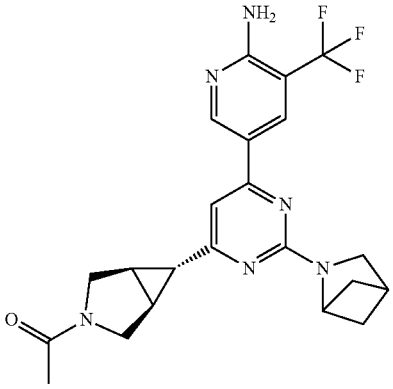 <br>1-[(1R,5S)-6-[6-[6-amino-5-(trifluoromethyl)-3-pyridyl]-2-(3-azabicyclo[2.1.1]hexan-3-yl)pyrimidin-4-yl]-3-azabicyclo[3.1.0]hexan-3-yl]ethanone | $^1$H NMR (400 MHz, DMSO-d6) δ 8.92 (s, 1H), 8.37 (s, 1H), 7.09 (s, 1H), 6.94 (s, 2H), 4.84-4.82 (m, 1H), 3.71-3.64 (m, 3H), 3.43-3.35 (m, 2H), 3.34-3.31 (m, 1H), 3.26-3.21 (m, 1H), 2.89-2.87 (m, 1H), 2.21-2.14 (m, 2H), 1.94-1.90 (m, 4H), 1 73-1.71 (m, 1H), 1.31 (d, J = 4.0 Hz, 2H). | 445.0 | C |
| 20 | 0.01 | 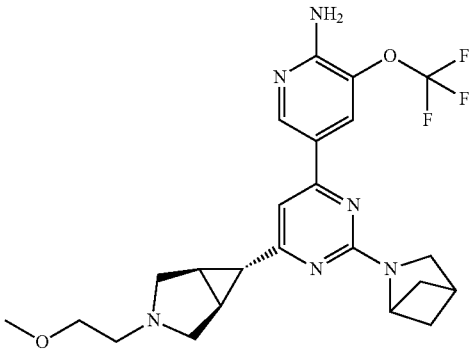 <br>5-[2-(3-azabicyclo[2.1.1]hexan-3-yl)-6-[(1R,5S)-3-(2-methoxyethyl)-3-azabicyclo[3.1.0]hexan-6-yl]pyrimidin-4-yl]-3-(trifluoromethoxy)pyridin-2-amine | $^1$H NMR (400 MHz, Methanol-d4) δ 8.62 (s, 1H), 8.17 (s, 1H), 6.85 (s, 1H), 3.80-3.70 (m, 1H), 3.54-3.50 (m, 3H), 3.38 (s, 3H), 3.20 (d, J = 9.6 Hz, 2H), 2.95-2.90 (m, 1H), 2.71-2.69 (m, 2H), 2.58-2.55 (m, 2H), 2.29 (s, 1H), 2.09-2.04 (m, 3H), 1.42-1.41 (m, 1H), 1.29 (s, 3H). | 477.14 | C |
| 21 | 0.007 | 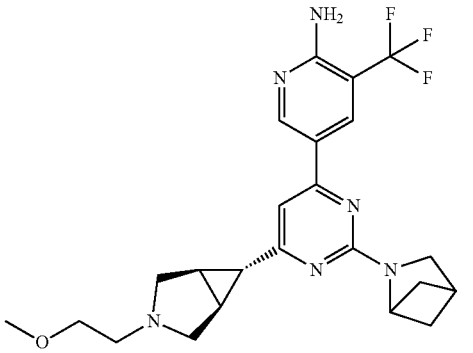 <br>5-[2-(3-azabicyclo[2.1.1]hexan-3-yl)-6-[(1R,5S)-3-(2-methoxyethyl)-3-azabicyclo[3.1.0]hexan-6-yl]pyrimidin-4-yl]-3-(trifluoromethyl)pyridin-2-amine | $^1$H NMR (400 MHz, DMSO-d6) δ 8.92 (s, 1H), 8.38 (s, 1H), 7.09 (s, 1H), 6.91 (s, 2H), 4.82-4.81 (m, 1H), 3.42-3.37 (m, 8H), 3.36-3.34 (m, 2H), 3.21 (s, 2H), 3.06 (d, J = 9.2 Hz, 1H), 2.87-2.84 (m, 1H), 2.58-2.57 (m, 1H), 2.39 (d, J = 8.8 Hz, 1H), 2.20 (s, 1H), 1.97-1.93 (m, 3H), 1.29 (d, J = 2.4 Hz, 1H). | 461.0 | C |

TABLE 1-continued

| No | DLK Ki (μM) | Structure | $^1$H NMR | MS [MS]$^+$ | Method |
|---|---|---|---|---|---|
| 22 | 0.03 | 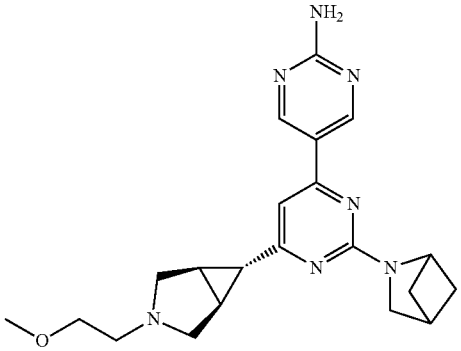 5-[2-(3-azabicyclo[2.1.1]hexan-3-yl)-6-[(1R,5S)-3-(2-methoxyethyl)-3-azabicyclo[3.1.0]hexan-6-yl]pyrimidin-4-yl]pyrimidin-2-amine | $^1$H NMR (400 MHz, Chloroform-d) δ 8.94 (s, 2H), 6.66 (s, 1H), 5.21 (s, 2H), 4.96 (d, J = 6.8 Hz, 1H), 3.54 (s, 2H), 3.50-3.47 (m, 2H), 3.38 (s, 3H), 3.22 (d, J = 8.8 Hz, 2H), 2.96-2.94 (m, 1H), 2.72-2.69 (m, 2H), 2.51 (d, J = 8.4 Hz, 2H), 2.35-2.32 (m, 1H), 2.09 (s, 2H), 1.99 (s, 2H), 1.46-1.44 (m, 2H). | 393.9 | C |
| 23 | 0.02 | 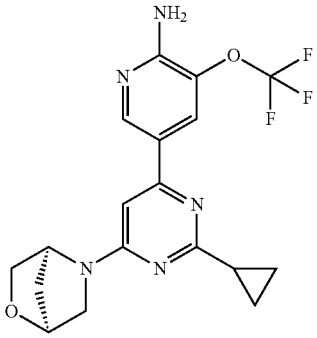 5-[2-cyclopropyl-6-[(1S,4S)-2-oxa-5-azabicyclo[2.2.1]heptan-5-yl]pyrimidin-4-yl]-3-(trifluoromethoxy)pyridin-2-amine | $^1$H NMR (400 MHz, Methanol-d4) δ 8.57 (s, 1H), 8.10 (s, 1H), 6.52 (br.s, 1H), 5.08 (br.s, 1H), 4.71 (s, 1H), 3.86 (d, J = 6.8 Hz, 1H), 3.78 (d, J = 7.2 Hz, 1H), 3.52 (d, J = 10.0 Hz, 1H), 3.35-3.31 (m, 1H), 2.06-2.02 (m, 1H), 2.01-1.96 (m, 2H), 1.08-1.05 (m, 2H), 0.95-0.92 (m, 2H). | 394.19 | A |
| 24 | 1.61 | 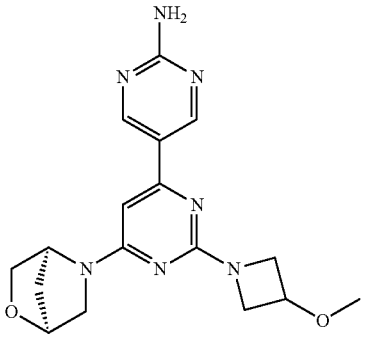 5-[2-(3-methoxyazetidin-1-yl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.88 (s, 2H), 6.98 (s, 2H), 4.96 (s, 1H), 4.66 (s, 1H), 4.30-4.22 (m, 1H), 4.21-4.13 (m, 2H), 3.86-3.73 (m, 3H), 3.71-3.61 (m, 2H), 3.43 (d, J = 10.4, 2.5 Hz, 1H), 3.24 (s, 3H), 1.89 (s, 2H). | 355 | E |

TABLE 1-continued

| No | DLK Ki (μM) | Structure | $^1$H NMR | MS [MS]$^+$ | Method |
|---|---|---|---|---|---|
| 25 | 1.09 | 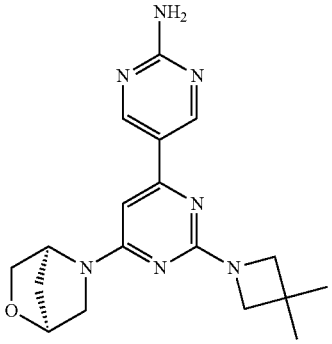 <br>5-[2-(3,3-dimethylazetidin-1-yl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.87 (s, 2H), 6.98 (s, 2H), 4.95 (s, 1H), 4.66 (s, 1H), 3.76 (d, J = 7.2, 1.5 Hz, 1H), 3.68 (s, 3H), 3.64 (d, J = 7.2 Hz, 1H), 3.43 (d, J = 10.5, 1.4 Hz, 1H), 1.85 (s, 2H), 1.26 (s, 5H). | 353 | E |
| 26 | 0.01 | 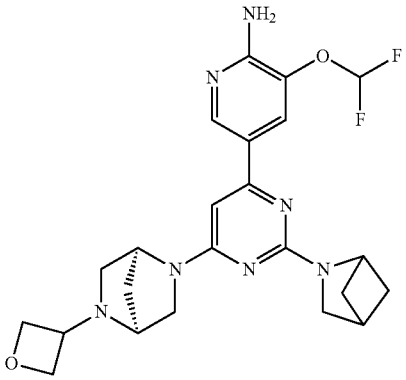 <br>[5-(5-((1R,5S,6s)-3-oxabicyclo[3.1.0]]<br>[hexan-6-yl)-1-isopropyl-1H-pyrazol-3-yl)-]<br>[3-fluoro-1H-pyrrolo[2,3-b]pyridine]<br>*5-[2-(2-azabicyclo[2.1.1]hexan-2-yl)-6-[(1S,4S)-5-(oxetan-3-yl)-2,5-diazabicyclo[2.2.1]heptan-2-yl]pyrimidin-4-yl]-3-(difluoromethoxy)pyridin-2-amine* | $^1$H NMR (400 MHz, Methanol-d4) δ 8.36 (s, 1H), 7.86 (s, 1H), 6.92 (t, J = 72.0 Hz, 1H), 6.24 (br.s, 1H), 4.96-4.90 (m, 3H), 4.79-4.74 (m, 2H), 4.55 (s, 2H), 4.10 (s, 1H), 3.81 (s, 1H), 3.62 (s, 2H), 3.55-3.52 (m, 1H), 3.04-2.97 (m, 3H), 2.11-2.06 (m, 3H), 1.96-1.94 (m, 1H), 1.51-1.44 (m, 2H). | 472.0 | B |
| 27 | 0.001 | 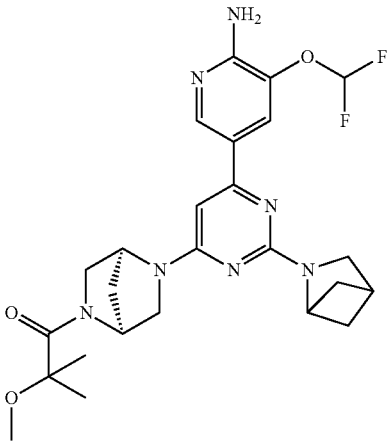 <br>1-[(1S,4S)-5-[6-[6-amino-5-(difluoromethoxy)-3-pyridyl]-2-(3-azabicyclo[2.1.1]hexan-3-yl)pyrimidin-4-yl]-2,5-diazabicyclo[2.2.1]heptan-2-yl]-2-methoxy-2-methyl-propan-1-one | $^1$H NMR (400 MHz, DMSO-d6) δ 8.58 (s, 1H), 7.97 (s, 1H), 7.12 (t, J = 74.0 Hz, 1H), 6.27 (s, 1H), 6.10 (s, 2H), 5.30 (br.s, 1H), 4.97 (s, 1H), 4.86 (d, J = 7.2 Hz, 1H), 3.65-3.57 (m, 2H), 3.48 (s, 3H), 3.44-3.42 (m, 1H), 3.16-3.11 (m, 3H), 2.91-2.89 (m, 1H), 1.95-1.88 (m, 4H), 1.34-1.20 (m, 8H). | 516.0 | B |

TABLE 1-continued

| No | DLK Ki (μM) | Structure | $^1$H NMR | MS [MS]$^+$ | Method |
|---|---|---|---|---|---|
| 28 | 0.001 | 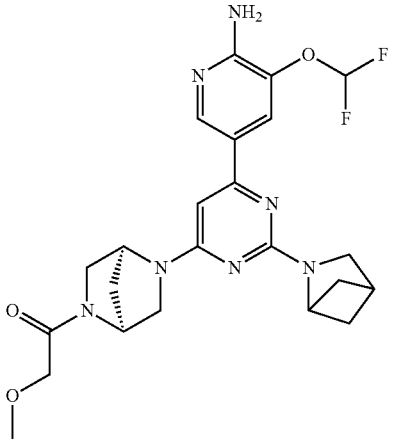 <br>[[6-amino-5-(difluoromethoxy)-3-]<br>[pyridyl]-2-(3-azabicyclo[2.1.1]hexan-]<br>[3-yl)pyrimidin-4-yl]-2,5-diazabicyclo[2.2.1]]<br>[heptan-2-yl]-2-methoxy-ethanone]<br>*1-[(1S,4S)-5-[6-[6-amino-5-(difluoromethoxy)-3-pyridyl]-2-(3-azabicycko[2.1.1]hexan-3-yl) pyrimidin-4-yl]-2,5-diazabicyclo[2.2.1]heptan-2-yl]-3-methoxy-ethanone* | $^1$H NMR (400 MHz, DMSO-d6) δ 8.59 (s, 1H), 7.97 (s, 1H), 7.18 (t, J = 73.6 Hz, 1H), 6.47 (s, 2H), 6.16 (br.s, 1H), 4.99 (br.s, 1H), 4.84-4.70 (m, 2H), 4.13-4.09 (m, 1H), 3.92-3.91 (m, 1H), 3.56-3.50 (m, 5H), 3.30-3.24 (m, 5H), 2.90-2.88 (m, 1H), 1.94-1.85 (m, 3H), 1.31-1.20 (m 2H). | 488.0 | B |
| 29 | 0.005 | 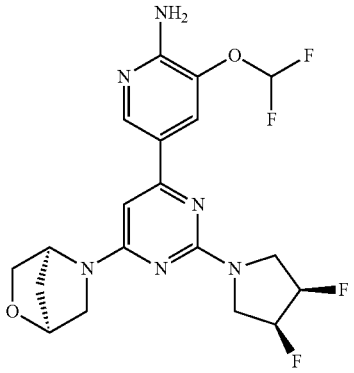 <br>3-(difluoromethoxy)-5-[2-[(3R,4S)-3,4-difluoropyrrolidin-1-yl]-6-[(1S,4S)-2-oxa-5-azabicyclo[2.2.1]heptan-5-yl]pyrimidin-4-yl]pyridin-2-amine | 1H NMR (400 MHz, DMSO-d6) δ 8.61 (s, 1H), 7.99 (s, 1H), 7.39-6.96 (m, 1H), 6.66-6.12 (m, 3H), 5.51-5.39 (m, 1H), 5.38-5.26 (m, 1H), 5.01 (s, 1H), 4.68 (s, 1H), 4.02-3.84 (m, 2H), 3.79 (d, J = 7.2, 1.6 Hz, 1H), 3.75-3.56 (m, 3H), 3.47 (d, J = 10.4, 1.4 Hz, 1H), 3.37 (s, 1H), 1.87 (s, 2H). | 441 | E |
| 30 | 0.81 | 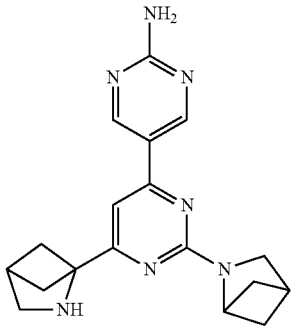 <br>5-[2-(3-azabicyclo[2.1.1]hexan-3-yl)-6-(3-azabicyclo[2.1.1]hexan-4-yl) pyrimidin-4-yl]pyrimidin-2-amine | $^1$H NMR (400 MHz, DMSO) δ 8.95 (s, 2H), 7.13 (s, 2H), 7.11 (s, 1H), 4.93 (d, J = 7.0 Hz, 1H), 3.51 (s, 2H), 2.98-2.91 (m, 3H), 2.76 (t, J = 2.8 Hz, 1H), 2.01 (d, J = 16.4 Hz, 4H), 1.47 (dd, J = 3.9, 1.7 Hz, 2H), 1.36 (dd, J = 4.3, 1.7 Hz, 2H), 1.24 (s, 1H). | 336 | C |

TABLE 1-continued

| No | DLK Ki (μM) | Structure | $^1$H NMR | MS [MS]$^+$ | Method |
|---|---|---|---|---|---|
| 31 | 0.03 | 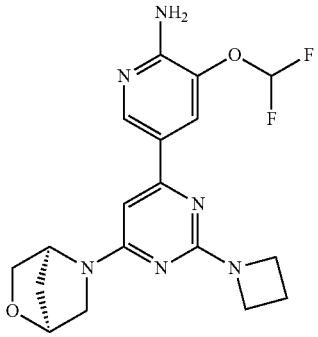 <br>5-[2-(azetidin-1-yl)-6-[(1S,4S)-2-oxa-5-azabicyclo[2.2.1]heptan-5-yl]pyrimidin-4-yl]-3-(difluoromethoxy)pyridin-2-amine | 1H NMR (400 MHz, DMSO-d6) δ 8.57 (s, 1H), 7.94 (s, 1H), 7.35-6.93 (m, 1H), 6.43 (s, 2H), 4.96 (s, 1H), 4.66 (s, 1H), 3.99 (t, J = 7.4 Hz, 4H), 3.77 (d, J = 7.5, 1.5 Hz, 1H), 3.64 (d, J = 7.4 Hz, 1H), 3.44 (d, J = 10.0 Hz, 1H), 2.31-2.18 (m, 2H), 1.85 (s, 2H). | 391 | E |
| 32 | 0.02 | 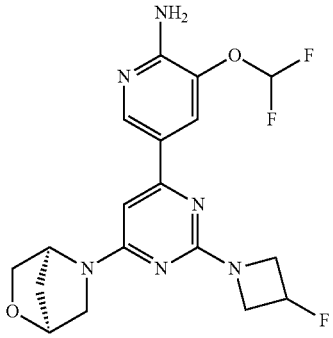 <br>3-(difluoromethoxy)-5-[2-(3-fluoroazetidin-1-yl)-6-[(1S,4S)-2-oxa-5-azabicyclo[2.2.1]heptan-5-yl]pyrimidin-4-yl]pyridin-2-amine | 1H NMR (400 MHz, DMSO-d6) δ 8.59 (s, 1H), 7.95 (s, 1H), 7.36-6.95 (m, 1H), 6.46 (s, 2H), 5.58-5.33 (m, 1H), 4.98 (s, 1H), 4.67 (s, 1H), 4.40-4.26 (m, 2H), 4.06 (d, 1H), 4.00 (d, J = 11.1, 3.2 Hz, 1H), 3.78 (d, J = 7.2, 1.5 Hz, 1H), 3.65 (d, J = 7.4 Hz, 1H), 3.45 (d, J = 10.4 Hz, 1H), 1.86 (s, 2H). | 409 | E |
| 33 | 1.07 | 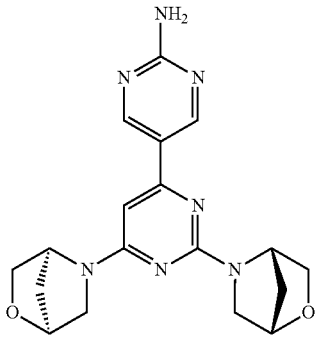 <br>5-[2,6-bis[(1S,4S)-2-oxa-5-azabicyclo[2.2.1]heptan-5-yl]pyrimidin-4-yl]pyrimidin-2-amine | 1H NMR (400 MHz, DMSO-d6) δ 8.90 (s, 2H), 6.97 (s, 2H), 6.32 (s, 1H), 4.97 (s, 2H), 4.69-4.59 (m, 2H), 3.82-3.74 (m, 2H), 3.67 (dd, J = 7.3, 5.9 Hz, 2H), 3.45 (td, J = 8.6, 7.4, 4.3 Hz, 3H), 3.33 (d, J = 8.9 Hz, 2H), 1.89-1.77 (m, 4H). | 368 | E |

TABLE 1-continued

| No | DLK Ki (μM) | Structure | $^1$H NMR | MS [MS]$^+$ | Method |
|---|---|---|---|---|---|
| 34 | 0.024 | 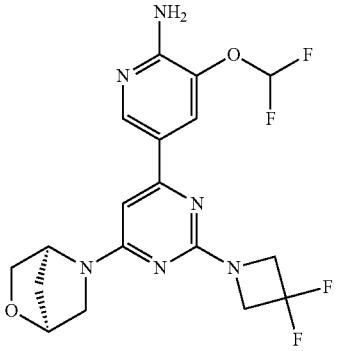 5-[2-(3,3-difluoroazetidin-1-yl)-6-[(1S,4S)-2-oxa-5-azabicyclo[2.2.1]heptan-5-yl]pyrimidin-4-yl]-3-(difluoromethoxy)pyridin-2-amine | | 427 | E |
| 35 | 0.17 | 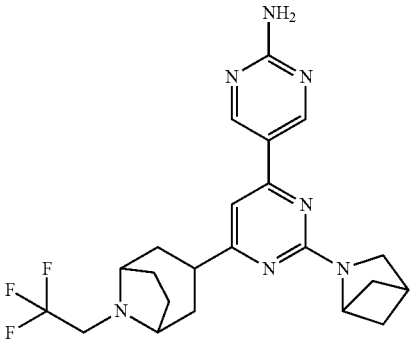 5-[2-(3-azabicyclo[2.1.1]hexan-3-yl)-6-[8-(2,2,2-trifluoroethyl)-8-azabicyclo[3.2.1]octan-3-yl]pyrimidin-4-yl]pyrimidin-2-amine | 1H NMR (400 MHz, DMSO) δ 8.95 (s, 2H), 7.10 (s, 2H), 6.99 (s, 1H), 4.91 (d, J = 7.0 Hz, 1H), 3.50 (s, 2H), 3.15 (q, J = 10.2 Hz, 3H), 2.96-2.90 (m, 1H), 2.88-2.80 (m, 1H), 2.01-1.88 (m, 6H), 1.72-1.65 (m, 2H), 1.65-1.56 (m, 2H), 1.35 (dd, J = 4.3, 1.7 Hz, 2H). | 446 | C |
| 36 | 0.22 | 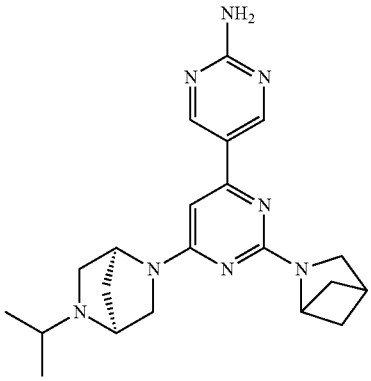 5-[2-(3-azabicyclo[2.1.1]hexan-3-yl)-6-[(1S,4S)-2-isopropyl-2,5-diazabicyclo[2.2.1]heptan-5-yl]pyrimidin-4-yl]pyrimidin-2-amine | $^1$H NMR (400 MHz, Methanol-d4) δ 8.85 (s, 2H), 6.07 (br.s, 1H), 4.87 (d, J = 6.8 Hz, 1H), 4.54 (br.s, 1H), 3.83 (s, 1H), 3.51 (s, 3H), 3.34-3.30 (m, 1H), 3.11-3.08 (m, 1H), 2.89-2.88 (m, 1H), 2.61-2.50 (m, 2H), 1.98-1.92 (m, 4H), 1.38 (d, J = 4.0 Hz, 2H), 1.06 (dd, J = 6.0, 15.2 Hz, 6H). | 393.22 | B |

TABLE 1-continued

| No | DLK Ki (μM) | Structure | $^1$H NMR | MS [MS]$^+$ | Method |
|---|---|---|---|---|---|
| 37 | 0.22 | 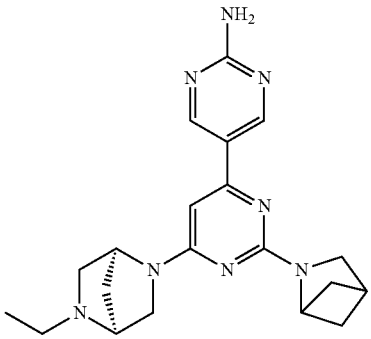 <br>5-[2-(3-azabicyclo[2.1.1]hexan-3-yl)-6-[(1S,4S)-5-ethyl-2,5-diazabicyclo[2.2.1]heptan-2-yl]pyrimidin-4-yl]pyrimidin-2-amine | $^1$H NMR (400 MHz, Methanol-d4) δ 8.86 (s, 2H), 6.11 (br.s, 1H), 4.88 (d, J = 6.8 Hz, 1H), 4.60 (br.s, 1H), 3.70 (s, 4H), 3.40-3.31 (m, 1H), 2.95-2.91 (m, 2H), 2.66-2.56 (m, 3H), 2.00-1.86 (m, 4H), 1.41-1.40 (m, 2H), 1.10 (t, J = 3.2 Hz, 3H). | 379.23 | B |
| 38 | 0.29 | 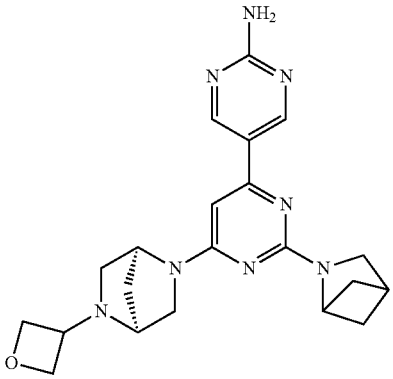 <br>5-[2-(3-azabicyclo[2.1.1]hexan-3-yl)-6-[(1S,4S)-2-(oxetan-3-yl)-2,5-diazabicyclo[2.2.1]heptan-5-yl]pyrimidin-4-yl]pyrimidin-2-amine | $^1$H NMR (400 MHz, DMSO-d6) δ 8.90 (s, 2H), 6.95 (d, J = 6.4 Hz, 2H), 6.25 (br.s, 1H), 4.83 (d, J = 7.6 Hz, 2H), 4.56 (t, J = 6.8 Hz, 2H), 4.35 (t, J = 6.0 Hz, 1H), 4.28 (t, J = 6.4 Hz, 1H), 3.90-3.88 (m, 1H), 3.60-3.50 (m, 1H), 3.45 (s, 2H), 3.20-3.15 (m, 2H), 2.89-2.87 (m, 1H), 2.85-2.81 (m, 1H), 2.68-2.66 (m, 1H), 1.93 (s, 2H), 1.84-1.82 (m, 1H), 1.80-1.75 (m, 1H), 1.32-1.15 (m, 2H). | 407.2 | B |
| 39 | 0.07 | 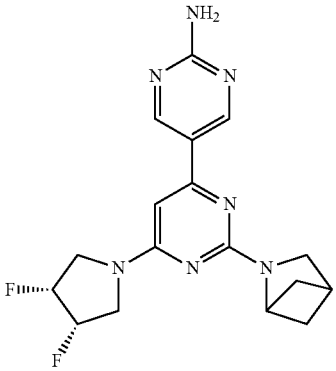 <br>5-[2-(3-azabicyclo[2.1.1]hexan-3-yl)-6-[(3S,4R)-3,4-difluoropyrrolidin-1-yl]pyrimidin-4-yl]pyrimidin-2-amine | $^1$H NMR (400 MHz, DMSO-d6) δ 8.93 (s, 2H), 7.04 (s, 2H), 6.31 (s, 1H), 5.49-5.34 (m, 2H), 4.85 (d, J = 6.4 Hz, 1H), 3.91-3.84 (m, 2H), 3.69-3.61 (m, 2H), 3.47 (s, 2H), 2.90-2.88 (m, 1H), 1.94 (s, 2H), 1.32-1.23 (m, 2H). | 359.8 | B |

TABLE 1-continued

| No | DLK Ki (μM) | Structure | $^1$H NMR | MS [MS]$^+$ | Method |
|---|---|---|---|---|---|
| 40 | 0.004 | 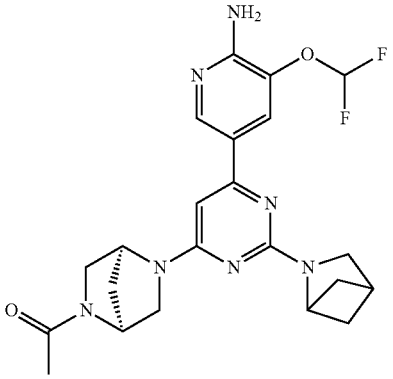 1-[(1S,4S)-5-[6-[6-amino-5-(difluoromethoxy)-3-pyridyl]-2-(3-azabicyclo[2.1.1]hexan-3-yl)pyrimidin-4-yl]-2,5-diazabicyclo[2.2.1]heptan-2-yl]ethanone | $^1$H NMR (400 MHz, DMSO-d6) δ 8.59 (s, 1H), 7.97 (s, 1H), 7.18 (t, J = 74.0 Hz, 1H), 6.47 (s, 2H), 6.17 (br.s, 1H), 4.98 (br.s, 1H), 4.84-4.67 (m, 2H), 3.56-3.54 (m, 1H), 3.50-3.38 (m, 4H), 3.33-3.26 (m, 2H), 2.88 (d, J = 3.2 Hz, 1H), 2.03 (s, 1H), 1.94 (s, 3H), 1.87-1.84 (m, 2H), 1.32-1.31 (m, 2H). | 457.9 | B |
| 41 | 0.28 | 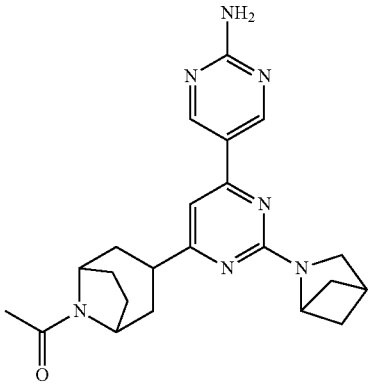 1-[3-[6-(2-aminopyrimidin-5-yl)-2-(3-azabicyclo[2.1.1]hexan-3-yl)pyrimidin-4-yl]-8-azabicyclo[3.2.1]octan-8-yl]ethanone | 1H NMR (400 MHz, DMSO) δ 8.95 (s, 2H), 7.11 (s, 2H), 7.02 (s, 1H), 4.89 (d, J = 7.0 Hz, 1H), 4.57-4.50 (m, 1H), 4.31-4.21 (m, 1H), 3.48 (s, 2H), 3.18-3.09 (m, 1H), 2.95-2.90 (m, 1H), 2.00 (s, 3H), 2.00-1.94 (m, 3H), 1.91-1.70 (m, 7H), 1.34 (dd, J = 4.4, 1.8 Hz, 2H). | 406 | C |
| 42 | 0.17 | 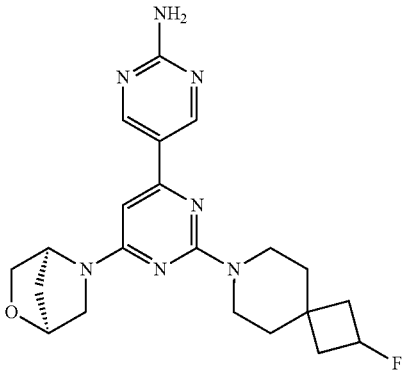 5-[2-(2-fluoro-7-azaspiro[3.5]nonan-7-yl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.90 (s, 2H), 6.98 (s, 2H), 5.91-5.77 (m, 1H), 5.18-5.08 (m, 2H), 4.96 (s, 1H), 4.67 (s, 1H), 4.53-4.44 (m, 2H), 3.77 (d, J = 7.2, 1.5 Hz, 1H), 3.41-3.32 (m, 1H), 3.65 (d, J = 7.3 Hz, 1H), 3.45 (dd, J = 10.6, 1.5 Hz, 1H), 3.18 (t, J = 12.1 Hz, 2H), 2.43 (d, J = 7.2 Hz, 1H), 2.37 (d, J = 7.4 Hz, 1H), 1.86 (s, 2H), 1.83-1.72 (m, 2H), 1.72-1.51 (m, 2H). | 412 | E |

TABLE 1-continued

| No | DLK Ki (μM) | Structure | $^1$H NMR | MS [MS]$^+$ | Method |
|---|---|---|---|---|---|
| 43 | 1.61 | 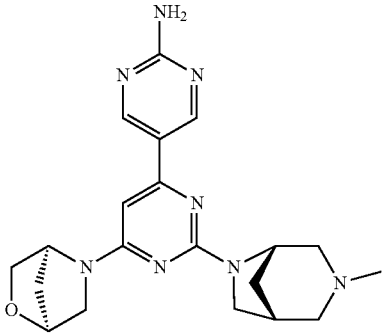 <br>5-[2-[(1R,5S)-3-methyl-3,6-diazabicyclo[3.2.1]octan-6-yl]-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 3.14-2.98 (m, 1H), 2.82-2.72 (m, 1H), 2.41 (s, 1H), 2.13 (d, J = 3.4 Hz, 3H), 1.96 (d, J = 10.5 Hz, 1H), 1.86 (s, 3H), 1.53 (d, J = 10.6 Hz, 1H), 3.38-3.31 (m, 1H), 8.89 (d, J = 10.6 Hz, 2H), 6.94 (s, 2H), 5.02-4.88 (m, 1H), 4.66 (s, 1H), 4.47-4.27 (m, 1H), 3.77 (d, J = 7.2 Hz, 1H), 3.66 (s, 1H), 3.55-3.39 (m, 3H). | 395 | E |
| 44 | 0.07 | 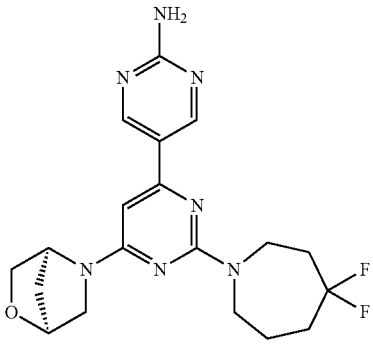 <br>5-[2-(4,4-difluoroazepan-1-yl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.90 (s, 2H), 6.97 (s, 2H), 4.96 (s, 1H), 4.67 (s, 1H), 3.87-3.72 (m, 5H), 3.41-3.32 (m, 1H), 3.66 (d, J = 7.2 Hz, 1H), 3.46 (d, J = 10.5, 1.4 Hz, 1H), 2.31-2.17 (m, 2H), 2.10-1.96 (m, 2H), 1.92-1.78 (m, 4H). | 404 | E |
| 45 | 1.75 | 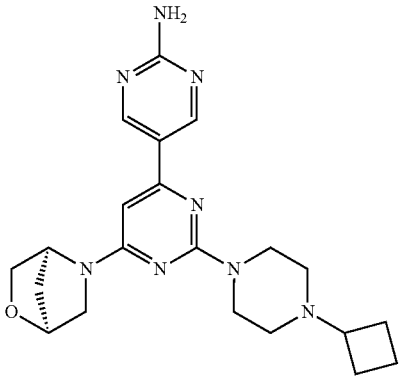 <br>5-[2-(4-cyclobutylpiperazin-1-yl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.89 (s, 2H), 6.97 (s, 2H), 4.96 (s, 1H), 4.66 (s, 1H), 3.77 (d, J = 7.5, 1.4 Hz, 1H), 3.71 (t, J = 4.9 Hz, 4H), 3.65 (d, J = 7.3 Hz, 1H), 3.44 (d, J = 10.5, 1.4 Hz, 1H), 3.33 (s, 1H), 2.74-2.64 (m, 1H), 2.27 (t, J = 5.0 Hz, 4H), 1.97 (qd, J = 7.2 3.1 Hz, 2H), 1.92-1.72 (m, 4H), 1.72-1.54 (m, 2H). | 409 | E |

TABLE 1-continued

| No | DLK Ki (μM) | Structure | $^1$H NMR | MS [MS]$^+$ | Method |
|---|---|---|---|---|---|
| 46 | 1.61 | 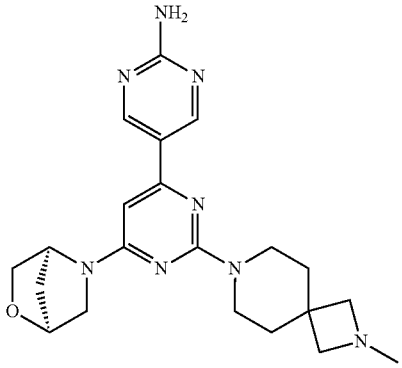 <br>5-[2-(2-methyl-2,7-diazaspiro[3.5]nonan-7-yl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.88 (s, 2H), 6.97 (s, 2H), 4.95 (s, 1H), 4.66 (s, 1H), 3.76 (d, J = 7.2, 1.5 Hz, 1H), 3.68 (s, 4H), 3.64 (d, J = 7.3 Hz, 1H), 3.43 (d, J = 10.5, 1.4 Hz, 1H), 2.24 (s, 4H), 2.13 (s, 3H), 1.85 (s, 2H), 1.71 (t, J = 5.3 Hz, 4H). | 409 | E |
| 47 | 0.07 | 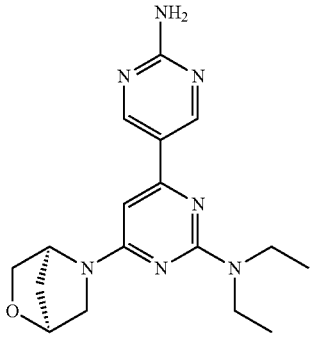 <br>4-(2-aminopyrimidin-5-yl)-N,N-diethyl-6-[(1S,4S)-2-oxa-5-azabicyclo[2.2.1]heptan-5-yl]pyrimidin-2-amine | 1H NMR (400 MHz, DMSO-d6) δ 8.88 (s, 2H), 6.94 (s, 2H), 4.93 (s, 1H), 4.66 (s, 1H), 3.77 (d, J = 7.2, 1.6 Hz, 1H), 3.66 (d, J = 7.2 Hz, 1H), 3.63-3.51 (m, 4H), 3.45 (d, J = 10.5, 1.4 Hz, 1H), 1.87 (t, 2H), 1.14 (t, 6H). | 342 | E |
| 48 | 1.61 | 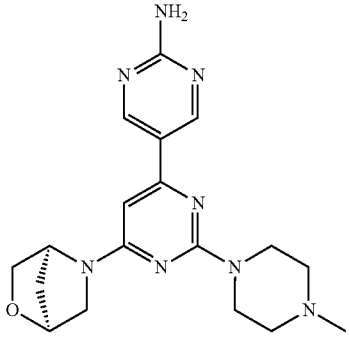 <br>5-[2-(4-methylpiperazin-1-yl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.90 (s, 2H), 6.98 (s, 2H), 4.97 (s, 1H), 4.66 (s, 1H), 3.77 (d, J = 7.5, 1.5 Hz, 1H), 3.75-3.68 (m, 4H), 3.41-3.32 (m, 1H), 3.65 (d, J = 7.3 Hz, 1H), 3.45 (d, J = 10.5, 1.4 Hz, 1H), 3.17 (s, 1H), 2.34 (t, J = 5.0 Hz, 4H), 2.20 (s, 3H), 1.86 (s, 2H). | 369 | E |

TABLE 1-continued

| No | DLK Ki (μM) | Structure | $^1$H NMR | MS [MS]$^+$ | Method |
|---|---|---|---|---|---|
| 49 | 0.54 | 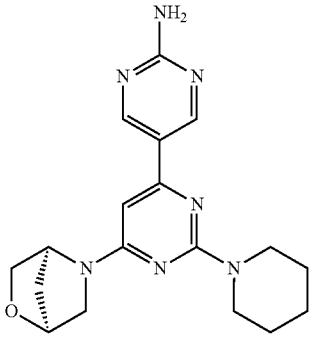 <br>5-[6-[(1S,4S)-2-oxa-5-azabicyclo[2.2.1]heptan-5-yl]-2-(1-piperidyl)pyrimidin-4-yl]pyrimidin-2-amine | 1H NMR (400 MHz, DMSO-d6) δ 8.89 (s, 2H), 6.96 (s, 2H), 4.95 (s, 1H), 4.66 (s, 1H), 3.82-3.69 (m, 5H), 3.65 (d, J = 7.3 Hz, 1H), 3.49-3.41 (m, 1H), 3.40-3.32 (m, 1H), 1.92-1.80 (m, 2H), 1.67-1.56 (m, 2H), 1.56-1.45 (m, 4H). | 354 | E |
| 50 | 0.41 | 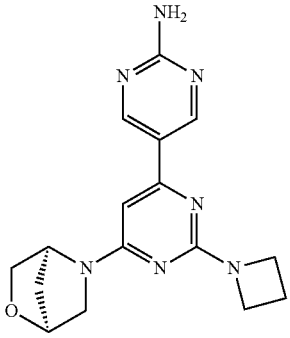 <br>5-[2-(azetidin-1-yl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.87 (s, 2H), 6.97 (s, 2H), 4.95 (s, 1H), 4.66 (s, 1H), 3.99 (t, J = 7.5 Hz, 4H), 3.77 (dd, J = 7.3, 1.5 Hz, 1H), 3.64 (d, J = 7.3 Hz, 1H), 3.43 (dd, J = 10.5, 1.5 Hz, 1H), 3.40-3.32 (m, 1H), 3.17 (s, 1H), 2.24 (p, J = 7.5 Hz, 2H), 1.85 (s, 2H). | 326 | E |
| 51 | 0.20 | 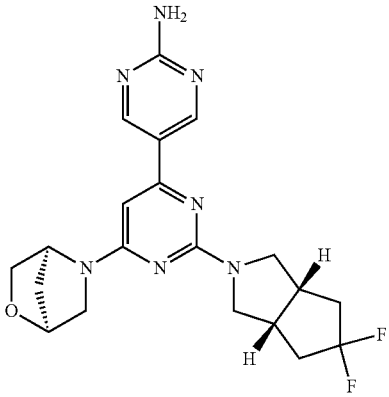 <br>5-[2-[(3aS,6aR)-5,5-difluoro-1,3,3a,4,6,6a-hexahydrocyclopenta[c]pyrrol-2-yl]-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.91 (s, 2H), 6.97 (s, 2H), 6.31 (s, 1H), 4.97 (s, 1H), 4.66 (s, 1H), 3.84-3.69 (m, 3H), 3.65 (d, J = 7.3 Hz, 1H), 3.51-3.41 (m, 3H), 2.89 (q, J = 9.3, 8.1 Hz, 2H), 2.48-2.31 (m, 2H), 2.16-1.98 (m, 2H), 1.86 (s, 2H). | 416 | E |

TABLE 1-continued

| No | DLK Ki (μM) | Structure | $^1$H NMR | MS [MS]$^+$ | Method |
|---|---|---|---|---|---|
| 52 | 0.086 | 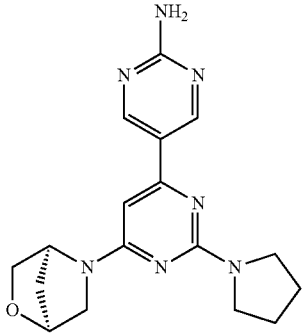 <br>5-[6-[(1S,4S)-2-oxa-5-azabicyclo[2.2.1]heptan-5-yl]-2-pyrrolidin-1-yl-pyrimidin-4-yl]pyrimidin-2-amine | 1H NMR (400 MHz, DMSO-d6) δ 8.90 (s, 2H), 6.95 (s, 2H), 6.27 (s, 1H), 4.96 (s, 1H), 4.66 (s, 1H), 3.77 (d, J = 7.3, 1.5 Hz, 1H), 3.65 (d, J = 7.3 Hz, 1H), 3.58-3.41 (m, 5H), 1.96-1.79 (m, 6H). | 340 | E |
| 53 | 0.27 | 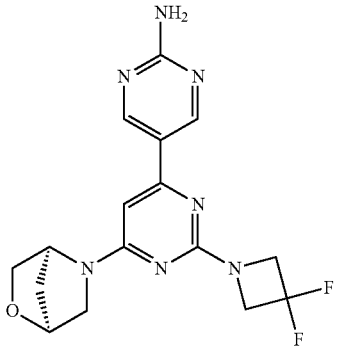 <br>5-[2-(3,3-difluoroazetidin-1-yl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.91 (s, 2H), 7.03 (s, 2H), 6.35 (s, 1H), 4.99 (s, 1H), 4.68 (s, 1H), 4.41 (t, J = 12.6 Hz, 4H), 3.78 (dd, J = 7.5, 1.5 Hz, 1H), 3.66 (d, J = 7.4 Hz, 1H), 3.50-3.42 (m, 1H), 3.40-3.31 (m, 1H), 1.87 (s, 2H). | 362 | E |
| 54 | 0.16 | 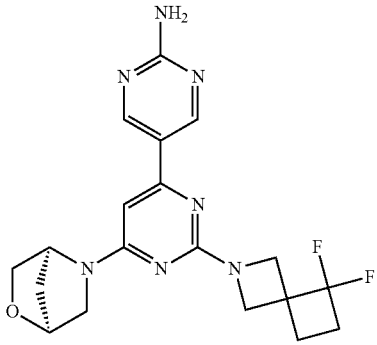 <br>5-[2-(7,7-difluoro-2-azaspiro[3.3]heptan-2-yl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.89 (s, 2H), 7.00 (s, 2H), 4.97 (s, 1H), 4.67 (s, 1H), 4.19 (d, J = 9.3, 3.2 Hz, 2H), 3.94 (d, J = 9.2, 2.8 Hz, 2H), 3.77 (d, J = 7.5, 1.5 Hz, 1H), 3.65 (d, J = 7.4 Hz, 1H), 3.44 (d, J = 10.5, 1.5 Hz, 1H), 2.11-1.99 (m, 2H), 1.86 (s, 2H). | 402 | E |

TABLE 1-continued

| No | DLK Ki (μM) | Structure | $^1$H NMR | MS [MS]$^+$ | Method |
|---|---|---|---|---|---|
| 55 | 0.13 | 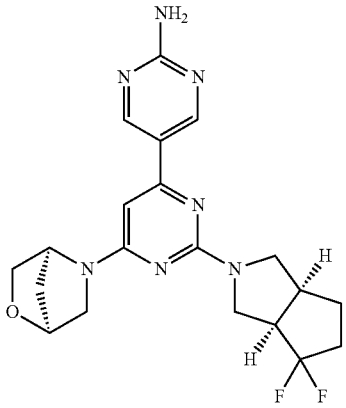 <br>5-[2-[(3aR,6aS)-4,4-difluoro-1,3,3a,5,6,6a-hexahydrocyclopenta[c]pyrrol-2-yl]-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.91 (s, 2H), 6.98 (s, 2H), 4.97 (s, 1H), 4.67 (s, 1H), 3.84-3.58 (m, 5H), 3.49-3.41 (m, 2H), 3.04-2.90 (m, 2H), 2.28-2.08 (m, 2H), 2.08-1.96 (m, 1H), 1.86 (s, 2H), 1.68-1.57 (m, 1H). | 416 | E |
| 56 | 1.61 | 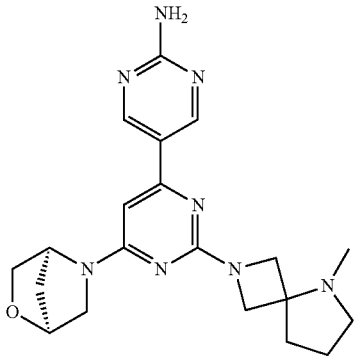 <br>5-[2-(5-methyl-2,5-diazaspiro[3.4]octan-2-yl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.88 (s, 2H), 6.98 (s, 2H), 4.96 (s, 1H), 4.66 (s, 1H), 4.08 (d, J = 9.0, 3.2 Hz, 2H), 3.82-3.71 (m, 3H), 3.65 (d, J = 7.2 Hz, 1H), 3.43 (d, J = 10.6, 1.5 Hz, 1H), 3.17 (d, J = 5.0 Hz, 1H), 2.62 (t, J = 7.2 Hz, 2H), 2.34 (s, 3H), 2.05-1.97 (m, 2H), 1.85 (s, 2H), 1.73-1.62 (m, 2H). | 395 | E |
| 57 | 0.12 | 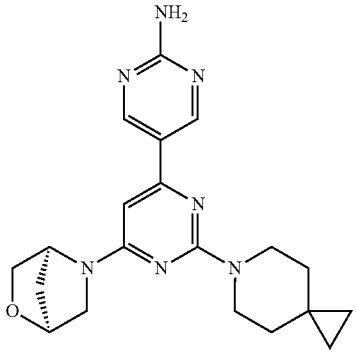 <br>5-[2-(6-azaspiro[2.5]octan-6-yl)-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.89 (s, 2H), 6.96 (s, 2H), 4.95 (s, 1H), 4.66 (s, 1H), 3.84-3.79 (m, 4H), 3.77 (d, J = 7.2, 1.4 Hz, 1H), 3.66 (d, J = 7.2 Hz, 1H), 3.45 (d, J = 10.5, 1.5 Hz, 1H), 1.86 (s, 2H), 1.41-1.28 (m, 4H), 0.34 (s, 4H). | 380 | E |

TABLE 1-continued

| No | DLK Ki (μM) | Structure | $^1$H NMR | MS [MS]$^+$ | Method |
|---|---|---|---|---|---|
| 58 | 0.21 | 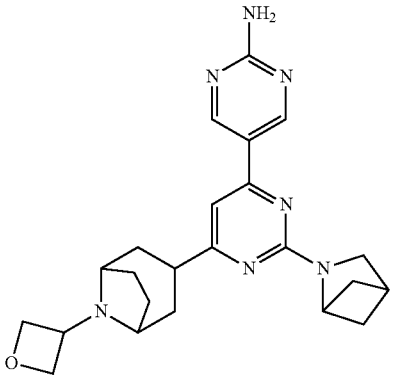 <br>5-[2-(3-azabicyclo[2.1.1]hexan-3-yl)-6-[8-(oxetan-3-yl)-8-azabicyclo[3.2.1]octan-3-yl]pyrimidin-4-yl]pyrimidin-2-amine | 1H NMR (400 MHz, DMSO) δ 8.95 (s, 2H), 7.09 (s, 2H), 6.99 (s, 1H), 4.92 (d, J = 7.0 Hz, 1H), 4.58 (t, J = 6.2 Hz, 2H), 4.35 (t, J = 5.7 Hz, 2H), 3.73-3.65 (m, 1H), 3.50 (s, 2H), 3.13 (s, 2H), 2.93 (dd, J = 6.8, 3.2 Hz, 1H), 2.90-2.79 (m, 1H), 2.02-1.81 (m, 6H), 1.69-1.57 (m, 4H), 1.35 (dd, J = 4.3, 1.8 Hz, 2H) | 420 | C |
| 59 | 0.02 | 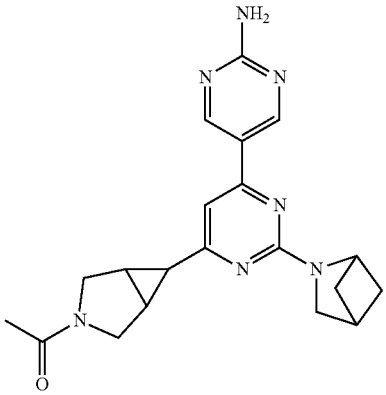 <br>1-[6-[6-(2-aminopyrimidin-5-yl)-2-(3-azabicyclo[2.1.1]hexan-3-yl)pyrimidin-4-yl]-3-azabicyclo[3.1.0]hexan-3-yl]ethanone | 1H NMR (400 MHz, Chloroform-d) δ 8.94 (s, 2H), 6.65 (s, 1H), 5.49 (s, 2H), 4.95 (d, J = 6.0 Hz, 1H), 3.97 (d, J = 12.0 Hz, 1H), 3.72 (s, 2H), 3.54 (s, 3H), 2.95 (s, 1H), 2.30 (s, 2H), 2.06 (s, 3H), 2.00 (s, 2H), 1.70 (s, 1H), 1.45 (s, 2H). | 377.8 | C |
| 60 | 0.01 | 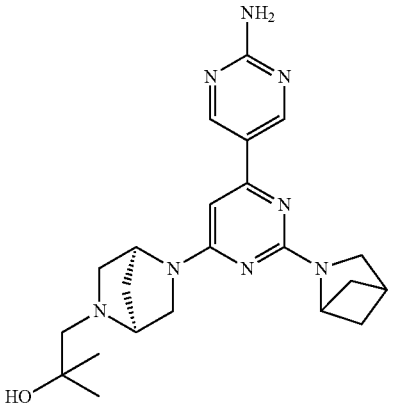 <br>1-[(1S,4S)-2-[6-(2-aminopyrimidin-5-yl)-2-(3-azabicyclo[2.1.1]hexan-3-yl)pyrimidin-4-yl]-2,5-diazabicyclo[2.2.1]heptan-5-yl]-2-methyl-propan-2-ol | $^1$H NMR (400 MHz, DMSO-d6) δ 8.90 (s, 2H), 6.97 (s, 2H), 6.40-6.14 (m, 1H), 4.83 (d, J = 6.8 Hz, 1H), 3.99 (s, 1H), 3.68-3.60 (m, 1H), 3.45 (s, 2H), 3.28-3.27 (m, 2H), 3.04 (d, J = 7.6 Hz, 1H), 2.89-2.87 (m, 1H), 2.57-2.54 (m, 1H), 2.45-2.41 (m, 2H), 1.93-1.91 (m, 2H), 1.82-1.71 (m, 2H), 1.32-1.29 (m, 2H), 1.23-1.15 (m, 1H), 1.04 (s, 6H). | 423.2 | B |

TABLE 1-continued

| No | DLK Ki (μM) | Structure | $^1$H NMR | MS [MS]$^+$ | Method |
|---|---|---|---|---|---|
| 61 | 0.01 | 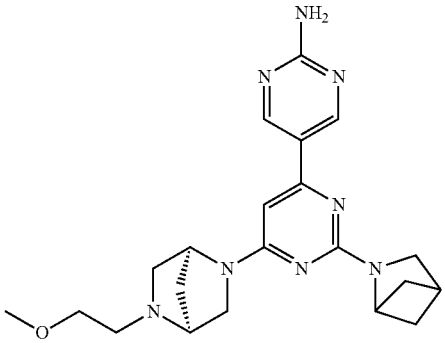 <br>5-[2-(3-azabicyclo[2.1.1]hexan-3-yl)-6-[(1S,4S)-5-(2-methoxyethyl)-2,5-diazabicyclo[2.2.1]heptan-2-yl]pyrimidin-4-yl]pyrimidin-2-amine | $^1$H NMR (400 MHz, Methanol-d4) δ 8.84 (s, 2H), 6.09 (br.s, 1H), 4.95-4.87 (m, 2H), 4.67 (br.s, 1H), 3.71 (s, 1H), 3.62-3.52 (m, 4H), 3.48-3.45 (m, 1H), 3.34-3.31 (m, 3H), 3.00-2.95 (m, 1H), 2.92-2.90 (m, 1H), 2.76-2.74 (m, 2H), 2.67-2.64 (m, 1H), 1.98-1.94 (m, 3H), 1.88-1.82 (m, 1H), 1.42-1.38 (m, 2H). | 409.2 | B |
| 62 | 0.003 | 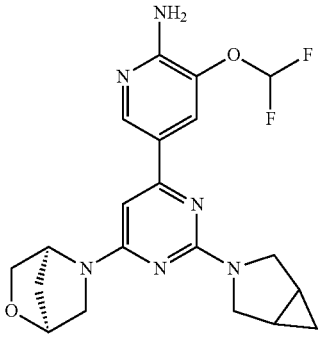 <br>5-[2-(3-azabicyclo[3.1.0]hexan-3-yl)-6-[(1S,4S)-2-oxa-5-azabicyclo[2.2.1]heptan-5-yl]pyrimidin-4-yl]-3-(difluoromethoxy)pyridin-2-amine | $^1$H NMR (400 MHz, DMSO-d6) δ 8.57 (s, 1H), 7.96 (s, 1H), 7.17 (t, J = 74.0 Hz, 1H), 6.44 (s, 2H), 6.30 (br.s, 1H), 4.96 (s, 1H), 4.66 (s, 1H), 3.86-3.76 (m, 3H), 3.64 (d, J = 7.2 Hz, 1H), 3.45-3.40 (m, 4H), 1.85 (s, 2H), 1.61-1.58 (m, 2H), 0.71-0.66 (m, 1H), 0.14-0.11 (m, 1H). | 416.8 | A |
| 63 | 0.53 | 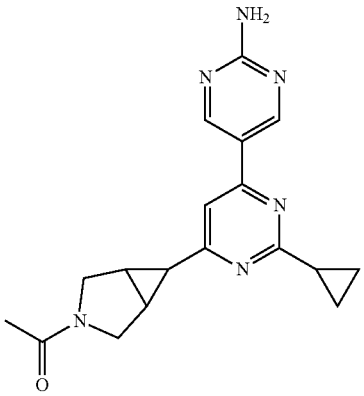 <br>1-[6-[6-(2-aminopyrimidin-5-yl)-2-cyclopropyl-pyrimidin-4-yl]-3-azabicyclo[3.1.0]hexan-3-yl]ethanone | $^1$H NMR (400 MHz, Chloroform-d) δ 8.98 (s, 2H), 1.17 (s, 1H), 5.32 (s, 2H), 3.99 (d, J = 12.0 Hz, 1H), 3.74-3.72 (m, 2H), 3.56 (dd, J = 4.0, 12.4 Hz, 1H), 2.33-2.29 (m, 2H), 2.25-2.20 (m, 1H), 2.07 (s, 3H), 1.80-1.78 (m, 1H), 1.13-1.11 (m, 2H), 1.04-1.02 (m, 2H). | 336.9 | C |

TABLE 1-continued

| No | DLK Ki (μM) | Structure | $^1$H NMR | MS [MS]$^+$ | Method |
|---|---|---|---|---|---|
| 64 | 0.27 | 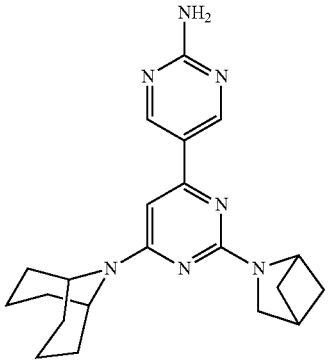 <br>5-[2-(3-azabicyclo[2.1.1]hexan-3-yl)-6-(9-azabicyclo[3.3.1]nonan-9-yl) pyrimidin-4-yl]pyrimidin-2-amine | $^1$H NMR (400 MHz, DMSO) δ 8.91 (s, 2H), 6.92 (br s, 2H), 6.50 (s, 1H), 5.03 (br s, 1H), 4.80 (d, J = 6.9 Hz, 1H), 4.36 (br s, 1H), 3.44 (s, 2H), 2.85 (m, 1H), 2.18-1.51 (m, 14H), 1.39-1.27 (m, 2H). | 378 | I |
| 65 | 0.04 | 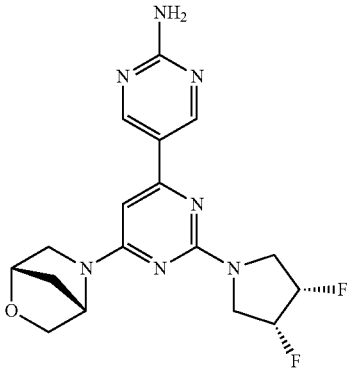 <br>5-[2-[(3S,4R)-3,4-difluoropyrrolidin-1-yl]-6-[(1S,4S)-2-oxa-5-azabicyclo[2.2.1] heptan-5-yl]pyrimidin-4-yl]pyrimidin-2-amine | 1H NMR (400 MHz, DMSO-d6) δ 8.93 (s, 2H), 6.99 (s, 2H), 5.49-5.38 (m, 1H), 5.38-5.26 (m, 1H), 5.00 (s, 1H), 4.68 (s, 1H), 3.44-3.32 (m, 1H), 4.03-3.84 (m, 2H), 3.78 (d, J = 7.5, 1.5 Hz, 1H), 3.75-3.57 (m, 3H), 3.46 (d, J = 10.5, 1.6 Hz, 1H), 3.37 (s, 1H), 1.95-1.80 (m, 2H). | 376 | E |
| 66 | 0.03 | 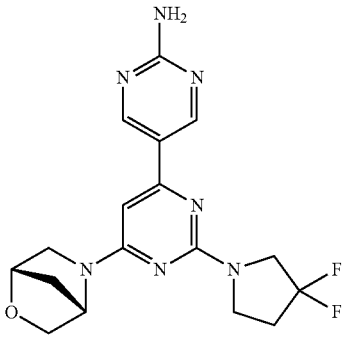 <br>5-[2-(3,3-difluoropyrrolidin-1-yl)-6-[(1S,4S)-2-oxa-5-azabicyclo[2.2.1] heptan-5-yl]pyrimidin-4-yl]pyrimidin-2-amine | 1H NMR (400 MHz, DMSO-d6) δ 8.93 (s, 2H), 6.99 (s, 2H), 5.00 (s, 1H), 4.67 (s, 1H), 3.91 (t, J = 13.5 Hz, 2H), 3.80-3.68 (m, 3H), 3.65 (d, J = 7.3 Hz, 1H), 3.46 (d, 1H), 3.37 (s, 1H), 1.87 (s, 2H). | 376 | E |

TABLE 1-continued

| No | DLK Ki (μM) | Structure | $^1$H NMR | MS [MS]$^+$ | Method |
|---|---|---|---|---|---|
| 67 | 0.65 | 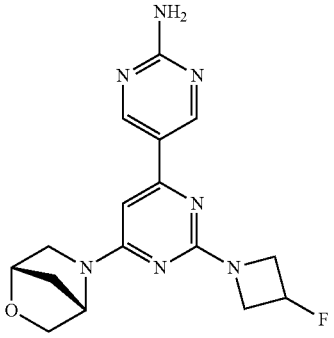 <br>5-[2-(3-fluoroazetidin-1-yl)-6-[(1S, 4S)-2-oxa-5-azabicyclo[2.2.1]heptan-5-yl]pyrimidin-4-yl]pyrimidin-2-amine | 1H NMR (400 MHz, DMSO-d6) δ 8.89 (s, 2H), 7.00 (s, 2H), 5.45 (d, J = 57.9, 6.1, 3.2 Hz, 1H), 4.97 (s, 1H), 4.67 (s, 1H), 4.40-4.25 (m, 2H), , 4.12-4.03 (m, 1H), 4.03-3.96 (m, 1H), 3.77 (d, J = 7.3, 1.5 Hz, 1H), 3.65 (d, J = 7.3 Hz, 1H), 3.44 (d, J = 10.5, 1.5 Hz, 1H), 3.41-3.31 (m, 1H), 3.35 (s, 1H), 1.86 (s, 2H). | 395 | E |
| 68 | 1.61 | 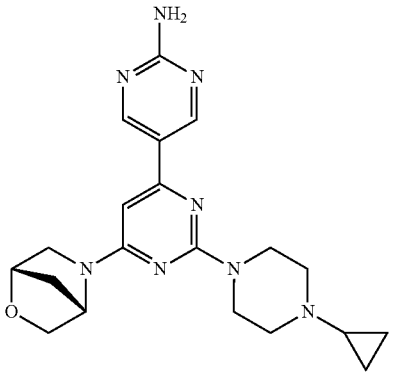 <br>5-[2-(4-cyclopropylpiperazin-1-yl)-6-[(1S,4S)-2-oxa-5-azabicyclo[2.2.1] heptan-5-yl]pyrimidin-4-yl]pyrimidin-2-amine | 1H NMR (400 MHz, DMSO-d6) δ 8.90 (s, 2H), 6.98 (s, 2H), 4.97 (s, 1H), 4.66 (s, 1H), 3.77 (d, J = 7.5, 1.7 Hz, 1H), 3.74-3.61 (m, 5H), 3.45 (d, J = 10.5, 1.5 Hz, 1H), 3.35 (s, 1H), 2.56 (t, J = 5.0 Hz, 4H), 1.86 (s, 2H), 1.68-1.59 (m, 1H), 0.43 (m, 2H), 0.36 (q, J = 3.2, 2.6 Hz, 2H). | 395 | E |
| 69 | 0.11 | 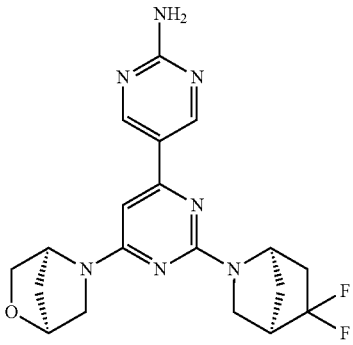 <br>5-[2-[(1R,4R)-5,5-difluoro-2-azabicyclo[2.2.1]heptan-2-yl]-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.90 (s, 2H), 6.98 (s, 2H), 4.97 (s, 2H), 4.75 (s, 2H), 4.67 (s, 2H), 3.77 (d, J = 7.5, 1.7 Hz, 2H), 3.66 (d, J = 7.4 Hz, 2H), 3.64-3.50 (m, 1H), ), 3.56 (t, J = 8.9 Hz, 1H), 3.50-3.40 (d, 1H), 3.40-3.35 (m, 3H), 3.45 (d, J = 9.9, 1.7 Hz, 1H), 2.93 (s, 1H), 2.28-2.10 (m, 1H), 2.10-1.96 (m 1H), 1.89 (d, J = 18.5 Hz, 4H). | 402 | E |

TABLE 1-continued

| No | DLK Ki (μM) | Structure | $^1$H NMR | MS [MS]$^+$ | Method |
|---|---|---|---|---|---|
| 70 | 0.22 | 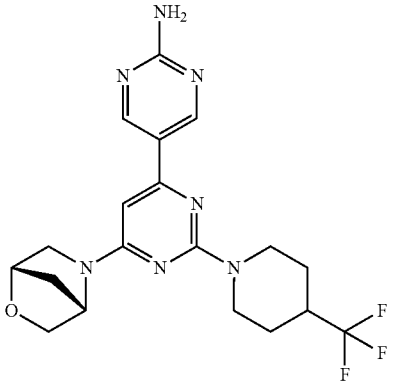 <br>5-[6-[(1S,4S)-2-oxa-5-azabicyclo[2.2.1]heptan-5-yl]-2-[4-(trifluoromethyl)-1-piperidyl]pyrimidin-4-yl]pyrimidin-2-amine | 1H NMR (400 MHz, DMSO-d6) δ 8.90 (s, 2H), 6.98 (s, 2H), 4.97 (s, 1H), 4.85 (d, J = 13.2 Hz, 2H), 4.67 (s, 1H), 3.78 (d, J = 7.3, 1.4 Hz, 1H), 2.64-2.52 (m, 1H), 3.65 (d, J = 7.4 Hz, 1H), 3.46 (d, J = 10.5, 1.4 Hz, 1H), 3.35 (s, 1H), 2.82 (t, J = 12.8 Hz, 2H), 1.86 (d, J = 11.0 Hz, 4H), 1.45-1.28 (m, 2H). | 422 | E |
| 71 | 0.09 | 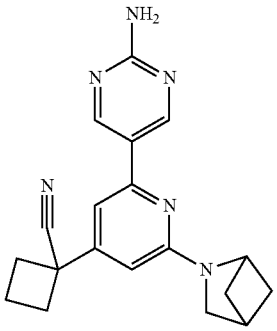 <br>1-[2-(2-aminopyrimidin-5-yl)-6-(3-azabicyclo[2.1.1]hexan-3-yl)-4-pyridyl]cyclobutanecarbonitrile | $^1$H NMR (400 MHz, DMSO) δ 8.92 (s, 2H), 7.10 (d, J = 1.1 Hz, 1H), 6.91 (br s, 2H), 6.46 (d, J = 1.1 Hz, 1H), 4.88 (d, J = 6.8 Hz, 1H), 3.44 (s, 2H), 3.01-2.90 (m, 1H), 2.75-2.64 (m, 4H), 2.39-2.18 (m, 1H), 2.11-1.92 (m, 3H), 1.41-1.27 (m, 2H). | 333 | G |
| 72 | 0.04 | 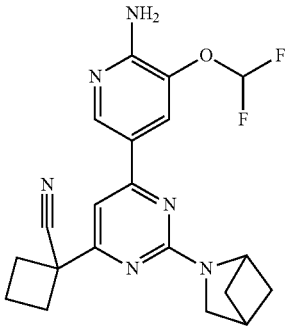 <br>1-[6-[6-amino-5-(difluoromethoxy)-3-pyridyl]-2-(3-azabicyclo[2.1.1]hexan-3-yl)pyrimidin-4-yl]cyclobutanecarbonitrile | $^1$H NMR (400 MHz, DMSO) δ 8.69 (s, 1H), 8.05 (s, 1H), 7.23 (t, J = 74.0 Hz, 2H), 7.20 (s, 1H), 6.70 (br s, 2H), 4.95 (m, 1H), 3.54 (s, 2H), 2.99-2.91 (m, 1H), 2.81 (m, 2H), 2.72-2.60 (m, 2H), 2.32-2.18 (m, 1H), 2.13-1.94 (m, 3H), 1.45-1.38 (m, 2H). | 399 | I |

TABLE 1-continued

| No | DLK Ki (μM) | Structure | $^1$H NMR | MS [MS]$^+$ | Method |
|---|---|---|---|---|---|
| 73 | 0.002 | 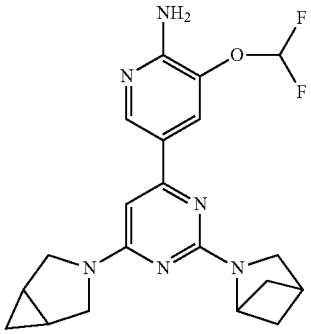 <br>5-[2-(3-azabicyclo[2.1.1]hexan-3-yl)-6-(3-azabicyclo[3.1.0]hexan-3-yl) pyrimidin-4-yl]-3-(difluoromethoxy) pyridin-2-amine | 1H NMR (400 MHz, Methanol-d4) δ 8.26 (s, 1H), 7.78 (s, 1H), 6.72 (t, J = 73.6 Hz, 1H), 5.90 (s, 1H), 4.73-4.68 (m, 1H), 3.62 (br.s, 2H), 3.37 (s, 2H), 3.30 (d, J = 10.4 Hz, 2H), 2.75-2.73 (m, 1H), 1.83 (s, 2H), 1.51-1.50 (m, 2H), 1.24-1.22 (m, 2H), 0.64-0.61 (m, 1H), 0.02-0.01 (m, 1H). | 401.0 | A |
| 74 | 0.05 | 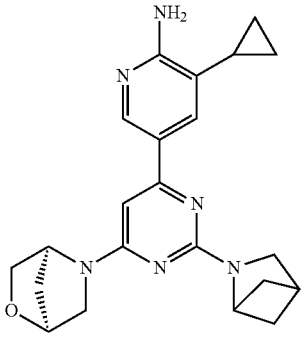 <br>5-[2-(3-azabicyclo[2.1.1]hexan-3-yl)-6-[(1S,4S)-2-oxa-5-azabicyclo[2.2.1] heptan-5-yl]pyrimidin-4-yl]-3-cyclopropyl-pyridin-2-amine | $^1$H NMR (400 MHz, Chloroform-d) δ 8.54 (s, 1H), 7.91 (s, 1H), 5.92 (s, 1H), 4.96 (d, J = 6.8 Hz, 2H), 4.89 (s, 2H), 4.70 (s, 1H), 3.92-3.87 (m, 2H), 3.58 (s, 2H), 3.52-4.94 (m, 2H), 2.92-2.90 (m, 1H), 1.96-1.93 (m, 4H), 1.68-1.66 (m, 1H), 1.48-1.46 (m, 2H), 0.96-0.94 (m, 2H), 0.69-0.67 (m, 2H). | 390.9 | A |
| 75 | 0.009 | 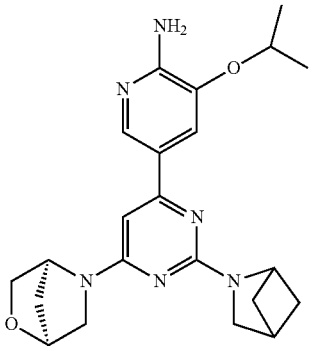 <br>5-[2-(3-azabicyclo[2.1.1]hexan-3-yl)-6-[(1S,4S)-2-oxa-5-azabicyclo[2.2.1] heptan-5-yl]pyrimidin-4-yl]-3-isopropoxy-pyridin-2-amine | $^1$H NMR (400 MHz, DMSO-d6) δ 8.28 (s, 1H), 7.23 (s, 1H), 6.21 (br.s, 2H), 5.92 (s, 2H), 4.96 (s, 1H), 4.80 (d, J = 7.2 Hz, 1H), 4.67-4.61 (m, 2H), 3.75 (d, J = 6.4 Hz, 1H), 3.63 (d, J = 7.2 Hz, 1H), 3.43-3.42 (m, 4H), 2.87-2.85 (m, 1H), 1.91-1.83 (m, 4H), 1.32-1.21 (m, 8H). | 409.2 | A |

TABLE 1-continued

| No | DLK Ki (μM) | Structure | $^1$H NMR | MS [MS]$^+$ | Method |
|---|---|---|---|---|---|
| 76 | 0.008 | 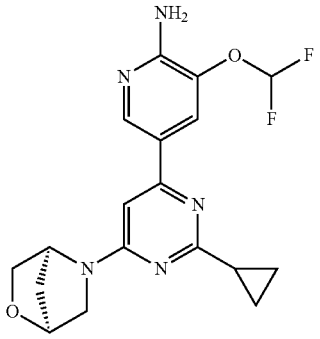 <br>5-[2-cyclopropyl-6-[(1S,4S)-2-oxa-5-azabicyclo[2.2.1]heptan-5-yl]pyrimidin-4-yl]-3-(difluoromethoxy)pyridin-2-amine | $^1$H NMR (400 MHz, Chloroform-d) δ 8.51 (s, 1H), 7.99 (s, 1H), 6.58 (t, J = 73.2 Hz, 1H), 6.29 (s, 1H), 5.12 (br.s, 1H), 4.91 (s, 2H), 4.74 (s, 1H), 3.91-3.87 (m, 2H), 3.51-3.44 (m, 2H), 2.12-2.05 (m, 1H), 2.00-1.92 (m, 2H), 1.15-1.07 (m, 2H), 0.97-0.95 (m, 2H).<br>$^1$H NMR (400 MHz, DMSO-d6) δ 8.63 (s, 1H), 7.99 (s, 1H), 7.18 (t, J = 74.0 Hz, 1H), 6.80 (br.s, 1H), 6.54 (s, 2H), 5.02 (s, 1H), 4.69 (s, 1H), 3.78 (d, J = 6.8 Hz, 1H), 3.64 (d, J = 7.2 Hz, 1H), 3.48-3.45 (m, 2H), 1.99-1.88 (m, 3H), 0.99-0.88 (m, 4H). | 376.1<br>376.1 | A |
| 77 | 0.16 | 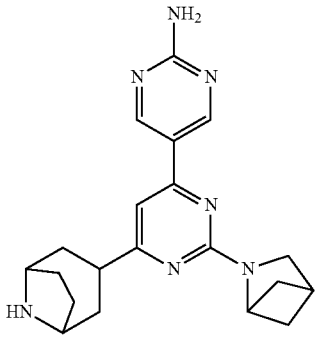 <br>5-[2-(3-azabicyclo[2.1.1]hexan-3-yl)-6-(8-azabicyclo[3.2.1]octan-3-yl)pyrimidin-4-yl]pyrimidin-2-amine | 1H NMR (400 MHz, DMSO) δ 8.94 (s, 2H), 8.40 (s, 1H), 7.12 (s, 2H), 7.03 (s, 1H), 4.93 (d, J = 7.1 Hz, 1H), 3.81 (s, 2H), 3.04-2.94 (m, 2H), 2.95-2.90 (m, 1H), 2.03-1.95 (m, 4H), 1.94-1.76 (m, 7H), 1.35 (dd, J = 4.4, 1.7 Hz, 2H). | 364 | C |
| 78 | 1.61 | 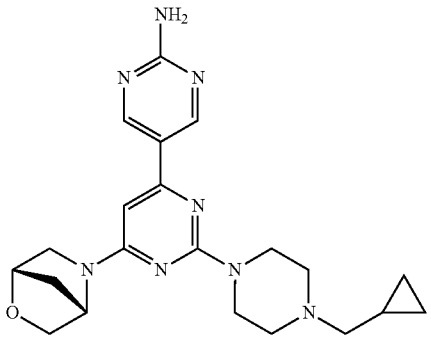 <br>5-[2-[4-(cyclopropylmethyl)piperazin-1-yl]-6-[(1S,4S)-2-oxa-5-azabicyclo[2.2.1]heptan-5-yl]pyrimidin-4-yl]pyrimidin-2-amine | 1H NMR (400 MHz, DMSO-d6) δ 8.92 (s, 2H), 7.00 (s, 2H), 4.98 (s, 1H), 4.68 (s, 1H), 3.78 (d, J = 6.7 Hz, 1H), 3.65 (d, J = 7.4 Hz, 1H), 3.46 (d, J = 10.1 Hz, 1H), 3.10-2.52 (m, 4H), 1.87 (s, 2H), 0.96 (s, 1H), 0.55 (d, J = 7.5 Hz, 2H), 0.21 (s, 2H), 3.10-2.52 (m, 4H). | 409 | E |

TABLE 1-continued

| No | DLK Ki (μM) | Structure | $^1$H NMR | MS [MS]$^+$ | Method |
|---|---|---|---|---|---|
| 79 | 0.06 | 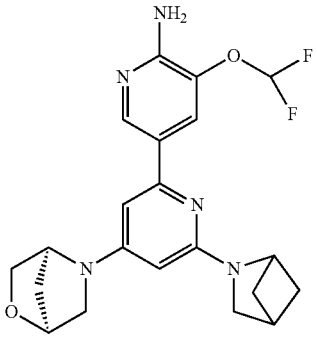 <br>5-[6-(3-azabicyclo[2.1.1]hexan-3-yl)-4-[(1S,4S)-2-oxa-5-azabicyclo[2.2.1]heptan-5-yl]-2-pyridyl]-3-(difluoromethoxy)pyridin-2-amine | 1H NMR (400 MHz, DMSO-d6) δ 8.48 (s, 1H), 7.91 (s, 1H), 7.15 (t, J = 74.0 Hz, 1H), 6.42 (s, 1H), 6.21 (s, 2H), 5.54 (s, 1H), 4.76-4.74 (m, 2H), 4.62 (s, 1H), 3.73 (d, J = 6.8 Hz, 1H), 3.63 (d, J = 7.6 Hz, 1H), 3.45 (d, J = 8.8 Hz, 1H), 3.33 (s, 2H), 3.10 (d, J = 10.4 Hz, 1H), 2.88-2.86 (m, 1H), 1.88-1.81 (m, 4H), 1.27-1.26 (m, 2H). | 416.1 | D |
| 80 | 0.08 | 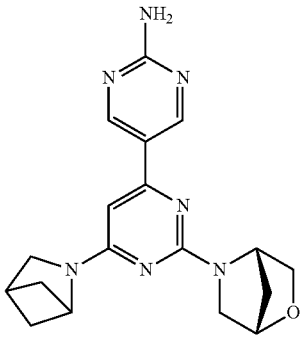 <br>5-[6-(3-azabicyclo[2.1.1]hexan-3-yl)-2-[(1S,4S)-2-oxa-5-azabicyclo[2.2.1]heptan-5-yl]pyrimidin-4-yl]pyrimidin-2-amine | $^1$H NMR (400 MHz, DMSO-d6) δ 8.91 (s, 2H), 6.99 (s, 2H), 6.38 (br.s, 1H), 4.97-4.91 (m, 2H), 4.62 (s, 1H), 3.78 (d, J = 6.4 Hz, 1H), 3.67 (d, J = 7.2 Hz, 1H), 3.47-3.41 (m, 4H), 2.96-2.90 (m, 1H), 1.98 (s, 2H), 1.87-1.79 (m, 2H), 1.33 (d, J = 2.8 Hz, 2H). | 351.8 | B |
| 81 | 0.038 | 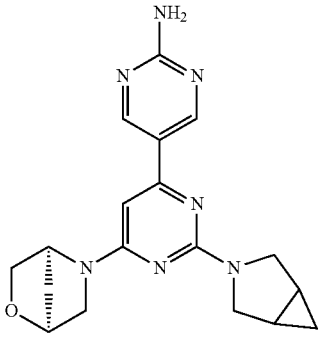 <br>5-[2-(3-azabicyclo[3.1.0]hexan-3-yl)-6-[(1S,4S)-2-oxa-5-azabicyclo[2.2.1]heptan-5-yl]pyrimidin-4-yl]pyrimidin-2-amine | $^1$H NMR (400 MHz, DMSO-d6) δ 8.89 (s, 2H), 7.00 (s, 2H), 6.54-6.10 (br.s, 1H), 5.08-4.96 (br.s, 1H), 4.66-4.62 (m, 1H), 3.84-3.81 (m, 2H), 3.77-3.75 (m, 1H), 3.63 (d, J = 7.2 Hz, 1H), 3.44-3.39 (m, 4H), 1.85 (s, 2H), 1.60-1.58 (m, 2H), 0.73-0.66 (m, 1H), 0.14-0.12 (m, 1H). | 352.19 | B |

TABLE 1-continued

| No | DLK Ki (μM) | Structure | $^1$H NMR | MS [MS]$^+$ | Method |
|---|---|---|---|---|---|
| 82 | 0.034 | 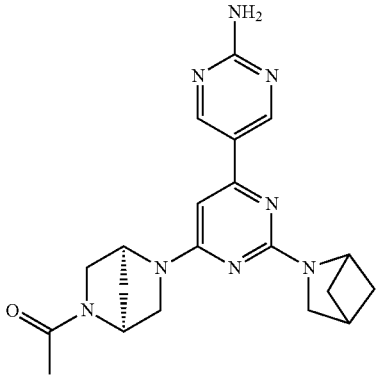 <br>1-[(1S,4S)-5-[6-(2-aminopyrimidin-5-yl)-2-(3-azabicyclo[2.1.1]hexan-3-yl)pyrimidin-4-yl]-2,5-diazabicyclo[2.2.1]heptan-2-yl]ethanone | $^1$H NMR (400 MHz, DMSO-d6) δ 8.91 (s, 2H), 7.00 (s, 2H), 6.68-6.12 (br.s, 1H), 5.11-4.95 (br.s, 1H), 4.88-4.65 (m, 2H), 3.55-3.33 (m, 5H), 3.28-3.23 (m, 1H), 2.88 (d, J = 6.8 Hz, 1H), 2.02 (s, 2H), 1.93 (s, 3H), 1.86-1.83 (m, 2H), 1.31 (s, 2H). | 393.15 | B |
| 83 | 0.17 | 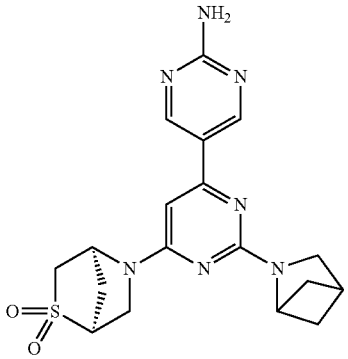 <br>[5-[2-(3-azabicyclo[2.1.1]hexan-3-yl)-][6-[(1S,4S)-2,2-dioxo-2$]]^[{6}-thia-][5-azabicyclo[2.2.1]heptan-5-yl]][pyrimidin-4-yl]pyrimidin-2-amine]<br>*5-[2-(3-azabicyclo[2.1.1]hexane-3-yl)-6-[(1S,4S)-2,2-dioxo-2λ6thia-5-azabicyclo[2.2.1]heptain-5-yl]pyrimidin-4-yl]pyrimidin-2-amine* | $^1$H NMR (400 MHz, Chloroform-d) δ 8.91 (s, 2H), 5.92 (s, 1H), 5.22 (s, 3H), 5.00-4.93 (m, 1H), 4.15-4.12 (m, 1H), 3.80 (s, 1H), 3.75-3.72 (m, 1H), 3.55 (s, 2H), 3.45-3.41 (m, 1H), 3.21-3.18 (m, 1H), 2.95-2.93 (m, 1H), 2.74-2.71 (m, 1H), 2.50-2.47 (m, 1H), 2.00 (s, 2H), 1.47 (d, J = 4.0 Hz, 2H). | 399.8 | B |
| 84 | 0.051 | 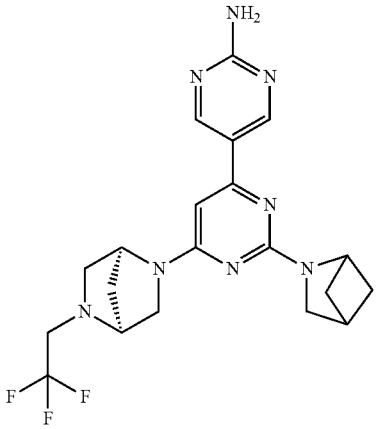 <br>5-[2-(3-azabicyclo[2.1.1]hexan-3-yl)-6-[(1S,4S)-5-(2,2,2-trifluoroethyl)-2,5-diazabicyclo[2.2.1]heptan-2-yl]pyrimidin-4-yl]pyrimidin-2-amine | $^1$H NMR (400 MHz, DMSO-d6) δ 8.91 (s, 2H), 7.00 (s, 2H), 6.50-6.15 (m, 1H), 4.83 (d, J = 6.8 Hz, 1H), 3.69 (s, 1H), 3.51-3.48 (m, 3H), 3.45-3.40 (m, 2H), 3.08-3.05 (m, 1H), 2.89-2.88 (m, 1H), 2.68-2.64 (m, 1H), 2.02 (s, 1H), 1.87-1.86 (m, 1H), 1.82-1.77 (m, 1H), 1.38 (s, 3H), 1.33-1.32 (m, 2H). | 433.1 | A |

TABLE 1-continued

| No | DLK Ki (μM) | Structure | $^1$H NMR | MS [MS]$^+$ | Method |
|---|---|---|---|---|---|
| 85 | 0.05 | 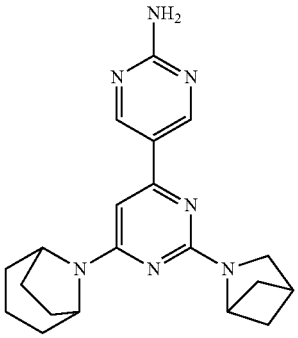 <br>5-[2-(3-azabicyclo[2.1.1]hexan-3-yl)-6-(8-azabicyclo[3.2.1]octan-8-yl) pyrimidin-4-yl]pyrimidin-2-amine | $^1$H NMR (400 MHz, DMSO-d6) δ 8.87 (s, 2H), 6.94 (s, 2H), 6.39 (s, 1H), 4.78-4.76 (m, 1H), 4.54 (br.s, 2H), 2.84-2.83 (m, 1H), 2.46 (s, 2H), 1.88 (s, 4H), 1.75-1.67 (m, 5H), 1.42-1.27 (m, 5H). | 363.9 | A |
| 86 | 0.21 | 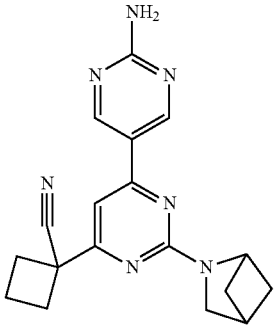 <br>1-[6-(2-aminopyrimidin-5-yl)-2-(3-azabicyclo[2.1.1]hexan-3-yl) pyrimidin-4-yl]cyclobutanecarbonitrile | 1H NMR (400 MHz, DMSO) δ 9.01 (s, 2H), 7.21 (br s, 2H), 7.20 (s, 1H), 5.06-4.80 (m, 1H), 3.54 (s, 2H), 2.99-2.89 (m, 1H), 2.85-2.73 (m, 2H), 2.70-2.59 (m, 2H), 2.34-2.14 (m, 1H), 2.14-1.90 (m, 3H), 1.45-1.33 (m, 2H). | 334 | I |
| 87 | 0.21 | 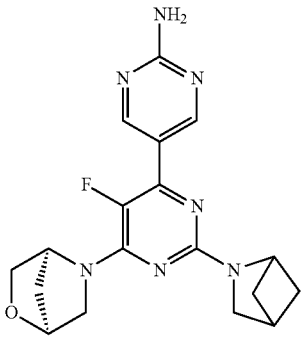 <br>5-[2-(3-azabicyclo[2.1.1]hexan-3-yl)-5-fluoro-6-[(1S,4S)-2-oxa-5-azabicyclo[2.2.1]heptan-5-yl] pyrimidin-4-yl]pyrimidin-2-amine | | 370 | B |

TABLE 1-continued

| No | DLK Ki (μM) | Structure | $^1$H NMR | MS [MS]$^+$ | Method |
|---|---|---|---|---|---|
| 88 | 0.41 | 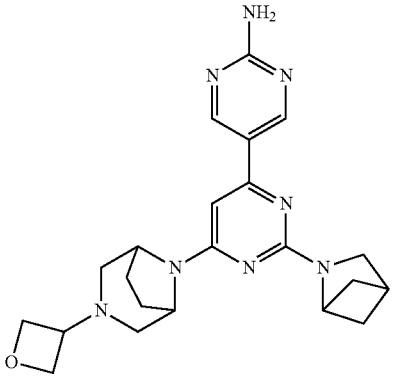 5-[2-(3-azabicyclo[2.1.1]hexan-3-yl)-6-[3-(oxetan-3-yl)-3-azabicyclo[3.2.1]octan-8-yl]pyrimidin-4-yl]pyrimidin-2-amine | 1H NMR (400 MHz, DMSO) δ 8.96 (s, 2H), 7.14-7.02 (m, 3H), 4.90 (d, J = 6.0 Hz, 1H), 4.49 (dt, J = 19.6, 6.2 Hz, 4H), 3.57-3.45 (m, 3H), 2.97-2.87 (m, 1H), 2.76-2.66 (m, 4H), 2.62 (s, 1H), 2.10-2.03 (m, 2H), 1.98 (s, 2H), 1.62 (s, 4H), 1.40-1.33 (m, 2H). | 420 | C |
| 89 | 0.01 | 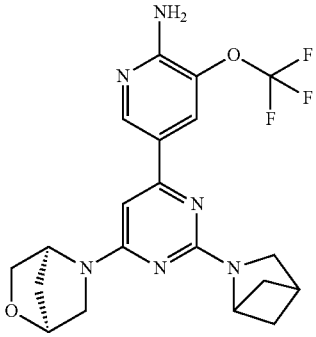 5-[2-(3-azabicyclo[2.1.1]hexan-3-yl)-6-[(1S,4S)-2-oxa-5-azabicyclo[2.2.1]heptan-5-yl]pyrimidin-4-yl]-3-(trifluoromethoxy)pyridin-2-amine | $^1$H NMR (400 MHz, DMSO-d6) δ 8.71 (s, 1H), 8.14 (s, 1H), 6.80 (s, 2H), 6.23 (br.s, 1H), 5.00 (br.s, 1H), 4.82 (d, J = 6.8 Hz, 1H), 4.67 (s, 1H), 3.77 (d, J = 6.4 Hz, 1H), 3.65 (d, J = 7.2 Hz, 1H), 3.47-3.45 (m, 4H), 2.90-2.88 (m, 1H), 1.94-1.86 (m, 4H), 1.32-1.31 (m, 2H). | 434.9 | A |
| 90 | 0.13 | 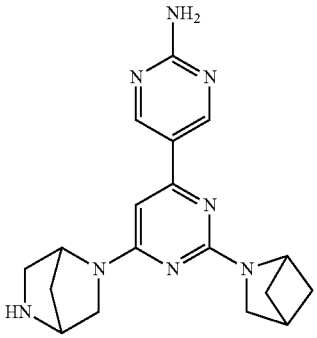 5-[2-(3-azabicyclo[2.1.1]hexan-3-yl)-6-(2,5-diazabicyclo[2.2.1]heptan-2-yl)pyrimidin-4-yl]pyrimidin-2-amine | $^1$H NMR (400 MHz, DMSO-d6) δ 8.90 (s, 2H), 6.98 (s, 2H), 6.43-6.09 (m, 1H), 4.90-4.65 (m, 2H), 3.69-3.61 (m, 1H), 3.50-3.39 (m, 5H), 2.88 (d, J = 8.0 Hz, 2H), 2.79-2.76 (m, 1H), 1.93 (s, 2H), 1.73-1.64 (m, 2H), 1.31-1.28 (m, 2H). | 351.18 | B |

TABLE 1-continued

| No | DLK Ki (μM) | Structure | $^1$H NMR | MS [MS]$^+$ | Method |
|---|---|---|---|---|---|
| 91 | 0.1 | 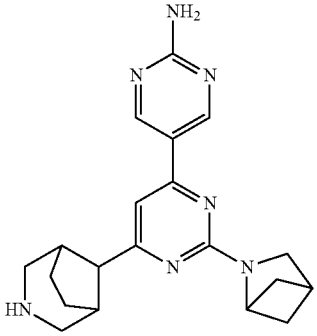 5-[2-(3-azabicyclo[2.1.1]hexan-3-yl)-6-(3-azabicyclo[3.2.1]octan-8-yl) pyrimidin-4-yl]pyrimidin-2-amine | 1H NMR (400 MHz, DMSO) δ 8.95 (s, 2H), 7.08 (s, 2H), 7.01 (s, 1H), 4.89 (d, J = 6.7 Hz, 1H), 3.49 (s, 2H), 2.96-2.90 (m, 1H), 2.81-2.68 (m, 5H), 2.55 (s, 2H), 1.97 (d, J = 1.2 Hz, 2H), 1.68-1.51 (m, 4H), 1.35 (dd, J = 4.3, 1.8 Hz, 2H) | 364 | C |
| 92 | 0.002 | 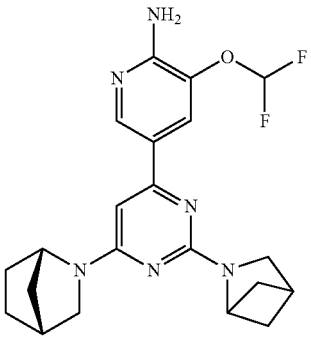 5-[6-[(1R,4S)-3-azabicyclo[2.2.1] heptan-3-yl]-2-(3-azabicyclo[2.1.1] hexan-3-yl)pyrimidin-4-yl]-3-(difluoromethoxy)pyridin-2-amine | 1H NMR (400 MHz, DMSO) δ 8.56 (s, 1H), 7.95 (s, 1H), 7.18 (t, J = 73.9 Hz, 1H), 6.38 (br s, 2H), 6.36-6.00 (m, 1H), 4.82 (d, J = 7.0 Hz, 1H), 4.77-4.45 (m, 1H), 3.45 (s, 2H), 3.42-3.34 (m, 1H), 3.16-3.04 (m, 1H), 2.88 (dd, J = 6.9, 3.1 Hz, 1H), 2.61 (s, 1H), 1.93 (s, 2H), 1.73-1.44 (m, 5H), 1.41-1.26 (m, 3H). | 415 | E |
| 93 | 0.01 | 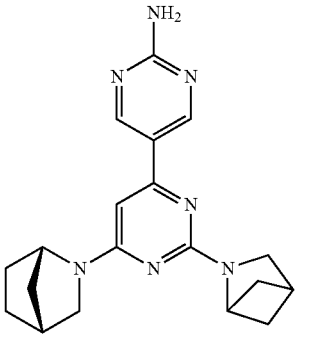 5-[6-[(1R,4S)-3-azabicyclo[2.2.1] heptan-3-yl]-2-(3-azabicyclo[2.1.1] hexan-3-yl)pyrimidin-4-yl]pyrimidin-2-amine | 1H NMR (400 MHz, DMSO) δ 8.88 (s, 2H), 6.93 (s, 2H), 6.35-6.10 (m, 1H), 4.82 (d, J = 7.0 Hz, 1H), 4.77-4.42 (m, 1H), 3.44 (s, 2H), 3.37 (d, J = 8.4 Hz, 1H), 3.21-2.98 (m, 1H), 2.91-2.83 (m, 1H), 2.61 (d, J = 1.9 Hz, 1H), 1.92 (s, 2H), 1.72-1.52 (m, 4H), 1.51-1.43 (m, 1H), 1.36 (t, J = 8.6 Hz, 1H), 1.31 (dd, J = 4.3, 1.6 Hz, 2H). | 350 | E |

TABLE 1-continued

| No | DLK Ki (μM) | Structure | $^1$H NMR | MS [MS]$^+$ | Method |
|---|---|---|---|---|---|
| 94 | 0.028 | 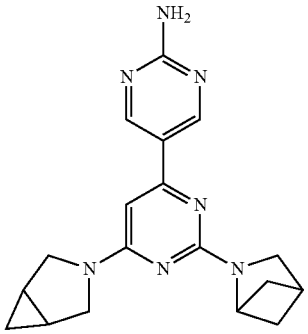 <br>5-[2-(3-azabicyclo[2.1.1]hexan-3-yl)-6-(3-azabicyclo[3.1.0]hexan-3-yl) pyrimidin-4-yl]pyrimidin-2-amine | $^1$H NMR (400 MHz, DMSO-d6) δ 8.89 (s, 2H), 6.97 (s, 2H), 6.19 (s, 1H), 4.82 (d, J = 6.4 Hz, 1H), 3.74 (br.s, 2H), 3.44-3.38 (m, 4H), 2.88-2.87 (m, 1H), 1.92-1.87 (m, 2H), 1.65 (s, 2H), 1.31 (s, 2H), 0.73-0.72 (m, 1H), 0.13-0.12 (m, 1H). | 335.8 | A |
| 95 | 0.68 | 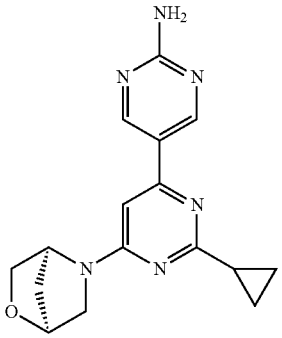 <br>5-[2-cyclopropyl-6-[(1S,4S)-2-oxa-5-azabicyclo[2.2.1]heptan-5-yl] pyrimidin-4-yl]pyrimidin-2-amine | $^1$H NMR (400 MHz, Methanol-d4) δ 8.76 (s, 2H), 6.45 (br.s, 1H), 5.02-4.98 (m, 1H), 4.63 (s, 1H), 3.78-3.77 (m, 1H), 3.70-3.68 (m, 1H), 3.43-3.42 (m, 1H), 3.38-3.30 (m, 1H), 1.98-1.97 (m, 1H), 1.88-1.85 (m, 2H), 1.18-0.97 (m, 2H), 0.86-0.83 (m, 2H). | 311.19 | A |
| 96 | 0.14 | 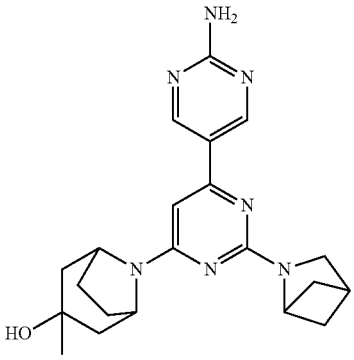 <br>8-[6-(2-aminopyrimidin-5-yl)-2-(3-azabicyclo[2.1.1]hexan-3-yl) pyrimidin-4-yl]-3-methyl-8-azabicyclo[3.2.1]octan-3-ol | $^1$H NMR (400 MHz, DMSO-d6) δ 8.90 (s, 2H), 6.97 (s, 2H), 6.41 (s, 1H), 4.81-4.79 (m, 1H), 4.70-4.44 (m, 2H), 3.43 (s, 2H), 2.70-2.69 (m, 2H), 2.25-2.24 (m, 2H), 1.92 (s, 2H), 1.80-1.73 (m, 4H), 1.64-1.61 (m, 2H), 1.31-1.30 (m, 2H), 0.95 (s, 3H). | 394.2 | A |

TABLE 1-continued

| No | DLK Ki (μM) | Structure | $^1$H NMR | MS [MS]$^+$ | Method |
|---|---|---|---|---|---|
| 97 | 0.32 | 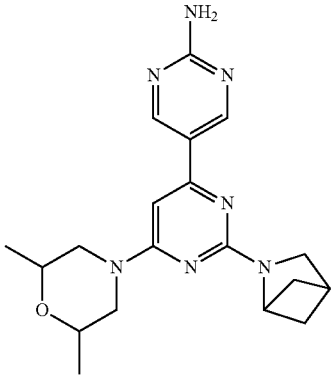 <br>5-[2-(3-azabicyclo[2.1.1]hexan-3-yl)-6-(2,6-dimethylmorpholin-4-yl) pyrimidin-4-yl]pyrimidin-2-amine | $^1$H NMR (400 MHz, Chloroform-d) δ 8.88 (s, 2H), 6.08 (s, 1H), 5.70 (s, 2H), 4.94 (d, J = 7.2 Hz, 1H), 4.21 (d, J = 12.8 Hz, 2H), 3.72-3.64 (m, 2H), 3.57 (s, 2H), 2.94-2.91 (m, 1H), 2.62-2.56 (m, 2H), 1.98 (d, J = 2.0 Hz, 2H), 1.47 (dd, J = 2.0, 4.4 Hz, 2H), 1.28 (d, J = 6.8 Hz, 6H). | 368.0 | A |
| 98 | 0.101 | 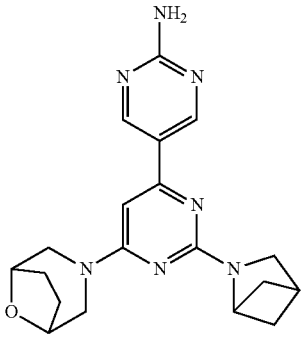 <br>5-[2-(3-azabicyclo[2.1.1]hexan-3-yl)-6-(8-oxa-3-azabicyclo[3.2.1] octan-3-yl)pyrimidin-4-yl]pyrimidin-2-amine | $^1$H NMR (400 MHz, Methanol-d4) δ 8.85 (s, 2H), 6.30 (s, 1H), 4.88-4.86 (m, 1H), 4.44-4.43 (m, 2H), 4.12-4.06 (m, 2H), 3.53 (s, 2H), 3.10 (dd, J = 2.0, 12.8 Hz, 2H), 2.92-2.90 (m, 1H), 2.00 (s, 1H), 1.95-1.91 (m, 2H), 1.87-1.79 (m, 3H), 1.40 (dd, J = 2.0, 4.4 Hz, 2H). | 365.9 | A |
| 99 | 0.043 | 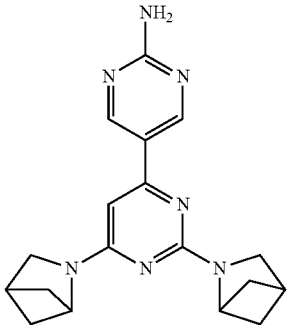 <br>5-[2,6-bis(3-azabicyclo[2.1.1] hexan-3-yl)pyrimidin-4-yl]pyrimidin-2-amine | $^1$H NMR (400 MHz, DMSO-d6) δ 8.90 (s, 2H), 6.97 (s, 2H), 6.34 (s, 1H), 4.84-4.82 (m, 2H), 3.40 (s, 4H), 2.96-2.86 (m, 2H), 1.95 (d, J = 19.6 Hz, 4H), 1.32-1.31 (m, 4H). | 336.1 | A |

TABLE 1-continued

| No | DLK Ki (μM) | Structure | $^1$H NMR | MS [MS]$^+$ | Method |
|---|---|---|---|---|---|
| 100 | 0.001 | 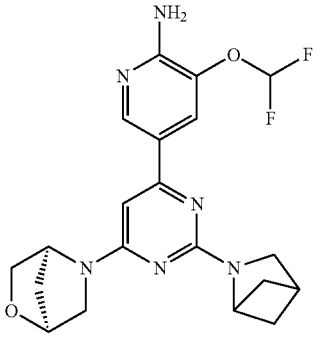 5-[2-(3-azabicyclo[2.1.1]hexan-3-yl)-6-[(1S,4S)-2-oxa-5-azabicyclo[2.2.1]heptan-5-yl]pyrimidin-4-yl]-3-(difluoromethoxy)pyridin-2-amine | $^1$H NMR (400 MHz, DMSO-d6) δ 8.58 (s, 1H), 7.97 (s, 1H), 7.18 (t, J = 73.6 Hz, 1H), 6.47 (s, 2H), 6.25 (br.s, 1H), 5.00-4.97 (m, 1H), 4.85-4.83 (m, 1H), 4.68 (s, 1H), 3.78 (d, J = 6.4 Hz, 1H), 3.66 (d, J = 7.2 Hz, 1H), 3.52-3.46 (m, 4H), 2.90-2.89 (m, 1H), 1.95-1.87 (m, 4H), 1.32 (s, 2H). | 416.9 | A |
| 101 | 0.026 | 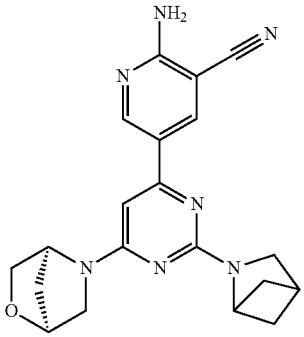 2-amino-5-[2-(3-azabicyclo[2.1.1]hexan-3-yl)-6-[(1S,4S)-2-oxa-5-azabicyclo[2.2.1]heptan-5-yl]pyrimidin-4-yl]pyridine-3-carbonitrile | $^1$H NMR (400 MHz, DMSO-d6) δ 8.95 (s, 1H), 8.54 (s, 1H), 7.26 (br.s, 2H), 6.50 (br.s, 1H), 5.04-5.01 (m, 1H), 4.86 (s, 1H), 4.68 (s, 1H), 3.78 (d, J = 7.2 Hz, 1H), 3.66 (d, J = 7.2 Hz, 1H), 3.47-3.44 (m, 4H), 2.92-2.89 (m, 1H), 1.95-1.87 (m, 4H), 1.35-1.33 (m, 2H). | 375.9 | A |
| 102 | 0.024 | 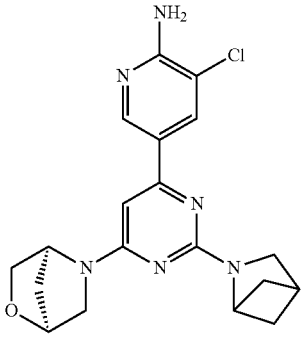 5-[2-(3-azabicyclo[2.1.1]hexan-3-yl)-6-[(1S,4S)-2-oxa-5-azabicyclo[2.2.1]heptan-5-yl]pyrimidin-4-yl]-3-chloro-pyridin-2-amine | $^1$H NMR (400 MHz, DMSO-d6) δ 8.67 (s, 1H), 8.23 (s, 1H), 6.66 (s, 2H), 6.30-6.20 (m, 1H), 5.04-4.98 (m, 1H), 4.93-4.83 (m, 1H), 4.71-4.67 (m, 1H), 3.77 (d, J = 6.0 Hz, 1H), 3.66 (d, J = 7.2 Hz, 1H), 3.52-3.44 (m, 4H), 2.90-2.88 (m, 1H), 1.94-1.91 (m, 2H), 1.90-1.86 (m, 2H), 1.33-1.31 (m, 2H). | 385.0 | A |

TABLE 1-continued

| No | DLK Ki (μM) | Structure | $^1$H NMR | MS [MS]$^+$ | Method |
|---|---|---|---|---|---|
| 103 | 0.018 | 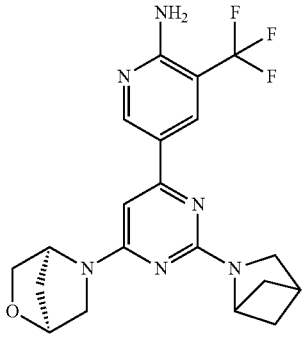 5-[2-(3-azabicyclo[2.1.1]hexan-3-yl)-6-[(1S,4S)-2-oxa-5-azabicyclo[2.2.1]heptan-5-yl]pyrimidin-4-yl]-3-(trifluoromethyl)pyridin-2-amine | $^1$H NMR (400 MHz, DMSO + $H_2O$-d6) δ 8.76-8.75 (m, 1H), 8.32-8.28 (m, 1H), 6.60-6.10 (m, 1H), 5.20-5.00 (m, 1H), 4.90-4.88 (m, 1H), 4.69-4.70 (m, 1H), 3.79-3.77 (m, 2H), 3.51-3.48 (m, 4H), 2.93-2.91 (m, 1H), 2.02-1.99 (m, 2H), 1.95-1.89 (m, 2H), 1.35 (s, 2H). | 419.0 | A |
| 104 | 0.069 | 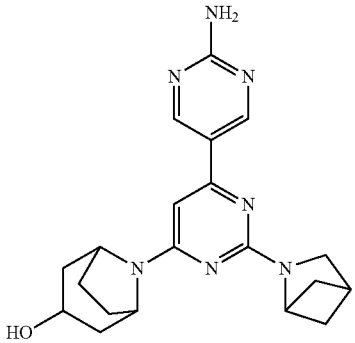 8-[6-(2-aminopyrimidin-5-yl)-2-(3-azabicyclo[2.1.1]hexan-3-yl)pyrimidin-4-yl]-8-azabicyclo[3.2.1]octan-3-ol | $^1$H NMR (400 MHz, DMSO-d6) δ 8.90 (s, 2H), 6.97 (s, 2H), 6.42 (s, 1H), 4.82-4.80 (m, 1H), 4.59-4.54 (m, 4H), 3.90-3.86 (m, 1H), 2.89-2.87 (m, 1H), 2.26-2.25 (m, 2H), 1.99-1.86 (m, 7H), 1.65-1.61 (m, 2H), 1.32-1.30 (m, 2H). | 380.1 | A |
| 105 | 1.36 | 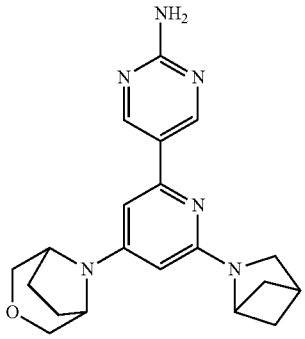 5-[6-(3-azabicyclo[2.1.1]hexan-3-yl)-4-(3-oxa-8-azabicyclo[3.2.1]octan-8-yl)-2-pyridyl]pyrimidin-2-amine | 1H NMR (400 MHz, DMSO) δ 8.86 (s, 2H), 6.75 (s, 2H), 6.61 (d, J = 1.7 Hz, 1H), 5.81 (d, J = 1.7 Hz, 1H), 4.82-4.72 (m, 1H), 4.35 (s, 2H), 3.68 (d, J = 10.8 Hz, 2H), 3.44 (d, J = 10.9 Hz, 2H), 3.37 (s, 2H), 2.95-2.87 (m, 1H), 1.97-1.91 (m, 6H), 1.30 (dd, J = 4.3, 1.8 Hz, 2H). | 365 | D |

TABLE 1-continued

| No | DLK Ki (μM) | Structure | $^1$H NMR | MS [MS]$^+$ | Method |
|---|---|---|---|---|---|
| 106 | 0.98 | 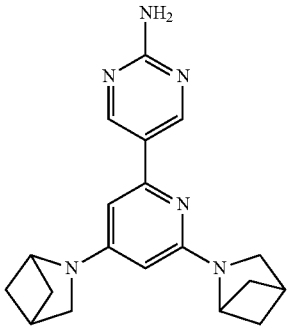 5-[4,6-bis(3-azabicyclo[2.1.1] hexan-3-yl)-2-pyridyl]pyrimidin-2-amine | 1H NMR (400 MHz, DMSO) δ 8.84 (s, 2H), 6.73 (s, 2H), 6.49 (d, J = 1.6 Hz, 1H), 5.67 (d, J = 1.6 Hz, 1H), 4.77 (dd, J = 5.4, 1.6 Hz, 1H), 4.63 (d, J = 6.8 Hz, 1H), 3.36 (s, 2H), 2.96-2.88 (m, 2H), 1.92 (dd, J = 16.5, 1.6 Hz, 4H), 1.35-1.25 (m, 4H). | 335 | D |
| 107 | 0.13 | 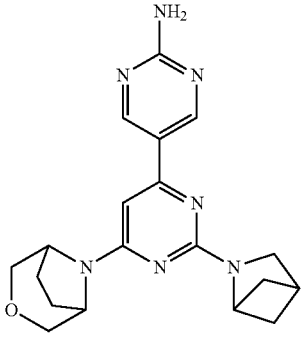 5-[2-(3-azabicyclo[2.1.1]hexan-3-yl)-6-(3-oxa-8-azabicyclo[3.2.1]octan-8-yl)pyrimidin-4-yl]pyrimidin-2-amine | $^1$H NMR (400 MHz, DMSO-d6) δ 8.92 (s, 2H), 7.00 (s, 2H), 6.52 (s, 1H), 4.82 (d, J = 6.8 Hz, 1H), 4.65-4.50 (m, 2H), 3.62 (d, J = 10.8 Hz, 4H), 3.53 (d, J = 10.4 Hz, 2H), 2.89-2.87 (m, 1H), 1.96-1.86 (m, 6H), 1.32 (dd, J = 2.0, 4.4 Hz, 2H). | 366.1 | A |
| 108 | 0.32 | 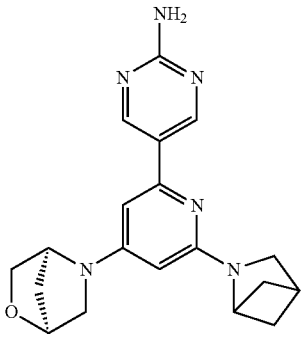 5-[6-(3-azabicyclo[2.1.1] hexan-3-yl)-4-[(1S,4S)-2-oxa-5-azabicyclo[2.2.1]heptan-5-yl]-2-pyridyl]pyrimidin-2-amine | 1H NMR (400 MHz, DMSO) δ 8.85 (s, 2H), 6.75 (s, 2H), 6.44 (s, 1H), 5.57 (s, 1H), 4.78-4.76 (m, 2H), 4.65 (s, 1H), 3.75 (dd, J = 7.3, 1.1 Hz, 1H), 3.66 (d, J = 7.4 Hz, 1H), 3.47 (dd, J = 9.7, 1.3 Hz, 1H), 3.36 (s, 2H), 3.12 (d, J = 9.8 Hz, 1H), 2.90 (dt, J = 6.2, 2.8 Hz, 1H), 1.93-1.82 (m, 4H), 1.33-1.27 (m, 2H). | 351 | D |

TABLE 1-continued

| No | DLK Ki (μM) | Structure | $^1$H NMR | MS [MS]$^+$ | Method |
|---|---|---|---|---|---|
| 109 | 0.48 | 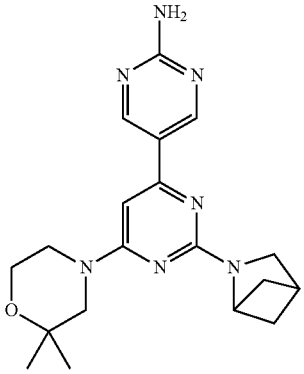 5-[2-(3-azabicyclo[2.1.1]hexan-3-yl)-6-(2,2-dimethylmorpholin-4-yl) pyrimidin-4-yl]pyrimidin-2-amine | No NMR | 368 | C |
| 110 | 0.02 | 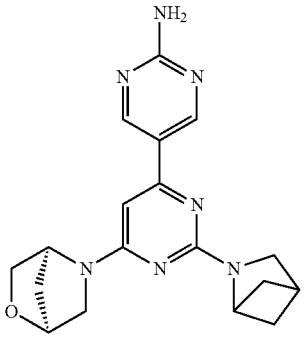 5-[2-(3-azabicyclo[2.1.1]hexan-3-yl)-6-[(1S,4S)-2-oxa-5-azabicyclo[2.2.1] heptan-5-yl]pyrimidin-4-yl]pyrimidin-2-amine | $^1$H NMR (400 MHz, DMSO-d6) δ 8.91 (s, 2H), 6.99 (s, 2H), 6.30-6.10 (m, 1H), 5.10-4.90 (m, 1H), 4.83 (d, J = 6.8 Hz, 1H), 4.70-4.64 (m, 1H), 3.85-3.76 (m, 1H), 3.66-3.64 (m, 1H), 3.45-3.38 (m, 4H), 2.91-2.87 (m, 1H), 1.93-1.86 (m, 4H), 1.34-1.29 (m, 2H). | 352.1 | A |
| 111 | 0.15 | 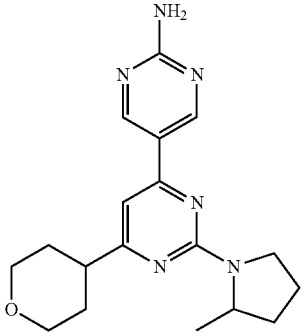 5-[2-(2-methylpyrrolidin-1-yl)-6-tetrahydropyran-4-yl-pyrimidin-4-yl]pyrimidin-2-amine | 1H NMR (400 MHz, DMSO) δ 8.95 (s, 2H), 7.08 (s, 2H), 6.98 (s, 1H), 4.29-4.21 (m, 1H), 3.96-3.91 (m, 2H), 3.63-3.48 (m, 2H), 3.43 (td, J = 11.2, 3.4 Hz, 2H), 2.78-2.70 (m, 1H), 2.09-1.96 (m, 2H), 1.92-1.85 (m, 1H), 1.82-1.73 (m, 4H), 1.71-1.64 (m, 1H), 1.25 (d, J = 6.2 Hz, 3H). | 341 | C |

TABLE 1-continued

| No | DLK Ki (μM) | Structure | $^1$H NMR | MS [MS]$^+$ | Method |
|---|---|---|---|---|---|
| 112 | 0.06 | 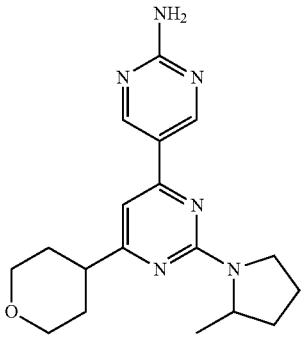 <br>5-[2-(2-methylpyrrolidin-1-yl)-6-tetrahydropyran-4-yl-pyrimidin-4-yl]pyrimidin-2-amine | 1H NMR (400 MHz, DMSO) δ 8.95 (s, 2H), 7.08 (s, 2H), 6.98 (s, 1H), 4.25 (dd, J = 6.1, 4.2 Hz, 1H), 3.94 (dd, J = 9.7, 2.3 Hz, 2H), 3.64-3.49 (m, 2H), 3.43 (td, J = 11.3, 3.1 Hz, 2H), 2.79-2.69 (m, 1H), 2.10-1.95 (m, 2H), 1.91-1.72 (m, 5H), 1.72-1.63 (m, 1H), 1.25 (d, J = 6.3 Hz, 3H). | 341 | C |
| 113 | 0.74 | 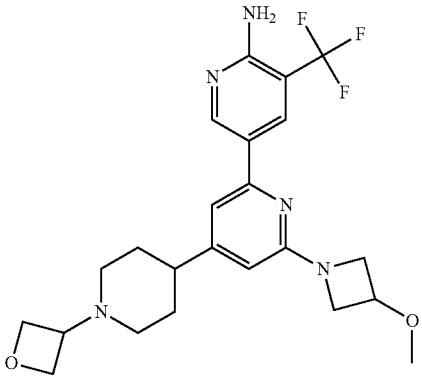 <br>5-[6-(3-methoxyazetidin-1-yl)-4-[1-(oxetan-3-yl)-4-piperidyl]-2-pyridyl]-3-(trifluoromethyl)pyridin-2-amine | $^1$H NMR (400 MHz, Chloroform-d) δ 8.75 (s, 1H), 8.36 (s, 1H), 6.96 (s, 1H), 6.11 (s, 1H), 5.64 (s, 2H), 4.74-4.67 (m, 4H), 4.38-4.23 (m, 3H), 3.93-3.90 (m, 2H), 3.63-3.56 (m, 1H), 3.35 (s, 3H), 2.98 (d, J = 10.8 Hz, 2H), 2.54-2.46 (m, 1H), 2.06-1.99 (m, 2H), 1.93-1.88 (m, 4H). | 464.0 | F |
| 114 | 0.69 | 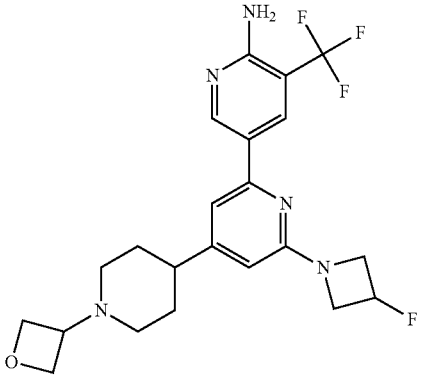 <br>5-[6-(3-fluoroazetidin-1-yl)-4-[1-(oxetan-3-yl)-4-piperidyl]-2-pyridyl]-3-(trifluoromethyl)pyridin-2-amine | $^1$H NMR (400 MHz, Chloroform-d) δ 8.76 (s, 1H), 8.36 (s, 1H), 6.89 (s, 1H), 6.14 (s, 1H), 5.53 (s, 2H), 4.74-4.69 (m, 5H), 4.38-4.31 (m, 2H), 4.20-4.11 (m, 2H), 3.63-3.60 (m, 1H), 3.00-2.98 (m, 2H), 2.54-2.49 (m, 1H), 2.04-1.90 (m, 6H). | 452.0 | F |

TABLE 1-continued

| No | DLK Ki (μM) | Structure | $^1$H NMR | MS [MS]$^+$ | Method |
|---|---|---|---|---|---|
| 115 | 0.49 | 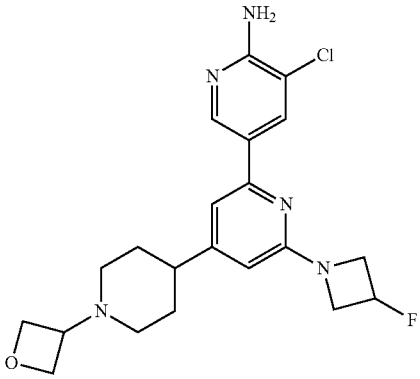 <br>3-chloro-5-[6-(3-fluoroazetidin-1-yl)-4-[1-(oxetan-3-yl)-4-piperidyl]-2-pyridyl]pyridin-2-amine | $^1$H NMR (400 MHz, Methanol-d4) δ 8.52 (s, 1H), 8.20 (s, 1H), 7.01 (s, 1H), 6.24 (s, 1H), 5.66-5.34 (m, 1H), 4.72-4.71 (m, 2H), 4.66-4.62 (m, 2H), 4.40-4.31 (m, 2H), 4.14-4.11 (m, 1H), 4.08-4.05 (m, 1H), 3.56-3.53 (m, 1H), 2.94-2.92 (m, 2H), 2.61-2.52 (m, 1H), 2.03-2.00 (m, 2H), 1.97-1.78 (m, 4H). | 418.15 | F |
| 116 | 1.61 | 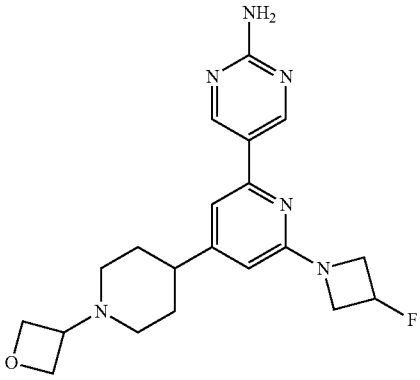 <br>5-[6-(3-fluoroazetidin-1-yl)-4-[1-(oxetan-3-yl)-4-piperidyl]-2-pyridyl]pyrimidin-2-amine | $^1$H NMR (400 MHz, Methanol-d4) δ 8.86 (s, 2H), 7.01 (s, 1H), 6.26 (s, 1H), 5.53-5.36 (m, 1H), 4.74-4.71 (m, 2H), 4.65-4.62 (m, 2H), 4.40-4.31 (m, 2H), 4.14-4.05 (m, 2H), 3.56-3.52 (m, 1H), 2.93 (d, J = 12.0 Hz, 2H), 2.64-2.56 (m, 1H), 2.03-1.99 (m, 2H), 1.97-1.81 (m, 4H). | 385.16 | F |
| 117 | 0.71 | 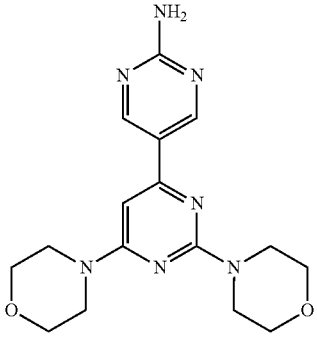 <br>5(2,6-dimorpholinopyrimidin-4-yl)pyrimidin-2-amine | 1H NMR (400 MHz, DMSO) δ 8.93 (s, 2H), 7.00 (s, 2H), 6.60 (s, 1H), 3.70-3.60 (m, 16H). | 344 | G |

TABLE 1-continued

| No | DLK Ki (μM) | Structure | $^1$H NMR | MS [MS]$^+$ | Method |
|---|---|---|---|---|---|
| 118 | 0.001 | 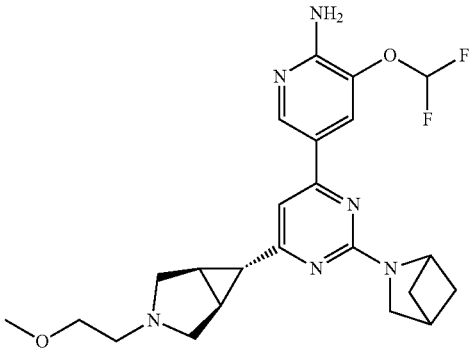 <br>5-[2-(3-azabicyclo[2.1.1]hexan-3-yl)-6-[(1R,5S)-3-(2-methoxyethyl)-3-azabicyclo[3.1.0]hexan-6-yl]pyrimidin-4-yl]-3-(difluoromethoxy)pyridin-2-amine | $^1$H NMR (400 MHz, Chloroform-d) δ 8.56 (s, 1H), 8.01 (s, 1H), 6.71 (s, 1H), 6.57 (t, J = 73.6 Hz, 1H), 4.97-4.93 (m, 3H), 3.55 (s, 2H), 3.50-3.47 (m, 2H), 3.38 (s, 3H), 3.22 (d, J = 8.4 Hz, 2H), 2.94-2.92 (m, 1H), 2.72-2.69 (m, 2H), 2.52-2.50 (m, 2H), 2.32 (s, 1H), 2.09 (s, 2H), 1.98 (s, 2H), 1.46-1.44 (m, 2H). | 459.15 | C |
| 119 | 0.002 | 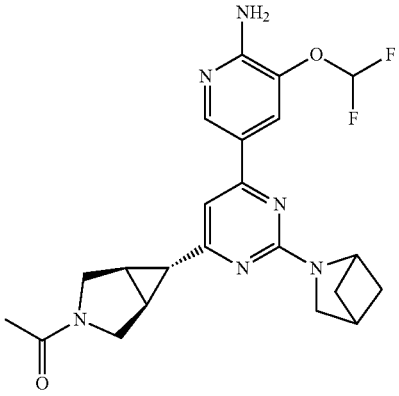 <br>1-[(1R,5S)-6-[6-[6-amino-5-(difluoromethoxy)-3-pyridyl]-2-(3-azabicyclo[2.1.1]hexan-3-yl)pyrimidin-4-yl]-3-azabicyclo[3.1.0]hexan-3-yl]ethanone | $^1$H NMR (400 MHz, Chloroform-d) δ 8.58 (s, 1H), 8.03 (s, 1H), 6.71 (s, 1H), 6.58 (t, J = 73.2 Hz, 1H), 4.96 (s, 3H), 3.97 (d, J = 12.0 Hz, 1H), 3.73 (s, 2H), 3.56 (s, 2H), 3.00-2.95 (m, 1H), 2.31 (s, 2H), 2.07-2.00 (m, 5H), 1.72 (s, 1H), 1.60 (d, J = 3.6 Hz, 1H), 1.47 (s, 2H). | 443.15 | C |
| 120 | 0.01 | 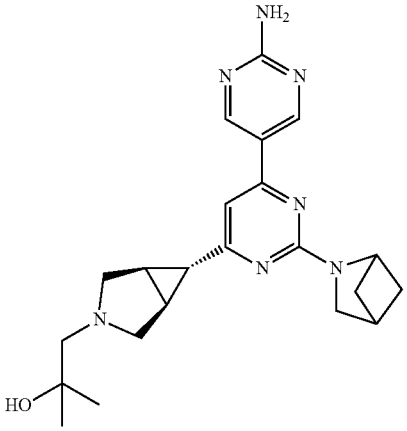 <br>1-[(1R,5S)-6-[6-(2-aminopyrimidin-5-yl)-2-(3-azabicyclo[2.1.1]hexan-3-yl)pyrimidin-4-yl]-3-azabicyclo[3.1.0]hexan-3-yl]-2-methyl-propan-2-ol | $^1$H NMR (400 MHz, Chloroform-d) δ 8.95 (s, 2H), 6.65 (s, 1H), 5.31 (s, 2H), 4.97 (d, J = 7.2 Hz, 1H), 3.56 (s, 2H), 3.30 (d, J = 9.2 Hz, 2H), 2.98-2.93 (m, 2H), 2.75 (d, J = 8.8 Hz, 2H), 2.50 (s, 2H), 2.10 (s, 1H), 2.02 (s, 2H), 1.99 (s, 2H), 1.46-1.45 (m, 2H), 1.19 (s, 6H). | 408.15 | C |

TABLE 1-continued

| No | DLK Ki (μM) | Structure | $^1$H NMR | MS [MS]$^+$ | Method |
|---|---|---|---|---|---|
| 121 | 0.003 | 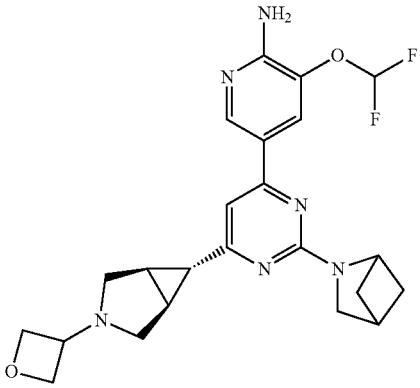 <br>5-[2-(3-azabicyclo[2.1.1]hexan-3-yl)-6-[(1R,5S)-3-(oxetan-3-yl)-3-azabicyclo[3.1.0]hexan-6-yl]pyrimidin-4-yl]-3-(difluoromethoxy)pyridin-2-amine | $^1$H NMR (400 MHz, Chloroform-d) δ 8.58 (s, 1H), 8.03 (s, 1H), 6.72 (s, 1H), 6.58 (t, J = 73.2 Hz, 1H), 4.97-4.93 (m, 3H), 4.71-4.67 (m, 2H), 4.69-4.61 (m, 2H), 3.82-3.79 (m, 1H), 3.56 (s, 2H), 3.14 (d, J = 8.8 Hz, 2H), 2.95-2.93 (m, 1H), 2.50 (d, J = 8.4 Hz, 2H), 2.35-2.34 (m, 1H), 2.13 (s, 2H), 1.99 (s, 2H), 1.49-1.45 (m, 2H). | 457.12 | C |
| 122 | 0.02 | 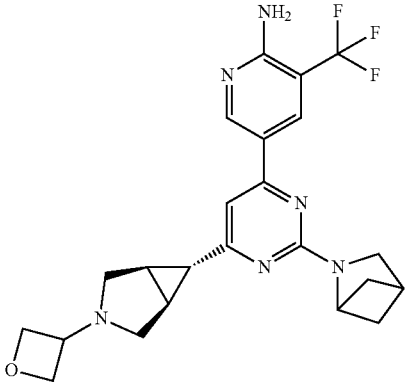 <br>5-[2-(3-azabicyclo[2.1.1]hexan-3-yl)-6-[(1R,5S)-3-(oxetan-3-yl)-3-azabicyclo[3.1.0]hexan-6-yl]pyrimidin-4-yl]-3-(trifluoromethyl)pyridin-2-amine | $^1$H NMR (400 MHz, Chloroform-d) δ 8.86 (s, 1H), 8.41 (s, 1H), 6.71 (s, 1H), 4.98-4.92 (m, 1H), 4.69-4.62 (m, 2H), 4.62-4.59 (m, 2H), 3.82-3.75 (m, 1H), 3.55 (s, 2H), 3.12 (d, J = 8.8 Hz, 2H), 2.93-2.92 (m, 1H), 2.49 (d, J = 8.4 Hz, 2H), 2.35-2.33 (m, 1H), 2.12 (s, 2H), 2.00-1.98 (m, 2H), 1.45-1.43 (m, 2H). | 458.9 | C |
| 123 | 0.02 | 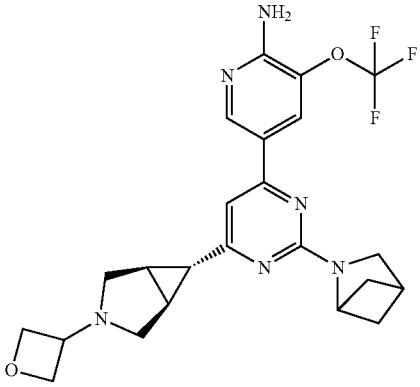 <br>5-[2-(3-azabicyclo[2.1.1]hexan-3-yl)-6-[(1R,5S)-3-(oxetan-3-yl)-3-azabicyclo[3.1.0]hexan-6-yl]pyrimidin-4-yl]-3-(trifluoromethoxy)pyridin-2-amine | $^1$H NMR (400 MHz, DMSO-d6) δ 8.73 (s, 1H), 8.15 (s, 1H), 7.10 (s, 1H), 6.92 (s, 2H), 4.85-4.83 (m, 1H), 4.57-4.54 (m, 2H), 4.46-4.43 (m, 2H), 3.72-3.69 (m, 1H), 3.45 (s, 2H), 3.06 (d, J = 8.8 Hz, 2H), 2.91-2.89 (m, 1H), 2.40 (d, J = 8.4 Hz, 2H), 2.29 (s, 1H), 2.05 (s, 2H), 1.96 (s, 2H), 1.33-1.32 (m, 2H). | 474.9 | C |

TABLE 1-continued

| No | DLK Ki (μM) | Structure | $^1$H NMR | MS [MS]$^+$ | Method |
|---|---|---|---|---|---|
| 124 | 0.02 | 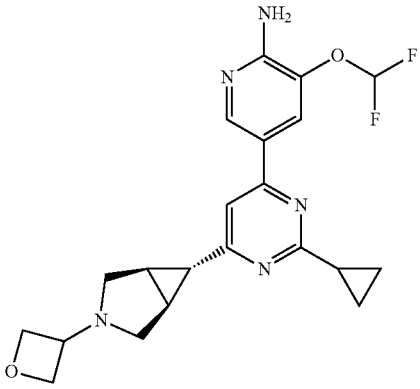 <br>5-[2-cyclopropyl-6-[(1R,5S)-3-(oxetan-3-yl)-3-azabicyclo[3.1.0]hexan-6-yl]pyrimidin-4-yl]-3-(difluoromethoxy)pyridin-2-amine | $^1$H NMR (400 MHz, Chloroform-d) δ 8.58 (s, 1H), 8.04 (s, 1H), 7.19 (s, 1H), 6.58 (t, J = 73.2 Hz, 1H), 4.97 (s, 2H), 4.69-4.59 (m, 4H), 3.81-3.75 (m, 1H), 3.12 (d, J = 8.8 Hz, 2H), 2.49 (d, J = 8.4 Hz, 2H), 2.42-2.40 (m, 1H), 2.18-2.15 (m, 1H), 2.11 (s, 2H), 1.11-1.08 (m, 2H), 1.00-0.97 (m, 2H). | 416.1 | C |
| 125 | 0.11 | 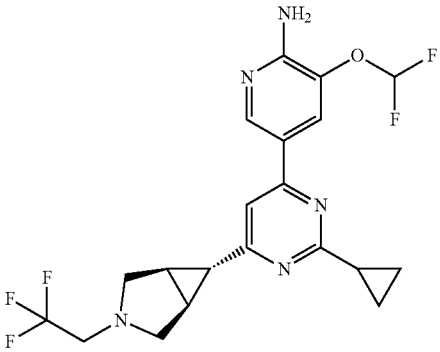 <br>5-[2-cyclopropyl-6-[(1R,5S)-3-(2,2,2-trifluoroethyl)-3-azabicyclo[3.1.0]hexan-6-yl]pyrimidin-4-yl]-3-(difluoromethoxy)pyridin-2-amine | $^1$H NMR (400 MHz, Chloroform-d) δ 8.53 (s, 1H), 7.97 (s, 1H), 7.14 (s, 1H), 6.52 (t, J = 73.6 Hz, 1H), 4.93 (s, 2H), 3.26-3.20 (m, 2H), 3.05-3.00 (m, 2H), 2.71 (d, J = 8.8 Hz, 2H), 2.27-2.25 (m, 1H), 2.11-2.10 (m, 1H), 2.04 (s, 2H), 1.18-1.03 (m, 2H), 0.96-0.91 (m, 2H). | 442.1 | C |
| 126 | 0.003 | 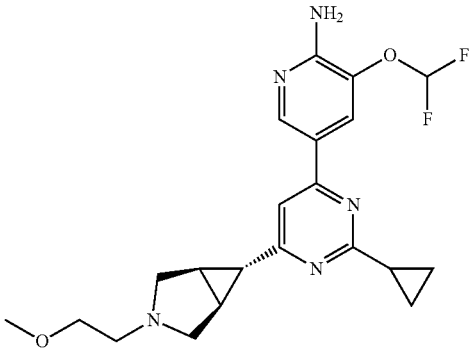 <br>5-[2-cyclopropyl-6-[(1R,5S)-3-(2-methoxyethyl)-3-azabicyclo[3.1.0]hexan-6-yl]pyrimidin-4-yl]-3-(difluoromethoxy)pyridin-2-amine | $^1$H NMR (400 MHz, Chloroform-d) δ 8.55 (s, 1H), 8.02 (s, 1H), 7.17 (s, 1H), 6.58 (t, J = 73.2 Hz, 1H), 4.96 (s, 2H), 3.46 (t, J = 6.4 Hz, 2H), 3.36 (s, 3H), 3.21 (d, J = 9.2 Hz, 2H), 2.70-2.67 (m, 2H), 2.49 (d, J = 8.8 Hz, 2H), 2.38 (s, 1H), 2.17-2.15 (m, 1H), 2.06 (s, 2H), 1.11-1.18 (m, 2H), 0.99-0.96 (m, 2H). | 418.2 | C |

TABLE 1-continued

| No | DLK Ki (μM) | Structure | $^1$H NMR | MS [MS]$^+$ | Method |
|---|---|---|---|---|---|
| 127 | 0.001 | 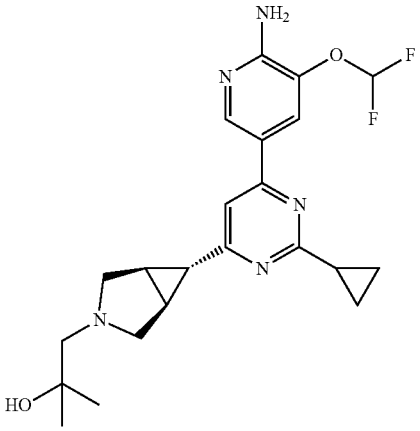 <br>1-[(1R,5S)-6-[6-[6-amino-5-(difluoromethoxy)-3-pyridyl]-2-cyclopropyl-pyrimidin-4-yl]-3-azabicyclo[3.1.0]hexan-3-yl]-2-methyl-propan-2-ol | $^1$H NMR (400 MHz, Chloroform-d) δ 8.60 (s, 1H), 8.05 (s, 1H), 7.18 (s, 1H), 6.60 (t, J = 73.2 Hz, 1H), 4.99 (s, 2H), 3.30 (d, J = 8.8 Hz, 2H), 2.92-2.85 (m, 1H), 2.75 (d, J = 8.4 Hz, 2H), 2.51 (s, 2H), 2.34 (s, 1H), 2.20-2.16 (m, 1H), 2.10 (s, 2H), 1.19 (s, 6H), 1.14-1.11 (m, 2H), 1.10-1.00 (m, 2H). | 432.2 | C |
| 128 | 0.008 | 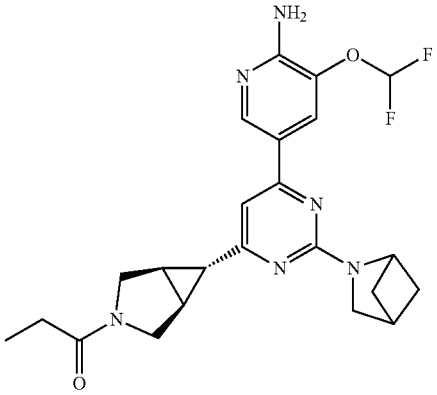 <br>1-[(1R,5S)-6-[6-[6-amino-5-(difluoromethoxy)-3-pyridyl]-2-(3-azabicyclo[2.1.1]hexan-3-yl)pyrimidin-4-yl]-3-azabicyclo[3.1.0]hexan-3-yl]propan-1-one | $^1$H NMR (400 MHz, Chloroform-d) δ 8.57 (s, 1H), 8.02 (s, 1H), 6.69 (s, 1H), 6.58 (t, J = 73.6 Hz, 1H), 5.01-4.94 (m, 3H), 3.98 (d, J = 8.4 Hz, 1H), 3.75-3.66 (m, 2H), 3.57-3.55 (m, 3H), 2.95-2.94 (m, 1H), 2.32-2.26 (m, 4H), 2.00 (s, 2H), 1.70-1.68 (m, 1H), 1.46-1.45 (m, 2H), 1.16 (t, J = 7.6 Hz, 3H). | 457.15 | C |
| 129 | 0.001 | 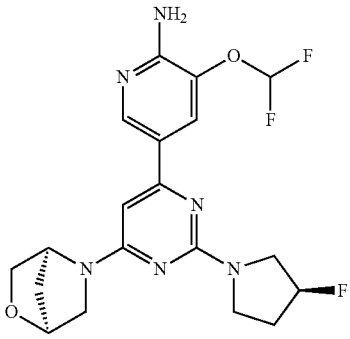 <br>3-(difluoromethoxy)-5-[2-[(3S)-3-fluoropyrrolidin-1-yl]-6-[(1S,4S)-2-oxa-5-azabicyclo[2.2.1]heptan-5-yl]pyrimidin-4-yl]pyridin-2-amine | 1H NMR (400 MHz, DMSO-d6) δ 8.60 (s, 1H), 7.99 (s, 1H), 7.17 (t, J = 73.8 Hz, 1H), 6.43 (s, 2H), 5.51-5.30 (m, 1H), 4.99 (s, 1H), , 4.67 (s, 1H), 3.93-3.74 (m, 3H), 3.74-3.44 (m, 4H), 3.35 (s, 1H), 2.28-2.01 (m, 2H), 1.92-1.82 (m, 2H). | 423 | E |

TABLE 1-continued

| No | DLK Ki (μM) | Structure | $^1$H NMR | MS [MS]$^+$ | Method |
|---|---|---|---|---|---|
| 130 | 0.022 | 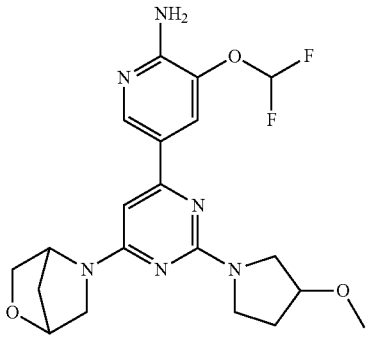 <br>3-(difluoromethoxy)-5-[2-(3-methoxypyrrolidin-1-yl)-6-(2-oxa-5-azabicyclo[2.2.1]heptan-5-yl)pyrimidin-4-yl]pyridin-2-amine | 1H NMR (400 MHz, DMSO-d6) δ 8.59 (s, 1H), 7.98 (s, 1H), 7.16 (t, 1H), 6.41 (s, 2H), 4.98 (s, 1H), 4.66 (s, 1H), 4.06-3.99 (m, 1H), 3.78 (d, J = 7.4 Hz, 1H), 3.70-3.53 (m, 4H), 3.46 (d, J = 10.1 Hz, 2H 3.35 (s, 1H), 3.26 (s, 3H), 2.06-1.93 (m, 2H), 1.86 (s, 2H). | 435 | E |
| 131 | 0.01 | 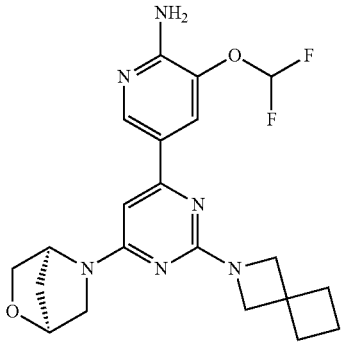 <br>5-[2-(2-azaspiro[3.3]heptan-2-yl)-6-[(1S,4S)-2-oxa-5-azabicyclo[2.2.1]heptan-5-yl]pyrimidin-4-yl]-3-(difluoromethoxy)pyridin-2-amine | 1H NMR (400 MHz, DMSO-d6) δ 8.57 (s, 1H), 7.94 (s, 1H), 7.15 (t, 1H), 6.43 (s, 2H), 4.95 (s, 1H), 4.66 (s, 1H), 3.95 (s, 4H), 3.77 (d, J = 7.3 Hz, 1H), 3.64 (d, J = 7.3 Hz, 1H), 3.43 (d, J = 10.4 Hz, 1H), 3.35 (s, 1H), 2.15 (t, J = 7.6 Hz, 4H), 1.91-1.71 (m, 4H). | 431 | E |
| 132 | 0.014 | 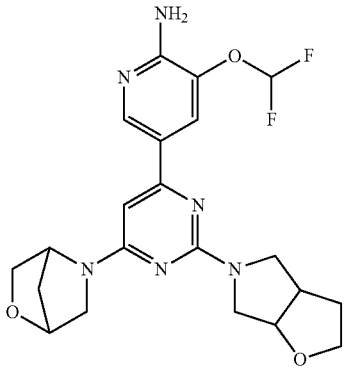 <br>5-[2-(2,3,3a,4,6,6a-hexahydrofuro[2,3-c]pyrrol-5-yl)-6-(2-oxa-5-azabicyclo[2.2.1]heptan-5-yl)pyrimidin-4-yl]-3-(difluoromethoxy)pyridin-2-amine | 1H NMR (400 MHz, DMSO-d6) δ 8.59 (s, 1H), 7.97 (s, 1H), 7.16 (t, J = 73.8 Hz, 1H), 6.42 (s, 2H), 4.98 (s, 1H), 4.66 (s, 1H), 4.50 (t, J = 5.6 Hz, 1H), 3.85 (q, J = 7.4 Hz, 1H), 3.81-3.68 (m, 4H), 3.65 (d, J = 7.3 Hz, 1H), 3.59-3.50 (m, 1H), 3.45 (d, J = 10.1 Hz, 1H), 3.35 (s, 1H), 2.99-2.87 (m, 1H), 2.14-1.98 (m, 1H), 1.93-1.73 (m, 3H). | 447 | E |

TABLE 1-continued

| No | DLK Ki (μM) | Structure | $^1$H NMR | MS [MS]$^+$ | Method |
|---|---|---|---|---|---|
| 133 | 0.08 | 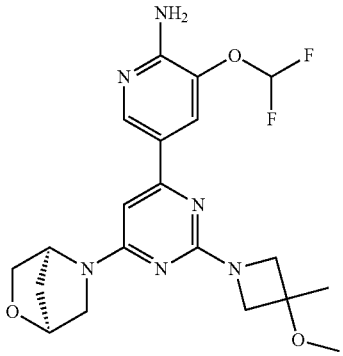 3-(difluoromethoxy)-5-[2-(3-methoxy-3-methyl-azetidin-1-yl)-6-[(1S,4S)-2-oxa-5-azabicyclo[2.2.1]heptan-5-yl]pyrimidin-4-yl]pyridin-2-amine | 1H NMR (400 MHz, DMSO-d6) δ 8.58 (s, 1H), 7.94 (s, 1H), 7.37-6.94 (m, 1H), 6.45 (s, 2H), 4.97 (s, 1H), 4.67 (s, 1H), 3.97-3.89 (m, 2H), 3.85-3.73 (m, 3H), 3.65 (d, J = 7.3 Hz, 1H), 3.44 (d, J = 10.4 Hz, 1H), 3.40-3.30 (m, 1H), 3.20 (s, 3H), 1.86 (s, 2H), 1.44 (s, 3H). | 435 | E |
| 134 | 0.02 | 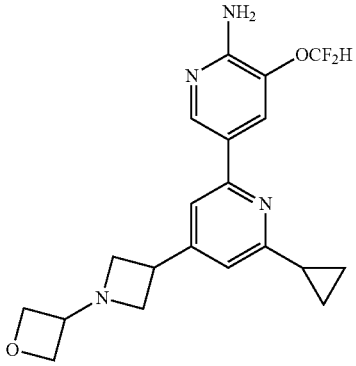 6-cyclopropyl-5'-(difluoromethoxy)-4-(1-(oxetan-3-yl)azetidin-3-yl)-[2,3'-bipyridin]-6'-amine | $^1$H NMR (400 MHz, DMSO) δ 8.53 (d, J = 1.9 Hz, 1H), 7.94 (s, 1H), 7.50 (d, J = 1.9 Hz, 1H), 7.17 (t, J = 74.0 Hz, 1H), 7.16 (s, 1H), 6.35 (br s, 2H), 4.62-4.50 (m, 2H), 4.45-4.32 (m, 2H), 3.82-3.70 (m, 1H), 3.70-3.60 (m, 3H), 3.28-3.23 (m, 2H), 2.17-2.03 (m, 1H), 1.05-0.85 (m, 4H) | | J |

Example 3

DLK TR-FRET inhibition assay: DLK kinase reactions (20 μL) containing 5 nM N-terminally GST-tagged DLK (catalytic domain amino acid 1-520) (Carna Bioscience), 40 nM N-terminally HIS-tagged MKK4 K131M substrate, and 30 μM ATP in kinase reaction buffer (50 mM HEPES, pH 7.5, 0.01% Triton X-100, 0.01% Bovine γ-Globulins, 2 mM DTT, 10 mM $MgCl_2$ and 1 mM EGTA), and testing compound 1:3 serial diluted starting at 20 uM were incubated at ambient temperature for 60 minutes in 384 well OptiPlate (Perkin Elmer). To quench kinase reactions and detect phosphorylated MKK4, 15 μL of TR-FRET antibody mixture containing 2 nM anti-phosphorylated MKK4 labeled with Europium cryptate (Cisbio) and 23 nM anti-HIS labeled with D2 (Cisbio) in detection buffer (25 mM Tris pH 7.5, 100 mM NaCl, 100 mM EDTA, 0.01% Tween-20, and 200 mM KF) was added to the reaction mixture. The detection mixture was incubated for 3 hours at ambient temperature and the TR-FRET was detected with an EnVision multilabel plate reader (Perkin-Elmer) using the LANCE/DELFIA Dual Enh label from Perkin-Elmer (excitation filter: UV2 (TRF) 320 and emission filters: APC 665 and Europium 615). Compounds of formula I as set forth in Table 1 in Example 1 inhibited the DLK kinase with the $K_i$s in micromolar (μM).

The invention claimed is:

1. [Compounds] *A compound* of formula (I)

(I)

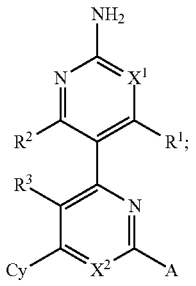

or [salts] *a pharmaceutically acceptable salt* thereof wherein $R^1$, $R^2$ and $R^3$ are each independently H, F, Cl, Br, I, *CN*, $C_{1-6}$ alkyl or $C_{1-6}$ haloalkyl;

$X^1$ is [N or] C—$R^4$, wherein $R^4$ is selected from the group consisting of —F, —Cl, —Br, [I -$(L^1)_{0-1}$-$C_{1-6}$ alkyl,] —*I, CN,* -$(L^1)_{0.1}$-$C_{1-6}$ *alkyl,* -$(L^1)_{0-1}$-$C_{1-6}$ haloalkyl, -$(L^1)_{0-1}$-$C_{1-6}$ heteroalkyl, -$(L^2)_{0-1}$-$C_{3-8}$ cycloalkyl, -$(L^2)_{0-1}$-3 to 7 membered heterocycloalkyl, -$(L^2)_{0-1}$-6-10 membered aryl, -$(L^2)_{0-1}$-5-10 membered heteroaryl, wherein $L^1$ is selected from the group consisting of —O—, —N(H)—, —S—, —N($C_{1-6}$alkyl)-, [=O] *and* —*C*(=*O*)—, and $L^2$ is selected from the group consisting of —O—, —N(H)—, —N($C_{1-6}$ alkyl)-, —S—, [=O] —*C*(=*O*)—, $C_{1-4}$ alkylene, $C_{1-4}$ alkenylene, $C_{1-4}$ alkynylene, $C_{1-4}$ alkoxylene, $C_{1-4}$ aminoalkylene, $C_{1-4}$ thioalkylene and $C_{1-4}$ heteroalkylene, and wherein $R^4$ is optionally substituted on carbon atoms and heteroatoms with $R^{R4}$ substituents selected from the group consisting of F, Cl, Br, I, $C_{1-6}$ alkyl, $C_{1-6}$ haloalkyl, 3-5 membered cycloalkyl, 3-5 membered heterocycloalkyl, $C_{1-6}$ alkoxy, $C_{1-6}$ alkylamino, $C_{1-6}$ dialkylamino, $C_{1-6}$ alkylthio, =O, —$NH_2$, —CN, —$NO_2$ and —$SF_5$;

$X^2$ is N;

A is selected from the group consisting of $C_{1-6}$ alkyl, $C_{1-6}$ haloalkyl, $C_{1-6}$ dialkylamino, 3 to 12 membered cycloalkyl, 3 to 12 membered heterocycloalkyl, wherein A is optionally substituted with 1-5 $R^A$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^A)_{0-1}$-3-8 membered cycloalkyl, -$(L^A)_{0-1}$-3-8 membered heterocycloalkyl, -$(L^A)_{0-1}$-5 to 6 membered heteroaryl, -$(L^A)_{0-1}$-$C_6$ aryl, -$(L^A)_{0-1}$-$NR^{R1a}R^{R1b}$, -$(L^A)_{0-1}$-$OR^{R1a}$, -$(L^A)_{0-1}$-$SR^{R1a}$, [-$(L^A)_{0-1}$-N($R^{R1a}$)C(=$Y^1$)$OR^{R1c}$,] -$(L^A)_{0-1}$-OC(=O)N($R^{R1a}$)($R^{R1b}$), -$(L^A)_{0-1}$-N($R^{R1a}$)C(=O)N($R^{R1a}$)($R^{R1b}$), -$(L^A)_{0-1}$-C(=O)N($R^{R1a}$)($R^{R1b}$), -$(L^A)_{0-1}$-N($R^{R1a}$)C(=O)$R^{R1b}$, -$(L^A)_{0-1}$-C(=O)$OR^{R1a}$, -$(L^A)_{0-1}$-OC(=O)$R^{R1a}$, -$(L^A)_{0-1}$-P(=O)($OR^{R1a}$)($OR^{R1b}$), -$(L^A)_{0-1}$-S(O)$_{1-2}$ $R^{R1c}$, -$(L^A)_{0-1}$-S(O)$_{1-2}$N($R^{R1a}$)($R^{R1b}$), -$(L^A)_{0-1}$-N($R^{R1a}$)S(O)$_{1-2}$N($R^{R1a}$)($R^{R1b}$) and -$(L^A)_{0-1}$-N($R^{R1a}$)S(O)$_{1-2}$($R^{R1c}$), wherein $L^A$ is selected from the group consisting of $C_{1-4}$ alkylene, $C_{1-4}$ heteroalkylene, $C_{1-4}$ alkoxylene, $C_{1-4}$ aminoalkylene, $C_{1-4}$ thioalkylene, $C_{2-4}$ alkenylene, and $C_{2-4}$ alkynylene; wherein $R^{R1a}$ and $R^{R1b}$ are independently selected from the group consisting of hydrogen, $C_{1-8}$ alkyl, $C_{1-8}$ haloalkyl, 3-8 membered cycloalkyl, phenyl, benzyl, 5 to 6 membered heteroaryl and 3 to 8 membered heterocycloalkyl; $R^{R1c}$ is selected from the group consisting of $C_{1-8}$ alkyl, $C_{1-8}$ haloalkyl, 3 to 8 membered cycloalkyl, phenyl, benzyl, 5 to 6 membered heteroaryl and 3 to 7 membered heterocycloalkyl, and wherein $R^A$ is optionally substituted on carbon atoms and heteroatoms with $R^{RA}$ substituents selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-S(O)$_{0-2}$—, $C_{1-4}$ (halo)alkyl-N(H)S(O)$_{0-2}$—, $C_{1-4}$ (halo)alkyl-S(O)$_{0-2}$N(H)—, (halo)alkyl-N(H)—S(O)$_{0-2}$ N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylthio, $C_{1-4}$ alkylamino and $C_{1-4}$ dialkylamino; and Cy is selected from the group consisting of $C_{1-6}$ alkyl, $C_{1-6}$ haloalkyl, 3 to 12 membered cycloalkyl, 3 to 12 membered heterocycloalkyl, wherein Cy is optionally substituted on carbon or heteroatoms with $R^{Cy}$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^{Cy})_{0-1}$-3-8 membered cycloalkyl, -$(L^{Cy})_{0-1}$-3-8 membered heterocycloalkyl, -$(L^{Cy})_{0-1}$-5 to 6 membered heteroaryl, -$(L^{Cy})_{0-1}$-phenyl, -$(L^{Cy})_{0-1}$-$NR^{RCa}R^{RCb}$, -$(L^{Cy})_{0-1}$-$OR^{RCa}$, -$(L^{Cy})_{0-1}$-$SR^{RCa}$, [-$(L^{Cy})_{0-1}$-N($R^{RCa}$)C(=$Y^1$)$OR^{RCc}$,] -$(L^{Cy})_{0-1}$-OC(=O)N($R^{RCa}$)($R^{RCb}$), -$(L^{Cy})_{0-1}$-N($R^{RCa}$)C(=O)N($R^{RCa}$)($R^{RCb}$), -$(L^{Cy})_{0-1}$-C(=O)N($R^{RCa}$)($R^{RCb}$), -$(L^{Cy})_{0-1}$-N($R^{RCa}$)C(=O)$R^{RCb}$, -$(L^{Cy})_{0-1}$-C(=O)$OR^{RCa}$, -$(L^{Cy})_{0-1}$-OC(=O)$R^{RCa}$, -$(L^{Cy})_{0-1}$-P(=O)($OR^{RCa}$)($OR^{RCb}$), -$(L^{Cy})_{0-1}$-S(O)$_{1-2}$$R^{RCc}$, -$(L^{Cy})_{0-1}$-S(O)$_{1-2}$N($R^{RCa}$)($R^{RCb}$), [-$(L^{Cy})_{0-1}$N($R^{RCa}$)S(O)$_{1-2}$N($R^{Rca}$)($R^{RCb}$)] -$(L^{Cy})_{0-1}$N($R^{RCa}$)S(O)$_{1-2}$N($R^{RCa}$)($R^{RCb}$) and -$(L^{Cy})_{0-1}$-N($R^{RCa}$)S(O)$_{1-2}$($R^{RCc}$), wherein $L^{Cy}$ is selected from the group consisting of $C_{1-4}$ alkylene, $C_{1-4}$ heteroalkylene, $C_{1-4}$ alkoxylene, $C_{1-4}$ aminoalkylene, $C_{1-4}$ thioalkylene, $C_{2-4}$ alkenylene, and $C_{2-4}$ alkynylene; wherein $R^{RCa}$ and $R^{RCb}$ are independently selected from the group consisting of hydrogen, $C_{1-8}$ alkyl, $C_{1-8}$ haloalkyl, 3-8 membered cycloalkyl, phenyl, benzyl, 5 to 6 membered heteroaryl and 3 to 8 membered heterocycloalkyl; $R^{RCc}$ is selected from the group consisting of $C_{1-8}$ alkyl, $C_{1-8}$ haloalkyl, 3 to 8 membered cycloalkyl, phenyl, benzyl, 5 to 6 membered heteroaryl and 3 to 7 membered heterocycloalkyl, and wherein $R^{Cy}$ is optionally substituted on carbon atoms and heteroatoms with from 1 to 5 $R^{RCy}$ [substitutents] *substituents* selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-S(O)$_{0-2}$—, $C_{1-4}$ (halo)alkyl-N(H)S(O)$_{0-2}$—, $C_{1-4}$ (halo)alkyl-S(O)$_{0-2}$N(H)—, (halo)alkyl-N(H)—S(O)$_{0-2}$ N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylthio, $C_{1-4}$ alkylamino and $C_{1-4}$ dialkylamino.

2. A compound according to claim 1, *or a pharmaceutically acceptable salt thereof,* wherein either A or Cy is a polycyclic carbocycle or polycyclic heterocycle.

[3. A compound according to claim 1, wherein $X^1$ is N.]

[4. A compound according to claim 1, wherein $X^1$ is C—$R^4$.]

5. A compound according to claim 1, *or a pharmaceutically acceptable salt thereof,* wherein $R^4$ is selected from the group consisting of —F, —Cl, —CN, -$(L^2)_{0-1}$-$C_{3-8}$ cycloalkyl, -$(L^2)_{0-1}$-3 to 7 membered heterocycloalkyl, -$(L^1)_{0-1}$-$C_{1-6}$ alkyl, -$(L^1)_{0-1}$-$C_{1-6}$ haloalkyl, -$(L^1)_{0-1}$-$C_{1-6}$ heteroalkyl, -$(L^2)_{0-1}$-6-10 membered aryl and -$(L^2)_{0-1}$-5-10 membered heteroaryl, and is optionally substituted.

6. A compound according to claim 1, *or a pharmaceutically acceptable salt thereof,* wherein $R^4$ is selected from the group consisting of —F, —Cl, $C_{3-8}$ cycloalkyl, 3 to 7 membered heterocycloalkyl, $C_{1-6}$ alkyl, $C_{1-6}$ haloalkyl, —(O)—$C_{3-8}$ cycloalkyl, —(O)—3 to 7 membered heterocycloalkyl, —(O)—$C_{1-6}$ alkyl and —(O)—$C_{1-6}$ haloalkyl, and is optionally substituted.

7. A compound of claim 1, *or a pharmaceutically acceptable salt thereof,* wherein $R^4$ is selected from the group consisting of methoxy, monofluoromethoxy, difluoromethoxy, trifluoromethoxy, ethoxy, propoxy, isopropoxy, butoxy, isobutoxy, tert-butoxy, cyclopropoxy, cyclobutoxy, cyclopentoxy, methyl, monofluoromethyl difluoromethyl, trifluoromethyl, cyclopropyl, cyclobutyl and cyclopentyl.

8. A compound of claim 1, *or a pharmaceutically acceptable salt thereof,* wherein $R^4$ is selected from the group consisting of [$(L^2)_{0-1}$-phenyl] -$(L^2)_{0-1}$-*phenyl*, -$(L^2)_{0-1}$-pyridyl, -$(L^2)_{0-1}$-pyrimidinyl, -$(L^2)_{0-1}$pyrazinyl, -$(L^2)_{0-1}$-pyridazinyl, -$(L^2)_{0-1}$-pyrrolyl, -$(L^2)_{0-1}$-pyrazolyl, -$(L^2)_{0-1}$-imidazolyl, -$(L^2)_{0-1}$-thienyl, -$(L^2)_{0-1}$-thiazolyl [and], -$(L^2)_{0-1}$-thiadiazolyl, -$(L^2)_{0-1}$-triazoloyl, -$(L^2)_{0-1}$-oxazolyl, -$(L^2)_{0-1}$-oxadiazolyl, *and* -$(L^2)_{0-1}$-furanyl and is optionally substituted.

9. A compound of claim 1, *or a pharmaceutically acceptable salt thereof,* wherein $R^4$ is selected from the group consisting of $-(L^2)_{0-1}$-phenyl and $-(L^2)_{0-1}$-pyridinyl, and is optionally substituted.

10. A compound of claim 1, *or a pharmaceutically acceptable salt thereof,* wherein $R^4$ is —OC(H)($CH_3$)-phenyl wherein said phenyl ring is optionally substituted.

11. A compound of claim 1, *or a pharmaceutically acceptable salt thereof,* wherein $R^1$, $R^2$ and $R^3$ are each independently selected from the group consisting of F, Cl, CN, hydrogen, $C_{1-4}$ alkyl and $C_{1-4}$ haloalkyl.

12. A compound of claim 1, *or a pharmaceutically acceptable salt thereof,* wherein $R^1$, $R^2$ and $R^3$ are each hydrogen.

13. A compound of claim 1, *or a pharmaceutically acceptable salt thereof,* wherein A and Cy are independently selected from the group consisting of pyrrolidine, piperidine, azetidine, azepane, piperazine, 7-azaspiro[3.5]nonane, 3,6-diazabicyclo[3.2.1]octane, 2-oxa-5-azabicyclo[2.2.1]heptane, 2,7-diazaspiro[3.5]nonane, octahydrocyclopenta[c]pyrrole, 2-azaspiro[3.3]heptane, 2,5-diazaspiro[3.4]octane, 6-azaspiro[2.5]octane, 3-azabicyclo[3.1.0]hexane, 3-oxabicyclo[3.1.0]hexane, morpholine, hexahydro-2H-furo[3,2-c]pyrrole, 2-azabicyclo[2.1.1]hexane, 2,5-diazabicyclo[2.2.1]heptane, 2-aza-tricyclo[3.3.1.1-3,7]decane, [2-azabicyclo[2.1.1]hexane,] 9-azabicyclo[4.2.1]nonane, 9-azabicyclo[3.3.1]nonane, cyclobutane, cyclopropane, cyclopentane, 2-Thia-5-aza-bicyclo[2.2.1]heptane 2,2-dioxide, 2-azabicyclo[2.2.1]heptane, tetrahydro-2H-pyran, 8-azabicyclo[3.2.1]octane and 3-oxa-8-azabicyclo[3.2.1]octane, and is optionally substituted.

14. A compound of claim 1, *or a pharmaceutically acceptable salt thereof,* wherein A is selected from the group consisting of pyrrolidine, piperidine, azetidine, azepane, piperazine, cyclopropane, cyclobutane, cyclopentane, 7-azaspiro[3.5]nonane, 3-oxabicyclo[3.1.0]hexane, 3,6-diazabicyclo[3.2.1]octane, 2-oxa-5-azabicyclo[2.2.1]heptane, 2,7-diazaspiro[3.5]nonane, octahydrocyclopenta[c]pyrrole, 2-azaspiro[3.3]heptane, 2,5-diazaspiro[3.4]octane, 6-azaspiro[2.5]octane, 3-azabicyclo[3.1.0]hexane, morpholine, hexahydro-2H-furo[3,2-c]pyrrole and 2-azabicyclo[2.1.1]hexane, and is optionally substituted.

15. A compound of claim 1, *or a pharmaceutically acceptable salt thereof,* wherein A is selected from the group consisting of 2-azabicyclo[2.1.1]hexane, 3-azabicyclo[3.1.0]hexane, [3oxabicyclo[3.1.0]hexane] *3-oxabicyclo[3.1.0]hexane*, azetidine, pyrrolidine, cyclopropane, cyclobutane, cyclopentane, and is optionally substituted.

16. A compound of claim 1, *or a pharmaceutically acceptable salt thereof,* wherein A is selected from the group consisting of (1S,4S)-2-oxa-5-azabicyclo[2.2.1]heptane, (1R,4R)-2-oxa-5-azabicyclo[2.2.1]heptane, (1R,5S)-3-azabicyclo[3.1.0]hexane, (1S,5R)-3-azabicyclo[3.1.0]hexane, 3-oxabicyclo[3.1.0]hexane, (1R,5S)-3-oxabicyclo[3.1.0]hexane, (1S,5R)-3-oxabicyclo[3.1.0]hexane, (1S,4S)-2,5-diazabicyclo[2.2.1]heptane and (1R,4R)-2,5-diazabicyclo[2.2.1]heptane, and is optionally substituted.

17. A compound of claim 1, *or a pharmaceutically acceptable salt thereof,* wherein [is] A is selected from the group consisting of methyl, ethyl, isopropyl,

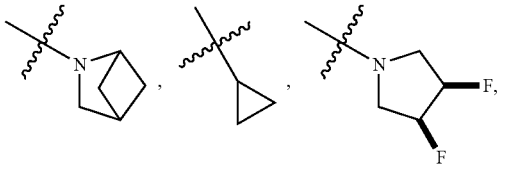

-continued

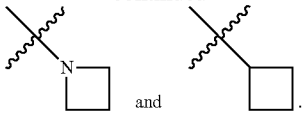

18. A compound of claim 1, *or a pharmaceutically acceptable salt thereof,* wherein Cy is selected from the group consisting of 2,5-diazabicyclo[2.2.1]heptane, piperidine, pyrrolidine, azetidine, 2-aza-tricyclo[3.3.1.1-3,7]decane, 2-oxa-5-azabicyclo[2.2.1]heptane, 3-azabicyclo[3.1.0]hexane, 3-oxabicyclo[3.1.0]hexane, 2-azabicyclo[2.1.1]hexane, 9-azabicyclo[4.2.1]nonane, 9-azabicyclo[3.3.1]nonane, cyclobutane, 2-Thia-5-aza-bicyclo[2.2.1]heptane 2,2-dioxide, 2-azabicyclo[2.2.1]heptane, tetrahydro-2H-pyran, 8-azabicyclo[3.2.1]octane, *and* 3-oxa-8-azabicyclo[3.2.1]octane, *and* is optionally substituted.

19. A compound of claim 1, *or a pharmaceutically acceptable salt thereof,* wherein Cy is selected from the group consisting of azetidine, (1S ,4S)-2-oxa-5-azabicyclo[2.2.1]heptane, (1R,4R)-2-oxa-5-azabicyclo[2.2.1]heptane, (1R,5S)-3-azabicyclo[3.1.0]hexane, (1S,5R)-3-azabicyclo[3.1.0]hexane, 3-oxabicyclo[3.1.0]hexane, (1R,5S)-3-oxabicyclo[3.1.0]hexane, (1S,5R)-3-oxabicyclo[3.1.0]hexane, (1S,4S)-2,5-diazabicyclo[2.2.1]heptane and (1R,4R)-2,5-diazabicyclo[2.2.1]heptane, and is optionally substituted.

20. A compound of claim 1, *or a pharmaceutically acceptable salt thereof,* wherein Cy is selected from the group consisting of

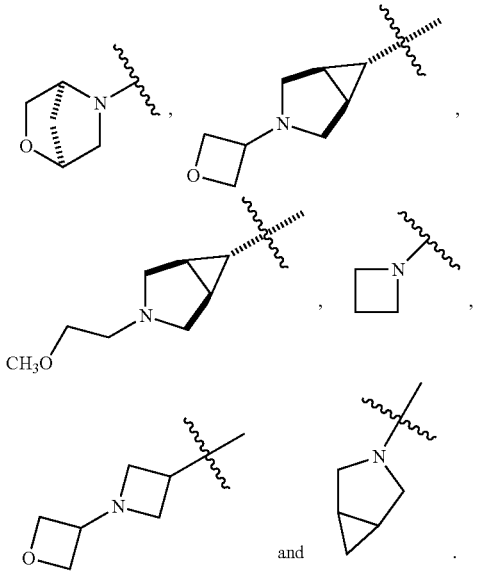

21. A compound of claim 1, *or a pharmaceutically acceptable salt thereof,* wherein A is $C_{1-6}$ alkyl or $C_{1-6}$ dialkylamino, and is optionally substituted.

22. A compound of claim 1, *or a pharmaceutically acceptable salt thereof,* wherein A is methyl or ethyl.

23. A compound of claim 1, *or a pharmaceutically acceptable salt thereof,* wherein Cy is $C_{1-6}$ alkyl, and is optionally substituted.

24. A compound of claim 1, *or a pharmaceutically acceptable salt thereof,* wherein A is optionally substituted with from 1 to 5 $R^A$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^A)_{0-1}$-3-8 membered cycloalkyl, -$(L^A)_{0-1}$-3-8 membered heterocycloalkyl, -$(L^A)_{0-1}$-5 to 6 membered heteroaryl, *and* -$(L^A)_{0-1}$-$C_6$ aryl, wherein $L^A$ is selected from the group consisting of —C(O)—, —C(O)$CH_2$—, —$OCH_2$—, —$CH_2O$—, —$CH_2$—, —$CH_2CH_2$—, —$CH_2OCH_2$—, —N(H)$CH_2$—, —N($C_{1-3}$ alkyl)$CH_2$—, [$CH_2$N(H)—] —*$CH_2$N(H)*—, *and* —$CH_2$N($C_{1-3}$ alkyl)-; wherein said 3-8 membered cycloalkyl is selected from the group consisting of propane, butane, pentane and hexane; wherein said 3 to 8 membered heterocycloalkyl is selected from the group consisting of oxetane, tetrahydrofuran, tetrahydropyran, oxepane, azetidine, pyrrolidine, piperidine and azepane; wherein said 5 to 6 membered heteroaryl is selected from the group consisting of pyrrole, pyrazole, imidazole, thiophene, thiazole, oxazole, [trizole] *triazole*, pyridine, pyrimidine, pyrazine, *and* pyridazine; wherein said $C_6$ aryl is phenyl; and [where in] *wherein* $R^A$ is optionally substituted with from 1 to 5 $R^{RA}$ [substitutents] *substituents* selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-S$(O)_{0-2}$—, $C_{1-4}$ (halo)alkyl-N(H)S$(O)_{0-2}$—, $C_{1-4}$ (halo)alkyl-S$(O)_{0-2}$N(H)—, (halo)alkyl-N(H)—S$(O)_{0-2}$N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—(=O)O—, ((halo)alkyl)$_2$N—C(=O)O—, $C_{1-4}$ alkylthio, $C_{1-4}$ alkylamino and $C_{1-4}$ dialkylamino.

25. A compound of claim 1, *or a pharmaceutically acceptable salt thereof,* wherein Cy is optionally substituted with from 1 to 5 $R^{Cy}$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^{Cy})_{0-1}$-3-8 membered cycloalkyl, -$(L^{Cy})_{0-1}$-3-8 membered heterocycloalkyl, -$(L^{Cy})_{0-1}$-5 to 6 membered heteroaryl, *and* -$(L^{Cy})_{0-1}$-$C_6$ aryl, wherein $L^{Cy}$ is selected from the group consisting of —C(O)—, —C(O)$CH_2$—, —$OCH_2$—, —$CH_2O$—, —$CH_2$—, —$CH_2CH_2$—, —$CH_2OCH_2$—, —N(H)$CH_2$—, —N($C_{1-3}$ alkyl)$CH_2$—, [$CH_2$N(H)—,] —*$CH_2$N(H)*—, *and* —$CH_2$N($C_{1-3}$ alkyl)-; wherein said 3-8 membered cycloalkyl is selected from the group consisting of propane, butane, pentane and hexane; wherein said 3 to 8 membered heterocycloalkyl is selected from the group consisting of oxetane, tetrahydrofuran, tetrahydropyran, oxepane, azetidine, pyrrolidine, piperidine and azepane; wherein said 5 to 6 membered heteroaryl is selected from the group consisting of pyrrole, pyrazole, imidazole, thiophene, thiazole, oxazole, [trizole] *triazole*, pyridine, pyrimidine, pyrazine, *and* pyridazine; wherein said $C_6$ aryl is phenyl; and where in $R^{Cy}$ is optionally substituted with from 1 to 5 $R^{RCy}$ [substitutents] *substituents* selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-S$(O)_{0-2}$—, $C_{1-4}$ (halo)alkyl-N(H)S$(O)_{0-2}$—, $C_{1-4}$ (halo)alkyl-S$(O)_{0-2}$N(H)—, (halo)alkyl-N(H)—S$(O)_{0-2}$N(H)—, $C_{1-4}$ (halo)alkyl-C(=O)N(H)—, $C_{1-4}$ (halo)alkyl-N(H)—(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—(=O)O—, ((halo)alkyl)$_2$N—C(=O)O—, $C_{1-4}$ alkylthio, $C_{1-4}$ alkylamino and $C_{1-4}$ dialkylamino.

26. A compound [of claim] of claim 1, *or a pharmaceutically acceptable salt thereof,* wherein Cy is optionally substituted with 1 to 5 $R^{Cy}$ substituents selected from the group consisting of F, Cl, Br, I, CN, OH, 2,3-difluorophen-1-yl-C(=O)—, 4-fluorophen-1-yl-C(=O)—, 3-fluorophen-1-yl-C(=O)—, 3,5-difluorophen-1-yl-C(=O)—, 3-fluoro-4-methyl-phen-1-yl-C(=O)—, 2,5-difluorophen-1-yl-C(=O)—, oxetane, oxetan-3-yl, thiazole, thiazol-2-yl, —$CH_3CH_2$C(=O)—, $CH_3$C(=O)—, $CF_3CH_2$—, (HO)C$(CH_3)_2CH_2$—, $CH_3OCH_2CH_2$—, $CH_3OC(CH_3)_2$C(=O)—, $CH_3OCH_2$C(=O)—, isopropyl, ethyl and methyl.

27. A compound of claim 1, *or a pharmaceutically acceptable salt thereof,* wherein A is optionally substituted with 1 to 5 $R^A$ substituents selected from the group consisting of F, Cl, Br, I, CN, $CH_3O$—, $CH_3$, cyclopropylmethyl, $CF_3$ and butyl.

28. A compound of claim 1, *or a pharmaceutically acceptable salt thereof,* wherein said compound is selected from the subformula consisting of

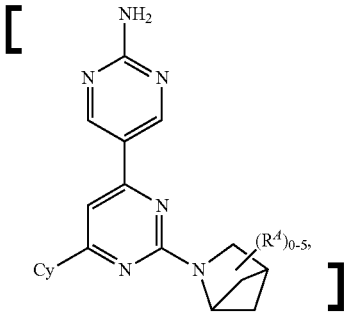

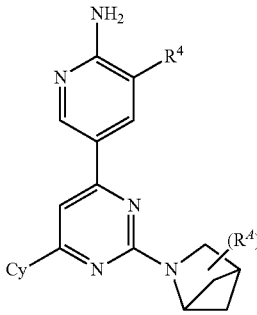

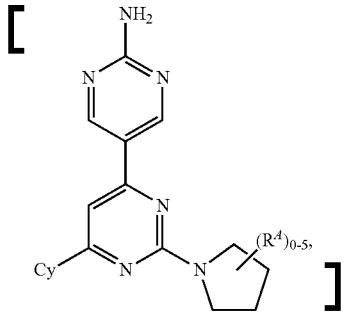

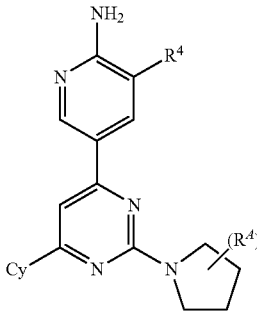

-continued
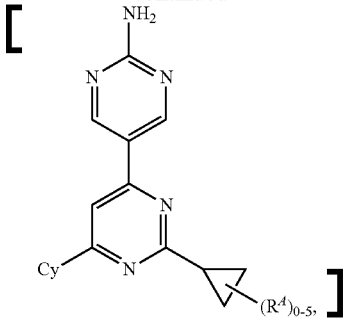
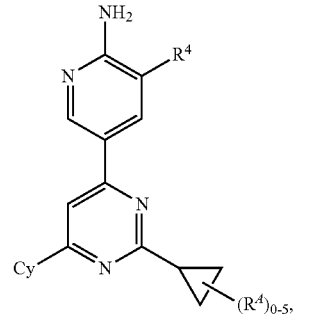
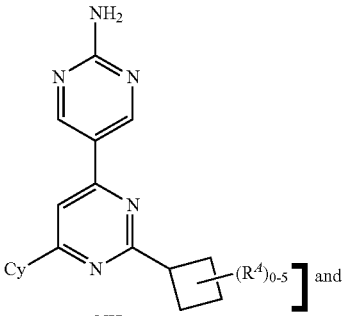
and
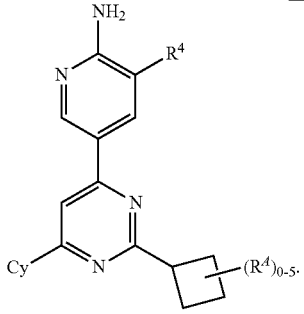
29. A compound of claim 1, *or a pharmaceutically acceptable salt thereof,* wherein said compound is selected from the subformula consisting of
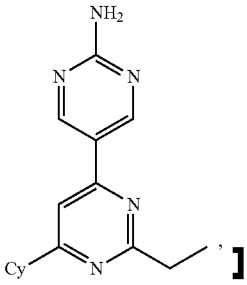
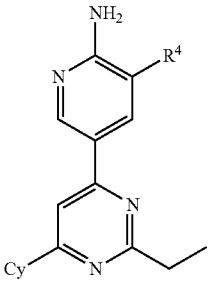
-continued
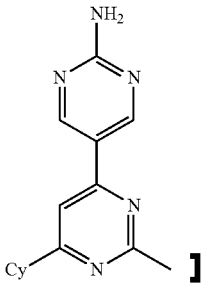
and
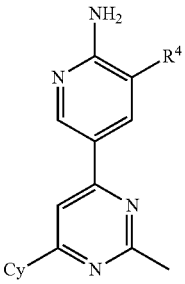
30. A compound of claim 1, *or a pharmaceutically acceptable salt thereof,* wherein said compound is selected from the subformula consisting of
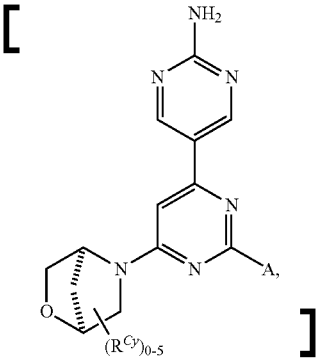
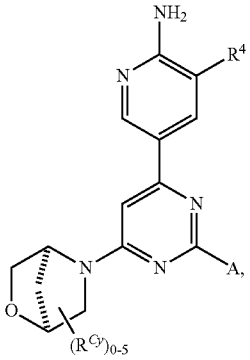
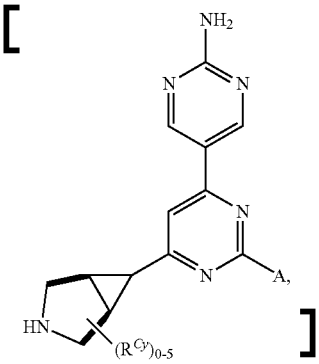

-continued

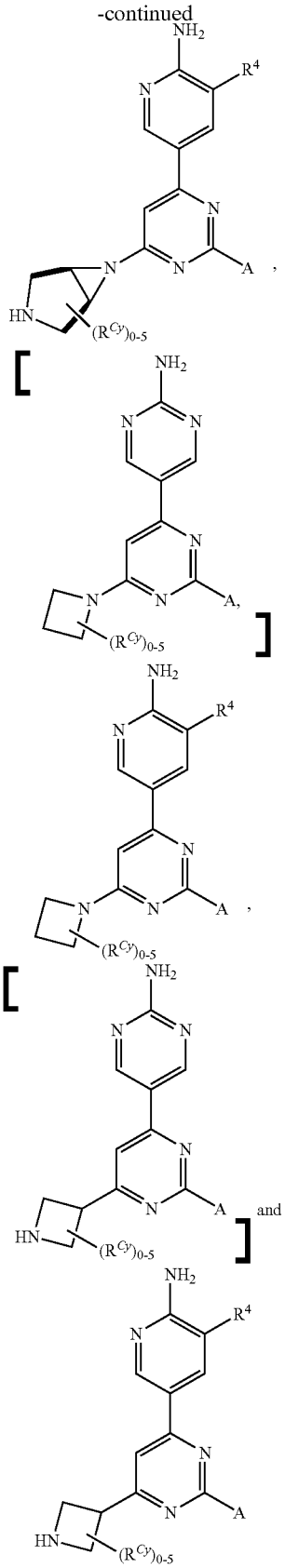

wherein $R^{Cy}$ if present replaces a hydrogen atom attached to a carbon or nitrogen atom of the Cy ring.

31. A compound of claim 1 selected from the group consisting of:

[[3-[6-[2-amino-4-(trifluoromethyl)pyrimidin-5-yl]-2-methyl-pyrimidin-4-yl]pyrrolidin-1-yl]-phenyl-methanone;

[3-[6-(2-aminopyrimidin-5-yl)-2-methyl-pyrimidin-4-yl]-1-piperidyl]-phenyl-methanone;

[3-[6-[2-amino-4-(trifluoromethyl)pyrimidin-5-yl]-2-methyl-pyrimidin-4-yl]-1-piperidyl]-phenyl-methanone;

[3-[6-(2-aminopyrimidin-5-yl)-2-methyl-pyrimidin-4-yl] pyrrolidin-1-yl]-phenyl-methanone 6-((1R,3R,5R,7R)-2-azaadamantan-2-yl)-2-(2-azabicyclo[2.1.1]hexan-2-yl)-[4,5'-bipyrimidin]-2'-amine;]

3-(difluoromethoxy)-5-[2-(3,3-difluoropyrrolidin-1-yl)-6-[(1S,4S)-2-oxa-5-azabicyclo[2.2.1]heptan-5-yl]pyrimidin-4-yl]pyridin-2-amine;

[5-[2-(3,3-difluoro-1-piperidyl)-6-[(1S,4S)-2-oxa-5-azabicyclo[2.2.1]heptan-5-yl]pyrimidin-4-yl]pyrimidin-2-amine;

5-[2-(4-fluoro-1-piperidyl)-6-[(1S,4S)-2-oxa-5-azabicyclo[2.2.1]heptan-5-yl]pyrimidin-4-yl]pyrimidin-2-amine;

5-[2-(3-azabicyclo[2.1.1]hexan-3-yl)-6-[(1R,5S)-3-(oxetan-3-yl)-3-azabicyclo[3.1.0]hexan-6-yl]pyrimidin-4-yl]pyrimidin-2-amine;]

1-[(1R,5S)-6-[6-[6-amino-5-(difluoromethoxy)-3-pyridyl]-2-cyclopropyl-pyrimidin-4-yl]-3-azabicyclo[3.1.0]hexan-3-yl]propan-1-one;

1-[(1R,5S)-6-[6-[6-amino-5-(difluoromethoxy)-3-pyridyl]-2-cyclopropyl-pyrimidin-4-yl]-3-azabicyclo[3.1.0]hexan-3-yl]ethanone;

1-[(1S,4S)-5-[6-[6-amino-5-(trifluoromethyl)-3-pyridyl]-2-(3-azabicyclo[2.1.1]hexan-3-yl)pyrimidin-4-yl]-2,5-diazabicyclo[2.2.1]heptan-2-yl]ethanone;

5-[2-(3-azabicyclo[2.1.1]hexan-3-yl)-6-[(1R,5S)-3-(2,2,2-trifluoroethyl)-3-azabicyclo[3.1.0]hexan-6-yl]pyrimidin-4-yl]-3-(difluoromethoxy)pyridin-2-amine;

[5-[2-(3-azabicyclo[2.1.1]hexan-3-yl)-6-[(1R,5S)-3-(2,2,2-trifluoroethyl)-3-azabicyclo[3.1.0]hexan-6-yl]pyrimidin-4-yl]pyrimidin-2-amine;]

1-[(1R,5S)-6-[6-[6-amino-5-(trifluoromethoxy)-3-pyridyl]-2-(3-azabicyclo[2.1.1]hexan-3-yl)pyrimidin-4-yl]-3-azabicyclo[3.1.0]hexan-3-yl]-2-methyl-propan-2-ol;

1-[(1R,5S)-6-[6-[6-amino-5-(trifluoromethyl)-3-pyridyl]-2-(3-azabicyclo[2.1.1]hexan-3-yl)pyrimidin-4-yl]-3-azabicyclo[3.1.0]hexan-3-yl]-2-methyl-propan-2-ol;

[[6-amino-5-(difluoromethoxy)-3-pyridyl]-2-(3-azabicyclo[2.1.1]hexan-3-yl)pyrimidin-4-yl]-3-azabicyclo[3.1.0]hexan-3-yl]-2-methyl-propan-2-ol;]

*1-[(1R,5S)-6-[6-[6-amino-5-(difluoromethoxy)-3-pyridyl]-2-(3-azabicyclo[2.1.1]hexan-3-yl)pyrimidin-4-yl]-3-azabicyclo[3.1.0]hexan-3-yl]-2-methyl-propan-2-ol;*

1-[(1R,5S)-6-[6-[6-amino-5-(trifluoromethoxy)-3-pyridyl]-2-(3-azabicyclo[2.1.1]hexan-3-yl)pyrimidin-4-yl]-3-azabicyclo[3.1.0]hexan-3-yl]ethanone;

[5-[2-(3,3-difluoro-1-piperidyl)-6-[(1S,4S)-2-oxa-5-azabicyclo[2.2.1]heptan-5-yl]pyrimidin-4-yl]pyrimidin-2-amine;

5-[2-(4-fluoro-1-piperidyl)-6-[(1S,4S)-2-oxa-5-azabicyclo[2.2.1]heptan-5-yl]pyrimidin-4-yl]pyrimidin-2-amine;

5-[2(3-azabicyclo[2.1.1]hexan-3-yl)-6-[(1R,5S)-3-(oxetan-3-yl)-3-azabicyclo[3.1.0]hexan-6-yl]pyrimidin-4-yl]pyrimidin-2-amine;

1-[(1R,5S)-6-[6-[6-amino-5-(difluoromethoxy)-3-pyridyl]-2-cyclopropyl-pyrimidin-4-yl]-3-azabicyclo[3.1.0]hexan-3-yl]propan-1-one;

1-[(1R,5S)-6-[6-[6-amino-5-(difluoromethoxy)-3-pyridyl]-2-cyclopropyl-pyrimidin-4-yl]-3-azabicyclo[3.1.0]hexan-3-yl]ethanone;

1-[(1S,4S)-5-[6-[6-amino-5-(trifluoromethyl)-3-pyridyl]-2-(3-azabicyclo[2.1.1]hexan-3-yl)pyrimidin-4-yl]-2,5-diazabicyclo[2.2.1]heptan-2-yl]ethanone;

5-[2-(3-azabicyclo[2.1.1]hexan-3-yl)-6-[(1R,5S)-3-(2,2,2-trifluoroethyl)-3-azabicyclo[3.1.0]hexan-6-yl]pyrimidin-4-yl]-3-(difluoromethoxy)pyridin-2-amine;

5-[2-(3-azabicyclo[2.1.1]hexan-3-yl)-6-[(1R,5S)-3-(2,2,2-trifluoroethyl)-3-azabicyclo[3.1.0]hexan-6-yl]pyrimidin-4-yl]pyrimidin-2-amine;

1-[(1R,5S)-6-[6-[6-amino-5-(trifluoromethoxy)-3-pyridyl]-2-(3-azabicyclo[2.1.1]hexan-3-yl)pyrimidin-4-yl]-3-azabicyclo[3.1.0]hexan-3-yl]-2-methyl-propan-2-ol;

1-[(1R,5S)-6-[6-[6-amino-5-(trifluoromethyl)-3-pyridyl]-2-(3-azabicyclo[2.1.1]hexan-3-yl)pyrimidin-4-yl]-3-azabicyclo[3.1.0]hexan-3-yl]-2-methyl-propan-2-ol;

[6-amino-5-(difluoromethoxy)-3-pyridyl]-2-(3-azabicyclo[2.1.1]hexan-3-yl)pyrimidin-4-yl]-3-azabicyclo[3.1.0]hexan-3-yl]-2-methyl-propan-2-ol;

1-[(1R,5S)-6-[6-[6-amino-5-(trifluoromethoxy)-3-pyridyl]-2-(3-azabicyclo[2.1.1]hexan-3-yl)pyrimidin-4-yl]-3-azabicyclo-[3.1.0]hexane-3-yl]ethanone;]

1-[(1R,5S)-6-[6-[6-amino-5-(trifluoromethyl)-3-pyridyl]-2-(3-azabicyclo[2.1.1]hexan-3-yl)pyrimidin-4-yl]-3-azabicyclo[3.1.0]hexan-3yl]-ethanone;

5-[2-(3-azabicyclo[2.1.1]hexan-3-yl)-6-[(1R,5S)-3-(2-methoxyethyl)-3-azabicyclo[3.1.0]hexan-6-yl]pyrimidin-4-yl]-3-(trifluoromethoxy)pyridin-2-amine;

5-[2-(3-azabicyclo[2.1.1]hexan-3-yl)-6-[(1R,5S)-3-(2-methoxyethyl)-3-azabicyclo[3.1.0]hexan-6-yl]pyrimidin-4-yl]-3-(trifluoromethyl)pyridin-2-amine;

[5-[2-(3-azabicyclo[2.1.1]hexan-3-yl)-6-[(1R,5S)-3-(2-methoxyethyl)-3-azabicyclo[3.1.0]hexan-6-yl]pyrimidin-4-yl]pyrimidin-2-amine; ]

5-[2-cyclopropyl-6-[(1S,4S)-2-oxa-5-azabicyclo[2.2.1]heptan-5-yl]pyrimidin-4-yl]-3-(trifluoromethoxy)pyridin-2-amine;

[5-[2-(3-methoxyazetidin-1-yl)-6-[(1S,4S)-2-oxa-5-azabicyclo[2.2.1]heptan-5-yl]pyrimidin-4-yl]pyrimidin-2-amine;

5-[2-(3,3-dimethylazetidin-1-yl)-6-[(1S,4S)-2-oxa-5-azabicyclo[2.2.1]heptan-5-yl]pyrimidin-4-yl]pyrimidin-2-amine;

5-(5-((1R,5S,6s)-3-oxabicyclo[3.1.0]hexan-6-yl)-1-isopropyl-1H-pyrazol-3-yl)-3-fluoro-1H-pyrrolo[2,3-b]pyridine;]

*5-[2-(2-azabicyclo[2.1.1]hexan-2-yl)-6-[(1S,4S)-5-(oxetan-3-yl)-2,5-diazabicyclo[2.2.1]heptan-2-yl]pyrimidin-4-yl]-3-(difluoromethoxy)pyridin-2-amine;*

1-[(1S,4S)-5-[6-[6-amino-5-(difluoromethoxy)-3-pyridyl]-2-(3-azabicyclo[2.1.1]hexan-3-yl)pyrimidin-4-yl]-2,5-diazabicyclo[2.2.1]heptan-2-yl]-2-methoxy-2-methyl-propan-1-one;

[[6-amino-5-(difluoromethoxy)-3-pyridyl]-2-(3-azabicyclo[2.1.1]hexan-3-yl)pyrimidin-4-yl]-2,5-diazabicyclo[2.2.1]heptan-2-yl]-2-methoxy-ethanone;]

*1-[(1S,4S)-5-[6-[6-amino-5-(difluoromethoxy)-3-pyridyl]-2-(3-azabicyclo[2.1.1]hexan-3-yl)pyrimidin-4-yl]-2,5-diazabicyclo[2.2.1]heptan-2-yl]-2-methoxy-ethanone;*

3-(difluoromethoxy)-5-[2-[(3R,4S)-3,4-difluoropyrrolidin-1-yl]-6-[(1S,4S)-2-oxa-5-azabicyclo[2.2.1]heptan-5-yl]pyrimidin-4-yl]pyridin-2-amine;

[5-[2-(3-azabicyclo[2.1.1]hexan-3-yl)-6-(3-azabicyclo[2.1.1]hexan-4-yl)pyrimidin-4-yl]pyrimidin-2-amine;]

5-[2-(azetidin-1-yl)-6-[(1S,4S)-2-oxa-5-azabicyclo[2.2.1]heptan-5-yl]pyrimidin-4-yl]-3-(difluoromethoxy)pyridin-2-amine;

3-(difluoromethoxy)-5-[2-(3-fluoroazetidin-1-yl)-6-[(1S,4S)-2-oxa-5-azabicyclo[2.2.1]heptan-5-yl]pyrimidin-4-yl]pyridin-2-amine;

[5-[2,6-bis[(1S,4S)-2-oxa-5-azabicyclo[2.2.1]heptan-5-yl]pyrimidin-4-yl]pyrimidin-2-amine;]

5-[2-(3,3-difluoroazetidin-1-yl)-6-[(1S,4S)-2-oxa-5-azabicyclo[2.2.1]heptan-5-yl]pyrimidin-4-yl]-3-(difluoromethoxy)pyridin-2-amine;

[5-[2-(3-azabicyclo[2.1.1]hexan-3-yl)-6-[8-(2,2,2-trifluoroethyl)-8-azabicyclo[3.2.1]octan-3-yl]pyrimidin-4-yl]pyrimidin-2-amine;

5-[2-(3-azabicyclo[2.1.1]hexan-3-yl)-6-[(1S,4S)-2-isopropyl-2,5-diazabicyclo[2.2.1]heptan-5-yl]pyrimidin-4-yl]pyrimidin-2-amine;

5-[2-(3-azabicyclo[2.1.1]hexan-3-yl)-6-[(1S,4S)-5-ethyl-2,5-diazabicyclo[2.2.1]heptan-2-yl]pyrimidin-4-yl]pyrimidin-2-amine;

5-[2-(3-azabicyclo[2.1.1]hexan-3-yl)-6-[(1S,4S)-2-(oxetan-3-yl)-2,5-diazabicyclo[2.2.1]heptan-5-yl]pyrimidin-4-yl]pyrimidin-2-amine;

5-[2-(3-azabicyclo[2.1.1]hexan-3-yl)-6-[(3S,4R)-3,4-difluoropyrrolidin-1-yl]pyrimidin-4-yl]pyrimidin-2-amine;]

1-[(1S,4S)-5-[6-[6-amino-5-(difluoromethoxy)-3-pyridyl]-2-(3-azabicyclo[2.1.1]hexan-3-yl)pyrimidin-4-yl]-2,5-diazabicyclo[2.2.1]heptan-2-yl]ethanone;

[1-[3-[6-(2-aminopyrimidin-5-yl)-2-(3-azabicyclo[2.1.1]hexan-3-yl)pyrimidin-4-yl]-8-azabicyclo[3.2.1]octan-8-yl]ethanone;

5-[2-(2-fluoro-7-azaspiro[3.5]nonan-7-yl)-6-[(1S,4S)-2-oxa-5-azabicyclo[2.2.1]heptan-5-yl]pyrimidin-4-yl]pyrimidin-2-amine;

5-[2-[(1R,5S)-3-methyl-3,6-diazabicyclo[3.2.1]octan-6-yl]-6-[(1S,4S)-2-oxa-5-azabicyclo[2.2.1]heptan-5-yl]pyrimidin-4-yl]pyrimidin-2-amine;

5-[2-(4,4-difluoroazepan-1-yl)-6-[(1S,4S)-2-oxa-5-azabicyclo[2.2.1]heptan-5-yl]pyrimidin-4-yl]pyrimidin-2-amine;

5-[2-(4-cyclobutylpiperazin-1-yl)-6-[(1S,4S)-2-oxa-5-azabicyclo[2.2.1]heptan-5-yl]pyrimidin-4-yl]pyrimidin-2-amine;

5-[2-(2-methyl-2,7-diazaspiro[3.5]nonan-7-yl)-6-[(1S,4S)-2-oxa-5-azabicyclo[2.2.1]heptan-5-yl]pyrimidin-4-yl]pyrimidin-2-amine;

4-(2-aminopyrimidin-5-yl)-N,N-diethyl-6-[(1S,4S)-2-oxa-5-azabicyclo[2.2.1]heptan-5-yl]pyrimidin-2-amine;

5-[2-(4-methylpip erazin- 1-yl)-6-[(1S,4S)-2-oxa-5-azabicyclo[2.2.1]heptan-5-yl]pyrimidin-4-yl]pyrimidin-2-amine;

5-[6-[(1S,4S)-2-oxa-5-azabicyclo[2.2.1]heptan-5-yl]-2-(1-piperidyl)pyrimidin-4-yl]pyrimidin-2-amine;

5-[2-(azetidin-1-yl)-6-[(1S,4S)-2-oxa-5-azabicyclo[2.2.1]heptan-5-yl]pyrimidin-4-yl]pyrimidin-2-amine;

5-[2-[(3aS,6aR)-5,5-difluoro-1,3,3a,4,6,6a-hexahydrocyclopenta[c]pyrrol-2-yl]-6-[(1S,4S)-2-oxa-5-azabicyclo[2.2.1]heptan-5-yl]pyrimidin-4-yl]pyrimidin-2-amine;

5-[6-[(1S,4S)-2-oxa-5-azabicyclo[2.2.1]heptan-5-yl]-2-pyrrolidin-1-yl-pyrimidin-4-yl]pyrimidin-2-amine;

5-[2-(3,3-difluoroazetidin-1-yl)-6-[(1S,4S)-2-oxa-5-azabicyclo[2.2.1]heptan-5-yl]pyrimidin-4-yl]pyrimidin-2-amine;

5-[2-(7,7-difluoro-2-azaspiro[3.3]heptan-2-yl)-6-[(1S,4S)-2-oxa-5-azabicyclo[2.2.1]heptan-5-yl]pyrimidin-4-yl]pyrimidin-2-amine;

5-[2-[(3aR,6aS)-4,4-difluoro-1,3,3a,5,6,6a-hexahydrocyclopenta[c]pyrrol-2-yl]-6-[(1S,4S)-2-oxa-5-azabicyclo[2.2.1]heptan-5-yl]pyrimidin-4-yl]pyrimidin-2-amine;

5-[2-(5-methyl-2,5-diazaspiro[3.4]octan-2-yl)-6-[(1S,4S)-2-oxa-5-azabicyclo[2.2.1]heptan-5-yl]pyrimidin-4-yl]pyrimidin-2-amine;

5-[2-(6-azaspiro[2.5]octan-6-yl)-6-[(1S,4S)-2-oxa-5-azabicyclo[2.2.1]heptan-5-yl]pyrimidin-4-yl]pyrimidin-2-amine;

5-[2-(3-azabicyclo[2.1.1]hexan-3-yl)-6-[8-(oxetan-3-yl)-8-azabicyclo[3.2.1]octan-3-yl]pyrimidin-4-yl]pyrimidin-2-amine;

1-[6-[6-(2-aminopyrimidin-5-yl)-2-(3-azabicyclo[2.1.1]hexan-3-yl)pyrimidin-4-yl]-3-azabicyclo[3.1.0]hexan-3-yl]ethanone;

1-[(1S,4S)-2-[6-(2-aminopyrimidin-5-yl)-2-(3-azabicyclo[2.1.1]hexan-3-yl)pyrimidin-4-yl]-2,5-diazabicyclo[2.2.1]heptan-5-yl]-2-methyl-propan-2-ol;

5-[2-(3-azabicyclo[2.1.1]hexan-3-yl)-6-[(1S,4S)-5-(2-methoxyethyl)-2,5-diazabicyclo[2.2.1]heptan-2-yl]pyrimidin-4-yl]pyrimidin-2-amine;]

5-[2-(3-azabicyclo[3.1.0]hexan-3-yl)-6-[(1S,4S)-2-oxa-5-azabicyclo[2.2.1]heptan-5-yl]pyrimidin-4-yl]-3-(difluoromethoxy)pyridin-2-amine;

[1-[6-[6-(2-aminopyrimidin-5-yl)-2-cyclopropyl-pyrimidin-4-yl]-3-azabicyclo[3.1.0]hexan-3-yl]ethanone;

5-[2-(3-azabicyclo[2.1.1]hexan-3-yl)-6-(9-azabicyclo[3.3.1]nonan-9-yl)pyrimidin-4-yl]pyrimidin-2-amine;

5-[2-[(3S,4R)-3,4-difluoropyrrolidin-1-yl]-6-[(1S,4S)-2-oxa-5-azabicyclo[2.2.1]heptan-5-yl]pyrimidin-4-yl]pyrimidin-2-amine;

5-[2-(3,3-difluoropyrrolidin-1-yl)-6-[(1S,4S)-2-oxa-5-azabicyclo[2.2.1]heptan-5-yl]pyrimidin-4-yl]pyrimidin-2-amine;

5-[2-(3-fluoroazetidin-1-yl)-6-[(1S,4S)-2-oxa-5-azabicyclo[2.2.1]heptan-5-yl]pyrimidin-4-yl]pyrimidin-2-amine;

5-[2-(4-cyclopropylpiperazin-1-yl)-6-[(1S,4S)-2-oxa-5-azabicyclo[2.2.1]heptan-5-yl]pyrimidin-4-yl]pyrimidin-2-amine;

5-[2-[(1R,4R)-5,5-difluoro-2-azabicyclo[2.2.1]heptan-2-yl]-6-[(1S,4S)-2-oxa-5-azabicyclo[2.2.1]heptan-5-yl]pyrimidin-4-yl]pyrimidin-2-amine;

5-[6-[(1S,4S)-2-oxa-5-azabicyclo[2.2.1]heptan-5-yl]-2-[4-(trifluoromethyl)-1-piperidyl]pyrimidin-4-yl]pyrimidin-2-amine;

1-[2-(2-aminopyrimidin-5-yl)-6-(3-azabicyclo[2.1.1]hexan-3-yl)-4-pyridyl]cyclobutanecarbonitrile;]

1-[6-[6-amino-5-(difluoromethoxy)-3-pyridyl]-2-(3-azabicyclo[2.1.1]hexan-3-yl)pyrimidin-4-yl]cyclobutanecarbonitrile;

5-[2-(3-azabicyclo[2.1.1]hexan-3-yl)-6-(3-azabicyclo[3.1.0]hexan-3-yl)pyrimidin-4-yl]-3-(difluoromethoxy)pyridin-2-amine;

5-[2-(3-azabicyclo[2.1.1]hexan-3-yl)-6-[(1S,4S)-2-oxa-5-azabicyclo[2.2.1]heptan-5-yl]pyrimidin-4-yl]-3-cyclopropyl-pyridin-2-amine;

5-[2-(3-azabicyclo[2.1.1]hexan-3-yl)-6-[(1S,4S)-2-oxa-5-azabicyclo[2.2.1]heptan-5-yl]pyrimidin-4-yl]-3-isopropoxy-pyridin-2-amine;

5-[2-cyclopropyl-6-[(1S,4S)-2-oxa-5-azabicyclo[2.2.1]heptan-5-yl]pyrimidin-4-yl]-3-(difluoromethoxy)pyridin-2-amine;

[5-[2-(3-azabicyclo[2.1.1]hexan-3-yl)-6-(8-azabicyclo[3.2.1]octan-3-yl)pyrimidin-4-yl]pyrimidin-2-amine;

5-[2-[4-(cyclopropylmethyl)piperazin-1-yl]-6-[(1S,4S)-2-oxa-5-azabicyclo[2.2.1]heptan-5-yl]pyrimidin-4-yl]pyrimidin-2-amine;

5-[6-(3-azabicyclo[2.1.1]hexan-3-yl)-4-[(1S,4S)-2-oxa-5-azabicyclo[2.2.1]heptan-5-yl]-2-pyridyl]-3-(difluoromethoxy)pyridin-2-amine;

5-[6-(3-azabicyclo[2.1.1]hexan-3-yl)-2-[(1S,4S)-2-oxa-5-azabicyclo[2.2.1]heptan-5-yl]pyrimidin-4-yl]pyrimidin-2-amine;

5-[2-(3-azabicyclo[3.1.0]hexan-3-yl)-6-[(1S,4S)-2-oxa-5-azabicyclo[2.2.1]heptan-5-yl]pyrimidin-4-yl]pyrimidin-2-amine;

1-[(1S,4S)-5-[6-(2-aminopyrimidin-5-yl)-2-(3-azabicyclo[2.1.1]hexan-3-yl)pyrimidin-4-yl]-2,5-diazabicyclo[2.2.1]heptan-2-yl]ethanone;

5-[2-(3-azabicyclo[2.1.1]hexan-3-yl)-6-[(1S,4S)-2,2-dioxo-2-thia-5-azabicyclo[2.2.1]heptan-5-yl]pyrimidin-4-yl]pyrimidin-2-amine;

5-[2-(3-azabicyclo[2.1.1]hexan-3-yl)-6-[(1S,4S)-5-(2,2,2-trifluoroethyl)-2,5-diazabicyclo[2.2.1]heptan-2-yl]pyrimidin-4-yl]pyrimidin-2-amine;

5-[2-(3-azabicyclo[2.1.1]hexan-3-yl)-6-(8-azabicyclo[3.2.1]octan-8-yl)pyrimidin-4-yl]pyrimidin-2-amine;

1-[6-(2-aminopyrimidin-5-yl)-2-(3-azabicyclo[2.1.1]hexan-3-yl)pyrimidin-4-yl]cyclobutanecarbonitrile;

5-[2-(3-azabicyclo[2.1.1]hexan-3-yl)-5-fluoro-6-[(1S,4S)-2-oxa-5-azabicyclo[2.2.1]heptan-5-yl]pyrimidin-4-yl]pyrimidin-2-amine;

5-[2-(3-azabicyclo[2.1.1]hexan-3-yl)-6-[3-(oxetan-3-yl)-3-azabicyclo[3.2.1]octan-8-yl]pyrimidin-4-yl]pyrimidin-2-amine;]

5-[2-(3-azabicyclo[2.1.1]hexan-3-yl)-6-[(1S,4S)-2-oxa-5-azabicyclo[2.2.1]heptan-5-yl]pyrimidin-4-yl]-3-(trifluoromethoxy)pyridin-2-amine;

[5-[2-(3-azabicyclo[2.1.1]hexan-3-yl)-6-(2,5-diazabicyclo[2.2.1]heptan-2-yl)pyrimidin-4-yl]pyrimidin-2-amine;

5-[2-(3-azabicyclo[2.1.1]hexan-3-yl)-6-(3-azabicyclo[3.2.1]octan-8-yl)pyrimidin-4-yl]pyrimidin-2-amine;]

5-[6-[(1R,4S)-3-azabicyclo[2.2.1]heptan-3-yl]-2-(3-azabicyclo[2.1.1]hexan-3-yl)pyrimidin-4-yl]-3-(difluoromethoxy)pyridin-2-amine;

[5-[6-[(1R,4S)-3-azabicyclo[2.2.1]heptan-3-yl]-2-(3-azabicyclo[2.1.1]hexan-3-yl)pyrimidin-4-yl]pyrimidin-2-amine;

5-[2-(3-azabicyclo[2.1.1]hexan-3-yl)-6-(3-azabicyclo[3.1.0]hexan-3-yl)pyrimidin-4-yl]pyrimidin-2-amine;

5-[2-cyclopropyl-6[(1S,4S)-2-oxa-5-azabicyclo[2.2.1]heptan-5-yl]pyrimidin-4-yl]pyrimidin-2-amine;

8-[6-(2-aminopyrimidin-5-yl)-2-(3-azabicyclo[2.1.1]hexan-3-yl)pyrimidin-4-yl]-3-methyl-8-azabicyclo[3.2.1]octan-3-ol;

5-[2-(3-azabicyclo[2.1.1]hexan-3-yl)-6-(2,6-dimethylmorpholin-4-yl)pyrimidin-4-yl]pyrimidin-2-amine;

5-[2-(3-azabicyclo[2.1.1]hexan-3-yl)-6-(8-oxa-3-azabicyclo[3.2.1]octan-3-yl)pyrimidin-4-yl]pyrimidin-2-amine;

5-[2,6-bis(3-azabicyclo[2.1.1]hexan-3-yl)pyrimidin-4-yl]pyrimidin-2-amine;]

5-[2-(3-azabicyclo[2.1.1]hexan-3-yl)-6-[(1S,4S)-2-oxa-5-azabicyclo[2.2.1]heptan-5-yl]pyrimidin-4-yl]-3-(difluoromethoxy)pyridin-2-amine;

2-amino-5-[2-(3-azabicyclo[2.1.1]hexan-3-yl)-6-[(1S,4S)-2-oxa-5-azabicyclo[2.2.1]heptan-5-yl]pyrimidin-4-yl]pyridine-3-carbonitrile;

5-[2-(3-azabicyclo[2.1.1]hexan-3-yl)-6-[(1S,4S)-2-oxa-5-azabicyclo[2.2.1]heptan-5-yl]pyrimidin-4-yl]-3-chloro-pyridin-2-amine;

5-[2-(3-azabicyclo[2.1.1]hexan-3-yl)-6-[(1S,4S)-2-oxa-5-azabicyclo[2.2.1]heptan-5-yl]pyrimidin-4-yl]-3-(trifluoromethyl)pyridin-2-amine;

[8-[6-(2-aminopyrimidin-5-yl)-2-(3-azabicyclo[2.1.1]hexan-3-yl)pyrimidin-4-yl]-8-azabicyclo[3.2.1]octan-3-ol;

5-[6-(3-azabicyclo[2.1.1]hexan-3-yl)-4-(3-oxa-8-azabicyclo[3.2.1]octan-8-yl)-2-pyridyl]pyrimidin-2-amine;

5-[4,6-bis(3-azabicyclo[2.1.1]hexan-3-yl)-2-pyridyl]pyrimidin-2-amine;

5-[2-(3-azabicyclo[2.1.1]hexan-3-yl)-6-(3-oxa-8-azabicyclo[3.2.1]octan-8-yl)pyrimidin-4-yl]pyrimidin-2-amine;

5-[6-(3-azabicyclo[2.1.1]hexan-3-yl)-4-[(1S,4S)-2-oxa-5-azabicyclo[2.2.1]heptan-5-yl]-2-pyridyl]pyrimidin-2-amine;

5-[2-(3-azabicyclo[2.1.1]hexan-3-yl)-6-(2,2-dimethylmorpholin-4-yl)pyrimidin-4-yl]pyrimidin-2-amine;

5-[2-(3-azabicyclo[2.1.1]hexan-3-yl)-6-[(1S,4S)-2-oxa-5-azabicyclo[2.2.1]heptan-5-yl]pyrimidin-4-yl]pyrimidin-2-amine;

5-[2-(2-methylpyrrolidin-1-yl)-6-tetrahydropyran-4-yl-pyrimidin-4-yl]pyrimidin-2-amine;

5-[6-(3-methoxyazetidin- 1-yl)-4-[1-(oxetan-3-yl)-4-piperidyl]-2-pyridyl]-3-(trifluoromethyl)pyridin-2-amine;

5-[6-(3-fluoroazetidin-1-yl)-4-[1-(oxetan-3-yl)-4-piperidyl]-2-pyridyl]-3-(trifluoromethyl)pyridin-2-amine;

3-chloro-5-[6-(3-fluoroazetidin- 1-yl)-4-[1-(oxetan-3-yl)-4-piperidyl]-2-pyridyl]pyridin-2-amine;

5-[6-(3-fluoroazetidin-1-yl)-4-[1-(oxetan-3-yl)-4-piperidyl]-2-pyridyl]pyrimidin-2-amine;

5-(2,6-dimorpholinopyrimidin-4-yl)pyrimidin-2-amine;]

5-[2-(3-azabicyclo[2.1.1]hexan-3-yl)-6-[(1R,5S)-3-(2-methoxyethyl)-3-azabicyclo [3.1.0]hexan-6-yl]pyrimidin-4-yl]-3-(difluoromethoxy)pyridin-2-amine;

1-[(1R,5S)-6-[6-[6-amino-5-(difluoromethoxy)-3-pyridyl]-2-(3-azabicyclo[2.1.1]hexan-3-yl)pyrimidin-4-yl]-3-azabicyclo[3.1.0]hexan-3-yl]ethanone;

[1-[(1R,5S)-6-[6-(2-aminopyrimidin-5-yl)-2-(3-azabicyclo[2.1.1]hexan-3-yl)pyrimidin-4-yl]-3-azabicyclo [3.1.0]hexan-3-yl]-2-methyl-propan-2-ol;]

5-[2-(3-azabicyclo[2.1.1]hexan-3-yl)-6-[(1R,5S)-3-(oxetan-3-yl)-3-azabicyclo[3.1.0]hexan-6-yl]pyrimidin-4-yl]-3-(difluoromethoxy)pyridin-2-amine;

5-[2-(3-azabicyclo[2.1.1]hexan-3-yl)-6-[(1R,5S)-3-(oxetan-3-yl)-3-azabicyclo[3.1.0]hexan-6-yl]pyrimidin-4-yl]-3-(trifluoromethyl)pyridin-2-amine;

5-[2-(3-azabicyclo[2.1.1]hexan-3-yl)-6-[(1R,5S)-3-(oxetan-3-yl)-3-azabicyclo[3.1.0]hexan-6-yl]pyrimidin-4-yl]-3-(trifluoromethoxy)pyridin-2-amine;

[5-[2-cyclopropyl-6-[(1R,5S)-3-(oxetan-3-yl)-3azabicyclo[3.1.0]hexan-6-yl]pyrimidin-4-yl]-3-(difluoromethoxy)pyridine-2-amine;]

*5-[2-cyclopropyl-6-[(1R,5S)-3-(oxetan-3-yl)-3-azabicyclo[3.1.0]hexan-6-yl]pyrimidin-4-yl]-3-(difluoromethoxy)pyridin-2-amine;*

[5-[2-cyclopropyl-6-[(1R,5S)-3-(2,2,2-trifluoroethyl)-3azabicyclo[3.1.0]hexan-6-yl]pyrimidin-4-yl]-3-(difluoromethoxy)pyridine-2amine;]

*5-[2-cyclopropyl-6-[(1R,5S)-3-(2,2,2-trifluoroethyl)-3-azabicyclo[3.1.0]hexan-6-yl]pyrimidin-4-yl]-3-(difluoromethoxy)pyridin-2-amine;*

5-[2-cyclopropyl-6-[(1R,5S)-3-(2-methoxyethyl)-3-azabicyclo[3.1.0]hexan-6-yl]pyrimidin-4-yl]-3-(difluoromethoxy)pyridin-2-amine;

[1-[(1R,5S)-6-[6-[6-amino 5-(difluromethoxy)-3-pyridyl]-2-cyclopropyl-pyrmidin-4-yl]-3-azabicyclo [3.1.0]hexan-3-yl]-2-methyl-propan-2-ol;]

*1-[(1R,5S)-6-[6-[6-amino-5-(difluoromethoxy)-3-pyridyl]-2-cyclopropyl-pyrimidin-4-yl]-3-azabicyclo [3.1.0]hexan-3-yl]-2-methyl-propan-2-ol;*

[1-[(1R,5S)-6-[6-[6-amino-5-(difluoromethoxy)-3-pyridyl]-2(3-azabicyclo[2.1.1]hexan-3-yl)pyrimidin-4-yl]-3-azabicyclo[3.1.0]hexan-3-yl]propan-1one;]

*1-[(1R,5S)-6-[6-[6-amino-5-(difluoromethoxy)-3-pyridyl]-2-(3-azabicyclo[2.1.1]hexan-3-yl)pyrimidin-4-yl]-3-azabicyclo[3.1.0]hexan-3-yl]propan-1-one;*

[3-(difluoromethoxy)-5-[2-[(3S)-3-fluoropyrrolodin-1-yl]-6-[(1S,4S)-2-oxa-5-azabicyclo[2.2.1]heptan-5yl] pyrimidin-4-yl]pyridin-2-amine;]

*3-(difluoromethoxy)-5-[2-[(3S)-3-fluoropyrrolidin-1-yl]-6-[(1S,4S)-2-oxa-5-azabicyclo[2.2.1]heptan-5-yl]pyrimidin-4-yl]pyridin-2-amine;*

3-(difluoromethoxy)-5-[2-3-methoxypyrrolidin-1-yl)-6-(2-oxa-5-azabicyclo[2.2.1]heptan-5-yl)pyrimidin-4-yl] pyridin-2-amine;

5-[2-(2-azaspiro[3.3]heptan-2-yl)-6-[(1S,4S)-2-oxa-5-azabicyclo[2.2.1]heptan-5-yl]pyrimidin-4-yl]-3-(difluoromethoxy)-pyridin-2-amine;

[5-[2-(2,3,3a,4,6,6a-hexahydrofuro[2,3-c]pyrrol-5yl)-6-(2-oxa-5-azabicyclo[2.2.1]heptan-5-yl)pyrimidin-4-yl]-3-(difluoromethoxy)pyridine-2-amine;]

*5-[2-(2,3,3a,4,6,6a-hexahydrofuro[2,3-c]pyrrol-5-yl)-6-(2-oxa-5-azabicyclo[2.2.1]heptan-5-yl)pyrimidin-4-yl]-3-(difluoromethoxy)pyridin-2-amine; and*

3-(difluoromethoxy)-5-[2-(3-methoxy-3-methyl-azetidin-1-yl)-6-[(1S,4S)-2-oxa-5-azabicyclo[2.2.1]heptan-5-yl]pyrimidin-4-yl]pyridin-2-amine; [and 6-cyclopropyl-5'-(difluoromethoxy)-4-(1-(oxetan-3-yl) azetidin-3-yl)-[2,3'-bipyridin]-6'-amine]

*or a pharmaceutically acceptable salt thereof.*

32. A pharmaceutical composition comprising a compound of claim 1, *or a pharmaceutically acceptable salt thereof,* and a pharmaceutically acceptable carrier, diluent or excipient.

33. A compound [of claim 1 which is 3-(difluoromethoxy)-5-[2-(3,3-difluoropyrrolidin-1-yl)-6-[(1S,4S)-2-oxa-5-azabicyclo[2.2.1]heptan-5-yl]pyrimidin-4]pyridin-2-amine] *wherein is 3-(difluoromethoxy)-5-[2-(3,3-difluoropyrrolidin-1-yl)-6-[(1S,4S)-2-oxa-5-azabicyclo [2.2.1]heptan-5-yl]pyrimidin-4-yl]pyridin-2-amine; or a pharmaceutically acceptable salt thereof.*

34. A compound [of claim 1] which is 1-[(1R,5S)-6-[6-[6-amino-5-(trifluoromethoxy)-3-pyridyl]-2-(3-azabicyclo [2.1.1]hexan-3-yl)pyrimidin-4-yl]-3-azabicyclo [3.1.0] hexan-3-yl]-2-methyl-propan-2-ol*; or a pharmaceutically acceptable salt thereof.*

35. A compound [of claim 1] which is 1-[(1R,5S)-6-[6-[6-amino-5-(trifluoromethyl)-3-pyridyl]-2-(3-azabicyclo [2.1.1]hexan-3-yl)pyrimidin-4-yl]-3-azabicyclo[3.1.0] hexan-3-yl]-2-methyl-propan-2-ol*; or a pharmaceutically acceptable salt thereof.*

36. A compound [of claim 1 which is [6-amino-5-(difluoromethoxy)-3-pyridyl]-2-(3-azabicyclo[2.1.1]hexan-3-yl) pyrimidin-4-yl]-3-azabicyclo[3.1.0]hexan-3-yl]-2-methyl-propan-2-ol] *which is 1-[(1R,5S)-6-[6-[6-amino-5-*

(*difluoromethoxy*)-*3-pyridyl*]-*2*-(*3-azabicyclo*[*2.1.1*]*hexan-3-yl*)-*pyrimidin-4-yl*]-*3-azabicyclo*[*3.1.0*]*hexan-3-yl*]-*2-methyl-propan-2-ol; or a pharmaceutically acceptable salt thereof.*

37. A compound [of claim 1] which is 5-[2-(3-azabicyclo[2.1.1]hexan-3-yl)-6-[(1R,5S)-3-(2-methoxyethyl)-3-azabicyclo[3.1.0]hexan-6-yl]pyrimidin-4-yl]-3-(trifluoromethyl)pyridin-2-amine*; or a pharmaceutically acceptable salt thereof.*

38. A compound [of claim 1] which is 1-[(1S,4S)-5-[6-[6-amino-5-(difluoromethoxy)-3-pyridyl]-2-(3-azabicyclo[2.1.1]hexan-3-yl)pyrimidin-4-yl]-2,5-diazabicyclo[2.2.1]heptan-2-yl]-2-methoxy-2-methyl-propan-1-one*; or a pharmaceutically acceptable salt thereof.*

39. A compound [of claim 1 which is [6-amino-5-(difluoromethoxy)-3-pyridyl]-2-(3-azabicyclo[2.1.1]hexan-3-yl)pyrimidin-4-yl]-2,5-diazabicyclo[2.2.1]heptan-2-yl]-2-methoxy-ethanone] *which is 1-*[*(1S,4S)-5-*[*6-*[*6-amino-5-*(*difluoromethoxy*)-*3-pyridyl*]-*2*-(*3-azabicyclo*[*2.1.1*]*hexan-3-yl*)*pyrimidin-4-yl*]-*2,5-diazabicyclo*[*2.2.1*]*heptan-2-yl*]-*2-methoxy-ethanone; or a pharmaceutically acceptable salt thereof.*

40. A compound [of claim 1] which is 3-(difluoromethoxy)-5-[2-[(3R,4S)-3,4-difluoropyrrolidin-1-yl]-6-[(1S,4S)-2-oxa-5-azabicyclo[2.2.1]heptan-5-yl]pyrimidin-4-yl]pyridin-2-amine*; or a pharmaceutically acceptable salt thereof.*

41. A compound [of claim 1] which is 1-[(1S,4S)-5-[6-[6-amino-5-(difluoromethoxy)-3-pyridyl]-2-(3-azabicyclo[2.1.1]hexan-3-yl)pyrimidin-4-yl]-2,5-diazabicyclo[2.2.1]heptan-2-yl]ethanone*; or a pharmaceutically acceptable salt thereof.*

42. A compound [of claim 1] which is 5-[2-(3-azabicyclo[3.1.0]hexan-3-yl)-6-[(1S,4S)-2-oxa-5-azabicyclo[2.2.1]heptan-5-yl]pyrimidin-4-yl]-3-(difluoromethoxy)pyridin-2-amine*; or a pharmaceutically acceptable salt thereof.*

43. A compound [of claim 1] which is 5-[2-(3-azabicyclo[2.1.1]hexan-3-yl)-6-(3-azabicyclo[3.1.0]hexan-3-yl)pyrimidin-4-yl]-3-(difluoromethoxy)pyridin-2-amine*; or a pharmaceutically acceptable salt thereof.*

44. A compound [of claim 1] which is 5-[2-(3-azabicyclo[2.1.1]hexan-3-yl)-6-[(1S,4S)-2-oxa-5-azabicyclo[2.2.1]heptan-5-yl]pyrimidin-4-yl]-3-isopropoxy-pyridin-2-amine*; or a pharmaceutically acceptable salt thereof.*

45. A compound [of claim 1] which is 5-[2-cyclopropyl-6-[(1S,4S)-2-oxa-5-azabicyclo[2.2.1]heptan-5-yl]pyrimidin-4-yl]-3-(difluoromethoxy)pyridin-2-amine*; or a pharmaceutically acceptable salt thereof.*

46. A compound [of claim 1] which is 5-[6-[(1R,4S)-3-azabicyclo[2.2.1]heptan-3-yl]-2-(3-azabicyclo[2.1.1]hexan-3-yl)pyrimidin-4-yl]-3-(difluoromethoxy)pyridin-2-amine*; or a pharmaceutically acceptable salt thereof.*

47. A compound [of claim 1] which is 5-[2-(3-azabicyclo[2.1.1]hexan-3-yl)-6-[(1S,4S)-2-oxa-5-azabicyclo[2.2.1]heptan-5-yl]pyrimidin-4-yl]-3-(difluoromethoxy)pyridin-2-amine*; or a pharmaceutically acceptable salt thereof.*

48. A compound [of claim 1] which is 5-[2-(3-azabicyclo[2.1.1]hexan-3-yl)-6-[(1R,5S)-3-(2-methoxyethyl)-3-azabicyclo[3.1.0]hexan-6-yl]pyrimidin-4-yl]-3-(difluoromethoxy)pyridin-2-amine*; or a pharmaceutically acceptable salt thereof.*

49. A compound [of claim 1] which is 1-[(1R,5S)-6-[6-[6-amino-5-(difluoromethoxy)-3-pyridyl]-2-(3-azabicyclo[2.1.1]hexan-3-yl)pyrimidin-4-yl]-3-azabicyclo[3.1.0]hexan-3-yl]ethanone*; or a pharmaceutically acceptable salt thereof.*

[50. A compound of claim 1 which is 1-[(1R,5S)-6-[6-(2-aminopyrimidin-5-yl)-2-(3-azabicyclo[2.1.1]hexan-3-yl)pyrimidin-4-yl]-3-azabicyclo[3.1.0]hexan-3-yl]-2-methyl-propan-2-ol.]

51. A compound [of claim 1] which is 5-[2-(3-azabicyclo[2.1.1]hexan-3-yl)-6-[(1R,5S)-3-(oxetan-3-yl)-3-azabicyclo[3.1.0]hexan-6-yl]pyrimidin-4-yl]-3-(difluoromethoxy)pyridin-2-amine*; or a pharmaceutically acceptable salt thereof.*

52. A compound [of claim 1] which is 5-[2-cyclopropyl-6-[(1R,5S)-3-(2-methoxyethyl)-3-azabicyclo[3.1.0]hexan-6-yl]pyrimidin-4-yl]-3-(difluoromethoxy)pyridin-2-amine*; or a pharmaceutically acceptable salt thereof.*

53. A compound [of claim 1] which is 1-[(1R,5S)-6-[6-[6-amino-5-(difluoromethoxy)-3-pyridyl]-2-cyclopropyl-pyrimidin-4-yl]-3-azabicyclo[3.1.0]hexan-3-yl]-2-methyl-propan-2-ol*; or a pharmaceutically acceptable salt thereof.*

54. A compound [of claim 1] which is 1-[(1R,5S)-6-[6-[6-amino-5-(difluoromethoxy)-3-pyridyl]-2-(3-azabicyclo[2.1.1]hexan-3-yl)pyrimidin-4-yl]-3-azabicyclo[3.1.0]hexan-3-yl]propan-1-one*; or a pharmaceutically acceptable salt thereof.*

55. A compound [of claim 1] which is 3-(difluoromethoxy)-5-[2-[(3S)-3-fluoropyrrolidin-1-yl]-6-[(1S,4S)-2-oxa-5-azabicyclo[2.2.1]heptan-5-yl]pyrimidin-4-yl]pyridin-2-amine*; or a pharmaceutically acceptable salt thereof.*

*56. A compound selected from the group consisting of:*

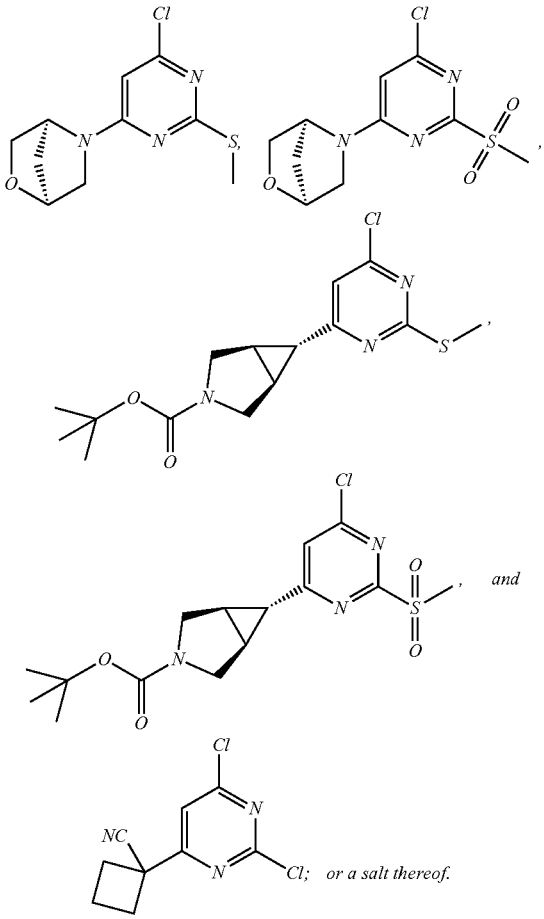

* * * * *